US011667712B2

(12) United States Patent
Ganesan et al.

(10) Patent No.: US 11,667,712 B2
(45) Date of Patent: Jun. 6, 2023

(54) MATERIALS AND METHODS FOR MODULATING T CELL MEDIATED IMMUNITY

(71) Applicant: Janssen Biotech, Inc., Horsham, PA (US)

(72) Inventors: Rajkumar Ganesan, Blue Bell, PA (US); Iqbal S. Grewal, Newtown, PA (US); Sanjaya Singh, Blue Bell, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 340 days.

(21) Appl. No.: 16/869,401

(22) Filed: May 7, 2020

(65) Prior Publication Data

US 2021/0032338 A1 Feb. 4, 2021

Related U.S. Application Data

(60) Provisional application No. 62/844,966, filed on May 8, 2019, provisional application No. 62/844,976, filed on May 8, 2019, provisional application No. 62/844,959, filed on May 8, 2019, provisional application No. 62/844,970, filed on May 8, 2019, provisional application No. 62/844,995, filed on May 8, 2019.

(51) Int. Cl.
*C07K 16/28* (2006.01)
*A61K 38/17* (2006.01)

(52) U.S. Cl.
CPC ...... *C07K 16/2809* (2013.01); *A61K 38/1709* (2013.01); *C07K 16/2866* (2013.01); *C07K 2317/24* (2013.01); *C07K 2317/31* (2013.01); *C07K 2317/565* (2013.01)

(58) Field of Classification Search
CPC ............ C07K 16/2809; C07K 16/2866; C07K 2317/24; C07K 2317/31; C07K 2317/565; C07K 16/30; C07K 2317/92; A61K 38/1709; A61K 2039/505; A61P 35/00
USPC ...................................................... 424/133.1
See application file for complete search history.

(56) References Cited

U.S. PATENT DOCUMENTS

| | | | |
|---|---|---|---|
| 6,737,056 | B1 | 5/2004 | Presta |
| 8,242,247 | B2 | 8/2012 | Klein et al. |
| 10,501,540 | B2 | 12/2019 | Van Der Vliet et al. |
| 2004/0018198 | A1 | 1/2004 | Gudas et al. |
| 2007/0287170 | A1 | 12/2007 | Davis et al. |
| 2009/0169547 | A1 | 7/2009 | Sahin et al. |
| 2009/0182127 | A1 | 7/2009 | Kjaergaard et al. |
| 2010/0015133 | A1 | 1/2010 | Igawa et al. |
| 2010/0028637 | A1 | 2/2010 | Tavsanli et al. |
| 2010/0261620 | A1 | 10/2010 | Almagro et al. |
| 2011/0052488 | A1 | 3/2011 | Dennis, Jr. et al. |
| 2011/0123532 | A1 | 5/2011 | Gurney et al. |
| 2012/0149876 | A1 | 6/2012 | von Kreudenstein et al. |
| 2013/0078249 | A1 | 3/2013 | Ast et al. |
| 2013/0195849 | A1 | 8/2013 | von Kreudenstein et al. |
| 2015/0119555 | A1 | 4/2015 | Jung et al. |
| 2017/0029506 | A1 | 2/2017 | Van de Vliet et al. |
| 2019/0144540 | A1 | 5/2019 | Koide et al. |
| 2019/0352397 | A1 | 11/2019 | Takahashi et al. |
| 2021/0284731 | A1 | 9/2021 | Ganesan et al. |
| 2022/0125947 | A1 | 4/2022 | Ganesan et al. |
| 2022/0306739 | A1 | 9/2022 | Ganesan et al. |

FOREIGN PATENT DOCUMENTS

| | | | |
|---|---|---|---|
| WO | WO 2006028936 | A2 | 3/2006 |
| WO | WO 2006028936 | A3 | 3/2006 |
| WO | WO 2009018386 | A1 | 2/2009 |
| WO | WO 2009080251 | A1 | 7/2009 |
| WO | WO 2009080252 | A1 | 7/2009 |
| WO | WO 2009080254 | A1 | 7/2009 |
| WO | WO 2011131746 | A2 | 10/2011 |
| WO | WO 2011131746 | A3 | 10/2011 |
| WO | WO 2012018767 | A2 | 2/2012 |
| WO | WO 2012018767 | A3 | 2/2012 |
| WO | WO 2015156673 | A1 | 10/2015 |
| WO | WO 2016196237 | A1 | 12/2016 |
| WO | WO 2021173896 | A1 | 9/2021 |
| WO | WO 2022093888 | A1 | 5/2022 |

OTHER PUBLICATIONS

U.S. Appl. No. 17/186,704, filed Feb. 26, 2021, U.S. Publ. No. 2022/0306739 (Sep. 29, 2022), Matrials and Methods for Modulating an Immune Response, Pending.
U.S. Appl. No. 17/202,004, filed Mar. 15, 2021, U.S. Publ. No. 2021/0284731 (Sep. 16, 2021), Methods and Materials for Modulating an Immune Response, Pending.
U.S. Appl. No. 17/512,195, filed Oct. 27, 2021, U.S. Publ. No. 2022/0125947 (Apr. 28, 2022), Compositions and Methods for Modulating Delta Gamma Chain Mediated Immunity, Pending.
Al-Lazikani et al., 1997, "Standard conformations for the canonical structures of immunoglobulins," J. Mol. Biol., 273(4):927-948.
Altschul et al., 1990, "Basic local alignment search tool," J. Mol. Biol., 215(3):403-410.
Altschul et al., 1997, "Gapped BLAST and PSI-BLAST: a new generation of protein database search programs," Nucleic Acids Res., 25(17):3389-3402.
Atwell et al., 1997, "Stable heterodimers from remodeling the domain interface of a homodimer using a phage display library," J. Mol. Biol., 270(1):26-35.

(Continued)

*Primary Examiner* — Yan Xiao
(74) *Attorney, Agent, or Firm* — Troutman Pepper Hamilton Sanders LLP

(57) ABSTRACT

Anti-TRGV9 antibodies or antigen binding fragments thereof are described. Also described are nucleic acids encoding the antibodies, compositions comprising the antibodies, methods of producing the antibodies, and methods of using the antibodies for treating or preventing diseases, such as cancer.

41 Claims, 22 Drawing Sheets

Specification includes a Sequence Listing.

(56) References Cited

OTHER PUBLICATIONS

Bel Ver et al., 2016, "The genetics and mechanisms of T cell acute lymphoblastic leukaemia," Nat. Rev. Cancer, 16(8):494-507.
Brown et al., 1998, "Affinity purification of human IgG using immobilised, mutated immunoglobulin-binding domains from protein A of *Staphylococcus aureus*," Biochem. Soc. Trans., 26(3):S249.
Bruin et al., 2017, "A bispecific nanobody approach to leverage the potent and widely applicable tumor cytolytic capacity of Vγ9Vδ2-T cells," Oncoimmunology, 7(1):e1375641 (15 pages).
Chames et al., 2009, "Bispecific antibodies for cancer therapy," Curr. Opin. Drug Discov. Devel., 12(2):276-283.
Chothia et al., 1987, "Canonical suuctures for the hypervariable regions of immunoglobulins," J. Mol. Biol., 196(4):901-917.
D'Asaro et al., 2010, "V gamma 9V delta 2 T lymphocytes efficiently recognize and kill zoledronate-sensitized, imatinib-sensitive, and imatinib-resistant chronic myelogenous leukemia cells," J. Immunol., 184(6):3260-3268.
Ebersbach et al., 2007, "Affilin-novel binding molecules based on human gamma-B-crystallin, an all beta-sheet protein," J. Mol. Biol., 372(1):172-185.
Ferrara et al., 2006, "Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II," Biotechnol. Bioeng., 93(5):851-861.
Ferrara et al., 2006, "The carbohydrate at FcgammaRIIIa Asn-162. An element required for high affinity binding to non-fucosylated IgG glycoforms," J. Biol. Chem., 281(8):5032-5036 (Epub 2005).
Ganesan et al., 2021, "Selective recruitment of γδ T cells by a bispecific antibody for the treatment of acute myeloid leukemia," Leukemia, 35(8):2274-2284.
Gebauer et al., 2009, "Engineered protein scaffolds as next-generation antibody therapeutics," Curr. Opin. Chem. Biol., 13(3):245-255.
GenBank Accession No. AY789109.1 (UnitProt P26951), "Interleukin-3 receptor subunit alpha • *Homo sapiens* (Human) • Gene: IL3RA (IL3R)," retrieved from internet <https://beta.uniprot.org/uniprotkb/P26951/entry> on Mar. 23, 2022, last released Feb. 23, 2022 (10 pages).
GenBank Accession No. BC028152.1 (UnitProt P20138), "Myeloid cell surface antigen CD33 • *Homo sapiens* (Human) • Gene: CD33 (SIGLEC3)," retrieved from internet <https://beta.uniprot.org/uniprotkb/P20138/entry> on Mar. 23, 2022, last released Feb. 23, 2022 (12 pages).
GenBank Accession No. NC_000007.14 (TRGC1), "*Homo sapiens* chromosome 7, GRCh38.p14 Primary Assembly," retrieved from internet <https://www.ncbi.nlm.nih.gov/nuccore/NC_000007.14?strand=2&report=genbank&from=38257879&to=38265678> on Sep. 20, 2022, last updated Apr. 6, 2022 (5 pages).
GenBank Accession No. NC_000007.14 (TRGC2), "*Homo sapiens* chromosome 7, GRCh38.p14 Primary Assembly," retrieved from internet <https://www.ncbi.nlm.nih.gov/nuccore/NC_000007.14?strand=2&report=genbank&from=38239580&to=38249572> on Sep. 20, 2022, last updated Apr. 6, 2022 (5 pages).
GenBank Accession No. NG_001336.2 (UnitProt Q99603), "T cell receptor gamma variable 9 • *Homo sapiens* (Human) • Gene: TRGV9 (TCRGV9)," retrieved from internet <https://beta.uniprot.org/uniprotkb/Q99603/entry> on Mar. 23, 2022, last released Feb. 23, 2022 (8 pages).
Grabulovski et al., 2007, "A novel, non-immunogenic Fyn SH3-derived binding protein with tumor vascular targeting properties," J. Biol. Chem., 282(5):3196-3204 (Epub 2006).
Hamuro et al., 2003, "Rapid analysis of protein structure and dynamics by hydrogen/deuterium exchange mass spectrometry," J. Biomol. Tech., 14(3):171-182.
Henikoff et al., 1992, "Amino acid substitution matrices from protein blocks," Proc. Natl. Acad. Sci. USA, 89(22):10915-10919.
Honegger et al., 2001, "Yet another numbering scheme for immunoglobulin variable domains: an automatic modeling and analysis tool," J. Mol. Biol., 309(3):657-670.
Horn et al., 2006, "The role of protein dynamics in increasing binding affinity for an engineered protein-protein interaction established by H/D exchange mass spectrometry," Biochemistry, 45(28):8488-8498.
Huang et al., 2018, "Hydrogen/deuterium exchange mass spectrometry and computational modeling reveal a discontinuous epitope of an antibody/TL1A Interaction," mAbs, 10(1):95-103 (Epub 2017).
International Search Authority, International Search Report and Written Opinion for International Patent Application No. PCT/US2020/031749 (Pub No. WO 2020227457) dated Oct. 9, 2020 (16 pages).
International Search Authority, International Search Report and Written Opinion for International Patent Application No. PCT/US2021/019766 (Pub No. WO 2021173896) dated Jul. 1, 2021 (10 pages).
International Search Authority, International Search Report and Written Opinion for International Patent Application No. PCT/US2021/056744 (Pub No. WO 2022093888) dated Mar. 2, 2022 (12 pages).
Itohara et al., 1990, "Selection of gamma delta T cells with canonical T-cell antigen receptors in fetal thymus," Proc. Natl. Acad. Sci. USA, 87(20):7935-7938.
Kabat et al., 1977, "Unusual distributions of amino acids in complementarity-determining (hypervariable) segments of heavy and light chains of immunoglobulins and their possible roles in specificity of antibody-combining sites," J. Biol. Chem., 252(19):6609-6616.
Kabat, 1978, "The structural basis of antibody complementarity," Adv. Protein. Chem., 32:1-75.
Karlin et al., 1993, "Applications and statistics for multiple high-scoring segments in molecular sequences," Proc. Natl. Acad. Sci. USA, 90(12):5873-5877.
Kiladjian et al., 2008, "Activation of cytotoxic T-cell receptor gammadelta T lymphocytes in response to specific stimulation in myelodysplastic syndromes," Haematologica, 93(3):381-389.
Kirkland et al., 1986, "Analysis of the fine specificity and cross-reactivity of monoclonal anti-lipid A antibodies," J. Immunol., 137(11):3614-3619.
Koide et al., 2007, "Monobodies: antibody mimics based on the scaffold of the fibronectin type III domain," Methods Mol. Biol., 352:95-109.
Kolmar, 2008, "Alternative binding proteins: biological activity and therapeutic potential of cystine-knot miniproteins," FEBS J., 275(11):2684-2690.
Konno et al., 2012, "Fucose content of monoclonal antibodies can be controlled by culture medium osmolality for high antibody-dependent cellular cytotoxicity," Cytotechnology, 64(3):249-265 (Epub 2011).
Krehenbrink et al., 2008, "Artificial binding proteins (Affitins) as probes for conformational changes in secretin PulD," J. Mol. Biol., 383(5):1058-1068.
Lefranc et al., 2003, "IMGT unique numbering for immunoglobulin and T cell receptor variable domains and Ig superfamily V-like domains," Dev. Comp. Immunol., 27(1):55-77.
Legut et al., 2015, "The promise of γδ T cells and the γδ T cell receptor for cancer immunotherapy," Cell Mol. Immunol., 12(6):656-668.
Litzow et al., 2015, "How I treat T-cell acute lymphoblastic leukemia in adults," Blood, 126(7):833-841.
Liu et al., 2017, "The genomic landscape of pediatric and young adult T-lineage acute lymphoblastic leukemia," Nat. Genet., 49(8):1211-1218 and Online Methods (10 pages).
Moldenhauer et al., 1990, "Identity of HML-1 antigen on intestinal intraepithelial T cells and of B-ly7 antigen on hairy cell leukaemia," Scand. J. Immunol., 32(2):77-82.
Morea et al., 2000, "Antibody modeling: implications for engineering and design," Methods, 20(3):267-279.
Morel et al., 1988, "Monoclonal antibodies to bovine serum albumin: affinity and specificity determinations," Mol. Immunol., 25(1):7-15.

(56) References Cited

OTHER PUBLICATIONS

Mori et al., 2004, "Engineering Chinese hamster ovary cells to maximize effector function of produced antibodies using FUT8 siRNA," Biotechnol. Bioeng., 88(7):901-908.

Needleman et al., 1970, "A general method applicable to the search for similarities in the amino acid sequence of two proteins," J. Mol. Biol., 48(3):443-453.

Nixon et al., 2006, "Engineered protein inhibitors of proteases," Curr. Opin. Drug Discov. Devel., 9(2):261-268.

Nunez-Prado et al., 2015, "The coming of age of engineered multivalent antibodies," Drug Discov. Today, 20(5):588-594.

Nygren, 2008, "Alternative binding proteins: affibody binding proteins developed from a small three-helix bundle scaffold," FEBS J., 275(11):2668-2676.

Oberg et al., 2014, "Novel bispecific antibodies increase γδ T-cell cytotoxicity against pancreatic cancer cells," Cancer Res., 74(5):1349-1360.

Oberg et al., 2015, "γδ T cell activation by bispecific antibodies," Cell Immunol., 296(1):41-49.

Olivier et al., 2010, "EB66 cell line, a duck embryonic stem cell-derived substrate for the industrial production of therapeutic monoclonal antibodies with enhanced ADCC activity," mAbs, 2(4):405-415.

Pascal et al., 2012, "HDX workbench: software for the analysis of H/D exchange MS data," J. Am. Soc. Mass Spectrom., 23(9):1512-1521.

Pearson et al., 1988, "Improved tools for biological sequence comparison," Proc. Natl. Acad. Sci. USA, 85(8):2444-2448.

Pui et al., 2015, "Childhood Acute Lymphoblastic Leukemia: Progress Through Collaboration," J. Clin. Oncol., 33(27):2938-2948.

Shields et al., 2002, "Lack of fucose on human IgG1 N-linked oligosaccharide improves binding to human Fcgamma RIII and antibody-dependent cellular toxicity," J. Biol. Chem., 277(30):26733-26740.

Shinkawa et al., 2003, "The absence of fucose but not the presence of galactose or bisecting N-acetylglucosamine of human IgG1 complex-type oligosaccharides shows the critical role of enhancing antibody-dependent cellular cytotoxicity," J. Biol, Chem., 278(5):3466-3473 (Epub 2002).

Silverman et al., 2005, "Multivalent avimer proteins evolved by exon shuffling of a family of human receptor domains," Nat. Biotechnol., 23(12):1556-1561.

Singh et al., 2015, "Selective targeting of the IL23 pathway: Generation and characterization of a novel high-affinity humanized anti-IL23A antibody," mAbs, 7(4):778-791.

Skerra, 2008, "Alternative binding proteins: anticalins—harnessing the structural plasticity of the lipocalin ligand pocket to engineer novel binding activities" FEBS J., 275(11):2677-2683.

Smith et al., 1981, "Comparison of biosequences," Advances in Applied Mathematics, 2(4):482-489.

Stahli et al., 1983, "Distinction of epitopes by monoclonal antibodies," Methods Enzymol., 92:242-253.

Stumpp et al., 2008, "DARPins: a new generation of protein therapeutics," Drug Discov. Today, 13(15-16):695-701.

Wesselborg et al., 1991, "Selective activation of gamma/delta + T cell clones by single anti-CD2 antibodies," J. Exp. Med., 173(2):297-304.

Wranik et al., 2012, "LUZ-Y, a novel platform for the mammalian cell production of full-length IgG-bispecific antibodies," J. Biol. Chem., 287(52):43331-43339.

Zhang et al., 2019, "CellMarker: a manually curated resource of cell markers in human and mouse," Nucleic Acids Res., 47(D1):D721-D728 (Epub 2018).

Zhou et al., 2008, "Development of a simple and rapid method for producing non-fucosylated oligomannose containing antibodies with increased effector function," Biotechnol. Bioeng., 99(3):652-665.

MATERIALS AND METHODS FOR MODULATING T CELL MEDIATED IMMUNITY

CROSS-REFERENCE TO RELATED APPLICATIONS

This application claims the benefit of U.S. Ser. No. 62/844,959 filed May 8, 2019; U.S. Ser. No. 62/844,966 filed May 8, 2019; U.S. Ser. No. 62/844,970 filed May 8, 2019; U.S. Ser. No. 62/844,976 filed May 8, 2019; and U.S. Ser. No. 62/844,995 filed May 8, 2019, each of which is incorporated herein by reference in its entirety.

FIELD

This invention relates to, among other things, anti-TRGV9 molecules, including anti-TRGV9 antibodies, anti-TRGV9/anti-cancer-associated antigen bispecific antibodies, as well as nucleic acids and expression vectors encoding the antibodies, recombinant cells containing the vectors, and compositions comprising the antibodies. Methods of making the antibodies, and methods of using the antibodies to kill cancer cells, are also provided.

REFERENCE TO SEQUENCE LISTING SUBMITTED ELECTRONICALLY

This application contains a sequence listing, which is submitted electronically via EFS-Web as an ASCII formatted sequence listing with a file name "14620-021-999_SEQLIST" and a creation date of May 5, 2020 and having a size of 349,546 bytes. The sequence listing submitted via EFS-Web is part of the specification and is herein incorporated by reference in its entirety.

SUMMARY

In one aspect, provided herein is an antibody that binds to T Cell Receptor Gamma Variable 9 (TRGV9). In some embodiments, the antibody comprises a heavy chain variable region (VH) and a light chain variable region (VL).

In another aspect, provided herein is an antibody that binds to TRGV9, wherein the antibody comprises: (i) a VH comprising a VH complementarity determining region (CDR) 1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the antibody comprises a VH having an amino acid sequence of SEQ ID NO:34. In some embodiments, the antibody comprises a VL having an amino acid sequence of SEQ ID NO:8. In some embodiments, the antibody comprises a VH having an amino acid sequence of SEQ ID NO:34, and a VL having an amino acid sequence of SEQ ID NO:8. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the antibody comprises a VH having an amino acid sequence of SEQ ID NO:35. In some embodiments, the antibody comprises a VL having an amino acid sequence of SEQ ID NO:8. In some embodiments, the antibody comprises a VH having an amino acid sequence of SEQ ID NO:35, and a VL having an amino acid sequence of SEQ ID NO:8. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the antibody comprises a VH having an amino acid sequence of SEQ ID NO:36. In some embodiments, the antibody comprises a VL having an amino acid sequence of SEQ ID NO:8. In some embodiments, the antibody comprises a VH having an amino acid sequence of SEQ ID NO:36, and a VL having an amino acid sequence of SEQ ID NO:8. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In some embodiments, the antibody comprises a VH having an amino acid sequence of SEQ ID NO:65. In some embodiments, the antibody comprises a VL having an amino acid sequence of SEQ ID NO:66. In some embodiments, the antibody comprises a VH having an amino acid sequence of SEQ ID NO:65, and a VL having an amino acid sequence of SEQ ID NO:66. In some embodiments, the antibody comprises a VH having an amino acid sequence of SEQ ID NO:67. In some embodiments, the antibody comprises a VL having an amino acid sequence of SEQ ID NO:68. In some embodiments, the antibody comprises a VH having an amino acid sequence of SEQ ID NO:67, and a VL having an amino acid sequence of SEQ ID NO:68. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100; and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In some embodiments, the antibody comprises a VH having an amino acid sequence of SEQ ID NO:104. In some embodiments, the antibody comprises a VL having an amino acid sequence of SEQ ID NO:105. In some embodiments, the antibody comprises a VH having an amino acid sequence of SEQ ID NO:104, and a VL having an amino acid sequence of SEQ ID NO:105. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109; and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In some embodiments, the antibody comprises a VH having an amino acid sequence of SEQ ID NO:113. In some embodiments, the antibody comprises a VL having an amino acid sequence of SEQ ID NO:114. In some embodiments, the antibody comprises a VH having an amino acid sequence of SEQ ID NO:113, and a VL having an amino acid sequence of SEQ ID NO:114. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119; and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In some embodiments, the antibody comprises a VH having an amino acid sequence of SEQ ID NO:123. In some embodiments, the antibody comprises a VL having an amino acid sequence of SEQ ID NO:124. In some embodiments, the antibody comprises a VH having an amino acid sequence of SEQ ID NO:123, and a VL having an amino acid sequence of SEQ ID NO:124. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In another aspect, provided herein is an antibody that binds to TRGV9, wherein the antibody comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129; and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In some embodiments, the antibody comprises a VH having an amino acid sequence of SEQ ID NO:133. In some embodiments, the antibody comprises a VL having an amino acid sequence of SEQ ID NO:134. In some embodiments, the antibody comprises a VH having an amino acid sequence of SEQ ID NO:133, and a VL having an amino acid sequence of SEQ ID NO:134. In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

Also provided is a nucleic acid encoding an antibody that binds to a TRGV9 provided herein. Also provided is a vector comprising a nucleic acid encoding an antibody that binds to a TRGV9 provided herein. Also provided is a host cell comprising a vector comprising a nucleic acid encoding an antibody that binds to a TRGV9 provided herein. Also provided is a kit comprising the vector comprising a nucleic acid encoding an antibody that binds to a TRGV9 provided herein, and packaging for the same.

Also provided is a pharmaceutical composition comprising an antibody that binds to a TRGV9 provided herein, and a pharmaceutically acceptable carrier. Also provided is a method of producing the pharmaceutical composition, comprising combining the antibody with a pharmaceutically acceptable carrier to obtain the pharmaceutical composition.

Also provided is a method of activating a γδ T cell expressing TRGV9, comprising contacting the γδ T cell with an antibody that binds to a TRGV9 provided herein. In some embodiments, the contacting results in an increase in CD69, CD25, and/or Granzyme B expression, as compared to a control γδ T cell expressing TRGV9. Also provided is a method of inactivating a γδ T cell expressing TRGV9, comprising contacting the γδ T cell with an antibody that binds to a TRGV9 provided herein. Also provided is a method of blocking activation a γδ T cell expressing TRGV9, comprising contacting the γδ T cell with an antibody that binds to a TRGV9 provided herein. Also provided is a method of modulating the activity of a γδ T cell expressing TRGV9, comprising contacting the γδ T cell with an antibody that binds to a TRGV9 provided herein.

In another aspect, provided herein is a bispecific antibody comprising: (a) a first binding domain that binds to TRGV9, and (b) a second binding domain that binds to a second target that is not TRGV9. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:7. In some embodiments, the first binding domain comprises a VL having an amino acid sequence of SEQ ID NO:8. In some embodiments, the first binding domain comprises a VH having an amino acid sequence of SEQ ID NO:7, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:34. In some embodiments, the first binding domain comprises a VL having an amino acid sequence of SEQ ID NO:8. In some embodiments, the first binding domain comprises a VH having an amino acid sequence of SEQ ID NO:34, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:35. In some embodiments, the first binding domain comprises a VL having an amino acid sequence of SEQ ID NO:8. In some embodiments, the first binding domain comprises a VH having an amino acid sequence of SEQ ID NO:35, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In some embodiments, the first binding domain comprises a VH having an amino acid sequence of SEQ ID NO:36. In some embodiments, the first binding domain comprises a VL having an amino acid sequence of SEQ ID NO:8. In some embodiments, the first binding domain comprises a VH having an amino acid sequence of SEQ ID NO:36, and a VL having an amino acid sequence of SEQ ID NO:8. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In some embodiments, the first binding domain comprises a VH having an amino acid sequence of SEQ ID NO:65. In some embodiments, the first binding domain comprises a VL having an amino acid sequence of SEQ ID NO:66. In some embodiments, the first binding domain comprises a VH having an amino acid sequence of SEQ ID NO:65, and a VL having an amino acid sequence of SEQ ID NO:66. In some embodiments, the first binding domain comprises a VH having an amino acid sequence of SEQ ID NO:67. In some embodiments, the first binding domain comprises a VL having an amino acid sequence of SEQ ID NO:68. In some embodiments, the first binding domain a VH having an amino acid sequence of SEQ ID NO:67, and a VL having an amino acid sequence of SEQ ID NO:68. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94. In some embodiments, the first binding domain comprises a VH having an amino acid sequence of SEQ ID NO:95. In some embodiments, the first binding domain comprises a VL having an amino acid sequence of SEQ ID NO:96. In some embodiments, the first binding domain comprises a VH having an amino acid sequence of SEQ ID NO:95, and a VL having an amino acid sequence of SEQ ID NO:96. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In some embodiments, the first binding domain comprises a VH having an amino acid sequence of SEQ ID NO:104. In some embodiments, the first binding domain comprises a VL having an amino acid sequence of SEQ ID NO:105. In some embodiments, the first binding domain comprises a VH having an amino acid sequence of SEQ ID NO:104, and a VL having an amino acid sequence of SEQ ID NO:105. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In some embodiments, the first binding domain comprises a VH having an amino acid sequence of SEQ ID NO:113. In some embodiments, the first binding domain comprises a VL having an amino acid sequence of SEQ ID NO:114. In some embodiments, the first binding domain comprises a VH having an amino acid sequence of SEQ ID NO:113, and a VL having an amino acid sequence of SEQ ID NO:114. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In some embodiments, the first binding domain comprises a VH having an amino acid sequence of SEQ ID NO:123. In some embodiments, the first binding domain comprises a VL having an amino acid sequence of SEQ ID NO:124. In some embodiments, the first binding domain comprises a VH having an amino acid sequence of SEQ ID NO:123, and a VL having an amino acid sequence of SEQ ID NO:124. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In some embodiments, the first binding domain comprises a VH having an amino acid sequence of SEQ ID NO:133. In some embodiments, the first binding domain comprises a VL having an amino acid sequence of SEQ ID NO:134. In some embodiments, the first binding domain comprises a VH having an amino acid sequence of SEQ ID NO:133, and a VL having an amino acid sequence of SEQ ID NO:134. In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to a cancer antigen present on the surface of a cancer cell. In some embodiments, the antigen on the surface of the cancer cell is a tumor-specific antigen, a tumor associated antigen, or a neoantigen. In certain embodiments, the first binding domain of the bispecific antibody specifically binds TRGV9. In some embodiments, the TRGV9 is present on the surface of a γδ T cell. In some embodiments, the cancer cell is killed when the bispecific antibody binds to the TRGV9 on the surface of the γδ T cell and the antigen on the surface of the cancer cell. In some embodiments, the first binding domain is humanized, the second binding domain is humanized, or both the first binding domain and the second binding domain are humanized. In some embodiments, the bispecific antibody is an IgG antibody. In some embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to CD123. In certain embodiments, the first binding domain of the bispecific antibody specifically binds TRGV9. In some embodiments, the TRGV9 is present on the surface of a γδ T cell. In some embodiments, the CD123 is on the surface of a cell. In certain embodiments, the TRGV9 is present on the surface of a γδ T cell, and the CD123 is on the surface of a cell. In some embodiments, the cell having the CD123 on the surface is killed when the bispecific antibody binds to the TRGV9 on the surface of the γδ T cell and the CD123 on the surface of the cell. In some embodiments, the CD123 is on the surface of a cancer cell. In certain embodiments, the TRGV9 is present on the surface of a γδ T cell, and the CD123 is on the surface of a cancer cell. In some embodiments, the cancer cell is killed when the bispecific antibody binds to the TRGV9 on the surface of the γδ T cell and the CD123 on the surface of the cell. In some embodiments, the first binding domain is humanized, the second binding domain is humanized, or both the first binding domain and the second binding domain are humanized. In some embodiments, the bispecific antibody is an IgG antibody. In some embodiments, the IgG antibody is an IgG1, IgG2, IgG3, or IgG4 antibody.

In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the CD123 is on the surface of a cell. In certain embodiments, the TRGV9 is present on the surface of a γδ T cell, and the CD123 is on the surface of a cell. In some embodiments, the cell having the CD123 on the surface is killed when the bispecific antibody binds to the TRGV9 on the surface of the γδ T cell and the CD123 on the surface of the cell. In some embodiments, the CD123 is on the surface of a cancer cell. In certain embodiments, the TRGV9 is present on the surface of a γδ T cell, and the CD123 is on the surface of a cancer cell. In some embodiments, the cancer cell is killed when the bispecific antibody binds to the TRGV9 on the surface of the γδ T cell and the CD123 on the surface of the cell. In some embodiments, the first binding domain is humanized, the second binding domain is humanized, or both the first binding domain and the second binding domain are humanized. In some embodiments, the bispecific antibody is an IgG antibody. In some embodiments, the IgG antibody is an IgG1, IgG2, IgG3, or IgG4 antibody.

In some embodiments of the various bispecific antibodies provided herein, the first binding domain that binds to TRGV9 comprises a VH CDR1, VH CDR2, VH CDR3, VL CDR1, VL CDR2 and VL CDR3 having amino acid sequences, as provided herein. In some embodiments, the first binding domain that binds to TRGV9 comprises a VH CDR1, VH CDR2 and VH CDR3 of a VH domain having an amino acid sequence, as provided herein. In some embodiments, the first binding domain that binds to TRGV9 comprises a VL CDR1, VL CDR2 and VL CDR3 of a VL domain having an amino acid sequence, as provided herein. In some embodiments, the first binding domain that binds to TRGV9 comprises a VH CDR1, VH CDR2 and VH CDR3 of a VH domain having an amino acid sequence, as provided herein; and a VL CDR1, VL CDR2 and VL CDR3 of a VL domain having an amino acid sequence, as provided herein. In some embodiments, the first binding domain that binds to TRGV9 comprises a VH domain having an amino acid sequence, as provided herein. In some embodiments, the first binding domain that binds to TRGV9 comprises a VL domain having an amino acid sequence, as provided herein. In some embodiments, the first binding domain that binds to TRGV9 comprises a VH domain having an amino acid sequence, as provided herein; and a VL domain having an amino acid sequence, as provided herein.

Also provided is a nucleic acid encoding a bispecific antibody comprising: (a) a first binding domain that binds to TRGV9, and (b) a second binding domain that binds to a second target that is not TRGV9, as provided herein. Also provided is a vector comprising a nucleic acid encoding a bispecific antibody that binds to a TRGV9 provided herein. Also provided is a host cell comprising a vector comprising a nucleic acid encoding a bispecific antibody that binds to a TRGV9 provided herein. Also provided is a kit comprising the vector comprising a nucleic acid encoding a bispecific antibody that binds to a TRGV9 provided herein, and packaging for the same.

In another aspect, provided herein is a pharmaceutical composition comprising a comprising: (a) a first binding domain that binds to TRGV9, and (b) a second binding domain that binds to a second target that is not TRGV9, and a pharmaceutically acceptable carrier. Any of the bispecific antibodies provided herein are contemplated in the pharmaceutical compositions. In certain embodiments, the second binding domain binds to CD123.

In another aspect, provided herein is a method of directing a γδ T cell expressing TRGV9 to a cancer cell, the method comprising contacting the γδ T cell with a bispecific antibody provided herein. In some embodiments, the contacting directs the γδ T cell to the cancer cell.

In another aspect, provided herein is a method of inhibiting growth or proliferation of cancer cells expressing a cancer antigen on the cell surface, the method comprising contacting the cancer cells with a bispecific antibody provided herein. In some embodiments, contacting the cancer cells with the pharmaceutical composition inhibits growth or proliferation of the cancer cells. In some embodiments, the cancer cells are in the presence of a γδ T cell expressing TRGV9 while in contact with the bispecific antibody.

In another aspect, provided herein is a method for eliminating cancer cells in a subject, comprising administering an effective amount of a bispecific antibody, as provided herein, to the subject. In some embodiments, the subject is a subject in need thereof. In some embodiments, the subject is a human.

In another aspect, provided herein is a method of activating a γδ T cell expressing TRGV9, comprising contacting the γδ T cell with the bispecific antibody, as provided herein.

Provided herein are isolated TRGV9 bispecific antibodies or antigen binding fragments thereof, the isolated TRGV9 bispecific antibody or antigen binding fragment thereof comprising:
a. a first heavy chain (HC1);
b. a second heavy chain (HC2);
c. a first light chain (LC1); and
d. a second light chain (LC2),
wherein HC1 is associated with LC1 and HC2 is associated with LC2, and wherein HC1 comprises a heavy chain complementarity determining region 1 (HCDR1), HCDR2, and HCDR3 comprising the amino acid sequences of:
i. SEQ ID NO:1, SEQ ID NO:2, and SEQ ID NO:3, respectively,
ii. SEQ ID NO:1, SEQ ID NO:2, and SEQ ID NO:31, respectively,
iii. SEQ ID NO:1, SEQ ID NO:2, and SEQ ID NO:32, respectively, or
iv. SEQ ID NO:1, SEQ ID NO:2, and SEQ ID NO:33, respectively,
and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:7, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:7, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d)

a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:34, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:34, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:35, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:35, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of: SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:36, and LC1 comprises an amino acid sequence having at least 95% identity to the amino acid sequence of SEQ ID NO:8. In another embodiment, the isolated TRGV9 bispecific antibody or antigen binding fragment thereof comprises an HC1 comprising the amino acid sequence of SEQ ID NO:36, and LC1 comprises the amino acid sequence of SEQ ID NO:8.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated TRGV9 bispecific antibody or antigen binding fragment thereof comprises an HC1 comprising the amino acid sequence of SEQ ID NO:65, and LC1 comprises the amino acid sequence of SEQ ID NO:66. In one embodiment, the isolated TRGV9 bispecific antibody or antigen binding fragment thereof comprises an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated TRGV9 bispecific antibody or antigen binding fragment thereof comprises an HC1 comprising the amino acid sequence of SEQ ID NO:67, and LC1 comprises the amino acid sequence of SEQ ID NO:68.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated TRGV9 bispecific antibody or antigen binding fragment thereof comprises an HC1 comprising the amino acid sequence of SEQ ID NO:65, and LC1 comprises the amino acid sequence of SEQ ID NO:66. In one embodiment, the isolated TRGV9 bispecific antibody or antigen binding fragment thereof comprises an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated TRGV9 bispecific antibody or antigen binding fragment thereof comprises an HC1 comprising the amino acid sequence of SEQ ID NO:67, and LC1 comprises the amino acid sequence of SEQ ID NO:68.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:95, and LC1 comprises an amino acid sequence having at least 95% identity to the amino acid sequence of SEQ ID NO:96. In another embodiment, the isolated TRGV9 bispecific antibody or antigen binding fragment thereof comprises an HC1 comprising the amino acid sequence of SEQ ID NO:95, and LC1 comprises the amino acid sequence of SEQ ID NO:96.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:104, and LC1 comprises an amino acid sequence having at least 95% identity to the amino acid sequence of SEQ ID NO:105. In another embodiment, the isolated TRGV9 bispecific antibody or antigen binding fragment thereof comprises an HC1 comprising the amino acid sequence of SEQ ID NO:104, and LC1 comprises the amino acid sequence of SEQ ID NO:105.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:113, and LC1 comprises an amino acid sequence having at least 95% identity to the amino acid sequence of SEQ ID NO:114. In another embodiment, the isolated TRGV9 bispecific antibody or antigen binding fragment thereof comprises an HC1 comprising the amino acid sequence of SEQ ID NO:113, and LC1 comprises the amino acid sequence of SEQ ID NO:114.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:123, and LC1 comprises an amino acid sequence having at least 95% identity to the amino acid sequence of SEQ ID NO:124. In another embodiment, the isolated TRGV9 bispecific antibody or antigen binding fragment thereof comprises an HC1 comprising the amino acid sequence of SEQ ID NO:123, and LC1 comprises the amino acid sequence of SEQ ID NO:124.

Also provided herein are isolated TRGV9 bispecific antibodies or antigen binding fragments thereof, the isolated TRGV9 bispecific antibody or antigen binding fragment thereof comprising: (a) a HC1; (b) a HC2; (c) a LC1; and (d) a LC2, wherein HC1 is associated with LC1 and HC2 is associated with LC2, and wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a binding site for a first antigen, and wherein HC2 and LC2 form a binding site for a second antigen. In one embodiment, the isolated TRGV9 bispecific antibody or antigen binding fragment thereof comprises an HC1 comprising an amino acid sequence having at least 95% identity to an amino acid sequence of SEQ ID NO:133, and LC1 comprises an amino acid sequence having at least 95% identity to the amino acid sequence of SEQ ID NO:134. In another embodiment, the isolated TRGV9 bispecific antibody or antigen binding fragment thereof comprises an HC1 comprising the amino acid sequence of SEQ ID NO:133, and LC1 comprises the amino acid sequence of SEQ ID NO:134.

In another embodiment, the binding site for a first antigen binds to TRGV9 on a γδ T cell.

In another embodiment, the binding site for a second antigen binds to a cancer antigen present on the surface of a cancer cell.

In another embodiment, the bispecific antibody binds to TRGV9 present on the surface of the γδ T cell and the binding of the cancer antigen present on the surface of the cancer cell results in the killing of the cancer cell.

In another embodiment, TRGV9 bispecific antibody comprises a humanized HC1 and a humanized LC1.

In another embodiment, the HC2 and LC2 of the TRGV9 antibody bind to CD123.

In another embodiment the bispecific antibody or antigen binding fragment thereof is an IgG1, an IgG2, an IgG3, or an IgG4 isotype.

In a specific embodiment, the bispecific antibody or antigen binding fragment thereof is an IgG4 isotype.

In another embodiment, the TRGV9 bispecific antibody or antigen binding fragment thereof induces γδ T cell dependent cytotoxicity of a cancer cell in vitro with an $EC_{50}$ of less than about 500 pM.

In another embodiment, the TRGV9 bispecific antibody or antigen binding fragment thereof induces γδ T cell dependent cytotoxicity of a cancer cell in vitro with an $EC_{50}$ of less than about 300 pM.

In another embodiment, the TRGV9 bispecific antibody or antigen binding fragment thereof induces γδ T cell dependent cytotoxicity of a cancer cell in vitro with an $EC_{50}$ of less than about 160 pM.

In one embodiment, the $EC_{50}$ is assessed with a mixture of γδ T effector cells and Kasumi3 AML target cells.

In another embodiment, effector cell to target cell ratio is about 0.01 to 1 to about 5 to 1.

In yet another embodiment, the effector cell to target cell ratio is about 0.1 to 1 to about 2 to 1.

In a specific embodiment, the effector cell to target cell ratio is about 1:1.

In another embodiment, the TRGV9 bispecific antibody or antigen binding fragment thereof is multivalent.

In another embodiment, the TRGV9 bispecific antibody or antigen binding fragment thereof is capable of binding at least three antigens.

In another embodiment, the TRGV9 bispecific antibody or antigen binding fragment thereof is capable of binding at least five antigens.

Also provided are isolated γδ T cell bispecific antibodies or antigen binding fragments thereof, the isolated γδ T cell bispecific antibody or antigen binding fragment thereof comprising:
 a. a HC1;
 b. a HC2;
 c. a LC1; and
 d. a LC2,
wherein HC1 is associated with LC1 and HC2 is associated with LC2,
wherein HC1 and LC1 form a binding site for a first antigen on a γδ T cell, and
wherein HC2 and LC2 form a binding site for a second antigen.

Also provided herein are bispecific antibodies comprising: a first means capable of specifically binding a T cell receptor gamma chain; and a second means capable of specifically binding a target molecule that is not a T cell receptor gamma chain.

Also provided are processes for making a molecule capable of specifically binding to more than one target molecule, the molecule comprising: a step for performing a function of obtaining an oligopeptide or polypeptide capable of binding to a T cell receptor gamma chain; a step for performing a function of obtaining an oligopeptide or polypeptide capable of binding to a target; and a step for performing a function of providing a molecule capable of specifically binding to a T cell receptor gamma chain and a target molecule.

In one embodiment, the step in the process for performing a function of obtaining an oligopeptide or polypeptide capable of binding to a target is repeated n times and further comprising n steps for performing a function of providing a molecule capable of specifically binding to a T cell receptor gamma chain and n number of target molecules, wherein n is at least 2.

Provided herein are isolated anti-TRGV9/anti-CD123 bispecific antibodies or antigen binding fragments thereof comprising:
 a. a HC1;
 b. a HC2;
 c. a LC1; and
 d. a LC2,
wherein HC1 is associated with LC1 and HC2 is associated with LC2, and wherein HC1 comprises a HCDR1, HCDR2, and HCDR3 comprising the amino acid sequences of:
 i. SEQ ID NO:1, SEQ ID NO:2, and SEQ ID NO:3, respectively,
 ii. SEQ ID NO:1, SEQ ID NO:2, and SEQ ID NO:31, respectively,
 iii. SEQ ID NO:1, SEQ ID NO:2, and SEQ ID NO:32, respectively, or
 iv. SEQ ID NO:1, SEQ ID NO:2, and SEQ ID NO:33, respectively,
and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:7, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:7, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:34, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:34, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:35, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:35, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:36, and LC1 comprises an amino acid sequence having at least 95% identity to the amino acid sequence of SEQ ID NO:8. In another embodiment, the isolated anti-TRGV9/anti-CD123 bispecific antibody or antigen binding fragment comprises an HC1 comprising the amino acid sequence of SEQ ID NO:36, and LC1 comprises the amino acid sequence of SEQ ID NO:8. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:65, and LC1 comprises an amino acid sequence having at least 95% identity to the amino acid sequence of SEQ ID NO:66. In another embodiment, the isolated anti-TRGV9/anti-CD123 bispecific antibody or antigen binding fragment comprises an HC1 comprising the amino acid sequence of SEQ ID NO:65, and LC1 comprises the amino acid sequence of SEQ ID NO:66. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:67, and LC1 comprises an amino acid sequence having at least 95% identity to the amino acid sequence of SEQ ID NO:68. In another embodiment, the isolated anti-TRGV9/anti-CD123 bispecific antibody or antigen binding fragment comprises an HC1 comprising the amino acid sequence of SEQ ID NO:67, and LC1 comprises the amino acid sequence of SEQ ID NO:68. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:65, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:65, and LC1 comprises an amino acid sequence having at least 95% identity to the amino acid sequence of SEQ ID NO:66. In another embodiment, the isolated anti-TRGV9/anti-CD123 bispecific antibody or antigen binding fragment comprises an HC1 comprising the amino acid sequence of SEQ ID NO:65, and LC1 comprises the amino acid sequence of SEQ ID NO:66. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:67, and LC1 comprises an amino acid sequence having at least 95% identity to the amino acid sequence of SEQ ID NO:68. In another embodiment, the isolated anti-TRGV9/anti-CD123 bispecific antibody or antigen binding fragment comprises an HC1 comprising the amino acid sequence of SEQ ID NO:67, and LC1 comprises the amino acid sequence of SEQ ID NO:68. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:95, and LC1 comprises an amino acid sequence having at least 95% identity to the amino acid sequence of SEQ ID NO:96. In another embodiment, the isolated anti-TRGV9/anti-CD123 bispecific antibody or antigen binding fragment comprises an HC1 comprising the amino acid sequence of SEQ ID NO:95, and LC1 comprises the amino acid sequence of SEQ ID NO:96. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:104, and LC1 comprises an amino acid sequence having at least 95% identity to the amino acid sequence of SEQ ID NO:105. In another embodiment, the isolated anti-TRGV9/anti-CD123 bispecific antibody or antigen binding fragment comprises an HC1 comprising the amino acid sequence of SEQ ID NO:104, and LC1 comprises the amino acid sequence of SEQ ID NO:105. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:113, and LC1 comprises an amino acid sequence having at least 95% identity to the amino acid sequence of SEQ ID NO:114. In another embodiment, the isolated anti-TRGV9/anti-CD123 bispecific antibody or antigen binding fragment comprises an HC1 comprising the amino acid sequence of SEQ ID NO:113, and LC1 comprises the amino acid sequence of SEQ ID NO:114. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:123, and LC1 comprises an amino acid sequence having at least 95% identity to the amino acid sequence of SEQ ID NO:124. In another embodiment, the isolated anti-TRGV9/anti-CD123 bispecific antibody or antigen binding fragment comprises an HC1 comprising the amino acid sequence of SEQ ID NO:123, and LC1 comprises the amino acid sequence of SEQ ID NO:124. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

Also provided herein are isolated anti-TRGV9/anti-CD123 bispecific antibodies or antigen binding fragments thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a binding site for a first antigen that specifically binds Vγ9, and wherein HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In one embodiment, the isolated anti-TRGV9/anti-CD123 bispecific antibody or antigen binding fragment comprises an HC1 comprising an amino acid sequence having at least 95% identity to an amino acid sequence selected of SEQ ID NO:133, and LC1 comprises an amino acid sequence having at least 95% identity to the amino acid sequence of SEQ ID NO:134. In another embodiment, the isolated anti-TRGV9/anti-CD123 bispecific antibody or antigen binding fragment comprises an HC1 comprising the amino acid sequence of SEQ ID NO:133, and LC1 comprises the amino acid sequence of SEQ ID NO:134. In another embodiment, the isolated anti-TRGV9/anti-CD123 bispecific antibody or antigen binding fragment comprises an HC2 comprising an amino acid sequence having at least 95% identity to the amino acid sequence of SEQ ID NO:15 and LC2 comprises an amino acid sequence having at least 95% identity to the amino acid sequence of SEQ ID NO:16. In another embodiment, the isolated anti-TRGV9/anti-CD123 bispecific antibody or antigen binding fragment comprises an HC2 comprising the amino acid sequence of SEQ ID NO:15 and LC2 comprises the amino acid sequence of SEQ ID NO:16.

In another embodiment, the TRGV9 is on the surface of a γδ T cell.

In another embodiment, the CD123 is on the surface of a tumor cell or a CD34+ stem cell.

In another embodiment, the binding of the bispecific antibody to TRGV9 present on the surface of the γδ T cell and the binding of the CD123 on the surface of the cancer cell results in the killing of the cancer cell.

In another embodiment, the isolated anti-TRGV9/anti-CD123 bispecific antibody or antigen binding fragment thereof comprises a humanized HC1 and a humanized LC1.

In another embodiment, the isolated anti-TRGV9/anti-CD123 bispecific antibody or antigen binding fragment comprises a humanized HC2 and a humanized LC2.

In another embodiment, the isolated anti-TRGV9/anti-CD123 bispecific antibody or antigen binding fragment thereof is an IgG1, an IgG2, an IgG3, or an IgG4 isotype. In a specific embodiment, the bispecific antibody is an IgG4 isotype.

In another embodiment, the isolated anti-TRGV9/anti-CD123 bispecific antibody or antigen binding fragment thereof induces γδ T cell dependent cytotoxicity of a cancer cell in vitro with an $EC_{50}$ of less than about 500 pM.

In another embodiment, the isolated anti-TRGV9/anti-CD123 bispecific antibody or antigen binding fragment thereof induces γδ T cell dependent cytotoxicity of a cancer cell in vitro with an $EC_{50}$ of less than about 300 pM.

In another embodiment, the isolated anti-TRGV9/anti-CD123 bispecific antibody or antigen binding fragment thereof induces γδ T cell dependent cytotoxicity of a cancer cell in vitro with an $EC_{50}$ of less than about 160 pM.

In one embodiment, the $EC_{50}$ is assessed with a mixture of γδ T effector cells and Kasumi3 AML target cells.

In another embodiment, the effector cell to target cell ratio is about 0.01 to 1 to about 5 to 1.

In yet another embodiment, the effector cell to target cell ratio is about 0.1 to 1 to about 2 to 1.

In a specific embodiment, the effector cell to target cell ratio is about 1:1.

Also provided are methods of making the isolated anti-TRGV9/anti-CD123 bispecific antibody or antigen binding fragment provided herein, the method comprising culturing a cell comprising a nucleic acid encoding the anti-TRGV9/anti-CD123 bispecific antibody or antigen binding fragment thereof under conditions to produce the bispecific antibody or antigen binding fragment thereof and recovering the bispecific antibody or antigen binding fragment thereof.

In another aspect, provided herein are isolated TRGV9 bispecific antibodies or antigen epitope binding fragments thereof, wherein the isolated TRGV9 bispecific antibodies or antigen epitope binding fragments thereof comprise a binding site for a first antigen and a binding site for a second antigen, wherein the binding site for the first antigen binds a TRGV9 epitope on a γδ T cell and the binding site for the second antigen binds an epitope of the second antigen on a surface of a target cell, and the binding of the TRGV9 epitope on the γδ T cell and the binding of the second antigen epitope on the target cell results in the killing of the target cell.

In one embodiment, the TRGV9 bispecific antibodies or antigen binding fragments comprise:
 a. a HC1;
 b. a HC2;
 c. a LC1; and
 d. a LC2,
wherein HC1 is associated with LC1 and HC2 is associated with LC2, and wherein HC1 comprises a HCDR1, HCDR2, and HCDR3 comprising the amino acid sequences of:
 i. SEQ ID NO:1, SEQ ID NO:2, and SEQ ID NO:3, respectively,
 ii. SEQ ID NO:1, SEQ ID NO:2, and SEQ ID NO:31, respectively,
 iii. SEQ ID NO:1, SEQ ID NO:2, and SEQ ID NO:32, respectively, or
 iv. SEQ ID NO:1, SEQ ID NO:2, and SEQ ID NO:33, respectively,
and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:7, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:7, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:34, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:34, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:35, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:35, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:36, and LC1 comprises an amino acid sequence having at least 95% identity to the amino acid sequence of SEQ ID NO:8. In another embodiment, the TRGV9 bispecific antibodies or antigen binding fragments comprise an HC1 comprising the amino acid sequence of SEQ ID NO:36, and LC1 comprises the amino acid sequence of SEQ ID NO:8.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR2 comprising the amino acid sequences of SEQ ID NO:77, SEQ ID NO:5, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the TRGV9 bispecific antibodies or antigen binding fragments comprise an HC1 comprising the amino acid sequence of SEQ ID NO:65, and LC1 comprises the amino acid sequence of SEQ ID NO:66. In another embodiment, the TRGV9 bispecific antibodies or antigen binding fragments comprise an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the TRGV9 bispecific antibodies or antigen binding fragments comprise an HC1 comprising the amino acid sequence of SEQ ID NO:67, and LC1 comprises the amino acid sequence of SEQ ID NO:68.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR2 comprising the amino acid sequences of SEQ ID NO:63, SEQ ID NO:64, and SEQ ID NO:6, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the TRGV9 bispecific antibodies or antigen binding fragments comprise an HC1 comprising the amino acid sequence of SEQ ID NO:65, and LC1 comprises the amino acid sequence of SEQ ID NO:66. In another embodiment, the TRGV9 bispecific antibodies or antigen binding fragments comprise an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the TRGV9 bispecific antibodies or antigen binding fragments comprise an HC1 comprising the amino acid sequence of SEQ ID NO:67, and LC1 comprises the amino acid sequence of SEQ ID NO:68.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR2 comprising the amino acid sequences of SEQ ID NO:92, SEQ ID NO:93, and SEQ ID NO:94, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:95, and LC1 comprises an amino acid sequence having at least 95% identity to the amino acid sequence of SEQ ID NO:96. In another embodiment, the TRGV9 bispecific antibodies or antigen binding fragments comprise an HC1 comprising the amino acid sequence of SEQ ID NO:95, and LC1 comprises the amino acid sequence of SEQ ID NO:96.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR2 comprising the amino acid sequences of SEQ ID NO:101, SEQ ID NO:102, and SEQ ID NO:103, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:104, and LC1 comprises an amino acid sequence having at least 95% identity to the amino acid sequence of SEQ ID NO:105. In another embodiment, the TRGV9 bispecific antibodies or antigen binding fragments comprise an HC1 comprising the amino acid sequence of SEQ ID NO:104, and LC1 comprises the amino acid sequence of SEQ ID NO:105.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR2 comprising the amino acid sequences of SEQ ID NO:110, SEQ ID NO:111, and SEQ ID NO:112, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:113, and LC1 comprises an amino acid sequence having at least 95% identity to the amino acid sequence of SEQ ID NO:114. In another embodiment, the TRGV9 bispecific antibodies or antigen binding fragments comprise an HC1 comprising the amino acid sequence of SEQ ID NO:113, and LC1 comprises the amino acid sequence of SEQ ID NO:114.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR2 comprising the amino acid sequences of SEQ ID NO:120, SEQ ID NO:121, and SEQ ID NO:122, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:123, and LC1 comprises an amino acid sequence having at least 95% identity to the amino acid sequence of SEQ ID NO:124. In another embodiment, the TRGV9 bispecific antibodies or antigen binding fragments comprise an HC1 comprising the amino acid sequence of SEQ ID NO:123, and LC1 comprises the amino acid sequence of SEQ ID NO:124.

In one embodiment, the TRGV9 bispecific antibodies or antigen binding fragments comprise: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR2 comprising the amino acid sequences of SEQ ID NO:130, SEQ ID NO:131, and SEQ ID NO:132, respectively, to form the binding site for the first antigen, and wherein HC2 and LC2 form the binding site for the second antigen epitope. In another embodiment, the TRGV9 bispecific antibodies or antigen binding fragments comprise an HC1 comprising an amino acid sequence having at least 95% identity to an amino acid sequence of SEQ ID NO:133, and LC1 comprises an amino acid sequence having at least 95% identity to the amino acid sequence of SEQ ID NO:134. In another embodiment, the TRGV9 bispecific antibodies or antigen binding fragments comprise an HC1 comprising the amino acid sequence of SEQ ID NO:133, and LC1 comprises the amino acid sequence of SEQ ID NO:134.

In another embodiment, the TRGV9 bispecific antibodies or antigen binding fragments comprise a humanized HC1 and a humanized LC.

In another embodiment, the TRGV9 bispecific antibodies or antigen binding fragments bind to a CD123 epitope.

In another embodiment, the TRGV9 bispecific antibodies or antigen binding fragments comprise and HC2 comprising an amino acid sequence having at least 95% identity to the amino acid sequence of SEQ ID NO:15 and LC2 comprises an amino acid sequence having at least 95% identity to the amino acid sequence of SEQ ID NO:16.

In another embodiment, the TRGV9 bispecific antibodies or antigen binding fragments comprise an HC2 comprising the amino acid sequence of SEQ ID NO:15 and LC2 comprises the amino acid sequence of SEQ ID NO:16.

In another embodiment, the TRGV9 bispecific antibodies or antigen binding fragments thereof are an IgG1, an IgG2, an IgG3, or an IgG4 isotype. In a specific embodiment, the bispecific antibodies or antigen binding fragments thereof fragment thereof are an IgG4 isotype.

In another embodiment, the TRGV9 bispecific antibodies or antigen binding fragments thereof induce γδ T cell dependent cytotoxicity of a cancer cell in vitro with an $EC_{50}$ of less than about 500 pM.

In another embodiment, the TRGV9 bispecific antibodies or antigen binding fragments thereof induce γδ T cell dependent cytotoxicity of a cancer cell in vitro with an $EC_{50}$ of less than about 300 pM.

In another embodiment, the TRGV9 bispecific antibodies or antigen binding fragments thereof induce γδ T cell dependent cytotoxicity of a cancer cell in vitro with an $EC_{50}$ of less than about 160 pM.

In one embodiment, the $EC_{50}$ is assessed with a mixture of γδ T effector cells and Kasumi3 AML target cells.

In another embodiment, the effector cell to target cell ratio is about 0.01 to 1 to about 5 to 1. In another embodiment, the effector cell to target cell ratio is about 0.1 to 1 to about 2 to 1. In a specific embodiment, the effector cell to target cell ratio is about 1:1.

Also provided are isolated γδ T cell bispecific antibodies or antigen binding fragments thereof, wherein the isolated γδ T cell bispecific antibody or antigen binding fragment thereof comprises a binding site for a first antigen epitope and a binding site for a second antigen epitope, wherein the binding site for the first antigen epitope binds a first antigen on a γδ T cell and the binding site for the second antigen epitope binds the second antigen epitope on a surface of a target cell, and the binding of the first antigen epitope on the γδ T cell and the binding of the second antigen epitope on the target cell results in the killing of the target cell.

In another aspect, provided herein are isolated nucleic acids encoding a TRGV9 bispecific antibody or antigen binding fragment thereof, the isolated TRGV9 bispecific antibody or antigen binding fragment thereof comprising:
 a. a HC1;
 b. a HC2;
 c. a LC1; and
 d. a LC2,
wherein HC1 is associated with LC1 and HC2 is associated with LC2, and wherein HC1 comprises a HCDR1, HCDR2, and HCDR3 comprising the amino acid sequences of:
 i. SEQ ID NO:1, SEQ ID NO:2, and SEQ ID NO:3, respectively,
 ii. SEQ ID NO:1, SEQ ID NO:2, and SEQ ID NO:31, respectively,
 iii. SEQ ID NO:1, SEQ ID NO:2, and SEQ ID NO:32, respectively, or
 iv. SEQ ID NO:1, SEQ ID NO:2, and SEQ ID NO:33, respectively,
and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence selected from SEQ ID NO:7, SEQ ID NO:34, SEQ ID NO:35, or SEQ ID NO:36, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:7, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:7, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:34, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:34, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:35, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:35, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:36, and LC1 comprises an amino acid sequence having at least 95% identity to the amino acid sequence of SEQ ID NO:8. In another embodiment, the isolated nucleic acid encodes a TRGV9 bispecific antibody comprising an HC1 comprising the amino acid sequence of SEQ ID NO:36, and LC1 comprises the amino acid sequence of SEQ ID NO:8.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR2 comprising the amino acid sequences of SEQ ID NO:77, SEQ ID NO:5, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated nucleic acid encodes a TRGV9 bispecific antibody comprising an HC1 comprising the amino acid sequence of SEQ ID NO:65, and LC1 comprises the amino acid sequence of SEQ ID NO:66. In one embodiment, the isolated nucleic acid encodes a TRGV9 bispecific antibody comprising an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated nucleic acid encodes a TRGV9 bispecific antibody comprising an HC1 comprising the amino acid sequence of SEQ ID NO:67, and LC1 comprises the amino acid sequence of SEQ ID NO:68.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR2 comprising the amino acid sequences of SEQ ID NO:63, SEQ ID NO:64, and SEQ ID NO:6, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:65, and LC1 comprises an amino acid sequence having at least 95% identity to the amino acid sequence of SEQ ID NO:66. In another embodiment, the isolated nucleic acid encodes a TRGV9 bispecific antibody comprising an HC1 comprising the amino acid sequence of SEQ ID NO:65, and LC1 comprises the amino acid sequence of SEQ ID NO:66. In one embodiment, the isolated nucleic acid encodes a TRGV9 bispecific antibody comprising an HC1 comprising an amino acid sequence having at least 95% identity to an amino acid sequence of SEQ ID NO:67, and LC1 comprises an amino acid sequence having at least 95% identity to the amino acid sequence of SEQ ID NO:68. In another embodiment, the isolated nucleic acid encodes a TRGV9 bispecific antibody comprising an HC1 comprising the amino acid sequence of SEQ ID NO:67, and LC1 comprises the amino acid sequence of SEQ ID NO:68.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR2 comprising the amino acid sequences of SEQ ID NO:92, SEQ ID NO:93, and SEQ ID NO:94, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:95, and LC1 comprises an amino acid sequence having at least 95% identity to the amino acid sequence of SEQ ID NO:96. In another embodiment, the isolated nucleic acid encodes a TRGV9 bispecific antibody comprising an HC1 comprising the amino acid sequence of SEQ ID NO:95, and LC1 comprises the amino acid sequence of SEQ ID NO:96.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR2 comprising the amino acid sequences of SEQ ID NO:101, SEQ ID NO:102, and SEQ ID NO:103, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:104, and LC1 comprises an amino acid sequence having at least 95% identity to the amino acid sequence of SEQ ID NO:105. In another embodiment, the isolated nucleic acid encodes a TRGV9 bispecific antibody comprising an HC1 comprising the amino acid sequence of SEQ ID NO:104, and LC1 comprises the amino acid sequence of SEQ ID NO:105.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR2 comprising the amino acid sequences of SEQ ID NO:110, SEQ ID NO:111, and SEQ ID NO:112, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:113, and LC1 comprises an amino acid sequence having at least 95% identity to the amino acid sequence of SEQ ID NO:114. In another embodiment, the isolated nucleic acid encodes a TRGV9 bispecific antibody comprising an HC1 comprising the amino acid sequence of SEQ ID NO:113, and LC1 comprises the amino acid sequence of SEQ ID NO:114.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR2 comprising the amino acid sequences of SEQ ID NO:120, SEQ ID NO:121, and SEQ ID NO:122, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:123, and LC1 comprises an amino acid sequence having at least 95% identity to the amino acid sequence of SEQ ID NO:124. In another embodiment, the isolated nucleic acid encodes a TRGV9 bispecific antibody comprising an HC1 comprising the amino acid sequence of SEQ ID NO:123, and LC1 comprises the amino acid sequence of SEQ ID NO:124.

In another aspect, provided herein are isolated nucleic acids encoding a TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR2 comprising the amino acid sequences of SEQ ID NO:130, SEQ ID NO:131, and SEQ ID NO:132, respectively, to form a binding site for a first antigen, and wherein HC2 and LC2 form a binding site for a second antigen. In one embodiment, the isolated nucleic acid encodes a TRGV9 bispecific antibody comprising an HC1 comprising an amino acid sequence having at least 95% identity to an amino acid sequence of SEQ ID NO:133, and LC1 comprises an amino acid sequence having at least 95% identity to the amino acid sequence of SEQ ID NO:134. In another embodiment, the isolated nucleic acid encodes a TRGV9 bispecific antibody comprising an HC1 comprising the amino acid sequence of SEQ ID NO:133, and LC1 comprises the amino acid sequence of SEQ ID NO:134.

In another embodiment, the isolated nucleic acid encodes a TRGV9 bispecific antibody comprising a binding site comprising a first antigen that binds to TRGV9 on a γδ T cell.

In another embodiment, the isolated nucleic acid encodes a TRGV9 bispecific antibody comprising a binding site for a second antigen that binds to a cancer antigen present on the surface of a cancer cell.

In another embodiment, the isolated nucleic acid encodes a TRGV9 bispecific antibody, wherein the binding of the bispecific antibody to TRGV9 present on the surface of the γδ T cell and the binding of the cancer antigen present on the surface of the cancer cell results in the killing of the cancer cell.

In another embodiment, the isolated nucleic acid encodes a TRGV9 bispecific antibody, wherein HC1 and LC1 are humanized.

In another embodiment, the isolated nucleic acid encodes a TRGV9 bispecific antibody, wherein HC2 and LC2 bind to CD123.

In another embodiment, the isolated nucleic acid encodes a TRGV9 bispecific antibody, wherein the bispecific antibody or antigen binding fragment thereof is an IgG1, an IgG2, an IgG3, or an IgG4 isotype.

In a specific embodiment, the bispecific antibody or antigen binding fragment thereof is an IgG4 isotype.

In another embodiment, the isolated nucleic acid encodes a TRGV9 bispecific antibody, wherein the bispecific antibody or antigen binding fragment thereof induces γδ T cell dependent cytotoxicity of a cancer cell in vitro with an $EC_{50}$ of less than about 500 pM.

In another embodiment, the isolated nucleic acid encodes a TRGV9 bispecific antibody, wherein the bispecific antibody or antigen binding fragment thereof induces γδ T cell dependent cytotoxicity of a cancer cell in vitro with an $EC_{50}$ of less than about 300 pM.

In another embodiment, the isolated nucleic acid encodes a TRGV9 bispecific antibody, wherein the bispecific antibody or antigen binding fragment thereof induces γδ T cell dependent cytotoxicity of a cancer cell in vitro with an $EC_{50}$ of less than about 160 pM.

In another embodiment, the isolated nucleic acid encodes a TRGV9 bispecific antibody, wherein the $EC_{50}$ is assessed with a mixture of γδ T effector cells and Kasumi3 AML target cells.

In another embodiment, the isolated nucleic acid encodes a TRGV9 bispecific antibody, wherein the effector cell to target cell ratio is about 0.01 to 1 to about 5 to 1. In one embodiment, the effector cell to target cell ratio is about 0.1 to 1 to about 2 to 1. In yet another embodiment, the effector cell to target cell ratio is about 1:1.

In another embodiment, the isolated nucleic acid encodes a TRGV9 bispecific antibody, wherein the bispecific antibody or antigen binding fragment thereof is multivalent.

In another embodiment, the isolated nucleic acid encodes a TRGV9 bispecific antibody, wherein the bispecific antibody or antigen binding fragment thereof is capable of binding at least three antigens.

In another embodiment, the isolated nucleic acid encodes a TRGV9 bispecific antibody, wherein the bispecific antibody or antigen binding fragment thereof is capable of binding at least five antigens.

Also provided are vectors comprising the isolated nucleic acids provided herein.

Also provided are host cells comprising the vectors provided herein.

Also provided are kits comprising the vectors provided herein and packaging for the same.

Provided herein are pharmaceutical compositions comprising: (A) an isolated TRGV9 bispecific antibody or antigen binding fragment thereof, the isolated TRGV9 bispecific antibody or antigen binding fragment thereof comprising:
  a. a HC1;
  b. a HC2;
  c. a LC1; and
  d. a LC2,
wherein HC1 is associated with LC1 and HC2 is associated with LC2, and wherein HC1 comprises a HCDR1, HCDR2, and HCDR3 comprising the amino acid sequences of:
  i. SEQ ID NO:1, SEQ ID NO:2, and SEQ ID NO:3, respectively,
  ii. SEQ ID NO:1, SEQ ID NO:2, and SEQ ID NO:31, respectively,
  iii. SEQ ID NO:1, SEQ ID NO:2, and SEQ ID NO:32, respectively, or
  iv. SEQ ID NO:1, SEQ ID NO:2, and SEQ ID NO:33, respectively,
and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen;
and (B) a pharmaceutically acceptable carrier. In one embodiment, the pharmaceutical composition comprises a bispecific antibody comprising an HC1 comprising an amino acid sequence having at least 95% identity to an amino acid sequence selected from SEQ ID NO:7, SEQ ID NO:34, SEQ ID NO:35, or SEQ ID NO:36, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence selected from SEQ ID NO:7, SEQ ID NO:34, SEQ ID NO:35, or SEQ ID NO:36, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:3, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:7, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:7, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:34, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:34, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:35, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:35, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively; and LC1 comprises a LCDR1, LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:36, and an LC1 comprising an amino acid sequence having at least 95% identity to the amino acid sequence of SEQ ID NO:8. In another embodiment, the pharmaceutical composition comprises a bispecific antibody comprising an HC1 comprising the amino acid sequence of SEQ ID NO:36, and an LC1 comprising the amino acid sequence of SEQ ID NO:8.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively; and LC1 comprises a LCDR1, LCDR2, and LCDR2 comprising the amino acid sequences of SEQ ID NO:77, SEQ ID NO:5, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:65, and an LC1 comprising an amino acid sequence having at least 95% identity to the amino acid sequence of SEQ ID NO:66. In another embodiment, the pharmaceutical composition comprises a bispecific antibody comprising an HC1 comprising the amino acid sequence of SEQ ID NO:65, and an LC1 comprising the amino acid sequence of SEQ ID NO:66. In one embodiment, the pharmaceutical composition comprises a bispecific antibody comprising an HC1 comprising an amino acid sequence having at least 95% identity to an amino acid sequence of SEQ ID NO:67, and an LC1 comprising an amino acid sequence having at least 95% identity to the amino acid sequence of SEQ ID NO:68. In another embodiment, the pharmaceutical composition comprises a bispecific antibody comprising an HC1 comprising the amino acid sequence of SEQ ID NO:67, and an LC1 comprising the amino acid sequence of SEQ ID NO:68.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively; and LC1 comprises a LCDR1, LCDR2, and LCDR2 comprising the amino acid sequences of SEQ ID NO:63, SEQ ID NO:64, and SEQ ID NO:6, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:65, and an LC1 comprising an amino acid sequence having at least 95% identity to the amino acid sequence of SEQ ID NO:66. In another embodiment, the pharmaceutical composition comprises a bispecific antibody comprising an HC1 comprising the amino acid sequence of SEQ ID NO:65, and an LC1 comprising the amino acid sequence of SEQ ID NO:66. In one embodiment, the pharmaceutical composition comprises a bispecific antibody comprising an HC1 comprising an amino acid sequence having at least 95% identity to an amino acid sequence of SEQ ID NO:67, and an LC1 comprising an amino acid sequence having at least 95% identity to the amino acid sequence of SEQ ID NO:68. In another embodiment, the pharmaceutical composition comprises a bispecific antibody comprising an HC1 comprising the amino acid sequence of SEQ ID NO:67, and an LC1 comprising the amino acid sequence of SEQ ID NO:68.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively; and LC1 comprises a LCDR1, LCDR2, and LCDR2 comprising the amino acid sequences of SEQ ID NO:92, SEQ ID NO:93, and SEQ ID NO:94, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:95, and an LC1 comprising an amino acid sequence having at least 95% identity to the amino acid sequence of SEQ ID NO:96. In another embodiment, the pharmaceutical composition comprises a bispecific antibody comprising an HC1 comprising the amino acid sequence of SEQ ID NO:95, and an LC1 comprising the amino acid sequence of SEQ ID NO:96.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2;

wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively; and LC1 comprises a LCDR1, LCDR2, and LCDR2 comprising the amino acid sequences of SEQ ID NO:101, SEQ ID NO:102, and SEQ ID NO:103, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:104, and an LC1 comprising an amino acid sequence having at least 95% identity to the amino acid sequence of SEQ ID NO:105. In another embodiment, the pharmaceutical composition comprises a bispecific antibody comprising an HC1 comprising the amino acid sequence of SEQ ID NO:104, and an LC1 comprising the amino acid sequence of SEQ ID NO:105.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively; and LC1 comprises a LCDR1, LCDR2, and LCDR2 comprising the amino acid sequences of SEQ ID NO:110, SEQ ID NO:111, and SEQ ID NO:112, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:113, and an LC1 comprising an amino acid sequence having at least 95% identity to the amino acid sequence of SEQ ID NO:114. In another embodiment, the pharmaceutical composition comprises a bispecific antibody comprising an HC1 comprising the amino acid sequence of SEQ ID NO:113, and an LC1 comprising the amino acid sequence of SEQ ID NO:114.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively; and LC1 comprises a LCDR1, LCDR2, and LCDR2 comprising the amino acid sequences of SEQ ID NO:120, SEQ ID NO:121, and SEQ ID NO:122, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:123, and an LC1 comprising an amino acid sequence having at least 95% identity to the amino acid sequence of SEQ ID NO:124. In another embodiment, the pharmaceutical composition comprises a bispecific antibody comprising an HC1 comprising the amino acid sequence of SEQ ID NO:123, and an LC1 comprising the amino acid sequence of SEQ ID NO:124.

Also provided herein are pharmaceutical compositions comprising: (A) an isolated TRGV9 bispecific antibody or antigen binding fragment thereof, the isolated TRGV9 bispecific antibody or antigen binding fragment thereof comprising: (a) a HC1; (b) a HC2; (c) a LC1; and (d) a LC2; wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively; and LC1 comprises a LCDR1, LCDR2, and LCDR2 comprising the amino acid sequences of SEQ ID NO:130, SEQ ID NO:131, and SEQ ID NO:132, respectively, to form a binding site for a first antigen, and wherein HC2 and LC2 form a binding site for a second antigen; and (B) a pharmaceutically acceptable carrier. In one embodiment, the pharmaceutical composition comprises a bispecific antibody comprising an HC1 comprising an amino acid sequence having at least 95% identity to an amino acid sequence of SEQ ID NO:133, and an LC1 comprising an amino acid sequence having at least 95% identity to the amino acid sequence of SEQ ID NO:134. In another embodiment, the pharmaceutical composition comprises a bispecific antibody comprising an HC1 comprising the amino acid sequence of SEQ ID NO:133, and an LC1 comprising the amino acid sequence of SEQ ID NO:134.

In another embodiment, the pharmaceutical composition comprises a bispecific antibody comprising a binding site for a first antigen binds to TRGV9 on a γδ T cell.

In another embodiment, the pharmaceutical composition comprises a bispecific antibody, wherein the binding site for a second antigen binds to a cancer antigen present on the surface of a cancer cell.

In another embodiment, the pharmaceutical composition comprises a bispecific antibody, wherein the binding of the bispecific antibody to TRGV9 present on the surface of the γδ T cell and the binding of the cancer antigen present on the surface of the cancer cell results in the killing of the cancer cell.

In another embodiment, the pharmaceutical composition comprises a bispecific antibody, wherein HC1 and LC1 are humanized.

In another embodiment, the pharmaceutical composition comprises a bispecific antibody, wherein HC2 and LC2 bind to CD123.

In another embodiment, the pharmaceutical composition comprises a bispecific antibody, wherein the bispecific antibody or antigen binding fragment thereof is an IgG1, an IgG2, an IgG3, or an IgG4 isotype.

Also provided are methods of directing a Vγ9-expressing γδ T cell to a cancer cell, the method comprising contacting a Vγ9-expressing γδ T cell with the pharmaceutical compositions provided herein, wherein contacting the Vγ9-expressing γδ T cell with the pharmaceutical composition directs the Vγ9-expressing γδ T cell to a cancer cell.

Also provided are methods of inhibiting growth or proliferation of cancer cells expressing a cancer antigen on the cell surface, the method comprising contacting the cancer cells with the pharmaceutical compositions provided herein, wherein contacting the cancer cells with the pharmaceutical composition inhibits growth or proliferation of the cancer cells.

In one embodiment, the cancer cell is in the presence of a Vγ9-expressing γδ T cell while in contact with anti-TRGV9 bispecific antibody or antigen binding fragment thereof.

Also provided are methods for treating a cancer in a subject in need thereof, the method comprising:
a. identifying a subject in need of cancer treatment; and
b. administering to the subject in need thereof the pharmaceutical compositions provided herein,
wherein administering the pharmaceutical composition to the subject in need thereof treats the cancer in the subject.

Also provided are methods of activating a Vγ9-expressing γδ T cell, the method comprising contacting the Vγ9-expressing γδ T cell with the pharmaceutical composition provided herein, wherein contacting the Vγ9-expressing γδ T cell with the pharmaceutical composition results in an increase in CD69, CD25, and/or Granzyme B expression as compared to a control Vγ9-expressing γδ T cell.

Also provided are methods of producing the pharmaceutical composition provided herein, the method comprising combining the bispecific antibody or antigen binding fragment thereof with a pharmaceutically acceptable carrier to obtain the pharmaceutical composition.

BRIEF DESCRIPTION OF THE DRAWINGS

The foregoing summary, as well as the following detailed description of certain embodiments of the present application, will be better understood when read in conjunction with the appended drawings. It should be understood, however, that the application is not limited to the precise embodiments shown in the drawings.

FIG. 3A shows a schematic depiction of gates used to describe the differentiation of γδ T cells (left). Representative FACS-dot plots show the differentiation profile of Vγ9+ γδ T cells from fresh PBMCs (left) and PBMCs cultured ex vivo with Zoledronic acid+IL-2+IL-15 for 14 days (right). Numbers in quadrants mirror the frequency (mean±SEM) of the respective population among fresh and activated Vγ9+ γδ T cells. Represented data is mean (±SEM) of five donors (n=5) from a single experiment. FIG. 3B shows numbers in representative dot plots mirroring the frequency (mean±SEM) of Vγ9+ γδ T cells positive for respective activation marker either from fresh PBMCs (upper row) or PBMCs cultured with Zoledronic acid+IL-2+IL-15 for 14 days (lower row). Represented data is mean (±SEM) of seven donors (n=7) for CD62L, CD69, CD44 expression data from two independent experiments. n=5 donors for NKG2D and 2 donors for CD45RO and CD71 expression data respectively from a single experiment. FIG. 3C shows numbers above gates in dot plots depicting the frequency (mean±SEM) of Vγ9+ γδ T cells positive for respective inhibitory receptor surface expression either from fresh PBMCs (upper row) or PBMCs cultured with Zoledronic acid+IL-2+IL-15 for day 14 (lower row). Data shown here is mean (±SEM) of five donors (n=5) for PD1, CTLA4, TIGIT and LAG3 surface expression and seven donors (n=7) for 2B4 and TIM3 surface expression data from two independent experiments. FIG. 3D shows representative FACS dot plots demonstrating the frequency (mean±SEM) of Vγ9+ γδ T cells expressing intracellular Granzyme B (left column) and Perforin (right column) from fresh PBMCs (upper row) and PBMCs cultured ex vivo with Zoledronic acid+IL-2+IL-15 for 14 days (lower row). Depicted data is mean (±SEM) of four (n=4) and seven (n=7) donors for Granzyme B and Perforin data respectively from two independent experiments. FIG. 3E shows bars representing the mean (±SEM) concentration (pg/mL) of cytokine in the cell culture supernatant on day 0 and day 14 of PBMCs culture with Zoledronic acid+IL-2+IL-15. Represented data is mean (±SEM) of four wells (n=4) from a single donor.

DETAILED DESCRIPTION

Figure 1:
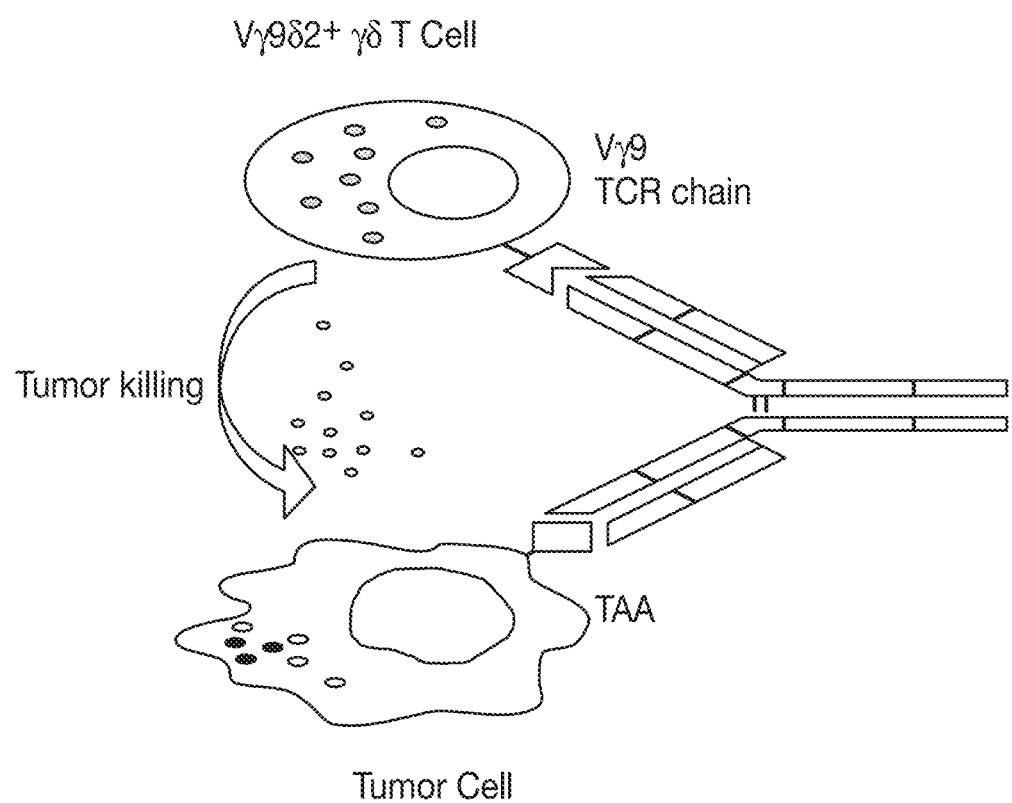
FIG. 1 shows a schematic demonstrating the binding of an anti-TRGV9/anti-tumor associated antigen (TAA) bispecific antibody to recruit γδ T cells to a cancer cell and to induce cancer cell death.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, such as a mammal, such as a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., or such as a human.

It should also be understood that the terms "about," "approximately," "generally," "substantially," and like terms, used herein when referring to a dimension or characteristic of a component, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-TRGV9/anti-cancer-associated antigen bispecific antibodies and polynucleotides that encode them, anti-TRGV9/anti-CD123 bispecific antibodies and polynucleotides that encode them, TRGV9 polypeptides and TRGV9 polynucleotides that encode them, CD123 polypeptides and CD123 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule provided herein. The "host cell" can be any type of cell, e.g., a primary cell, a cell in culture, or a cell from a cell line. In one embodiment, a "host cell" is a cell transfected with a nucleic acid molecule provided herein. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed bispecific antibody can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Antibodies

Provided herein are anti-TRGV9 antibodies or antigen-binding fragments thereof, nucleic acids and expression vectors encoding the antibodies, recombinant cells containing the vectors, and compositions comprising the antibodies. Also provided herein are anti-TRGV9 bispecific antibodies or antigen-binding fragments thereof, nucleic acids and expression vectors encoding the bispecific antibodies, recombinant cells containing the vectors, and compositions comprising the bispecific antibodies. Also provided herein are anti-TRGV9/anti-CD123 bispecific antibodies or antigen-binding fragments thereof, nucleic acids and expression vectors encoding the bispecific antibodies, recombinant cells containing the vectors, and compositions comprising the bispecific antibodies. Methods of making the antibodies, and methods of using the antibodies to treat diseases, including cancer, are also provided. The antibodies disclosed herein possess one or more desirable functional properties, including but not limited to high-affinity binding to TRGV9 and/or high affinity binding to CD123, high specificity to TRGV9 and/or high specificity to CD123, and the ability to treat or prevent cancer when administered alone or in combination with other anti-cancer therapies.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies provided herein can be of any of the five major classes or corresponding sub-classes. In certain embodiments, the antibodies provided herein are IgG1. In some embodiments, the antibodies provided herein are IgG2. In some embodiments, the antibodies provided herein are IgG3. In some embodiments, the antibodies provided herein are IgG4. Antibody light chains of vertebrate species can be assigned to one of two clearly distinct types, namely kappa and lambda, based on the amino acid sequences of their constant domains. Accordingly, the antibodies provided herein can contain a kappa or lambda light chain constant domain. According to particular embodiments, the antibodies provided herein include heavy and/or light chain constant regions from rat or human antibodies.

In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). A "CDR" refers to one of three hypervariable regions (HCDR1, HCDR2 or HCDR3) within the non-framework region of the immunoglobulin (Ig or antibody) VH β-sheet framework, or one of three hypervariable regions (LCDR1, LCDR2 or LCDR3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. CDR region sequences have also been defined by AbM, Contact and IMGT. Exemplary CDR region sequences are illustrated herein, for example, in the Sequence Listing, and tables provided in the Examples below. The positions of CDRs within a canonical antibody variable region have been determined by comparison of numerous structures (Al-Lazikani et al., *J. Mol. Biol.* 273: 927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The light chain variable region CDR1 domain is interchangeably referred to herein as LCDR1 or VL CDR1. The light chain variable region CDR2 domain is interchangeably referred to herein as LCDR2 or VL CDR2. The light chain variable region CDR3 domain is interchangeably referred to herein as LCDR3 or VL CDR3. The heavy chain variable region CDR1 domain is interchangeably referred to herein as HCDR1 or VH CDR1. The heavy chain variable region CDR2 domain is interchangeably referred to herein as HCDR2 or VH CDR2. The heavy chain variable region CDR1 domain is interchangeably referred to herein as HCDR3 or VH CDR3.

The term "hypervariable region", such as a VH or VL, when used herein refers to the regions of an antibody variable region that are hypervariable in sequence and/or form structurally defined loops. Generally, antibodies comprise six hypervariable regions; three in the VH (HCDR1, HCDR2, HCDR3), and three in the VL (LCDR1, LCDR2, LCDR3). A number of hypervariable region delineations are in use and are encompassed herein. The "Kabat" CDRs are based on sequence variability and are the most commonly used (see, e.g., Kabat et al., *Sequences of Proteins of Immunological Interest*, 5th Ed. Public Health Service, National Institutes of Health, Bethesda, Md. (1991)). "Chothia" refers instead to the location of the structural loops (see, e.g., Chothia and Lesk, *J. Mol. Biol.* 196:901-917 (1987)). The end of the Chothia CDR-HCDR1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The "AbM" hypervariable regions represent a compromise between the Kabat CDRs and Chothia structural loops, and are used by Oxford Molecular's AbM antibody modeling software (see, e.g., Martin, in *Antibody Engineering*, Vol. 2, Chapter 3, Springer Verlag). "Contact" hypervariable regions are based on an analysis of the available complex crystal structures.

Recently, a universal numbering system has been developed and widely adopted, ImMunoGeneTics (IMGT) Information System® (Lafranc et al., *Dev. Comp. Immunol.* 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, *J. Mol. Biol.* 309: 657-670 (2001). Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). An Exemplary system, shown herein, combines Kabat and Chothia.

|  | Exemplary | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (LCDR1), 46-56 or 50-56 (LCDR2) and 89-97 or 89-96 (LCDR3) in the VL and 26-35 or 26-35A (HCDR1), 50-65 or 49-65 (HCDR2) and 93-102, 94-102, or 95-102 (HCDR3) in the VH. CDR sequences, reflecting each of the above numbering schemes, are provided herein, including in the Sequence Listing.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term "framework" or "FR" residues are those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

As used herein, the term an "isolated antibody" refers to an antibody which is substantially free of other antibodies having different antigenic specificities (e.g., an isolated antibody that specifically binds to TRGV9 is substantially free of antibodies that do not bind to Vγ9; an isolated antibody that specifically binds to CD123 is substantially free of antibodies that do not bind to CD123). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies provided herein can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdAb) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin variable domain sequence which has binding specificity for a first epitope (e.g., an epitope on a TRGV9 antigen) and a second immunoglobulin variable domain sequence that has binding specificity for a second epitope (e.g., an epitope on a tumor-associated antigen (e.g., a CD123 antigen)). In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on TRGV9 and the second epitope is located on CD123. In an embodiment, the first epitope is located on TRGV9 and the second epitope is located on PD-1, PD-L1, CTLA-4, EGFR, HER-2, CD19, CD20, CD3 and/or other cancer associated immune suppressors or surface antigens.

The term "half antibody" as used herein refers to one immunoglobulin heavy chain associated with one immunoglobulin light chain. An exemplary half-antibody is depicted in SEQ ID NO:17. One skilled in the art will readily appreciate that a half-antibody can encompass a fragment thereof and can also have an antigen binding domain consisting of a single variable domain, e.g., originating from a camelidae.

As used herein, the term "TRGV9" refers to a polypeptide capable of forming a T cell receptor when expressed on the surface of γδ T cells. TRGV9-expressing γδ T cells are among the first T cells to develop in the human fetus and are the predominant γδ T cell subset in healthy adult peripheral blood cells. The term "TRGV9" includes any TRGV9 variant, isoform, and species homolog, which is naturally expressed by cells (including T cells) or can be expressed on cells transfected with genes or cDNA encoding the polypeptide. Unless noted, the TRGV9, in specific embodiments, is a human TRGV9. A human TRGV9 amino acid sequence is provided by GenBank Accession Number NG 001336.2.

The term "CD123" refers to a molecule that is found on cells which helps transmit the signal of interleukin-3, a soluble cytokine that is important in the immune system. CD123 can also be referred to as the "interleukin-3 receptor." The receptor belongs to the type I cytokine receptor family and is a heterodimer with a unique alpha chain paired with the common beta subunit (beta c or CD131). The CD123 receptor can be found on pluripotent progenitor cells and can induce tyrosine phosphorylation within the cell and promote proliferation and differentiation within hematopoietic cell lines. CD123 can also be expressed in acute myeloid leukemia (AML) subtypes. The term "CD123" includes any CD123 variant, isoform, and species homolog, which is naturally expressed by cells (including T cells) or can be expressed on cells transfected with genes or cDNA encoding those polypeptides, unless noted, in specific embodiments the "CD123" is a human CD123. A human CD123 amino acid sequence is provided by GenBank Accession Number AY789109.1.

As used herein, an antibody that "specifically binds to TRGV9" refers to an antibody that binds to a TRGV9, such as a human TRGV9, with a KD of $1\times10^{-7}$ M or less, such as $1\times10^{-8}$ M or less, $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

As used herein, an antigen binding domain or antigen binding fragment that "specifically binds to a tumor-associated antigen" refers to an antigen binding domain or antigen binding fragment that binds a tumor-associated antigen, with a KD of $1\times10^{-7}$ M or less, such as $1\times10^{-8}$ M or less, $5\times10^{-9}$ M or less, $1\times10^{-9}$ M or less, $5\times10^{-10}$ M or less, or $1\times10^{-10}$ M or less.

The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antigen binding domain or antigen binding fragment can be determined by using surface plasmon resonance, such as by using a biosensor system, e.g., a Biacore® system, or by using bio-layer interferometry technology, such as an Octet RED96 system.

As used herein, an antibody that "specifically binds to CD123" refers to an antibody that binds to a CD123, such as a human CD123, with a KD of $1\times10^{-7}$ M or less, such as $1\times10^{-8}$ M or less, $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

In one aspect, provided herein is an antibody that binds to TRGV9. In some embodiments, the antibody comprises a heavy chain variable region and a light chain variable region. In a some embodiments, the TRGV9 antibody is not a single domain antibody or nanobody. In some embodiments, the TRGV1 antibody is a humanized antibody.

In certain embodiments, provided herein is an anti-TRGV9 antibody comprising a VH region, VL region, VH CDR1, VH CDR2, VH CDR3, VL CDR1, VL CDR2, and/or VL CDR3 of any one of the antibodies described herein. In some embodiments, provided herein is an anti-TRGV9 antibody comprising a VH region of any one of the antibodies described herein. In some embodiments, provided herein is an anti-TRGV9 antibody comprising a VL region of any one of the antibodies described herein. In some embodiments, provided herein is an anti-TRGV9 antibody comprising a VH region of any one of the antibodies described herein, and a VL region of any one of the antibodies described herein. In some embodiments, provided herein is an anti-TRGV9 antibody comprising a VH CDR1, VH CDR2, and VH CDR3 of any one of the antibodies described herein. In some embodiments, provided herein is an anti-TRGV9 antibody comprising a VL CDR1, VL CDR2, and VL CDR3 of any one of the antibodies described herein. In some embodiments, provided herein is an anti-TRGV9 antibody comprising a VH CDR1, VH CDR2, and VH CDR3 of any one of the antibodies described herein; and a VL CDR1, VL CDR2, and VL CDR3 of any one of the antibodies described herein. Representative VH and VL amino acid sequences, including VH CDR1, VH CDR2, VH CDR3, VL CDR1, VL CDR2 and VL CDR3 amino acid sequences, of TRGV9 antibodies provided herein are provided in the Sequence Listing, as well as Tables 1-31.

In certain embodiments, provided herein is an anti-TRGV9 bispecific antibody comprising a binding domain that binds to TRGV9 having a VH region, VL region, VH CDR1, VH CDR2, VH CDR3, VL CDR1, VL CDR2, and/or VL CDR3 of any one of the antibodies described herein. In some embodiments, provided herein is an anti-TRGV9 bispecific antibody comprising a binding domain that binds to TRGV9 having a VH region of any one of the antibodies described herein. In some embodiments, provided herein is an anti-TRGV9 bispecific antibody comprising a binding domain that binds to TRGV9 having a VL region of any one of the antibodies described herein. In some embodiments, provided herein is an anti-TRGV9 bispecific antibody comprising a binding domain that binds to TRGV9 having a VH region of any one of the antibodies described herein, and a VL region of any one of the antibodies described herein. In some embodiments, provided herein is an anti-TRGV9 bispecific antibody comprising a binding domain that binds to TRGV9 having a VH CDR1, VH CDR2, and VH CDR3 of any one of the antibodies described. In some embodiments, provided herein is an anti-TRGV9 bispecific antibody comprising a binding domain that binds to TRGV9 having a VL CDR1, VL CDR2, and VL CDR3 of any one of the antibodies described herein. In some embodiments, provided herein is an anti-TRGV9 bispecific antibody comprising a binding domain that binds to TRGV9 having a VH CDR1, VH CDR2, and VH CDR3 of any one of the antibodies described herein; and a VL CDR1, VL CDR2, and VL CDR3 of any one of the antibodies described herein.

In certain embodiments, the anti-TRGV9 antibody is a bispecific antibody. In some embodiments, the anti-TRGV9 bispecific antibody further comprises a second binding domain that binds to CD123 having a VH region, VL region, VH CDR1, VH CDR2, VH CDR3, VL CDR1, VL CDR2, and/or VL CDR3 of an anti-CD123 antibody provided herein. In some embodiments, the anti-TRGV9 bispecific antibody further comprises a second binding domain that binds to CD123 having a VH region of an anti-CD123 antibody provided herein. In some embodiments, the anti-TRGV9 bispecific antibody further comprises a second binding domain that binds to CD123 having a VL region of an anti-CD123 antibody provided herein. In some embodiments, the anti-TRGV9 bispecific antibody further comprises a second binding domain that binds to CD123 having a VH region of an anti-CD123 antibody provided herein, and a VL region of an anti-CD123 antibody provided herein. In some embodiments, the anti-TRGV9 bispecific antibody further comprises a second binding domain that binds to CD123 having a VH CDR1, VH CDR2, and VH CDR3 of an anti-CD123 antibody provided herein. In some embodiments, the anti-TRGV9 bispecific antibody further comprises a second binding domain that binds to CD123 having a VL CDR1, VL CDR2, and VL CDR3 of an anti-CD123 antibody provided herein. In some embodiments, the anti-TRGV9 bispecific antibody further comprises a second binding domain that binds to CD123 having a VH CDR1, VH CDR2, and VH CDR3 of an anti-CD123 antibody provided herein, and a VL CDR1, VL CDR2, and VL CDR3 of an anti-CD123 antibody provided herein.

In certain embodiments, provided is an anti-TRGV9 antibody that is an intact antibody. In other embodiments, provided is an anti-TRGV9 antibody is an antigen binding fragment of the anti-TRGV9 antibody. In some embodiments, the antigen binding fragment of the anti-TRGV9 antibody is a functional fragment. In some embodiments, the antigen binding fragment is a diabody. In some embodiments, the antigen binding fragment is a Fab. In some embodiments, the antigen binding fragment is a Fab'. In some embodiments, the antigen binding fragment is a F(ab')2. In some embodiments, the antigen binding fragment is a Fv fragment. In some embodiments, the antigen binding fragment is a disulfide stabilized Fv fragment (dsFv). In some embodiments, the antigen binding fragment is a (dsFv)$_2$. In some embodiments, the antigen binding fragment is a bispecific dsFv (dsFv-dsFv'). In some embodiments, the antigen binding fragment is a disulfide stabilized diabody (ds diabody). In some embodiments, the antigen binding fragment is a single-chain antibody molecule (scFv). In some embodiments, the antigen binding fragment is a single domain antibody (sdAb). In some embodiments, the antigen binding fragment is an scFv dimer (bivalent diabody). In some embodiments, the antigen binding fragment is a multispecific antibody formed from a portion of an antibody comprising one or more CDRs. In some embodiments, the antigen binding fragment is a camelized single domain antibody. In some embodiments, the antigen binding fragment is a nanobody. In some embodiments, the antigen binding fragment is a domain antibody. In some embodiments, the antigen binding fragment is a bivalent domain antibody. In some embodiments, the antigen binding fragment is an antibody fragment that binds to an antigen but does not comprise a complete antibody structure.

In specific embodiments, the anti-TRGV9 antibody comprises a VH region and a VL region. In some embodiments, the anti-TRGV9 antibody is not a single chain antibody. In some embodiments, the anti-TRGV9 antibody is not a single domain antibody. In some embodiments, the anti-TRGV9 antibody is not a nanobody. In certain embodiments, the anti-TRGV9 antibody is not a VHH antibody. In certain embodiments, the anti-TRGV9 antibody is not a llama antibody. In some embodiments, the anti-TRGV9 bispecific antibody does not comprise a single chain antibody. In some embodiments, the anti-TRGV9 bispecific antibody does not comprise a single domain antibody. In certain embodiments, the anti-TRGV9 bispecific antibody does not comprise a nanobody. In certain embodiments, the anti-TRGV9 bispecific antibody does not comprise a VHH antibody. In certain embodiments, the anti-TRGV9 bispecific antibody does not comprise a llama antibody. In some embodiments, the anti-TRGV9 antibody is a multispecific antibody. In other embodiments, the anti-TRGV9 antibody is a bispecific antibody. In certain embodiments, the multispecific antibody comprises an antigen binding fragment of an anti-TRGV9 antibody provided herein. In other embodiments, the bispecific antibody comprises an antigen binding fragment of an anti-TRGV9 antibody provided herein. In some embodiments, the anti-TRGV9 antibody is an agonistic antibody. In certain embodiments, the anti-TRGV9 antibody activates γδ T cells. In other embodiments, the anti-TRGV9 antibody is an antagonistic antibody. In certain embodiments, the anti-TRGV9 antibody inactivates γδ T cells. In some embodiments, the anti-TRGV9 antibody blocks activation of γδ T cells. In some embodiments, the anti-TRGV9 antibody modulates the activity of γδ T cells. In some embodiments, the anti-TRGV9 antibody neither activates or inactivates the activity of γδ T cells. In specific embodiments, the γδ T cells are human γδ T cells. In specific embodiments, provided is a bispecific antibody comprising a TRGV9 antibody provided herein in a knob-in-hole format. In some embodiments, an anti-TRGV9 antibody provided herein may be comprised in a bispecific antibody. In some embodiments, an anti-TRGV9 bispecific antibody provided herein may be comprised in a multispecific antibody. In certain embodiments, a bispecific antibody provided herein comprises a first binding domain comprising an anti-TRGV9 antibody provided herein that binds to a first TRGV9 epitope, and a second binding domain comprising an anti-TRGV9 antibody provided herein that binds to a second TRGV9 epitope, wherein the first TRGV9 epitope and the second TRGV9 epitope are not the same. In a specific embodiment, a TRGV9 antibody, or antigen binding fragment thereof, provided herein specifically binds to TRGV9. In certain embodiments, a TRGV9 antibody, or antigen binding fragment thereof, provided herein does not bind to an epitope of Vδ2.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:196, a VH CDR2 having an amino acid sequence of SEQ ID NO:197, and a VH CDR3 having an amino acid sequence of SEQ ID NO:198; and (ii) a VL comprising a VL CDR1 having an amino acid sequence of SEQ ID NO:199, a VL CDR2 having an amino acid sequence of SEQ ID NO:200, and a VL CDR3 having an amino acid sequence of SEQ ID NO:201. In another aspect, provided herein is an antibody that binds to TRGV9, wherein the antibody comprises: (i) a VH comprising a VH CDR1 having an amino acid sequence of SEQ ID NO:202, a VH CDR2 having an amino acid sequence of SEQ ID NO:203, and a VH CDR3 having an amino acid sequence of SEQ ID NO:204; and (ii) a VL comprising a VL CDR1 having an amino acid sequence of SEQ ID NO:205, a VL CDR2 having an amino acid sequence of SEQ ID NO:206, and a VL CDR3 having an amino acid sequence of SEQ ID NO:207. In another aspect, provided herein is an antibody that binds to TRGV9, wherein the antibody comprises: (i) a VH comprising a VH CDR1 having an amino acid sequence of SEQ ID NO:208, a VH CDR2 having an amino acid sequence of SEQ ID NO:209, and a VH CDR3 having an amino acid sequence of SEQ ID NO:210; and (ii) a VL comprising a VL CDR1 having an amino acid sequence of SEQ ID NO:211, a VL CDR2 having an amino acid sequence of SEQ ID NO:212, and a VL CDR3 having an amino acid sequence of SEQ ID NO:213. In another aspect, provided herein is an antibody that binds to TRGV9, wherein the antibody comprises: (i) a VH comprising a VH CDR1 having an amino acid sequence of SEQ ID NO:214, a VH CDR2 having an amino acid sequence of SEQ ID NO:215, and a VH CDR3 having an amino acid sequence of SEQ ID NO:216; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is an antibody that binds to TRGV9, wherein the antibody comprises: (i) a VH comprising a VH CDR1 having an amino acid sequence of SEQ ID NO:214, a VH CDR2 having an amino acid sequence of SEQ ID NO:702, and a VH CDR3 having an amino acid sequence of SEQ ID NO:703; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is an antibody that binds to TRGV9, wherein the antibody comprises: (i) a VH comprising a VH CDR1 having an amino acid sequence of SEQ ID NO:220, a VH CDR2 having an amino acid sequence of SEQ ID NO:221, and a VH CDR3 having an amino acid sequence of SEQ ID NO:222; and (ii) a VL comprising a VL CDR1 having an amino acid sequence of SEQ ID NO:223, a VL CDR2 having an amino acid sequence of SEQ ID NO:224, and a VL CDR3 having an amino acid sequence of SEQ ID NO:225. In another aspect, provided herein is an antibody that binds to TRGV9, wherein the antibody comprises: (i) a VH comprising a VH CDR1 having an amino acid sequence of SEQ ID NO:226, a VH CDR2 having an amino acid sequence of SEQ ID NO:227, and a VH CDR3 having an amino acid sequence of SEQ ID NO:228; and (ii) a VL comprising a VL CDR1 having an amino acid sequence of SEQ ID NO:229, a VL CDR2 having an amino acid sequence of SEQ ID NO:230, and a VL CDR3 having an amino acid sequence of SEQ ID NO:231. In some embodiments, the antibody comprises a VH having an amino acid sequence of SEQ ID NO:34. In some embodiments, the antibody comprises a VL having an amino acid sequence of SEQ ID NO:8. In some embodiments, the antibody comprises a VH having an amino acid sequence of SEQ ID NO:34, and a VL having an amino acid sequence of SEQ ID NO:8. In some embodiments, the antibody comprises a VH comprising an amino acid sequence having at least 95% identity to the amino acid sequence of SEQ ID NO:34. In some embodiments, the antibody comprises a VL comprising an amino acid sequence having at least 95% identity to the amino acid sequence of SEQ ID NO:8. In some embodiments, the antibody comprises a VH comprising an amino acid sequence having at least 95% identity to the amino acid sequence of SEQ ID NO:34, and a VL comprising an amino acid sequence having at least 95% identity to the amino acid sequence of SEQ ID NO:8.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:232, a VH CDR2 having an amino acid sequence of SEQ ID NO:233, and a VH CDR3 having an amino acid sequence of SEQ ID NO:234; and (ii) a VL comprising a VL CDR1 having an amino acid sequence of SEQ ID NO:235, a VL CDR2 having an amino acid sequence of SEQ ID NO:236, and a VL CDR3 having an amino acid sequence of SEQ ID NO:237. In another aspect, provided herein is an antibody that binds to TRGV9, wherein the antibody comprises: (i) a VH comprising a VH CDR1 having an amino acid sequence of SEQ ID NO:238, a VH CDR2 having an amino acid sequence of SEQ ID NO:239, and a VH CDR3 having an amino acid sequence of SEQ ID NO:240; and (ii) a VL comprising a VL CDR1 having an amino acid sequence of SEQ ID NO:241, a VL CDR2 having an amino acid sequence of SEQ ID NO:242, and a VL CDR3 having an amino acid sequence of SEQ ID NO:243. In another aspect, provided herein is an antibody that binds to TRGV9, wherein the antibody comprises: (i) a VH comprising a VH CDR1 having an amino acid sequence of SEQ ID NO:244, a VH CDR2 having an amino acid sequence of SEQ ID NO:245, and a VH CDR3 having an amino acid sequence of SEQ ID NO:246; and (ii) a VL comprising a VL CDR1 having an amino acid sequence of SEQ ID NO:247, a VL CDR2 having an amino acid sequence of SEQ ID NO:248, and a VL CDR3 having an amino acid sequence of SEQ ID NO:249. In another aspect, provided herein is an antibody that binds to TRGV9, wherein the antibody comprises: (i) a VH comprising a VH CDR1 having an amino acid sequence of SEQ ID NO:250, a VH CDR2 having an amino acid sequence of SEQ ID NO:251, and a VH CDR3 having an amino acid sequence of SEQ ID NO:252; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is an antibody that binds to TRGV9, wherein the antibody comprises: (i) a VH comprising a VH CDR1 having an amino acid sequence of SEQ ID NO:250, a VH CDR2 having an amino acid sequence of SEQ ID NO:704, and a VH CDR3 having an amino acid sequence of SEQ ID NO:705; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is an antibody that binds to TRGV9, wherein the antibody comprises: (i) a VH comprising a VH CDR1 having an amino acid sequence of SEQ ID NO:256, a VH CDR2 having an amino acid sequence of SEQ ID NO:257, and a VH CDR3 having an amino acid sequence of SEQ ID NO:258; and (ii) a VL comprising a VL CDR1 having an amino acid sequence of SEQ ID NO:259, a VL CDR2 having an amino acid sequence of SEQ ID NO:260, and a VL CDR3 having an amino acid sequence of SEQ ID NO:261. In another aspect, provided herein is an antibody that binds to TRGV9, wherein the antibody comprises: (i) a VH comprising a VH CDR1 having an amino acid sequence of SEQ ID NO:262, a VH CDR2 having an amino acid sequence of SEQ ID NO:263, and a VH CDR3 having an amino acid sequence of SEQ ID NO:264; and (ii) a VL comprising a VL CDR1 having an amino acid sequence of SEQ ID NO:265, a VL CDR2 having an amino acid sequence of SEQ ID NO:266, and a VL CDR3 having an amino acid sequence of SEQ ID NO:267. In some embodiments, the antibody comprises a VH having an amino acid sequence of SEQ ID NO:35. In some embodiments, the antibody comprises a VL having an amino acid sequence of SEQ ID NO:8. In some embodiments, the antibody comprises a VH having an amino acid sequence of SEQ ID NO:35, and a VL having an amino acid sequence of SEQ ID NO:8. In some embodiments, the antibody comprises a VH comprising an amino acid sequence having at least 95% identity to the amino acid sequence of SEQ ID NO:35. In some embodiments, the antibody comprises a VL comprising an amino acid sequence having at least 95% identity to the amino acid sequence of SEQ ID NO:8. In some embodiments, the antibody comprises a VH comprising an amino acid sequence having at least 95% identity to the amino acid sequence of SEQ ID NO:35, and a VL comprising an amino acid sequence having at least 95% identity to the amino acid sequence of SEQ ID NO:8.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:268, a VH CDR2 having an amino acid sequence of SEQ ID NO:269, and a VH CDR3 having an amino acid sequence of SEQ ID NO:270; and (ii) a VL comprising a VL CDR1 having an amino acid sequence of SEQ ID NO:271, a VL CDR2 having an amino acid sequence of SEQ ID NO:272, and a VL CDR3 having an amino acid sequence of SEQ ID NO:273. In another aspect, provided herein is an antibody that binds to TRGV9, wherein the antibody comprises: (i) a VH comprising a VH CDR1 having an amino acid sequence of SEQ ID NO:274, a VH CDR2 having an amino acid sequence of SEQ ID NO:275, and a VH CDR3 having an amino acid sequence of SEQ ID NO:276; and (ii) a VL comprising a VL CDR1 having an amino acid sequence of SEQ ID NO:277, a VL CDR2 having an amino acid sequence of SEQ ID NO:278, and a VL CDR3 having an amino acid sequence of SEQ ID NO:279. In another aspect, provided herein is an antibody that binds to TRGV9, wherein the antibody comprises: (i) a VH comprising a VH CDR1 having an amino acid sequence of SEQ ID NO:280, a VH CDR2 having an amino acid sequence of SEQ ID NO:281, and a VH CDR3 having an amino acid sequence of SEQ ID NO:282; and (ii) a VL comprising a VL CDR1 having an amino acid sequence of SEQ ID NO:283, a VL CDR2 having an amino acid sequence of SEQ ID NO:284, and a VL CDR3 having an amino acid sequence of SEQ ID NO:285. In another aspect, provided herein is an antibody that binds to TRGV9, wherein the antibody comprises: (i) a VH comprising a VH CDR1 having an amino acid sequence of SEQ ID NO:286, a VH CDR2 having an amino acid sequence of SEQ ID NO:287, and a VH CDR3 having an amino acid sequence of SEQ ID NO:288; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is an antibody that binds to TRGV9, wherein the antibody comprises: (i) a VH comprising a VH CDR1 having an amino acid sequence of SEQ ID NO:286, a VH CDR2 having an amino acid sequence of SEQ ID NO:706, and a VH CDR3 having an amino acid sequence of SEQ ID NO:707; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is an antibody that binds to TRGV9, wherein the antibody comprises: (i) a VH comprising a VH CDR1 having an amino acid sequence of SEQ ID NO:292, a VH CDR2 having an amino acid sequence of SEQ ID NO:293, and a VH CDR3 having an amino acid sequence of SEQ ID NO:294; and (ii) a VL comprising a VL CDR1 having an amino acid sequence of SEQ ID NO:295, a VL CDR2 having an amino acid sequence of SEQ ID NO:296, and a VL CDR3 having an amino acid sequence of SEQ ID NO:297. In another aspect, provided herein is an antibody that binds to TRGV9, wherein the antibody comprises: (i) a VH comprising a VH CDR1 having an amino acid sequence of SEQ ID NO:298, a VH CDR2 having an amino acid sequence of SEQ ID NO:299, and a VH CDR3 having an amino acid sequence of SEQ ID NO:300; and (ii) a VL comprising a VL CDR1 having an amino acid sequence of SEQ ID NO:301, a VL CDR2 having an amino acid sequence of SEQ ID NO:302, and a VL CDR3 having an amino acid sequence of SEQ ID NO:303. In some embodiments, the antibody comprises a VH having an amino acid sequence of SEQ ID NO:36. In some embodiments, the antibody comprises a VL having an amino acid sequence of SEQ ID NO:8. In some embodiments, the antibody comprises a VH having an amino acid sequence of SEQ ID NO:36, and a VL having an amino acid sequence of SEQ ID NO:8. In some embodiments, the antibody comprises a VH comprising an amino acid sequence having at least 95% identity to the amino acid sequence of SEQ ID NO:36. In some embodiments, the antibody comprises a VL comprising an amino acid sequence having at least 95% identity to the amino acid sequence of SEQ ID NO:8. In some embodiments, the antibody comprises a VH comprising an amino acid sequence having at least 95% identity to the amino acid sequence of SEQ ID NO:36, and a VL comprising an amino acid sequence having at least 95% identity to the amino acid sequence of SEQ ID NO:8.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is an antibody that binds to TRGV9, wherein the antibody comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In another aspect, provided herein is an antibody that binds to TRGV9, wherein the antibody comprises: (i) a VH comprising a VH CDR1 having an amino acid sequence of SEQ ID NO:304, a VH CDR2 having an amino acid sequence of SEQ ID NO:305, and a VH CDR3 having an amino acid sequence of SEQ ID NO:306; and (ii) a VL comprising a VL CDR1 having an amino acid sequence of SEQ ID NO:307, a VL CDR2 having an amino acid sequence of SEQ ID NO:308, and a VL CDR3 having an amino acid sequence of SEQ ID NO:309. In another aspect, provided herein is an antibody that binds to TRGV9, wherein the antibody comprises: (i) a VH comprising a VH CDR1 having an amino acid sequence of SEQ ID NO:310, a VH CDR2 having an amino acid sequence of SEQ ID NO:311, and a VH CDR3 having an amino acid sequence of SEQ ID NO:312; and (ii) a VL comprising a VL CDR1 having an amino acid sequence of SEQ ID NO:313, a VL CDR2 having an amino acid sequence of SEQ ID NO:314, and a VL CDR3 having an amino acid sequence of SEQ ID NO:315. In another aspect, provided herein is an antibody that binds to TRGV9, wherein the antibody comprises: (i) a VH comprising a VH CDR1 having an amino acid sequence of SEQ ID NO:316, a VH CDR2 having an amino acid sequence of SEQ ID NO:317, and a VH CDR3 having an amino acid sequence of SEQ ID NO:318; and (ii) a VL comprising a VL CDR1 having an amino acid sequence of SEQ ID NO:319, a VL CDR2 having an amino acid sequence of SEQ ID NO:320, and a VL CDR3 having an amino acid sequence of SEQ ID NO:321. In another aspect, provided herein is an antibody that binds to TRGV9, wherein the antibody comprises: (i) a VH comprising a VH CDR1 having an amino acid sequence of SEQ ID NO:322, a VH CDR2 having an amino acid sequence of SEQ ID NO:323, and a VH CDR3 having an amino acid sequence of SEQ ID NO:324; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is an antibody that binds to TRGV9, wherein the antibody comprises: (i) a VH comprising a VH CDR1 having an amino acid sequence of SEQ ID NO:322, a VH CDR2 having an amino acid sequence of SEQ ID NO:708, and a VH CDR3 having an amino acid sequence of SEQ ID NO:709; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is an antibody that binds to TRGV9, wherein the antibody comprises: (i) a VH comprising a VH CDR1 having an amino acid sequence of SEQ ID NO:328, a VH CDR2 having an amino acid sequence of SEQ ID NO:329, and a VH CDR3 having an amino acid sequence of SEQ ID NO:330; and (ii) a VL comprising a VL CDR1 having an amino acid sequence of SEQ ID NO:331, a VL CDR2 having an amino acid sequence of SEQ ID NO:332, and a VL CDR3 having an amino acid sequence of SEQ ID NO:333. In another aspect, provided herein is an antibody that binds to TRGV9, wherein the antibody comprises: (i) a VH comprising a VH CDR1 having an amino acid sequence of SEQ ID NO:334, a VH CDR2 having an amino acid sequence of SEQ ID NO:335, and a VH CDR3 having an amino acid sequence of SEQ ID NO:336; and (ii) a VL comprising a VL CDR1 having an amino acid sequence of SEQ ID NO:337, a VL CDR2 having an amino acid sequence of SEQ ID NO:338, and a VL CDR3 having an amino acid sequence of SEQ ID NO:339. In another aspect, provided herein is an antibody that binds to TRGV9, wherein the antibody comprises: (i) a VH comprising a VH CDR1 having an amino acid sequence of SEQ ID NO:340, a VH CDR2 having an amino acid sequence of SEQ ID NO:341, and a VH CDR3 having an amino acid sequence of SEQ ID NO:342; and (ii) a VL comprising a VL CDR1 having an amino acid sequence of SEQ ID NO:343, a VL CDR2 having an amino acid sequence of SEQ ID NO:344, and a VL CDR3 having an amino acid sequence of SEQ ID NO:345. In another aspect, provided herein is an antibody that binds to TRGV9, wherein the antibody comprises: (i) a VH comprising a VH CDR1 having an amino acid sequence of SEQ ID NO:346, a VH CDR2 having an amino acid sequence of SEQ ID NO:347, and a VH CDR3 having an amino acid sequence of SEQ ID NO:348; and (ii) a VL comprising a VL CDR1 having an amino acid sequence of SEQ ID NO:349, a VL CDR2 having an amino acid sequence of SEQ ID NO:350, and a VL CDR3 having an amino acid sequence of SEQ ID NO:351. In another aspect, provided herein is an antibody that binds to TRGV9, wherein the antibody comprises: (i) a VH comprising a VH CDR1 having an amino acid sequence of SEQ ID NO:352, a VH CDR2 having an amino acid sequence of SEQ ID NO:353, and a VH CDR3 having an amino acid sequence of SEQ ID NO:354; and (ii) a VL comprising a VL CDR1 having an amino acid sequence of SEQ ID NO:355, a VL CDR2 having an amino acid sequence of SEQ ID NO:356, and a VL CDR3 having an amino acid sequence of SEQ ID NO:357. In another aspect, provided herein is an antibody that binds to TRGV9, wherein the antibody comprises: (i) a VH comprising a VH CDR1 having an amino acid sequence of SEQ ID NO:358, a VH CDR2 having an amino acid sequence of SEQ ID NO:359, and a VH CDR3 having an amino acid sequence of SEQ ID NO:360; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is an antibody that binds to TRGV9, wherein the antibody comprises: (i) a VH comprising a VH CDR1 having an amino acid sequence of SEQ ID NO:358, a VH CDR2 having an amino acid sequence of SEQ ID NO:710, and a VH CDR3 having an amino acid sequence of SEQ ID NO:711; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is an antibody that binds to TRGV9, wherein the antibody comprises: (i) a VH comprising a VH CDR1 having an amino acid sequence of SEQ ID NO:364, a VH CDR2 having an amino acid sequence of SEQ ID NO:365, and a VH CDR3 having an amino acid sequence of SEQ ID NO:366; and (ii) a VL comprising a VL CDR1 having an amino acid sequence of SEQ ID NO:367, a VL CDR2 having an amino acid sequence of SEQ ID NO:368, and a VL CDR3 having an amino acid sequence of SEQ ID NO:369. In another aspect, provided herein is an antibody that binds to TRGV9, wherein the antibody comprises: (i) a VH comprising a VH CDR1 having an amino acid sequence of SEQ ID NO:370, a VH CDR2 having an amino acid sequence of SEQ ID NO:371, and a VH CDR3 having an amino acid sequence of SEQ ID NO:372; and (ii) a VL comprising a VL CDR1 having an amino acid sequence of SEQ ID NO:373, a VL CDR2 having an amino acid sequence of SEQ ID NO:374, and a VL CDR3 having an amino acid sequence of SEQ ID NO:375. In some embodiments, the antibody comprises a VH having an amino acid sequence of SEQ ID NO:65. In some embodiments, the antibody comprises a VL having an amino acid sequence of SEQ ID NO:66. In some embodiments, the antibody comprises a VH having an amino acid sequence of SEQ ID NO:65, and a VL having an amino acid sequence of SEQ ID NO:66. In some embodiments, the antibody comprises a VH having an amino acid sequence of SEQ ID NO:67. In some embodiments, the antibody comprises a VL having an amino acid sequence of SEQ ID NO:68. In some embodiments, the antibody comprises a VH having an amino acid sequence of SEQ ID NO:67, and a VL having an amino acid sequence of SEQ ID NO:68. In some embodiments, the antibody comprises a heavy chain having an amino acid sequence of SEQ ID NO:71. In some embodiments, the antibody comprises a light chain having an amino acid sequence of SEQ ID NO:72. In some embodiments, the antibody comprises a heavy chain having an amino acid sequence of SEQ ID NO:71, and a light chain having an amino acid sequence of SEQ ID NO:72. In some embodiments, the antibody comprises an amino acid sequence of SEQ ID NO:70. In some embodiments, the antibody comprises a heavy chain having an amino acid sequence of SEQ ID NO:74. In some embodiments, the antibody comprises a light chain having an amino acid sequence of SEQ ID NO:75. In some embodiments, the antibody comprises a heavy chain having an amino acid sequence of SEQ ID NO:74, and a light chain having an amino acid sequence of SEQ ID NO:75. In some embodiments, the antibody comprises an amino acid sequence of SEQ ID NO:73. In some embodiments, the antibody comprises a VH comprising an amino acid sequence having at least 95% identity to the amino acid sequence of SEQ ID NO:65. In some embodiments, the antibody comprises a VL comprising an amino acid sequence having at least 95% identity to the amino acid sequence of SEQ ID NO:66. In some embodiments, the antibody comprises a VH comprising an amino acid sequence having at least 95% identity to the amino acid sequence of SEQ ID NO:65, and a VL comprising an amino acid sequence having at least 95% identity to the amino acid sequence of SEQ ID NO:66. In some embodiments, the antibody comprises a VH comprising an amino acid sequence having at least 95% identity to the amino acid sequence of SEQ ID NO:67. In some embodiments, the antibody comprises a VL comprising an amino acid sequence having at least 95% identity to the amino acid sequence of SEQ ID NO:68. In some embodiments, the antibody comprises a VH comprising an amino acid sequence having at least 95% identity to the amino acid sequence of SEQ ID NO:67, and a VL comprising an amino acid sequence having at least 95% identity to the amino acid sequence of SEQ ID NO:68. In some embodiments, the antibody comprises a heavy chain comprising an amino acid sequence having at least 95% identity to the amino acid sequence of SEQ ID NO:71. In some embodiments, the antibody comprises a light chain comprising an amino acid sequence having at least 95% identity to the amino acid sequence of SEQ ID NO:72. In some embodiments, the antibody comprises a heavy chain comprising an amino acid sequence having at least 95% identity to the amino acid sequence of SEQ ID NO:71, and a light chain comprising an amino acid sequence having at least 95% identity to the amino acid sequence of SEQ ID NO:72. In some embodiments, the antibody comprises an amino acid sequence of SEQ ID NO:70. In some embodiments, the antibody comprises a heavy chain comprising an amino acid sequence having at least 95% identity to the amino acid sequence of SEQ ID NO:74. In some embodiments, the antibody comprises a light chain comprising an amino acid sequence having at least 95% identity to the amino acid sequence of SEQ ID NO:75. In some embodiments, the antibody comprises a heavy chain comprising an amino acid sequence having at least 95% identity to the amino acid sequence of SEQ ID NO:74, and a light chain comprising an amino acid sequence having at least 95% identity to the amino acid sequence of SEQ ID NO:75. In some embodiments, the antibody comprises an amino acid sequence of SEQ ID NO:73.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is an antibody that binds to TRGV9, wherein the antibody comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100; and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In another aspect, provided herein is an antibody that binds to TRGV9, wherein the antibody comprises: (i) a VH comprising a VH CDR1 having an amino acid sequence of SEQ ID NO:412, a VH CDR2 having an amino acid sequence of SEQ ID NO:413, and a VH CDR3 having an amino acid sequence of SEQ ID NO:414; and (ii) a VL comprising a VL CDR1 having an amino acid sequence of SEQ ID NO:415, a VL CDR2 having an amino acid sequence of SEQ ID NO:416, and a VL CDR3 having an amino acid sequence of SEQ ID NO:417. In another aspect, provided herein is an antibody that binds to TRGV9, wherein the antibody comprises: (i) a VH comprising a VH CDR1 having an amino acid sequence of SEQ ID NO:418, a VH CDR2 having an amino acid sequence of SEQ ID NO:419, and a VH CDR3 having an amino acid sequence of SEQ ID NO:420; and (ii) a VL comprising a VL CDR1 having an amino acid sequence of SEQ ID NO:421, a VL CDR2 having an amino acid sequence of SEQ ID NO:422, and a VL CDR3 having an amino acid sequence of SEQ ID NO:423. In another aspect, provided herein is an antibody that binds to TRGV9, wherein the antibody comprises: (i) a VH comprising a VH CDR1 having an amino acid sequence of SEQ ID NO:424, a VH CDR2 having an amino acid sequence of SEQ ID NO:425, and a VH CDR3 having an amino acid sequence of SEQ ID NO:426; and (ii) a VL comprising a VL CDR1 having an amino acid sequence of SEQ ID NO:427, a VL CDR2 having an amino acid sequence of SEQ ID NO:428, and a VL CDR3 having an amino acid sequence of SEQ ID NO:429. In another aspect, provided herein is an antibody that binds to TRGV9, wherein the antibody comprises: (i) a VH comprising a VH CDR1 having an amino acid sequence of SEQ ID NO:430, a VH CDR2 having an amino acid sequence of SEQ ID NO:431, and a VH CDR3 having an amino acid sequence of SEQ ID NO:432; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is an antibody that binds to TRGV9, wherein the antibody comprises: (i) a VH comprising a VH CDR1 having an amino acid sequence of SEQ ID NO:430, a VH CDR2 having an amino acid sequence of SEQ ID NO:714, and a VH CDR3 having an amino acid sequence of SEQ ID NO:715; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is an antibody that binds to TRGV9, wherein the antibody comprises: (i) a VH comprising a VH CDR1 having an amino acid sequence of SEQ ID NO:436, a VH CDR2 having an amino acid sequence of SEQ ID NO:437, and a VH CDR3 having an amino acid sequence of SEQ ID NO:438; and (ii) a VL comprising a VL CDR1 having an amino acid sequence of SEQ ID NO:439, a VL CDR2 having an amino acid sequence of SEQ ID NO:440, and a VL CDR3 having an amino acid sequence of SEQ ID NO:441. In another aspect, provided herein is an antibody that binds to TRGV9, wherein the antibody comprises: (i) a VH comprising a VH CDR1 having an amino acid sequence of SEQ ID NO:442, a VH CDR2 having an amino acid sequence of SEQ ID NO:443, and a VH CDR3 having an amino acid sequence of SEQ ID NO:444; and (ii) a VL comprising a VL CDR1 having an amino acid sequence of SEQ ID NO:445, a VL CDR2 having an amino acid sequence of SEQ ID NO:446, and a VL CDR3 having an amino acid sequence of SEQ ID NO:447. In some embodiments, the antibody comprises a VH having an amino acid sequence of SEQ ID NO:104. In some embodiments, the antibody comprises a VL having an amino acid sequence of SEQ ID NO:105. In some embodiments, the antibody comprises a VH having an amino acid sequence of SEQ ID NO:104, and a VL having an amino acid sequence of SEQ ID NO:105. In some embodiments, the antibody comprises an amino acid sequence of SEQ ID NO:106. In some embodiments, the antibody comprises a VH comprising an amino acid sequence having at least 95% identity to the amino acid sequence of SEQ ID NO:104. In some embodiments, the antibody comprises a VL comprising an amino acid sequence having at least 95% identity to the amino acid sequence of SEQ ID NO:105. In some embodiments, the antibody comprises a VH comprising an amino acid sequence having at least 95% identity to the amino acid sequence of SEQ ID NO:104, and a VL comprising an amino acid sequence having at least 95% identity to the amino acid sequence of SEQ ID NO:105. In some embodiments, the antibody comprises an amino acid sequence of SEQ ID NO:106.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is an antibody that binds to TRGV9, wherein the antibody comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109; and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In another aspect, provided herein is an antibody that binds to TRGV9, wherein the antibody comprises: (i) a VH comprising a VH CDR1 having an amino acid sequence of SEQ ID NO:448, a VH CDR2 having an amino acid sequence of SEQ ID NO:449, and a VH CDR3 having an amino acid sequence of SEQ ID NO:450; and (ii) a VL comprising a VL CDR1 having an amino acid sequence of SEQ ID NO:451, a VL CDR2 having an amino acid sequence of SEQ ID NO:452, and a VL CDR3 having an amino acid sequence of SEQ ID NO:453. In another aspect, provided herein is an antibody that binds to TRGV9, wherein the antibody comprises: (i) a VH comprising a VH CDR1 having an amino acid sequence of SEQ ID NO:454, a VH CDR2 having an amino acid sequence of SEQ ID NO:455, and a VH CDR3 having an amino acid sequence of SEQ ID NO:456; and (ii) a VL comprising a VL CDR1 having an amino acid sequence of SEQ ID NO:457, a VL CDR2 having an amino acid sequence of SEQ ID NO:458, and a VL CDR3 having an amino acid sequence of SEQ ID NO:459. In another aspect, provided herein is an antibody that binds to TRGV9, wherein the antibody comprises: (i) a VH comprising a VH CDR1 having an amino acid sequence of SEQ ID NO:460, a VH CDR2 having an amino acid sequence of SEQ ID NO:461, and a VH CDR3 having an amino acid sequence of SEQ ID NO:462; and (ii) a VL comprising a VL CDR1 having an amino acid sequence of SEQ ID NO:463, a VL CDR2 having an amino acid sequence of SEQ ID NO:464, and a VL CDR3 having an amino acid sequence of SEQ ID NO:465. In another aspect, provided herein is an antibody that binds to TRGV9, wherein the antibody comprises: (i) a VH comprising a VH CDR1 having an amino acid sequence of SEQ ID NO:466, a VH CDR2 having an amino acid sequence of SEQ ID NO:467, and a VH CDR3 having an amino acid sequence of SEQ ID NO:468; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is an antibody that binds to TRGV9, wherein the antibody comprises: (i) a VH comprising a VH CDR1 having an amino acid sequence of SEQ ID NO:466, a VH CDR2 having an amino acid sequence of SEQ ID NO:716, and a VH CDR3 having an amino acid sequence of SEQ ID NO:717; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is an antibody that binds to TRGV9, wherein the antibody comprises: (i) a VH comprising a VH CDR1 having an amino acid sequence of SEQ ID NO:472, a VH CDR2 having an amino acid sequence of SEQ ID NO:473, and a VH CDR3 having an amino acid sequence of SEQ ID NO:474; and (ii) a VL comprising a VL CDR1 having an amino acid sequence of SEQ ID NO:475, a VL CDR2 having an amino acid sequence of SEQ ID NO:476, and a VL CDR3 having an amino acid sequence of SEQ ID NO:477. In another aspect, provided herein is an antibody that binds to TRGV9, wherein the antibody comprises: (i) a VH comprising a VH CDR1 having an amino acid sequence of SEQ ID NO:478, a VH CDR2 having an amino acid sequence of SEQ ID NO:479, and a VH CDR3 having an amino acid sequence of SEQ ID NO:480; and (ii) a VL comprising a VL CDR1 having an amino acid sequence of SEQ ID NO:481, a VL CDR2 having an amino acid sequence of SEQ ID NO:482, and a VL CDR3 having an amino acid sequence of SEQ ID NO:483. In some embodiments, the antibody comprises a VH having an amino acid sequence of SEQ ID NO:113. In some embodiments, the antibody comprises a VL having an amino acid sequence of SEQ ID NO:114. In some embodiments, the antibody comprises a VH having an amino acid sequence of SEQ ID NO:113, and a VL having an amino acid sequence of SEQ ID NO:114. In some embodiments, the antibody comprises a heavy chain having an amino acid sequence of SEQ ID NO:115. In some embodiments, the antibody comprises a light chain having an amino acid sequence of SEQ ID NO:116. In some embodiments, the antibody comprises a heavy chain having an amino acid sequence of SEQ ID NO:115, and a light chain having an amino acid sequence of SEQ ID NO:116. In some embodiments, the antibody comprises a VH comprising an amino acid sequence having at least 95% identity to the amino acid sequence of SEQ ID NO:113. In some embodiments, the antibody comprises a VL comprising an amino acid sequence having at least 95% identity to the amino acid sequence of SEQ ID NO:114. In some embodiments, the antibody comprises a VH comprising an amino acid sequence having at least 95% identity to the amino acid sequence of SEQ ID NO:113, and a VL comprising an amino acid sequence having at least 95% identity to the amino acid sequence of SEQ ID NO:114. In some embodiments, the antibody comprises a heavy chain comprising an amino acid sequence having at least 95% identity to the amino acid sequence of SEQ ID NO:115. In some embodiments, the antibody comprises a light chain comprising an amino acid sequence having at least 95% identity to the amino acid sequence of SEQ ID NO:116. In some embodiments, the antibody comprises a heavy chain comprising an amino acid sequence having at least 95% identity to the amino acid sequence of SEQ ID NO:115, and a light chain comprising an amino acid sequence having at least 95% identity to the amino acid sequence of SEQ ID NO:116.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is an antibody that binds to TRGV9, wherein the antibody comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119; and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In another aspect, provided herein is an antibody that binds to TRGV9, wherein the antibody comprises: (i) a VH comprising a VH CDR1 having an amino acid sequence of SEQ ID NO:484, a VH CDR2 having an amino acid sequence of SEQ ID NO:485, and a VH CDR3 having an amino acid sequence of SEQ ID NO:486; and (ii) a VL comprising a VL CDR1 having an amino acid sequence of SEQ ID NO:487, a VL CDR2 having an amino acid sequence of SEQ ID NO:488, and a VL CDR3 having an amino acid sequence of SEQ ID NO:489. In another aspect, provided herein is an antibody that binds to TRGV9, wherein the antibody comprises: (i) a VH comprising a VH CDR1 having an amino acid sequence of SEQ ID NO:490, a VH CDR2 having an amino acid sequence of SEQ ID NO:491, and a VH CDR3 having an amino acid sequence of SEQ ID NO:492; and (ii) a VL comprising a VL CDR1 having an amino acid sequence of SEQ ID NO:493, a VL CDR2 having an amino acid sequence of SEQ ID NO:494, and a VL CDR3 having an amino acid sequence of SEQ ID NO:495. In another aspect, provided herein is an antibody that binds to TRGV9, wherein the antibody comprises: (i) a VH comprising a VH CDR1 having an amino acid sequence of SEQ ID NO:496, a VH CDR2 having an amino acid sequence of SEQ ID NO:497, and a VH CDR3 having an amino acid sequence of SEQ ID NO:498; and (ii) a VL comprising a VL CDR1 having an amino acid sequence of SEQ ID NO:499, a VL CDR2 having an amino acid sequence of SEQ ID NO:500, and a VL CDR3 having an amino acid sequence of SEQ ID NO:501. In another aspect, provided herein is an antibody that binds to TRGV9, wherein the antibody comprises: (i) a VH comprising a VH CDR1 having an amino acid sequence of SEQ ID NO:502, a VH CDR2 having an amino acid sequence of SEQ ID NO:503, and a VH CDR3 having an amino acid sequence of SEQ ID NO:504; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is an antibody that binds to TRGV9, wherein the antibody comprises: (i) a VH comprising a VH CDR1 having an amino acid sequence of SEQ ID NO:502, a VH CDR2 having an amino acid sequence of SEQ ID NO:718, and a VH CDR3 having an amino acid sequence of SEQ ID NO:719; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is an antibody that binds to TRGV9, wherein the antibody comprises: (i) a VH comprising a VH CDR1 having an amino acid sequence of SEQ ID NO:508, a VH CDR2 having an amino acid sequence of SEQ ID NO:509, and a VH CDR3 having an amino acid sequence of SEQ ID NO:510; and (ii) a VL comprising a VL CDR1 having an amino acid sequence of SEQ ID NO:511, a VL CDR2 having an amino acid sequence of SEQ ID NO:512, and a VL CDR3 having an amino acid sequence of SEQ ID NO:513. In another aspect, provided herein is an antibody that binds to TRGV9, wherein the antibody comprises: (i) a VH comprising a VH CDR1 having an amino acid sequence of SEQ ID NO:514, a VH CDR2 having an amino acid sequence of SEQ ID NO:515, and a VH CDR3 having an amino acid sequence of SEQ ID NO:516; and (ii) a VL comprising a VL CDR1 having an amino acid sequence of SEQ ID NO:517, a VL CDR2 having an amino acid sequence of SEQ ID NO:518, and a VL CDR3 having an amino acid sequence of SEQ ID NO:519. In some embodiments, the antibody comprises a VH having an amino acid sequence of SEQ ID NO:123. In some embodiments, the antibody comprises a VL having an amino acid sequence of SEQ ID NO:124. In some embodiments, the antibody comprises a VH having an amino acid sequence of SEQ ID NO:123, and a VL having an amino acid sequence of SEQ ID NO:124. In some embodiments, the antibody comprises a heavy chain having an amino acid sequence of SEQ ID NO:125. In some embodiments, the antibody comprises a light chain having an amino acid sequence of SEQ ID NO:126. In some embodiments, the antibody comprises a heavy chain having an amino acid sequence of SEQ ID NO:125, and a light chain having an amino acid sequence of SEQ ID NO:126. In some embodiments, the antibody comprises a VH comprising an amino acid sequence having at least 95% identity to the amino acid sequence of SEQ ID NO:123. In some embodiments, the antibody comprises a VL comprising an amino acid sequence having at least 95% identity to the amino acid sequence of SEQ ID NO:124. In some embodiments, the antibody comprises a VH comprising an amino acid sequence having at least 95% identity to the amino acid sequence of SEQ ID NO:123, and a VL comprising an amino acid sequence having at least 95% identity to the amino acid sequence of SEQ ID NO:124. In some embodiments, the antibody comprises a heavy chain comprising an amino acid sequence having at least 95% identity to the amino acid sequence of SEQ ID NO:125. In some embodiments, the antibody comprises a light chain comprising an amino acid sequence having at least 95% identity to the amino acid sequence of SEQ ID NO:126. In some embodiments, the antibody comprises a heavy chain comprising an amino acid sequence having at least 95% identity to the amino acid sequence of SEQ ID NO:125, and a light chain comprising an amino acid sequence having at least 95% identity to the amino acid sequence of SEQ ID NO:126.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In another aspect, provided herein is an antibody that binds to TRGV9, wherein the antibody comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129; and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In another aspect, provided herein is an antibody that binds to TRGV9, wherein the antibody comprises: (i) a VH comprising a VH CDR1 having an amino acid sequence of SEQ ID NO:520, a VH CDR2 having an amino acid sequence of SEQ ID NO:521, and a VH CDR3 having an amino acid sequence of SEQ ID NO:522; and (ii) a VL comprising a VL CDR1 having an amino acid sequence of SEQ ID NO:523, a VL CDR2 having an amino acid sequence of SEQ ID NO:524, and a VL CDR3 having an amino acid sequence of SEQ ID NO:525. In another aspect, provided herein is an antibody that binds to TRGV9, wherein the antibody comprises: (i) a VH comprising a VH CDR1 having an amino acid sequence of SEQ ID NO:526, a VH CDR2 having an amino acid sequence of SEQ ID NO:527, and a VH CDR3 having an amino acid sequence of SEQ ID NO:528; and (ii) a VL comprising a VL CDR1 having an amino acid sequence of SEQ ID NO:529, a VL CDR2 having an amino acid sequence of SEQ ID NO:530, and a VL CDR3 having an amino acid sequence of SEQ ID NO:531. In another aspect, provided herein is an antibody that binds to TRGV9, wherein the antibody comprises: (i) a VH comprising a VH CDR1 having an amino acid sequence of SEQ ID NO:532, a VH CDR2 having an amino acid sequence of SEQ ID NO:533, and a VH CDR3 having an amino acid sequence of SEQ ID NO:534; and (ii) a VL comprising a VL CDR1 having an amino acid sequence of SEQ ID NO:535, a VL CDR2 having an amino acid sequence of SEQ ID NO:536, and a VL CDR3 having an amino acid sequence of SEQ ID NO:537. In another aspect, provided herein is an antibody that binds to TRGV9, wherein the antibody comprises: (i) a VH comprising a VH CDR1 having an amino acid sequence of SEQ ID NO:538, a VH CDR2 having an amino acid sequence of SEQ ID NO:539, and a VH CDR3 having an amino acid sequence of SEQ ID NO:540; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is an antibody that binds to TRGV9, wherein the antibody comprises: (i) a VH comprising a VH CDR1 having an amino acid sequence of SEQ ID NO:538, a VH CDR2 having an amino acid sequence of SEQ ID NO:720, and a VH CDR3 having an amino acid sequence of SEQ ID NO:721; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is an antibody that binds to TRGV9, wherein the antibody comprises: (i) a VH comprising a VH CDR1 having an amino acid sequence of SEQ ID NO:544, a VH CDR2 having an amino acid sequence of SEQ ID NO:545, and a VH CDR3 having an amino acid sequence of SEQ ID NO:546; and (ii) a VL comprising a VL CDR1 having an amino acid sequence of SEQ ID NO:547, a VL CDR2 having an amino acid sequence of SEQ ID NO:548, and a VL CDR3 having an amino acid sequence of SEQ ID NO:549. In another aspect, provided herein is an antibody that binds to TRGV9, wherein the antibody comprises: (i) a VH comprising a VH CDR1 having an amino acid sequence of SEQ ID NO:550, a VH CDR2 having an amino acid sequence of SEQ ID NO:551, and a VH CDR3 having an amino acid sequence of SEQ ID NO:552; and (ii) a VL comprising a VL CDR1 having an amino acid sequence of SEQ ID NO:553, a VL CDR2 having an amino acid sequence of SEQ ID NO:554, and a VL CDR3 having an amino acid sequence of SEQ ID NO:555. In some embodiments, the antibody comprises a VH having an amino acid sequence of SEQ ID NO:133. In some embodiments, the antibody comprises a VL having an amino acid sequence of SEQ ID NO:134. In some embodiments, the antibody comprises a VH having an amino acid sequence of SEQ ID NO:133, and a VL having an amino acid sequence of SEQ ID NO:134. In some embodiments, the antibody comprises a heavy chain having an amino acid sequence of SEQ ID NO:135. In some embodiments, the antibody comprises a light chain having an amino acid sequence of SEQ ID NO:136. In some embodiments, the antibody comprises a heavy chain having an amino acid sequence of SEQ ID NO:135, and a light chain having an amino acid sequence of SEQ ID NO:136. In some embodiments, the antibody comprises a VH comprising an amino acid sequence having at least 95% identity to the amino acid sequence of SEQ ID NO:133. In some embodiments, the antibody comprises a VL comprising an amino acid sequence having at least 95% identity to the amino acid sequence of SEQ ID NO:134. In some embodiments, the antibody comprises a VH comprising an amino acid sequence having at least 95% identity to the amino acid sequence of SEQ ID NO:133, and a VL comprising an amino acid sequence having at least 95% identity to the amino acid sequence of SEQ ID NO:134. In some embodiments, the antibody comprises a heavy chain comprising an amino acid sequence having at least 95% identity to the amino acid sequence of SEQ ID NO:135. In some embodiments, the antibody comprises a light chain comprising an amino acid sequence having at least 95% identity to the amino acid sequence of SEQ ID NO:136. In some embodiments, the antibody comprises a heavy chain comprising an amino acid sequence having at least 95% identity to the amino acid sequence of SEQ ID NO:135, and a light chain comprising an amino acid sequence having at least 95% identity to the amino acid sequence of SEQ ID NO:136.

In some embodiments, the anti-TRGV9 antibody is not a single chain antibody. In some embodiments, the anti-TRGV9 antibody is not a single domain antibody. In some embodiments, the anti-TRGV9 antibody is not a nanobody. In certain embodiments, the anti-TRGV9 antibody is not a VHH antibody. In certain embodiments, the anti-TRGV9 antibody is not a llama antibody.

In some embodiments, an anti-TRGV9 antibody provided herein does not comprise a VH CDR1, VH CDR2, and VH CDR3 having the amino acid sequence of SEQ ID NOs:730, 731, and 732, respectively. In some embodiments, an anti-TRGV9 antibody provided herein does not comprise a VH CDR1, VH CDR2, and VH CDR3 having the amino acid sequence of SEQ ID NOs:733, 734, and 735, respectively. In some embodiments, an anti-TRGV9 antibody provided herein does not comprise a VH CDR1, VH CDR2, and VH CDR3 having the amino acid sequence of SEQ ID NOs:736, 737, and 738, respectively. In some embodiments, an anti-TRGV9 antibody provided herein does not comprise a VH CDR1, VH CDR2, and VH CDR3 having the amino acid sequence of SEQ ID NOs:739, 740, and 741, respectively. In some embodiments, an anti-TRGV9 antibody provided herein does not comprise a VH CDR1, VH CDR2, and VH CDR3 having the amino acid sequence of SEQ ID NOs:742, 743, and 744, respectively. In some embodiments, an anti-TRGV9 antibody provided herein does not comprise a VH CDR1, VH CDR2, and VH CDR3 having the amino acid sequence of SEQ ID NOs:745, 746, and 747, respectively. In some embodiments, an anti-TRGV9 antibody provided herein does not comprise a VH CDR1, VH CDR2, and VH CDR3 having the amino acid sequence of SEQ ID NOs:748, 749, and 750, respectively. In some embodiments, an anti-TRGV9 antibody provided herein does not comprise a VH domain having the amino acid sequence of SEQ ID NO:751. In some embodiments, an anti-TRGV9 antibody provided herein does not comprise a VH domain having the amino acid sequence of SEQ ID NO:752. In some embodiments, an anti-TRGV9 antibody provided herein does not comprise a VH domain having the amino acid sequence of SEQ ID NO:753. In some embodiments, an anti-TRGV9 antibody provided herein does not comprise a VH domain having the amino acid sequence of SEQ ID NO:754. In some embodiments, an anti-TRGV9 antibody provided herein does not comprise a VH domain having the amino acid sequence of SEQ ID NO:755. In some embodiments, an anti-TRGV9 antibody provided herein does not comprise a VH domain having the amino acid sequence of SEQ ID NO:756. In some embodiments, an anti-TRGV9 antibody provided herein does not comprise a VH domain having the amino acid sequence of SEQ ID NO:757.

In another aspect, provided herein is an anti-TRGV9 antibody, comprising a VH domain comprising a VH CDR3 having the amino acid sequence of APNxGzYTbDF (SEQ ID NO:758), wherein x is Y or M, z is M or D, and b is I or L. In another aspect, provided herein is an anti-TRGV9 antibody, comprising a VH domain comprising the amino acid sequence of SEQ ID NO:758. In another aspect, provided herein is an anti-TRGV9 antibody, comprising a VH domain comprising a VH CDR1 having the amino acid sequence of GxTFzz (SEQ ID NO:761), wherein x is F, D or G, and z is S or N. In another aspect, provided herein is an anti-TRGV9 antibody, comprising a VH domain comprising the amino acid sequence of SEQ ID NO:761. In another aspect, provided herein is an anti-TRGV9 antibody, comprising a VL domain comprising a VL CDR1 having the amino acid sequence of RxSQSz (SEQ ID NO:762), wherein x is A or S, and z is V or L. In another aspect, provided herein is an anti-TRGV9 antibody, comprising a VL domain comprising the amino acid sequence of SEQ ID NO:761.

In another aspect, provided herein is an antibody that binds to TRGV9, wherein the antibody comprises: (i) a VH comprising a VH CDR1, a VH CDR2, and a VH CDR3; and (ii) a VL comprising a VL CDR1, a VL CDR2, and a VL CDR3. In some embodiments, the VH CDR1 comprises a first polar amino acid. In some embodiments, the VH CDR1 comprises a last polar uncharged amino acid. In some embodiments, the VH CDR1 comprises at least one tyrosine. In some embodiments, the VH CDR1 comprises at least 20% hydrophobic amino acids. In some embodiments, the VH CDR1 comprises at least two hydrophobic amino acids. In some embodiments, the VH CDR1 comprises at least about 40% hydrophobic amino acids. In some embodiments, the VH CDR1 comprises the VH CDR1 comprises a first polar amino acid, a last polar uncharged amino acid, at least one tyrosine, at least 20% hydrophobic amino acids, at least two hydrophobic amino acids, and at least about 40% hydrophobic amino acids. Any combination of two or more of the above-mentioned VH CDR1 structural features are also contemplated. In some embodiments, the VH CDR2 comprises a polar amino acid at residue 13. In some embodiments, the VH CDR2 comprises a hydrophobic at amino acid position 15. In some embodiments, the VH CDR2 comprises a phenylalanine (F) or leucine (L) at position 15. In some embodiments, the VH CDR2 comprises a polar amino acid at position 14. In some embodiments, the VH CDR2 comprises a lysine (K) or serine (S) at position 14. In some embodiments, the VH CDR2 comprises a hydrophobic amino acid at position 2. In some embodiments, the VH CDR2 comprises a hydrophobic amino acid at position 3. In some embodiments, the VH CDR2 comprises and a polar penultimate amino acid. In some embodiments, the VH CDR2 comprises a polar amino acid at residue 13, a hydrophobic at amino acid position 15, a phenylalanine (F) or leucine (L) at position 15, a polar amino acid at position 14, a lysine (K) or serine (S) at position 14, a hydrophobic amino acid at position 2 or 3, and a polar penultimate amino acid. Any combination of two or more of the above-mentioned VH CDR2 structural features are also contemplated. In some embodiments, the VH CDR3 does not comprise a polar charged amino acid at position 3. In some embodiments, the VH CDR3 comprises a hydrophobic or polar charged amino acid at position 7. In some embodiments, the VH CDR3 comprises a polar uncharged or hydrophobic amino acid at position 6. In some embodiments, the VH CDR3 comprises no polar charged amino acid at position 3, a hydrophobic or polar charged amino acid at position 7, and a polar uncharged or hydrophobic amino acid at position 6. Any combination of two or more of the above-mentioned VH CDR3 structural features are also contemplated. In some embodiments, the VL CDR1 comprises a polar amino acid at position 4. In some embodiments, the VL CDR1 comprises a first amino acid that is polar charged. In some embodiments, the VL CDR1 comprises a polar uncharged or hydrophobic amino acid at position 2. In some embodiments, the VL CDR1 comprises a serine at position 3. In some embodiments, the VL CDR1 comprises a polar amino acid at position 5. In some embodiments, the VL CDR1 comprises a hydrophobic amino acid at position 6. In some embodiments, the VL CDR1 comprises a polar amino acid at position 4, a first amino acid that is polar charged, a polar uncharged or hydrophobic amino acid at position 2, a serine at position 3, a polar amino acid at position 5, and a hydrophobic amino acid at position 6. Any combination of two or more of the above-mentioned VL CDR1 structural features are also contemplated. In some embodiments, the VL CDR2 comprises a polar amino acid at position 7. In some embodiments, the VL CDR2 comprises a polar charged or hydrophobic amino acid at position 6. In some embodiments, the VL CDR2 comprises a polar charged amino acid at position 3. In some embodiments, the VL CDR2 comprises a polar uncharged amino acid at position 4. In some embodiments, the VL CDR2 comprises a hydrophobic amino acid at position 2. In some embodiments, the VL CDR2 comprises a polar amino acid at position 7, a polar charged or hydrophobic amino acid at position 6, a polar charged amino acid at position 3, a polar uncharged amino acid at position 4, and a hydrophobic amino acid at position 2. Any combination of two or more of the above-mentioned VL CDR2 structural features are also contemplated. In some embodiments, the VL CDR3 comprises a hydrophobic terminal amino acid. In some embodiments, the VL CDR3 comprises a terminal tyrosine. In some embodiments, the VL CDR3 comprises a polar uncharged amino acid at position 5. In some embodiments, the VL CDR3 comprises a polar amino acid at position 2. In some embodiments, the VL CDR3 comprises a polar uncharged or hydrophobic amino acid at position 1. In some embodiments, the VL CDR3 comprises a hydrophobic amino acid at position 3. In some embodiments, the VL CDR3 comprises a hydrophylic or polar uncharged amino acid at position 6. In some embodiments, the VL CDR3 comprises no polar or hydrophobic amino acid at position 7. In some embodiments, the VL CDR3 comprises a hydrophobic terminal amino acid, a terminal tyrosine, a polar uncharged amino acid at position 5, a polar amino acid at position 2, a polar uncharged or hydrophobic amino acid at position 1, a hydrophobic amino acid at position 3, a hydrophylic or polar uncharged amino acid at position 6, and no polar or hydrophobic amino acid at position 7. Any combination of two or more of the above-mentioned VL CDR3 structural features are also contemplated. In specific embodiments, residue position numbering is according to Exemplary numbering.

In some embodiments, the anti-TRGV9 antibody is a multispecific antibody. In other embodiments, the anti-TRGV9 antibody is a bispecific antibody. In certain embodiments, the multispecific antibody comprises an antigen binding fragment of an anti-TRGV9 antibody provided herein. In some embodiments, the multispecific antibody comprises a first binding domain that binds to a first TRGV9 epitope and a second domain that binds to a second TRGV9 epitope, wherein the first TRGV9 epitope and the second TRGV9 epitope are different. In certain embodiments, the multispecific antibody further comprises a third binding domain that binds to a target that is not TRGV9.

In another aspect, provided herein is a bispecific antibody comprising: (a) a first binding domain that binds to TRGV9, and (b) a second binding domain that binds to a second target that is not TRGV9.

In some embodiments, the bispecific antibody comprises heavy chain variable regions and light chain variable region. In some embodiments, the first binding domain comprises a heavy chain variable region and a light chain variable region. In some embodiments, the second binding domain comprises a heavy chain variable region and a light chain variable region. In some embodiments, the first binding domain comprises a heavy chain variable region and a light chain variable region, and the second binding domain comprises a heavy chain variable region and a light chain variable region. In a some embodiments, the TRGV9 antibody is not a single domain antibody or nanobody.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:160, a VH CDR2 having an amino acid sequence of SEQ ID NO:161, and a VH CDR3 having an amino acid sequence of SEQ ID NO:162; and (ii) a VL comprising a VL CDR1 having an amino acid sequence of SEQ ID NO:163, a VL CDR2 having an amino acid sequence of SEQ ID NO:164, and a VL CDR3 having an amino acid sequence of SEQ ID NO:165. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:166, a VH CDR2 having an amino acid sequence of SEQ ID NO:167, and a VH CDR3 having an amino acid sequence of SEQ ID NO:168; and (ii) a VL comprising a VL CDR1 having an amino acid sequence of SEQ ID NO:169, a VL CDR2 having an amino acid sequence of SEQ ID NO:170, and a VL CDR3 having an amino acid sequence of SEQ ID NO:171. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:172, a VH CDR2 having an amino acid sequence of SEQ ID NO:173, and a VH CDR3 having an amino acid sequence of SEQ ID NO:174; and (ii) a VL comprising a VL CDR1 having an amino acid sequence of SEQ ID NO:175, a VL CDR2 having an amino acid sequence of SEQ ID NO:176, and a VL CDR3 having an amino acid sequence of SEQ ID NO:177. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:178, a VH CDR2 having an amino acid sequence of SEQ ID NO:179, and a VH CDR3 having an amino acid sequence of SEQ ID NO:180; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:178, a VH CDR2 having an amino acid sequence of SEQ ID NO:700, and a VH CDR3 having an amino acid sequence of SEQ ID NO:701; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:184, a VH CDR2 having an amino acid sequence of SEQ ID NO:185, and a VH CDR3 having an amino acid sequence of SEQ ID NO:186; and (ii) a VL comprising a VL CDR1 having an amino acid sequence of SEQ ID NO:187, a VL CDR2 having an amino acid sequence of SEQ ID NO:188, and a VL CDR3 having an amino acid sequence of SEQ ID NO:189. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:190, a VH CDR2 having an amino acid sequence of SEQ ID NO:191, and a VH CDR3 having an amino acid sequence of SEQ ID NO:192; and (ii) a VL comprising a VL CDR1 having an amino acid sequence of SEQ ID NO:193, a VL CDR2 having an amino acid sequence of SEQ ID NO:194, and a VL CDR3 having an amino acid sequence of SEQ ID NO:195. In some embodiments, the first binding domain comprises a VH having an amino acid sequence of SEQ ID NO:7. In some embodiments, the first binding domain comprises a VL having an amino acid sequence of SEQ ID NO:8. In some embodiments, the first binding domain comprises a VH having an amino acid sequence of SEQ ID NO:7, and a VL having an amino acid sequence of SEQ ID NO:8. In some embodiments, the first binding domain comprises a heavy chain having an amino acid sequence of SEQ ID NO:23. In some embodiments, the first binding domain comprises a light chain having an amino acid sequence of SEQ ID NO:24. In some embodiments, the first binding domain comprises a heavy chain having an amino acid sequence of SEQ ID NO:23, and a light chain having an amino acid sequence of SEQ ID NO:24. In some embodiments, the first binding domain comprises an amino acid sequence of SEQ ID NO:17. In some embodiments, the first binding domain comprises a heavy chain having an amino acid sequence of SEQ ID NO:69. In some embodiments, the first binding domain comprises a light chain having an amino acid sequence of SEQ ID NO:24. In some embodiments, the first binding domain comprises a heavy chain having an amino acid sequence of SEQ ID NO:69, and a light chain having an amino acid sequence of SEQ ID NO:24. In some embodiments, the first binding domain comprises a VH comprising an amino acid sequence having at least 95% identity to the amino acid sequence of SEQ ID NO:7. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:7, and a VL comprising an amino acid sequence having at least 95% identity to the amino acid sequence of SEQ ID NO:8. In some embodiments, the first binding domain comprises a heavy chain comprising an amino acid sequence having at least 95% identity to the amino acid sequence of SEQ ID NO:23. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:23, and a light chain comprising an amino acid sequence having at least 95% identity to the amino acid sequence of SEQ ID NO:24. In some embodiments, the first binding domain comprises an amino acid sequence of SEQ ID NO:17. In some embodiments, the first binding domain comprises a heavy chain comprising an amino acid sequence having at least 95% identity to the amino acid sequence of SEQ ID NO:69. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:69, and a light chain comprising an amino acid sequence having at least 95% identity to the amino acid sequence of SEQ ID NO:24.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:196, a VH CDR2 having an amino acid sequence of SEQ ID NO:197, and a VH CDR3 having an amino acid sequence of SEQ ID NO:198; and (ii) a VL comprising a VL CDR1 having an amino acid sequence of SEQ ID NO:199, a VL CDR2 having an amino acid sequence of SEQ ID NO:200, and a VL CDR3 having an amino acid sequence of SEQ ID NO:201. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:202, a VH CDR2 having an amino acid sequence of SEQ ID NO:203, and a VH CDR3 having an amino acid sequence of SEQ ID NO:204; and (ii) a VL comprising a VL CDR1 having an amino acid sequence of SEQ ID NO:205, a VL CDR2 having an amino acid sequence of SEQ ID NO:206, and a VL CDR3 having an amino acid sequence of SEQ ID NO:207. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:208, a VH CDR2 having an amino acid sequence of SEQ ID NO:209, and a VH CDR3 having an amino acid sequence of SEQ ID NO:210; and (ii) a VL comprising a VL CDR1 having an amino acid sequence of SEQ ID NO:211, a VL CDR2 having an amino acid sequence of SEQ ID NO:212, and a VL CDR3 having an amino acid sequence of SEQ ID NO:213. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:214, a VH CDR2 having an amino acid sequence of SEQ ID NO:215, and a VH CDR3 having an amino acid sequence of SEQ ID NO:216; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:214, a VH CDR2 having an amino acid sequence of SEQ ID NO:702, and a VH CDR3 having an amino acid sequence of SEQ ID NO:703; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:220, a VH CDR2 having an amino acid sequence of SEQ ID NO:221, and a VH CDR3 having an amino acid sequence of SEQ ID NO:222; and (ii) a VL comprising a VL CDR1 having an amino acid sequence of SEQ ID NO:223, a VL CDR2 having an amino acid sequence of SEQ ID NO:224, and a VL CDR3 having an amino acid sequence of SEQ ID NO:225. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:226, a VH CDR2 having an amino acid sequence of SEQ ID NO:227, and a VH CDR3 having an amino acid sequence of SEQ ID NO:228; and (ii) a VL comprising a VL CDR1 having an amino acid sequence of SEQ ID NO:229, a VL CDR2 having an amino acid sequence of SEQ ID NO:230, and a VL CDR3 having an amino acid sequence of SEQ ID NO:231. In some embodiments, the first binding domain comprises a VH having an amino acid sequence of SEQ ID NO:34. In some embodiments, the first binding domain comprises a VL having an amino acid sequence of SEQ ID NO:8. In some embodiments, the first binding domain comprises a VH having an amino acid sequence of SEQ ID NO:34, and a VL having an amino acid sequence of SEQ ID NO:8. In some embodiments, the first binding domain comprises a VH comprising an amino acid sequence having at least 95% identity to the amino acid sequence of SEQ ID NO:34. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:34, and a VL comprising an amino acid sequence having at least 95% identity to the amino acid sequence of SEQ ID NO:8.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:232, a VH CDR2 having an amino acid sequence of SEQ ID NO:233, and a VH CDR3 having an amino acid sequence of SEQ ID NO:234; and (ii) a VL comprising a VL CDR1 having an amino acid sequence of SEQ ID NO:235, a VL CDR2 having an amino acid sequence of SEQ ID NO:236, and a VL CDR3 having an amino acid sequence of SEQ ID NO:237. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:238, a VH CDR2 having an amino acid sequence of SEQ ID NO:239, and a VH CDR3 having an amino acid sequence of SEQ ID NO:240; and (ii) a VL comprising a VL CDR1 having an amino acid sequence of SEQ ID NO:241, a VL CDR2 having an amino acid sequence of SEQ ID NO:242, and a VL CDR3 having an amino acid sequence of SEQ ID NO:243. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:244, a VH CDR2 having an amino acid sequence of SEQ ID NO:245, and a VH CDR3 having an amino acid sequence of SEQ ID NO:246; and (ii) a VL comprising a VL CDR1 having an amino acid sequence of SEQ ID NO:247, a VL CDR2 having an amino acid sequence of SEQ ID NO:248, and a VL CDR3 having an amino acid sequence of SEQ ID NO:249. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:250, a VH CDR2 having an amino acid sequence of SEQ ID NO:251, and a VH CDR3 having an amino acid sequence of SEQ ID NO:252; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:250, a VH CDR2 having an amino acid sequence of SEQ ID NO:704, and a VH CDR3 having an amino acid sequence of SEQ ID NO:705; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:256, a VH CDR2 having an amino acid sequence of SEQ ID NO:257, and a VH CDR3 having an amino acid sequence of SEQ ID NO:258; and (ii) a VL comprising a VL CDR1 having an amino acid sequence of SEQ ID NO:259, a VL CDR2 having an amino acid sequence of SEQ ID NO:260, and a VL CDR3 having an amino acid sequence of SEQ ID NO:261. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:262, a VH CDR2 having an amino acid sequence of SEQ ID NO:263, and a VH CDR3 having an amino acid sequence of SEQ ID NO:264; and (ii) a VL comprising a VL CDR1 having an amino acid sequence of SEQ ID NO:265, a VL CDR2 having an amino acid sequence of SEQ ID NO:266, and a VL CDR3 having an amino acid sequence of SEQ ID NO:267. In some embodiments, the first binding domain comprises a VH having an amino acid sequence of SEQ ID NO:35. In some embodiments, the first binding domain comprises a VL having an amino acid sequence of SEQ ID NO:8. In some embodiments, the first binding domain comprises a VH having an amino acid sequence of SEQ ID NO:35, and a VL having an amino acid sequence of SEQ ID NO:8. In some embodiments, the first binding domain comprises a VH comprising an amino acid sequence having at least 95% identity to the amino acid sequence of SEQ ID NO:35. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:35, and a VL comprising an amino acid sequence having at least 95% identity to the amino acid sequence of SEQ ID NO:8.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:268, a VH CDR2 having an amino acid sequence of SEQ ID NO:269, and a VH CDR3 having an amino acid sequence of SEQ ID NO:270; and (ii) a VL comprising a VL CDR1 having an amino acid sequence of SEQ ID NO:271, a VL CDR2 having an amino acid sequence of SEQ ID NO:272, and a VL CDR3 having an amino acid sequence of SEQ ID NO:273. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:274, a VH CDR2 having an amino acid sequence of SEQ ID NO:275, and a VH CDR3 having an amino acid sequence of SEQ ID NO:276; and (ii) a VL comprising a VL CDR1 having an amino acid sequence of SEQ ID NO:277, a VL CDR2 having an amino acid sequence of SEQ ID NO:278, and a VL CDR3 having an amino acid sequence of SEQ ID NO:279. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:280, a VH CDR2 having an amino acid sequence of SEQ ID NO:281, and a VH CDR3 having an amino acid sequence of SEQ ID NO:282; and (ii) a VL comprising a VL CDR1 having an amino acid sequence of SEQ ID NO:283, a VL CDR2 having an amino acid sequence of SEQ ID NO:284, and a VL CDR3 having an amino acid sequence of SEQ ID NO:285. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:286, a VH CDR2 having an amino acid sequence of SEQ ID NO:287, and a VH CDR3 having an amino acid sequence of SEQ ID NO:288; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:286, a VH CDR2 having an amino acid sequence of SEQ ID NO:706, and a VH CDR3 having an amino acid sequence of SEQ ID NO:707; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:292, a VH CDR2 having an amino acid sequence of SEQ ID NO:293, and a VH CDR3 having an amino acid sequence of SEQ ID NO:294; and (ii) a VL comprising a VL CDR1 having an amino acid sequence of SEQ ID NO:295, a VL CDR2 having an amino acid sequence of SEQ ID NO:296, and a VL CDR3 having an amino acid sequence of SEQ ID NO:297. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:298, a VH CDR2 having an amino acid sequence of SEQ ID NO:299, and a VH CDR3 having an amino acid sequence of SEQ ID NO:300; and (ii) a VL comprising a VL CDR1 having an amino acid sequence of SEQ ID NO:301, a VL CDR2 having an amino acid sequence of SEQ ID NO:302, and a VL CDR3 having an amino acid sequence of SEQ ID NO:303. In some embodiments, the first binding domain comprises a VH having an amino acid sequence of SEQ ID NO:36. In some embodiments, the first binding domain comprises a VL having an amino acid sequence of SEQ ID NO:8. In some embodiments, the first binding domain comprises a VH having an amino acid sequence of SEQ ID NO:36, and a VL having an amino acid sequence of SEQ ID NO:8. In some embodiments, the first binding domain comprises a VH comprising an amino acid sequence having at least 95% identity to the amino acid sequence of SEQ ID NO:36. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:36, and a VL comprising an amino acid sequence having at least 95% identity to the amino acid sequence of SEQ ID NO:8.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:304, a VH CDR2 having an amino acid sequence of SEQ ID NO:305, and a VH CDR3 having an amino acid sequence of SEQ ID NO:306; and (ii) a VL comprising a VL CDR1 having an amino acid sequence of SEQ ID NO:307, a VL CDR2 having an amino acid sequence of SEQ ID NO:308, and a VL CDR3 having an amino acid sequence of SEQ ID NO:309. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:310, a VH CDR2 having an amino acid sequence of SEQ ID NO:311, and a VH CDR3 having an amino acid sequence of SEQ ID NO:312; and (ii) a VL comprising a VL CDR1 having an amino acid sequence of SEQ ID NO:313, a VL CDR2 having an amino acid sequence of SEQ ID NO:314, and a VL CDR3 having an amino acid sequence of SEQ ID NO:315. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:316, a VH CDR2 having an amino acid sequence of SEQ ID NO:317, and a VH CDR3 having an amino acid sequence of SEQ ID NO:318; and (ii) a VL comprising a VL CDR1 having an amino acid sequence of SEQ ID NO:319, a VL CDR2 having an amino acid sequence of SEQ ID NO:320, and a VL CDR3 having an amino acid sequence of SEQ ID NO:321. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:322, a VH CDR2 having an amino acid sequence of SEQ ID NO:323, and a VH CDR3 having an amino acid sequence of SEQ ID NO:324; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:322, a VH CDR2 having an amino acid sequence of SEQ ID NO:708, and a VH CDR3 having an amino acid sequence of SEQ ID NO:709; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:328, a VH CDR2 having an amino acid sequence of SEQ ID NO:329, and a VH CDR3 having an amino acid sequence of SEQ ID NO:330; and (ii) a VL comprising a VL CDR1 having an amino acid sequence of SEQ ID NO:331, a VL CDR2 having an amino acid sequence of SEQ ID NO:332, and a VL CDR3 having an amino acid sequence of SEQ ID NO:333. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:334, a VH CDR2 having an amino acid sequence of SEQ ID NO:335, and a VH CDR3 having an amino acid sequence of SEQ ID NO:336; and (ii) a VL comprising a VL CDR1 having an amino acid sequence of SEQ ID NO:337, a VL CDR2 having an amino acid sequence of SEQ ID NO:338, and a VL CDR3 having an amino acid sequence of SEQ ID NO:339. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:340, a VH CDR2 having an amino acid sequence of SEQ ID NO:341, and a VH CDR3 having an amino acid sequence of SEQ ID NO:342; and (ii) a VL comprising a VL CDR1 having an amino acid sequence of SEQ ID NO:343, a VL CDR2 having an amino acid sequence of SEQ ID NO:344, and a VL CDR3 having an amino acid sequence of SEQ ID NO:345. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:346, a VH CDR2 having an amino acid sequence of SEQ ID NO:347, and a VH CDR3 having an amino acid sequence of SEQ ID NO:348; and (ii) a VL comprising a VL CDR1 having an amino acid sequence of SEQ ID NO:349, a VL CDR2 having an amino acid sequence of SEQ ID NO:350, and a VL CDR3 having an amino acid sequence of SEQ ID NO:351. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:352, a VH CDR2 having an amino acid sequence of SEQ ID NO:353, and a VH CDR3 having an amino acid sequence of SEQ ID NO:354; and (ii) a VL comprising a VL CDR1 having an amino acid sequence of SEQ ID NO:355, a VL CDR2 having an amino acid sequence of SEQ ID NO:356, and a VL CDR3 having an amino acid sequence of SEQ ID NO:357. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:358, a VH CDR2 having an amino acid sequence of SEQ ID NO:359, and a VH CDR3 having an amino acid sequence of SEQ ID NO:360; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:358, a VH CDR2 having an amino acid sequence of SEQ ID NO:710, and a VH CDR3 having an amino acid sequence of SEQ ID NO:711; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:364, a VH CDR2 having an amino acid sequence of SEQ ID NO:365, and a VH CDR3 having an amino acid sequence of SEQ ID NO:366; and (ii) a VL comprising a VL CDR1 having an amino acid sequence of SEQ ID NO:367, a VL CDR2 having an amino acid sequence of SEQ ID NO:368, and a VL CDR3 having an amino acid sequence of SEQ ID NO:369. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:370, a VH CDR2 having an amino acid sequence of SEQ ID NO:371, and a VH CDR3 having an amino acid sequence of SEQ ID NO:372; and (ii) a VL comprising a VL CDR1 having an amino acid sequence of SEQ ID NO:373, a VL CDR2 having an amino acid sequence of SEQ ID NO:374, and a VL CDR3 having an amino acid sequence of SEQ ID NO:375. In some embodiments, the first binding domain comprises a VH having an amino acid sequence of SEQ ID NO:65. In some embodiments, the first binding domain comprises a VL having an amino acid sequence of SEQ ID NO:66. In some embodiments, the first binding domain comprises a VH having an amino acid sequence of SEQ ID NO:65, and a VL having an amino acid sequence of SEQ ID NO:66. In some embodiments, the first binding domain comprises a VH having an amino acid sequence of SEQ ID NO:67. In some embodiments, the first binding domain comprises a VL having an amino acid sequence of SEQ ID NO:68. In some embodiments, the first binding domain a VH having an amino acid sequence of SEQ ID NO:67, and a VL having an amino acid sequence of SEQ ID NO:68. In some embodiments, the first binding domain comprises a heavy chain having an amino acid sequence of SEQ ID NO:71. In some embodiments, the first binding domain comprises a light chain having an amino acid sequence of SEQ ID NO:72. In some embodiments, the first binding domain comprises a heavy chain having an amino acid sequence of SEQ ID NO:71, and a light chain having an amino acid sequence of SEQ ID NO:72. In some embodiments, the first binding domain comprises an amino acid sequence of SEQ ID NO:70. In some embodiments, the first binding domain comprises a heavy chain having an amino acid sequence of SEQ ID NO:74. In some embodiments, the first binding domain comprises a light chain having an amino acid sequence of SEQ ID NO:75. In some embodiments, the first binding domain comprises a heavy chain having an amino acid sequence of SEQ ID NO:74, and a light chain having an amino acid sequence of SEQ ID NO:75. In some embodiments, the first binding domain comprises an amino acid sequence of SEQ ID NO:73. In some embodiments, the first binding domain comprises a VH comprising an amino acid sequence having at least 95% identity to the amino acid sequence of SEQ ID NO:65. In some embodiments, the first binding domain comprises a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:65, and a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:67. In some embodiments, the first binding domain comprises a VL comprising an amino acid sequence having at least 95% identity to the amino acid sequence of SEQ ID NO:68. In some embodiments, the first binding domain a VH comprising an amino acid sequence having at least 95% identity to the amino acid sequence of SEQ ID NO:67, and a VL comprising an amino acid sequence having at least 95% identity to the amino acid sequence of SEQ ID NO:68. In some embodiments, the first binding domain comprises a heavy chain comprising an amino acid sequence having at least 95% identity to the amino acid sequence of SEQ ID NO:71. In some embodiments, the first binding domain comprises a light chain comprising an amino acid sequence having at least 95% identity to the amino acid sequence of SEQ ID NO:72. In some embodiments, the first binding domain comprises a heavy chain comprising an amino acid sequence having at least 95% identity to the amino acid sequence of SEQ ID NO:71, and a light chain comprising an amino acid sequence having at least 95% identity to the amino acid sequence of SEQ ID NO:72. In some embodiments, the first binding domain comprises an amino acid sequence having at least 95% identity to an amino acid sequence of SEQ ID NO:70. In some embodiments, the first binding domain comprises a heavy chain comprising an amino acid sequence having at least 95% identity to the amino acid sequence of SEQ ID NO:74. In some embodiments, the first binding domain comprises a light chain comprising an amino acid sequence having at least 95% identity to the amino acid sequence of SEQ ID NO:75. In some embodiments, the first binding domain comprises a heavy chain comprising an amino acid sequence having at least 95% identity to the amino acid sequence of SEQ ID NO:74, and a light chain comprising an amino acid sequence having at least 95% identity to the amino acid sequence of SEQ ID NO:75. In some embodiments, the first binding domain comprises an amino acid sequence having at least 95% identity to an amino acid sequence of SEQ ID NO:73.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:376, a VH CDR2 having an amino acid sequence of SEQ ID NO:377, and a VH CDR3 having an amino acid sequence of SEQ ID NO:378; and (ii) a VL comprising a VL CDR1 having an amino acid sequence of SEQ ID NO:379, a VL CDR2 having an amino acid sequence of SEQ ID NO:380, and a VL CDR3 having an amino acid sequence of SEQ ID NO:381. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:382, a VH CDR2 having an amino acid sequence of SEQ ID NO:383, and a VH CDR3 having an amino acid sequence of SEQ ID NO:384; and (ii) a VL comprising a VL CDR1 having an amino acid sequence of SEQ ID NO:385, a VL CDR2 having an amino acid sequence of SEQ ID NO:386, and a VL CDR3 having an amino acid sequence of SEQ ID NO:387. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:388, a VH CDR2 having an amino acid sequence of SEQ ID NO:389, and a VH CDR3 having an amino acid sequence of SEQ ID NO:390; and (ii) a VL comprising a VL CDR1 having an amino acid sequence of SEQ ID NO:391, a VL CDR2 having an amino acid sequence of SEQ ID NO:392, and a VL CDR3 having an amino acid sequence of SEQ ID NO:393. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:394, a VH CDR2 having an amino acid sequence of SEQ ID NO:395, and a VH CDR3 having an amino acid sequence of SEQ ID NO:396; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:394, a VH CDR2 having an amino acid sequence of SEQ ID NO:712, and a VH CDR3 having an amino acid sequence of SEQ ID NO:713; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:400, a VH CDR2 having an amino acid sequence of SEQ ID NO:401, and a VH CDR3 having an amino acid sequence of SEQ ID NO:402; and (ii) a VL comprising a VL CDR1 having an amino acid sequence of SEQ ID NO:403, a VL CDR2 having an amino acid sequence of SEQ ID NO:404, and a VL CDR3 having an amino acid sequence of SEQ ID NO:405. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:406, a VH CDR2 having an amino acid sequence of SEQ ID NO:407, and a VH CDR3 having an amino acid sequence of SEQ ID NO:408; and (ii) a VL comprising a VL CDR1 having an amino acid sequence of SEQ ID NO:409, a VL CDR2 having an amino acid sequence of SEQ ID NO:410, and a VL CDR3 having an amino acid sequence of SEQ ID NO:411. In some embodiments, the first binding domain comprises a VH having an amino acid sequence of SEQ ID NO:95. In some embodiments, the first binding domain comprises a VL having an amino acid sequence of SEQ ID NO:96. In some embodiments, the first binding domain comprises a VH having an amino acid sequence of SEQ ID NO:95, and a VL having an amino acid sequence of SEQ ID NO:96. In some embodiments, the first binding domain comprises an amino acid sequence of SEQ ID NO:97. In some embodiments, the first binding domain comprises a VH comprising an amino acid sequence having at least 95% identity to the amino acid sequence of SEQ ID NO:95. In some embodiments, the first binding domain comprises a VL comprising an amino acid sequence having at least 95% identity to the amino acid sequence of SEQ ID NO:96. In some embodiments, the first binding domain comprises a VH comprising an amino acid sequence having at least 95% identity to the amino acid sequence of SEQ ID NO:95, and a VL comprising an amino acid sequence having at least 95% identity to the amino acid sequence of SEQ ID NO:96. In some embodiments, the first binding domain comprises an amino acid sequence having at least 95% identity to an amino acid sequence of SEQ ID NO:97.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:412, a VH CDR2 having an amino acid sequence of SEQ ID NO:413, and a VH CDR3 having an amino acid sequence of SEQ ID NO:414; and (ii) a VL comprising a VL CDR1 having an amino acid sequence of SEQ ID NO:415, a VL CDR2 having an amino acid sequence of SEQ ID NO:416, and a VL CDR3 having an amino acid sequence of SEQ ID NO:417. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:418, a VH CDR2 having an amino acid sequence of SEQ ID NO:419, and a VH CDR3 having an amino acid sequence of SEQ ID NO:420; and (ii) a VL comprising a VL CDR1 having an amino acid sequence of SEQ ID NO:421, a VL CDR2 having an amino acid sequence of SEQ ID NO:422, and a VL CDR3 having an amino acid sequence of SEQ ID NO:423. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:424, a VH CDR2 having an amino acid sequence of SEQ ID NO:425, and a VH CDR3 having an amino acid sequence of SEQ ID NO:426; and (ii) a VL comprising a VL CDR1 having an amino acid sequence of SEQ ID NO:427, a VL CDR2 having an amino acid sequence of SEQ ID NO:428, and a VL CDR3 having an amino acid sequence of SEQ ID NO:429. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:430, a VH CDR2 having an amino acid sequence of SEQ ID NO:431, and a VH CDR3 having an amino acid sequence of SEQ ID NO:432; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:430, a VH CDR2 having an amino acid sequence of SEQ ID NO:714, and a VH CDR3 having an amino acid sequence of SEQ ID NO:715; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:436, a VH CDR2 having an amino acid sequence of SEQ ID NO:437, and a VH CDR3 having an amino acid sequence of SEQ ID NO:438; and (ii) a VL comprising a VL CDR1 having an amino acid sequence of SEQ ID NO:439, a VL CDR2 having an amino acid sequence of SEQ ID NO:440, and a VL CDR3 having an amino acid sequence of SEQ ID NO:441. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:442, a VH CDR2 having an amino acid sequence of SEQ ID NO:443, and a VH CDR3 having an amino acid sequence of SEQ ID NO:444; and (ii) a VL comprising a VL CDR1 having an amino acid sequence of SEQ ID NO:445, a VL CDR2 having an amino acid sequence of SEQ ID NO:446, and a VL CDR3 having an amino acid sequence of SEQ ID NO:447. In some embodiments, the first binding domain comprises a VH having an amino acid sequence of SEQ ID NO:104. In some embodiments, the first binding domain comprises a VL having an amino acid sequence of SEQ ID NO:105. In some embodiments, the first binding domain comprises a VH having an amino acid sequence of SEQ ID NO:104, and a VL having an amino acid sequence of SEQ ID NO:105. In some embodiments, the first binding domain comprises an amino acid sequence of SEQ ID NO:106. In some embodiments, the first binding domain comprises a VH comprising an amino acid sequence having at least 95% identity to the amino acid sequence of SEQ ID NO:104. In some embodiments, the first binding domain comprises a VL comprising an amino acid sequence having at least 95% identity to the amino acid sequence of SEQ ID NO:105. In some embodiments, the first binding domain comprises a VH comprising an amino acid sequence having at least 95% identity to the amino acid sequence of SEQ ID NO:104, and a VL comprising an amino acid sequence having at least 95% identity to the amino acid sequence of SEQ ID NO:105. In some embodiments, the first binding domain comprises an amino acid sequence having at least 95% identity to an amino acid sequence of SEQ ID NO:106.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:448, a VH CDR2 having an amino acid sequence of SEQ ID NO:449, and a VH CDR3 having an amino acid sequence of SEQ ID NO:450; and (ii) a VL comprising a VL CDR1 having an amino acid sequence of SEQ ID NO:451, a VL CDR2 having an amino acid sequence of SEQ ID NO:452, and a VL CDR3 having an amino acid sequence of SEQ ID NO:453. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:454, a VH CDR2 having an amino acid sequence of SEQ ID NO:455, and a VH CDR3 having an amino acid sequence of SEQ ID NO:456; and (ii) a VL comprising a VL CDR1 having an amino acid sequence of SEQ ID NO:457, a VL CDR2 having an amino acid sequence of SEQ ID NO:458, and a VL CDR3 having an amino acid sequence of SEQ ID NO:459. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:460, a VH CDR2 having an amino acid sequence of SEQ ID NO:461, and a VH CDR3 having an amino acid sequence of SEQ ID NO:462; and (ii) a VL comprising a VL CDR1 having an amino acid sequence of SEQ ID NO:463, a VL CDR2 having an amino acid sequence of SEQ ID NO:464, and a VL CDR3 having an amino acid sequence of SEQ ID NO:465. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:466, a VH CDR2 having an amino acid sequence of SEQ ID NO:467, and a VH CDR3 having an amino acid sequence of SEQ ID NO:468; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:466, a VH CDR2 having an amino acid sequence of SEQ ID NO:716, and a VH CDR3 having an amino acid sequence of SEQ ID NO:717; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:472, a VH CDR2 having an amino acid sequence of SEQ ID NO:473, and a VH CDR3 having an amino acid sequence of SEQ ID NO:474; and (ii) a VL comprising a VL CDR1 having an amino acid sequence of SEQ ID NO:475, a VL CDR2 having an amino acid sequence of SEQ ID NO:476, and a VL CDR3 having an amino acid sequence of SEQ ID NO:477. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:478, a VH CDR2 having an amino acid sequence of SEQ ID NO:479, and a VH CDR3 having an amino acid sequence of SEQ ID NO:480; and (ii) a VL comprising a VL CDR1 having an amino acid sequence of SEQ ID NO:481, a VL CDR2 having an amino acid sequence of SEQ ID NO:482, and a VL CDR3 having an amino acid sequence of SEQ ID NO:483. In some embodiments, the first binding domain comprises a VH having an amino acid sequence of SEQ ID NO:113. In some embodiments, the first binding domain comprises a VL having an amino acid sequence of SEQ ID NO:114. In some embodiments, the first binding domain comprises a VH having an amino acid sequence of SEQ ID NO:113, and a VL having an amino acid sequence of SEQ ID NO:114. In some embodiments, the first binding domain comprises a heavy chain having an amino acid sequence of SEQ ID NO:115. In some embodiments, the first binding domain comprises a light chain having an amino acid sequence of SEQ ID NO:116. In some embodiments, the first binding domain comprises a heavy chain having an amino acid sequence of SEQ ID NO:115, and a light chain having an amino acid sequence of SEQ ID NO:116. In some embodiments, the first binding domain comprises a VH comprising an amino acid sequence having at least 95% identity to the amino acid sequence of SEQ ID NO:113. In some embodiments, the first binding domain comprises a VL comprising an amino acid sequence having at least 95% identity to the amino acid sequence of SEQ ID NO:114. In some embodiments, the first binding domain comprises a VH comprising an amino acid sequence having at least 95% identity to the amino acid sequence of SEQ ID NO:113, and a VL comprising an amino acid sequence having at least 95% identity to the amino acid sequence of SEQ ID NO:114. In some embodiments, the first binding domain comprises a heavy chain comprising an amino acid sequence having at least 95% identity to the amino acid sequence of SEQ ID NO:115. In some embodiments, the first binding domain comprises a light chain comprising an amino acid sequence having at least 95% identity to the amino acid sequence of SEQ ID NO:116. In some embodiments, the first binding domain comprises a heavy chain comprising an amino acid sequence having at least 95% identity to the amino acid sequence of SEQ ID NO:115, and a light chain comprising an amino acid sequence having at least 95% identity to the amino acid sequence of SEQ ID NO:116.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:484, a VH CDR2 having an amino acid sequence of SEQ ID NO:485, and a VH CDR3 having an amino acid sequence of SEQ ID NO:486; and (ii) a VL comprising a VL CDR1 having an amino acid sequence of SEQ ID NO:487, a VL CDR2 having an amino acid sequence of SEQ ID NO:488, and a VL CDR3 having an amino acid sequence of SEQ ID NO:489. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:490, a VH CDR2 having an amino acid sequence of SEQ ID NO:491, and a VH CDR3 having an amino acid sequence of SEQ ID NO:492; and (ii) a VL comprising a VL CDR1 having an amino acid sequence of SEQ ID NO:493, a VL CDR2 having an amino acid sequence of SEQ ID NO:494, and a VL CDR3 having an amino acid sequence of SEQ ID NO:495. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:496, a VH CDR2 having an amino acid sequence of SEQ ID NO:497, and a VH CDR3 having an amino acid sequence of SEQ ID NO:498; and (ii) a VL comprising a VL CDR1 having an amino acid sequence of SEQ ID NO:499, a VL CDR2 having an amino acid sequence of SEQ ID NO:500, and a VL CDR3 having an amino acid sequence of SEQ ID NO:501. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:502, a VH CDR2 having an amino acid sequence of SEQ ID NO:503, and a VH CDR3 having an amino acid sequence of SEQ ID NO:504; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:502, a VH CDR2 having an amino acid sequence of SEQ ID NO:718, and a VH CDR3 having an amino acid sequence of SEQ ID NO:719; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:508, a VH CDR2 having an amino acid sequence of SEQ ID NO:509, and a VH CDR3 having an amino acid sequence of SEQ ID NO:510; and (ii) a VL comprising a VL CDR1 having an amino acid sequence of SEQ ID NO:511, a VL CDR2 having an amino acid sequence of SEQ ID NO:512, and a VL CDR3 having an amino acid sequence of SEQ ID NO:513. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:514, a VH CDR2 having an amino acid sequence of SEQ ID NO:515, and a VH CDR3 having an amino acid sequence of SEQ ID NO:516; and (ii) a VL comprising a VL CDR1 having an amino acid sequence of SEQ ID NO:517, a VL CDR2 having an amino acid sequence of SEQ ID NO:518, and a VL CDR3 having an amino acid sequence of SEQ ID NO:519. In some embodiments, the first binding domain comprises a VH having an amino acid sequence of SEQ ID NO:123. In some embodiments, the first binding domain comprises a VL having an amino acid sequence of SEQ ID NO:124. In some embodiments, the first binding domain comprises a VH having an amino acid sequence of SEQ ID NO:123, and a VL having an amino acid sequence of SEQ ID NO:124. In some embodiments, the first binding domain comprises a heavy chain having an amino acid sequence of SEQ ID NO:125. In some embodiments, the first binding domain comprises a light chain having an amino acid sequence of SEQ ID NO:126. In some embodiments, the first binding domain comprises a heavy chain having an amino acid sequence of SEQ ID NO:125, and a light chain having an amino acid sequence of SEQ ID NO:126. In some embodiments, the first binding domain comprises a VH comprising an amino acid sequence having at least 95% identity to the amino acid sequence of SEQ ID NO:123. In some embodiments, the first binding domain comprises a VL comprising an amino acid sequence having at least 95% identity to the amino acid sequence of SEQ ID NO:124. In some embodiments, the first binding domain comprises a VH comprising an amino acid sequence having at least 95% identity to the amino acid sequence of SEQ ID NO:123, and a VL comprising an amino acid sequence having at least 95% identity to the amino acid sequence of SEQ ID NO:124. In some embodiments, the first binding domain comprises a heavy chain comprising an amino acid sequence having at least 95% identity to the amino acid sequence of SEQ ID NO:125. In some embodiments, the first binding domain comprises a light chain comprising an amino acid sequence having at least 95% identity to the amino acid sequence of SEQ ID NO:126. In some embodiments, the first binding domain comprises a heavy chain comprising an amino acid sequence having at least 95% identity to the amino acid sequence of SEQ ID NO:125, and a light chain comprising an amino acid sequence having at least 95% identity to the amino acid sequence of SEQ ID NO:126.

In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:520, a VH CDR2 having an amino acid sequence of SEQ ID NO:521, and a VH CDR3 having an amino acid sequence of SEQ ID NO:522; and (ii) a VL comprising a VL CDR1 having an amino acid sequence of SEQ ID NO:523, a VL CDR2 having an amino acid sequence of SEQ ID NO:524, and a VL CDR3 having an amino acid sequence of SEQ ID NO:525. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:526, a VH CDR2 having an amino acid sequence of SEQ ID NO:527, and a VH CDR3 having an amino acid sequence of SEQ ID NO:528; and (ii) a VL comprising a VL CDR1 having an amino acid sequence of SEQ ID NO:529, a VL CDR2 having an amino acid sequence of SEQ ID NO:530, and a VL CDR3 having an amino acid sequence of SEQ ID NO:531. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:532, a VH CDR2 having an amino acid sequence of SEQ ID NO:533, and a VH CDR3 having an amino acid sequence of SEQ ID NO:534; and (ii) a VL comprising a VL CDR1 having an amino acid sequence of SEQ ID NO:535, a VL CDR2 having an amino acid sequence of SEQ ID NO:536, and a VL CDR3 having an amino acid sequence of SEQ ID NO:537. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:538, a VH CDR2 having an amino acid sequence of SEQ ID NO:539, and a VH CDR3 having an amino acid sequence of SEQ ID NO:540; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:538, a VH CDR2 having an amino acid sequence of SEQ ID NO:720, and a VH CDR3 having an amino acid sequence of SEQ ID NO:721; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:544, a VH CDR2 having an amino acid sequence of SEQ ID NO:545, and a VH CDR3 having an amino acid sequence of SEQ ID NO:546; and (ii) a VL comprising a VL CDR1 having an amino acid sequence of SEQ ID NO:547, a VL CDR2 having an amino acid sequence of SEQ ID NO:548, and a VL CDR3 having an amino acid sequence of SEQ ID NO:549. In another aspect, provided herein is a bispecific antibody comprising: (a) a first binding domain that binds to TRGV9, and (b) a second binding domain that binds to a second target that is not TRGV9, wherein the first binding domain comprises: (i) a VH comprising a VH CDR1 having an amino acid sequence of SEQ ID NO:550, a VH CDR2 having an amino acid sequence of SEQ ID NO:551, and a VH CDR3 having an amino acid sequence of SEQ ID NO:552; and (ii) a VL comprising a VL CDR1 having an amino acid sequence of SEQ ID NO:553, a VL CDR2 having an amino acid sequence of SEQ ID NO:554, and a VL CDR3 having an amino acid sequence of SEQ ID NO:555. In some embodiments, the first binding domain comprises a VH having an amino acid sequence of SEQ ID NO:133. In some embodiments, the first binding domain comprises a VL having an amino acid sequence of SEQ ID NO:134. In some embodiments, the first binding domain comprises a VH having an amino acid sequence of SEQ ID NO:133, and a VL having an amino acid sequence of SEQ ID NO:134. In some embodiments, the first binding domain comprises a heavy chain having an amino acid sequence of SEQ ID NO:135. In some embodiments, the first binding domain comprises a light chain having an amino acid sequence of SEQ ID NO:136. In some embodiments, the first binding domain comprises a heavy chain having an amino acid sequence of SEQ ID NO:135, and a light chain having an amino acid sequence of SEQ ID NO:136. In some embodiments, the first binding domain comprises a VH comprising an amino acid sequence having at least 95% identity to the amino acid sequence of SEQ ID NO:133. In some embodiments, the first binding domain comprises a VL comprising an amino acid sequence having at least 95% identity to the amino acid sequence of SEQ ID NO:134. In some embodiments, the first binding domain comprises a VH comprising an amino acid sequence having at least 95% identity to the amino acid sequence of SEQ ID NO:133, and a VL comprising an amino acid sequence having at least 95% identity to the amino acid sequence of SEQ ID NO:134. In some embodiments, the first binding domain comprises a heavy chain comprising an amino acid sequence having at least 95% identity to the amino acid sequence of SEQ ID NO:135. In some embodiments, the first binding domain comprises a light chain comprising an amino acid sequence having at least 95% identity to the amino acid sequence of SEQ ID NO:136. In some embodiments, the first binding domain comprises a heavy chain comprising an amino acid sequence having at least 95% identity to the amino acid sequence of SEQ ID NO:135, and a light chain comprising an amino acid sequence having at least 95% identity to the amino acid sequence of SEQ ID NO:136.

In another aspect, provided herein is a bispecific antibody comprising: (a) a first binding domain that binds to TRGV9, and (b) a second binding domain that binds to a cancer antigen present on the surface of a cancer cell. In some embodiments, the antigen on the surface of the cancer cell is a tumor-specific antigen. In some embodiments, the antigen on the surface of the cancer cell is a tumor associated antigen. In some embodiments, the antigen on the surface of the cancer cell is a neoantigen. In certain embodiments, the first binding domain of the bispecific antibody specifically binds TRGV9. In some embodiments, the TRGV9 is present on the surface of a γδ T cell. In some embodiments, cancer cell is killed when the bispecific antibody binds to the TRGV9 on the surface of the γδ T cell and the antigen on the surface of the cancer cell. Bispecific antibodies comprising any of the TRGV9 antibodies provided herein as the first binding domain are contemplated, in certain embodiments.

In another aspect, provided herein is a bispecific antibody comprising: (a) a first binding domain that binds to TRGV9, and (b) a second binding domain that binds to CD123. In certain embodiments, the first binding domain of the bispecific antibody specifically binds TRGV9. In some embodiments, the TRGV9 is present on the surface of a γδ T cell. In some embodiments, the CD123 is on the surface of a cell. In certain embodiments, the TRGV9 is present on the surface of a γδ T cell, and the CD123 is on the surface of a cell. In some embodiments, the cell having the CD123 on the surface is killed when the bispecific antibody binds to the TRGV9 on the surface of the γδ T cell and the CD123 on the surface of the cell. In some embodiments, the CD123 is on the surface of a cancer cell. In certain embodiments, the TRGV9 is present on the surface of a γδ T cell, and the CD123 is on the surface of a cancer cell. In some embodiments, the cancer cell is killed when the bispecific antibody binds to the TRGV9 on the surface of the γδ T cell and the CD123 on the surface of the cell. Bispecific antibodies comprising any of the TRGV9 antibodies provided herein as the first binding domain are contemplated, in certain embodiments. In addition, bispecific antibodies comprising any of the TRGV9 antibodies provided herein as the first binding domain, and a second binding domain that binds to CD123 are also contemplated in certain embodiments.

In another aspect, provided herein is a bispecific antibody comprising: (a) a first binding domain that binds to TRGV9, and (b) a second binding domain that binds to CD123, wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:556, a VH CDR2 having an amino acid sequence of SEQ ID NO:557, and a VH CDR3 having an amino acid sequence of SEQ ID NO:558; and (ii) a VL comprising a VL CDR1 having an amino acid sequence of SEQ ID NO:559, a VL CDR2 having an amino acid sequence of SEQ ID NO:560, and a VL CDR3 having an amino acid sequence of SEQ ID NO:561. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:562, a VH CDR2 having an amino acid sequence of SEQ ID NO:563, and a VH CDR3 having an amino acid sequence of SEQ ID NO:564; and (ii) a VL comprising a VL CDR1 having an amino acid sequence of SEQ ID NO:565, a VL CDR2 having an amino acid sequence of SEQ ID NO:566, and a VL CDR3 having an amino acid sequence of SEQ ID NO:567. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:568, a VH CDR2 having an amino acid sequence of SEQ ID NO:569, and a VH CDR3 having an amino acid sequence of SEQ ID NO:570; and (ii) a VL comprising a VL CDR1 having an amino acid sequence of SEQ ID NO:571, a VL CDR2 having an amino acid sequence of SEQ ID NO:572, and a VL CDR3 having an amino acid sequence of SEQ ID NO:573. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:574, a VH CDR2 having an amino acid sequence of SEQ ID NO:575, and a VH CDR3 having an amino acid sequence of SEQ ID NO:576; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:574, a VH CDR2 having an amino acid sequence of SEQ ID NO:722, and a VH CDR3 having an amino acid sequence of SEQ ID NO:723; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:580, a VH CDR2 having an amino acid sequence of SEQ ID NO:581, and a VH CDR3 having an amino acid sequence of SEQ ID NO:582; and (ii) a VL comprising a VL CDR1 having an amino acid sequence of SEQ ID NO:583, a VL CDR2 having an amino acid sequence of SEQ ID NO:584, and a VL CDR3 having an amino acid sequence of SEQ ID NO:585. In another aspect, provided herein is a bispecific antibody comprising: (a) a first binding domain that binds to TRGV9, and (b) a second binding domain that binds to CD123, wherein the second binding domain comprises: (i) a VH comprising a VH CDR1 having an amino acid sequence of SEQ ID NO:586, a VH CDR2 having an amino acid sequence of SEQ ID NO:587, and a VH CDR3 having an amino acid sequence of SEQ ID NO:588; and (ii) a VL comprising a VL CDR1 having an amino acid sequence of SEQ ID NO:589, a VL CDR2 having an amino acid sequence of SEQ ID NO:590, and a VL CDR3 having an amino acid sequence of SEQ ID NO:591. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence having at least 95% identity to an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:7. In some embodiments, the first binding domain comprises a VL having an amino acid sequence of SEQ ID NO:8. In some embodiments, the first binding domain comprises a VH having an amino acid sequence of SEQ ID NO:7, and a VL having an amino acid sequence of SEQ ID NO:8. In some embodiments, the first binding domain comprises a heavy chain having an amino acid sequence of SEQ ID NO:23. In some embodiments, the first binding domain comprises a light chain having an amino acid sequence of SEQ ID NO:24. In some embodiments, the first binding domain comprises a heavy chain having an amino acid sequence of SEQ ID NO:23, and a light chain having an amino acid sequence of SEQ ID NO:24. In some embodiments, the first binding domain comprises an amino acid sequence of SEQ ID NO:17. In some embodiments, the first binding domain comprises a heavy chain having an amino acid sequence of SEQ ID NO:69. In some embodiments, the first binding domain comprises a light chain having an amino acid sequence of SEQ ID NO:24. In some embodiments, the first binding domain comprises a heavy chain having an amino acid sequence of SEQ ID NO:69, and a light chain having an amino acid sequence of SEQ ID NO:24.

In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:7. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:7, and a VL comprising an amino acid sequence having at least 95% identity to the amino acid sequence of SEQ ID NO:8. In some embodiments, the first binding domain comprises a heavy chain comprising an amino acid sequence having at least 95% identity to the amino acid sequence of SEQ ID NO:23. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:23, and a light chain comprising an amino acid sequence having at least 95% identity to the amino acid sequence of SEQ ID NO:24. In some embodiments, the first binding domain comprises an amino acid sequence of SEQ ID NO:17. In some embodiments, the first binding domain comprises a heavy chain comprising an amino acid sequence having at least 95% identity to the amino acid sequence of SEQ ID NO:69. In some embodiments, the first binding domain comprises a light chain comprising an amino acid sequence having at least 95% identity to the amino acid sequence of SEQ ID NO:24. In some embodiments, the first binding domain comprises a heavy chain comprising an amino acid sequence having at least 95% identity to the amino acid sequence of SEQ ID NO:69, and a light chain comprising an amino acid sequence having at least 95% identity to the amino acid sequence of SEQ ID NO:24. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:34. In some embodiments, the first binding domain comprises a VL having an amino acid sequence of SEQ ID NO:8. In some embodiments, the first binding domain comprises a VH having an amino acid sequence of SEQ ID NO:34, and a VL having an amino acid sequence of SEQ ID NO:8. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:34. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:34, and a VL comprising an amino acid sequence having at least 95% identity to the amino acid sequence of SEQ ID NO:8. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:35. In some embodiments, the first binding domain comprises a VL having an amino acid sequence of SEQ ID NO:8. In some embodiments, the first binding domain comprises a VH having an amino acid sequence of SEQ ID NO:35, and a VL having an amino acid sequence of SEQ ID NO:8. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:35. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:35, and a VL comprising an amino acid sequence having at least 95% identity to the amino acid sequence of SEQ ID NO:8. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:36. In some embodiments, the first binding domain comprises a VL having an amino acid sequence of SEQ ID NO:8. In some embodiments, the first binding domain comprises a VH having an amino acid sequence of SEQ ID NO:36, and a VL having an amino acid sequence of SEQ ID NO:8. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:36. In some embodiments, the first binding domain comprises a VL comprising an amino acid sequence having at least 95% identity to the amino acid sequence of SEQ ID NO:8. In some embodiments, the first binding domain comprises a VH comprising an amino acid sequence having at least 95% identity to the amino acid sequence of SEQ ID NO:36, and a VL comprising an amino acid sequence having at least 95% identity to the amino acid sequence of SEQ ID NO:8. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:65. In some embodiments, the first binding domain comprises a VL having an amino acid sequence of SEQ ID NO:66. In some embodiments, the first binding domain comprises a VH having an amino acid sequence of SEQ ID NO:65, and a VL having an amino acid sequence of SEQ ID NO:66. In some embodiments, the first binding domain comprises a VH having an amino acid sequence of SEQ ID NO:67. In some embodiments, the first binding domain comprises a VL having an amino acid sequence of SEQ ID NO:68. In some embodiments, the first binding domain a VH having an amino acid sequence of SEQ ID NO:67, and a VL having an amino acid sequence of SEQ ID NO:68. In some embodiments, the first binding domain comprises a heavy chain having an amino acid sequence of SEQ ID NO:71. In some embodiments, the first binding domain comprises a light chain having an amino acid sequence of SEQ ID NO:72. In some embodiments, the first binding domain comprises a heavy chain having an amino acid sequence of SEQ ID NO:71, and a light chain having an amino acid sequence of SEQ ID NO:72. In some embodiments, the first binding domain comprises an amino acid sequence of SEQ ID NO:70. In some embodiments, the first binding domain comprises a heavy chain having an amino acid sequence of SEQ ID NO:74. In some embodiments, the first binding domain comprises a light chain having an amino acid sequence of SEQ ID NO:75. In some embodiments, the first binding domain comprises a heavy chain having an amino acid sequence of SEQ ID NO:74, and a light chain having an amino acid sequence of SEQ ID NO:75. In some embodiments, the first binding domain comprises an amino acid sequence of SEQ ID NO:73. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:65. In some embodiments, the first binding domain comprises a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:65, and a VL comprising an amino acid sequence having at least 95% identity to the amino acid sequence of SEQ ID NO:66. In some embodiments, the first binding domain comprises a VH comprising an amino acid sequence having at least 95% identity to the amino acid sequence of SEQ ID NO:67. In some embodiments, the first binding domain comprises a VL comprising an amino acid sequence having at least 95% identity to the amino acid sequence of SEQ ID NO:68. In some embodiments, the first binding domain a VH comprising an amino acid sequence having at least 95% identity to the amino acid sequence of SEQ ID NO:67, and a VL comprising an amino acid sequence having at least 95% identity to the amino acid sequence of SEQ ID NO:68. In some embodiments, the first binding domain comprises a heavy chain comprising an amino acid sequence having at least 95% identity to the amino acid sequence of SEQ ID NO:71. In some embodiments, the first binding domain comprises a light chain comprising an amino acid sequence having at least 95% identity to the amino acid sequence of SEQ ID NO:72. In some embodiments, the first binding domain comprises a heavy chain comprising an amino acid sequence having at least 95% identity to the amino acid sequence of SEQ ID NO:71, and a light chain comprising an amino acid sequence having at least 95% identity to the amino acid sequence of SEQ ID NO:72. In some embodiments, the first binding domain comprises an amino acid sequence of SEQ ID NO:70. In some embodiments, the first binding domain comprises a heavy chain comprising an amino acid sequence having at least 95% identity to the amino acid sequence of SEQ ID NO:74. In some embodiments, the first binding domain comprises a light chain comprising an amino acid sequence having at least 95% identity to the amino acid sequence of SEQ ID NO:75. In some embodiments, the first binding domain comprises a heavy chain comprising an amino acid sequence having at least 95% identity to the amino acid sequence of SEQ ID NO:74, and a light chain comprising an amino acid sequence having at least 95% identity to the amino acid sequence of SEQ ID NO:75. In some embodiments, the first binding domain comprises an amino acid sequence of SEQ ID NO:73. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and (ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:95. In some embodiments, the first binding domain comprises a VL having an amino acid sequence of SEQ ID NO:96. In some embodiments, the first binding domain comprises a VH having an amino acid sequence of SEQ ID NO:95, and a VL having an amino acid sequence of SEQ ID NO:96. In some embodiments, the first binding domain comprises an amino acid sequence of SEQ ID NO:97. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:95. In some embodiments, the first binding domain comprises a VL comprising an amino acid sequence having at least 95% identity to the amino acid sequence of SEQ ID NO:96. In some embodiments, the first binding domain comprises a VH comprising an amino acid sequence having at least 95% identity to the amino acid sequence of SEQ ID NO:95, and a VL comprising an amino acid sequence having at least 95% identity to the amino acid sequence of SEQ ID NO:96. In some embodiments, the first binding domain comprises an amino acid sequence of SEQ ID NO:97. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:104. In some embodiments, the first binding domain comprises a VL having an amino acid sequence of SEQ ID NO:105. In some embodiments, the first binding domain comprises a VH having an amino acid sequence of SEQ ID NO:104, and a VL having an amino acid sequence of SEQ ID NO:105. In some embodiments, the first binding domain comprises an amino acid sequence of SEQ ID NO:106. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:104. In some embodiments, the first binding domain comprises a VL comprising an amino acid sequence having at least 95% identity to the amino acid sequence of SEQ ID NO:105. In some embodiments, the first binding domain comprises a VH comprising an amino acid sequence having at least 95% identity to the amino acid sequence of SEQ ID NO:104, and a VL comprising an amino acid sequence having at least 95% identity to the amino acid sequence of SEQ ID NO:105. In some embodiments, the first binding domain comprises an amino acid sequence of SEQ ID NO:106. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VH having an amino acid sequence of SEQ ID NO:113. In some embodiments, the first binding domain comprises a VL having an amino acid sequence of SEQ ID NO:114. In some embodiments, the first binding domain comprises a VH having an amino acid sequence of SEQ ID NO:113, and a VL having an amino acid sequence of SEQ ID NO:114. In some embodiments, the first binding domain comprises a heavy chain having an amino acid sequence of SEQ ID NO:115. In some embodiments, the first binding domain comprises a light chain having an amino acid sequence of SEQ ID NO:116. In some embodiments, the first binding domain comprises a heavy chain having an amino acid sequence of SEQ ID NO:115, and a light chain having an amino acid sequence of SEQ ID NO:116. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VH comprising an amino acid sequence having at least 95% identity to the amino acid sequence of SEQ ID NO:113. In some embodiments, the first binding domain comprises a VL comprising an amino acid sequence having at least 95% identity to the amino acid sequence of SEQ ID NO:114. In some embodiments, the first binding domain comprises a VH comprising an amino acid sequence having at least 95% identity to the amino acid sequence of SEQ ID NO:113, and a VL comprising an amino acid sequence having at least 95% identity to the amino acid sequence of SEQ ID NO:114. In some embodiments, the first binding domain comprises a heavy chain comprising an amino acid sequence having at least 95% identity to the amino acid sequence of SEQ ID NO:115. In some embodiments, the first binding domain comprises a light chain comprising an amino acid sequence having at least 95% identity to the amino acid sequence of SEQ ID NO:116. In some embodiments, the first binding domain comprises a heavy chain comprising an amino acid sequence having at least 95% identity to the amino acid sequence of SEQ ID NO:115, and a light chain comprising an amino acid sequence having at least 95% identity to the amino acid sequence of SEQ ID NO:116. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122. In some embodiments, the first binding domain comprises a VH having an amino acid sequence of SEQ ID NO:123; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VL having an amino acid sequence of SEQ ID NO:124. In some embodiments, the first binding domain comprises a VH having an amino acid sequence of SEQ ID NO:123, and a VL having an amino acid sequence of SEQ ID NO:124. In some embodiments, the first binding domain comprises a heavy chain having an amino acid sequence of SEQ ID NO:125. In some embodiments, the first binding domain comprises a light chain having an amino acid sequence of SEQ ID NO:126. In some embodiments, the first binding domain comprises a heavy chain having an amino acid sequence of SEQ ID NO:125, and a light chain having an amino acid sequence of SEQ ID NO:126. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VL comprising an amino acid sequence having at least 95% identity to the amino acid sequence of SEQ ID NO:124. In some embodiments, the first binding domain comprises a VH comprising an amino acid sequence having at least 95% identity to the amino acid sequence of SEQ ID NO:123, and a VL comprising an amino acid sequence having at least 95% identity to the amino acid sequence of SEQ ID NO:124. In some embodiments, the first binding domain comprises a heavy chain comprising an amino acid sequence having at least 95% identity to the amino acid sequence of SEQ ID NO:125. In some embodiments, the first binding domain comprises a light chain comprising an amino acid sequence having at least 95% identity to the amino acid sequence of SEQ ID NO:126. In some embodiments, the first binding domain comprises a heavy chain comprising an amino acid sequence having at least 95% identity to the amino acid sequence of SEQ ID NO:125, and a light chain comprising an amino acid sequence having at least 95% identity to the amino acid sequence of SEQ ID NO:126. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16.

In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134; and wherein the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In another aspect, provided herein is a bispecific antibody comprising: (a) a first binding domain that binds to TRGV9, and (b) a second binding domain that binds to CD123, wherein the first binding domain comprises: (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132. In some embodiments, the first binding domain comprises a VH having an amino acid sequence of SEQ ID NO:133; and wherein the second binding domain comprises: (i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and (ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14. In some embodiments, the first binding domain comprises a VL having an amino acid sequence of SEQ ID NO:134. In some embodiments, the first binding domain comprises a VH having an amino acid sequence of SEQ ID NO:133, and a VL having an amino acid sequence of SEQ ID NO:134. In some embodiments, the first binding domain comprises a heavy chain having an amino acid sequence of SEQ ID NO:135. In some embodiments, the first binding domain comprises a light chain having an amino acid sequence of SEQ ID NO:136. In some embodiments, the first binding domain comprises a heavy chain having an amino acid sequence of SEQ ID NO:135, and a light chain having an amino acid sequence of SEQ ID NO:136. In some embodiments, the second binding domain comprises a VH having an amino acid sequence of SEQ ID NO:15. In some embodiments, the second binding domain comprises a VL having an amino acid sequence of SEQ ID NO:16. In some embodiments, the second binding domain comprises a VH having an amino acid sequence of SEQ ID NO:15, and a VL having an amino acid sequence of SEQ ID NO:16. In some embodiments, the second binding domain comprises a heavy chain having an amino acid sequence of SEQ ID NO:25. In some embodiments, the second binding domain comprises a light chain having an amino acid sequence of SEQ ID NO:26. In some embodiments, the second binding domain comprises a heavy chain having an amino acid sequence of SEQ ID NO:25, and a light chain having an amino acid sequence of SEQ ID NO:26. In some embodiments, the second binding domain comprises an amino acid sequence of SEQ ID NO:18. In some embodiments, the first binding domain comprises a VL comprising an amino acid sequence having at least 95% identity to the amino acid sequence of SEQ ID NO:134. In some embodiments, the first binding domain comprises a VH comprising an amino acid sequence having at least 95% identity to the amino acid sequence of SEQ ID NO:133, and a VL comprising an amino acid sequence having at least 95% identity to the amino acid sequence of SEQ ID NO:134. In some embodiments, the first binding domain comprises a heavy chain comprising an amino acid sequence having at least 95% identity to the amino acid sequence of SEQ ID NO:135. In some embodiments, the first binding domain comprises a light chain comprising an amino acid sequence having at least 95% identity to the amino acid sequence of SEQ ID NO:136. In some embodiments, the first binding domain comprises a heavy chain comprising an amino acid sequence having at least 95% identity to the amino acid sequence of SEQ ID NO:135, and a light chain comprising an amino acid sequence having at least 95% identity to the amino acid sequence of SEQ ID NO:136. In some embodiments, the second binding domain comprises a VH comprising an amino acid sequence having at least 95% identity to the amino acid sequence of SEQ ID NO:15. In some embodiments, the second binding domain comprises a VL comprising an amino acid sequence having at least 95% identity to the amino acid sequence of SEQ ID NO:16. In some embodiments, the second binding domain comprises a VH comprising an amino acid sequence having at least 95% identity to the amino acid sequence of SEQ ID NO:15, and a VL comprising an amino acid sequence having at least 95% identity to the amino acid sequence of SEQ ID NO:16. In some embodiments, the second binding domain comprises a heavy chain comprising an amino acid sequence having at least 95% identity to the amino acid sequence of SEQ ID NO:25. In some embodiments, the second binding domain comprises a light chain comprising an amino acid sequence having at least 95% identity to the amino acid sequence of SEQ ID NO:26. In some embodiments, the second binding domain comprises a heavy chain comprising an amino acid sequence having at least 95% identity to the amino acid sequence of SEQ ID NO:25, and a light chain comprising an amino acid sequence having at least 95% identity to the amino acid sequence of SEQ ID NO:26. In some embodiments, the second binding domain comprises an amino acid sequence of SEQ ID NO:18.

In another aspect, provided herein is a bispecific antibody comprising: (a) a first binding domain that binds to TRGV9, and (b) a second binding domain that binds to CD123. In some embodiments, the first binding domain that binds to TRGV9 comprises: (i) a VH comprising a VH CDR1 having an amino acid sequence of SEQ ID NO:160, a VH CDR2 having an amino acid sequence of SEQ ID NO:161, and a VH CDR3 having an amino acid sequence of SEQ ID NO:162; and (ii) a VL comprising a VL CDR1 having an amino acid sequence of SEQ ID NO:163, a VL CDR2 having an amino acid sequence of SEQ ID NO:164, and a VL CDR3 having an amino acid sequence of SEQ ID NO:165. In some embodiments, the first binding domain that binds to TRGV9 comprises: (i) a VH comprising a VH CDR1 having an amino acid sequence of SEQ ID NO:166, a VH CDR2 having an amino acid sequence of SEQ ID NO:167, and a VH CDR3 having an amino acid sequence of SEQ ID NO:168; and (ii) a VL comprising a VL CDR1 having an amino acid sequence of SEQ ID NO:169, a VL CDR2 having an amino acid sequence of SEQ ID NO:170, and a VL CDR3 having an amino acid sequence of SEQ ID NO:171. In some embodiments, the first binding domain that binds to TRGV9 comprises: (i) a VH comprising a VH CDR1 having an amino acid sequence of SEQ ID NO:172, a VH CDR2 having an amino acid sequence of SEQ ID NO:173, and a VH CDR3 having an amino acid sequence of SEQ ID NO:174; and (ii) a VL comprising a VL CDR1 having an amino acid sequence of SEQ ID NO:175, a VL CDR2 having an amino acid sequence of SEQ ID NO:176, and a VL CDR3 having an amino acid sequence of SEQ ID NO:177. In some embodiments, the first binding domain that binds to TRGV9 comprises: (i) a VH comprising a VH CDR1 having an amino acid sequence of SEQ ID NO:178, a VH CDR2 having an amino acid sequence of SEQ ID NO:179, and a VH CDR3 having an amino acid sequence of SEQ ID NO:180; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In some embodiments, the first binding domain that binds to TRGV9 comprises: (i) a VH comprising a VH CDR1 having an amino acid sequence of SEQ ID NO:178, a VH CDR2 having an amino acid sequence of SEQ ID NO:700, and a VH CDR3 having an amino acid sequence of SEQ ID NO:701; and (ii) a VL comprising a VL CDR1 having an amino acid sequence of SEQ ID NO:181, a VL CDR2 having an amino acid sequence of SEQ ID NO:182, and a VL CDR3 having an amino acid sequence of SEQ ID NO:183. In some embodiments, the first binding domain that binds to TRGV9 comprises: (i) a VH comprising a VH CDR1 having an amino acid sequence of SEQ ID NO:184, a VH CDR2 having an amino acid sequence of SEQ ID NO:185, and a VH CDR3 having an amino acid sequence of SEQ ID NO:186; and (ii) a VL comprising a VL CDR1 having an amino acid sequence of SEQ ID NO:187, a VL CDR2 having an amino acid sequence of SEQ ID NO:188, and a VL CDR3 having an amino acid sequence of SEQ ID NO:189. In some embodiments, the first binding domain that binds to TRGV9 comprises: (i) a VH comprising a VH CDR1 having an amino acid sequence of SEQ ID NO:190, a VH CDR2 having an amino acid sequence of SEQ ID NO:191, and a VH CDR3 having an amino acid sequence of SEQ ID NO:192; and (ii) a VL comprising a VL CDR1 having an amino acid sequence of SEQ ID NO:193, a VL CDR2 having an amino acid sequence of SEQ ID NO:194, and a VL CDR3 having an amino acid sequence of SEQ ID NO:195. In some embodiments, the first binding domain that binds to TRGV9 comprises: (i) a VH comprising a VH CDR1 having an amino acid sequence of SEQ ID NO:196, a VH CDR2 having an amino acid sequence of SEQ ID NO:197, and a VH CDR3 having an amino acid sequence of SEQ ID NO:198; and (ii) a VL comprising a VL CDR1 having an amino acid sequence of SEQ ID NO:199, a VL CDR2 having an amino acid sequence of SEQ ID NO:200, and a VL CDR3 having an amino acid sequence of SEQ ID NO:201. In some embodiments, the first binding domain that binds to TRGV9 comprises: (i) a VH comprising a VH CDR1 having an amino acid sequence of SEQ ID NO:202, a VH CDR2 having an amino acid sequence of SEQ ID NO:203, and a VH CDR3 having an amino acid sequence of SEQ ID NO:204; and (ii) a VL comprising a VL CDR1 having an amino acid sequence of SEQ ID NO:205, a VL CDR2 having an amino acid sequence of SEQ ID NO:206, and a VL CDR3 having an amino acid sequence of SEQ ID NO:207. In some embodiments, the first binding domain that binds to TRGV9 comprises: (i) a VH comprising a VH CDR1 having an amino acid sequence of SEQ ID NO:208, a VH CDR2 having an amino acid sequence of SEQ ID NO:209, and a VH CDR3 having an amino acid sequence of SEQ ID NO:210; and (ii) a VL comprising a VL CDR1 having an amino acid sequence of SEQ ID NO:211, a VL CDR2 having an amino acid sequence of SEQ ID NO:212, and a VL CDR3 having an amino acid sequence of SEQ ID NO:213. In some embodiments, the first binding domain that binds to TRGV9 comprises: (i) a VH comprising a VH CDR1 having an amino acid sequence of SEQ ID NO:214, a VH CDR2 having an amino acid sequence of SEQ ID NO:215, and a VH CDR3 having an amino acid sequence of SEQ ID NO:216; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In some embodiments, the first binding domain that binds to TRGV9 comprises: (i) a VH comprising a VH CDR1 having an amino acid sequence of SEQ ID NO:214, a VH CDR2 having an amino acid sequence of SEQ ID NO:702, and a VH CDR3 having an amino acid sequence of SEQ ID NO:703; and (ii) a VL comprising a VL CDR1 having an amino acid sequence of SEQ ID NO:217, a VL CDR2 having an amino acid sequence of SEQ ID NO:218, and a VL CDR3 having an amino acid sequence of SEQ ID NO:219. In some embodiments, the first binding domain that binds to TRGV9 comprises: (i) a VH comprising a VH CDR1 having an amino acid sequence of SEQ ID NO:220, a VH CDR2 having an amino acid sequence of SEQ ID NO:221, and a VH CDR3 having an amino acid sequence of SEQ ID NO:222; and (ii) a VL comprising a VL CDR1 having an amino acid sequence of SEQ ID NO:223, a VL CDR2 having an amino acid sequence of SEQ ID NO:224, and a VL CDR3 having an amino acid sequence of SEQ ID NO:225. In some embodiments, the first binding domain that binds to TRGV9 comprises: (i) a VH comprising a VH CDR1 having an amino acid sequence of SEQ ID NO:226, a VH CDR2 having an amino acid sequence of SEQ ID NO:227, and a VH CDR3 having an amino acid sequence of SEQ ID NO:228; and (ii) a VL comprising a VL CDR1 having an amino acid sequence of SEQ ID NO:229, a VL CDR2 having an amino acid sequence of SEQ ID NO:230, and a VL CDR3 having an amino acid sequence of SEQ ID NO:231. In some embodiments, the first binding domain that binds to TRGV9 comprises: (i) a VH comprising a VH CDR1 having an amino acid sequence of SEQ ID NO:232, a VH CDR2 having an amino acid sequence of SEQ ID NO:233, and a VH CDR3 having an amino acid sequence of SEQ ID NO:234; and (ii) a VL comprising a VL CDR1 having an amino acid sequence of SEQ ID NO:235, a VL CDR2 having an amino acid sequence of SEQ ID NO:236, and a VL CDR3 having an amino acid sequence of SEQ ID NO:237. In some embodiments, the first binding domain that binds to TRGV9 comprises: (i) a VH comprising a VH CDR1 having an amino acid sequence of SEQ ID NO:238, a VH CDR2 having an amino acid sequence of SEQ ID NO:239, and a VH CDR3 having an amino acid sequence of SEQ ID NO:240; and (ii) a VL comprising a VL CDR1 having an amino acid sequence of SEQ ID NO:241, a VL CDR2 having an amino acid sequence of SEQ ID NO:242, and a VL CDR3 having an amino acid sequence of SEQ ID NO:243. In some embodiments, the first binding domain that binds to TRGV9 comprises: (i) a VH comprising a VH CDR1 having an amino acid sequence of SEQ ID NO:244, a VH CDR2 having an amino acid sequence of SEQ ID NO:245, and a VH CDR3 having an amino acid sequence of SEQ ID NO:246; and (ii) a VL comprising a VL CDR1 having an amino acid sequence of SEQ ID NO:247, a VL CDR2 having an amino acid sequence of SEQ ID NO:248, and a VL CDR3 having an amino acid sequence of SEQ ID NO:249. In some embodiments, the first binding domain that binds to TRGV9 comprises: (i) a VH comprising a VH CDR1 having an amino acid sequence of SEQ ID NO:250, a VH CDR2 having an amino acid sequence of SEQ ID NO:251, and a VH CDR3 having an amino acid sequence of SEQ ID NO:252; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In some embodiments, the first binding domain that binds to TRGV9 comprises: (i) a VH comprising a VH CDR1 having an amino acid sequence of SEQ ID NO:250, a VH CDR2 having an amino acid sequence of SEQ ID NO:704, and a VH CDR3 having an amino acid sequence of SEQ ID NO:705; and (ii) a VL comprising a VL CDR1 having an amino acid sequence of SEQ ID NO:253, a VL CDR2 having an amino acid sequence of SEQ ID NO:254, and a VL CDR3 having an amino acid sequence of SEQ ID NO:255. In some embodiments, the first binding domain that binds to TRGV9 comprises: (i) a VH comprising a VH CDR1 having an amino acid sequence of SEQ ID NO:256, a VH CDR2 having an amino acid sequence of SEQ ID NO:257, and a VH CDR3 having an amino acid sequence of SEQ ID NO:258; and (ii) a VL comprising a VL CDR1 having an amino acid sequence of SEQ ID NO:259, a VL CDR2 having an amino acid sequence of SEQ ID NO:260, and a VL CDR3 having an amino acid sequence of SEQ ID NO:261. In some embodiments, the first binding domain that binds to TRGV9 comprises: (i) a VH comprising a VH CDR1 having an amino acid sequence of SEQ ID NO:262, a VH CDR2 having an amino acid sequence of SEQ ID NO:263, and a VH CDR3 having an amino acid sequence of SEQ ID NO:264; and (ii) a VL comprising a VL CDR1 having an amino acid sequence of SEQ ID NO:265, a VL CDR2 having an amino acid sequence of SEQ ID NO:266, and a VL CDR3 having an amino acid sequence of SEQ ID NO:267. In some embodiments, the first binding domain that binds to TRGV9 comprises: (i) a VH comprising a VH CDR1 having an amino acid sequence of SEQ ID NO:268, a VH CDR2 having an amino acid sequence of SEQ ID NO:269, and a VH CDR3 having an amino acid sequence of SEQ ID NO:270; and (ii) a VL comprising a VL CDR1 having an amino acid sequence of SEQ ID NO:271, a VL CDR2 having an amino acid sequence of SEQ ID NO:272, and a VL CDR3 having an amino acid sequence of SEQ ID NO:273. In some embodiments, the first binding domain that binds to TRGV9 comprises: (i) a VH comprising a VH CDR1 having an amino acid sequence of SEQ ID NO:274, a VH CDR2 having an amino acid sequence of SEQ ID NO:275, and a VH CDR3 having an amino acid sequence of SEQ ID NO:276; and (ii) a VL comprising a VL CDR1 having an amino acid sequence of SEQ ID NO:277, a VL CDR2 having an amino acid sequence of SEQ ID NO:278, and a VL CDR3 having an amino acid sequence of SEQ ID NO:279. In some embodiments, the first binding domain that binds to TRGV9 comprises: (i) a VH comprising a VH CDR1 having an amino acid sequence of SEQ ID NO:280, a VH CDR2 having an amino acid sequence of SEQ ID NO:281, and a VH CDR3 having an amino acid sequence of SEQ ID NO:282; and (ii) a VL comprising a VL CDR1 having an amino acid sequence of SEQ ID NO:283, a VL CDR2 having an amino acid sequence of SEQ ID NO:284, and a VL CDR3 having an amino acid sequence of SEQ ID NO:285. In some embodiments, the first binding domain that binds to TRGV9 comprises: (i) a VH comprising a VH CDR1 having an amino acid sequence of SEQ ID NO:286, a VH CDR2 having an amino acid sequence of SEQ ID NO:287, and a VH CDR3 having an amino acid sequence of SEQ ID NO:288; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In some embodiments, the first binding domain that binds to TRGV9 comprises: (i) a VH comprising a VH CDR1 having an amino acid sequence of SEQ ID NO:286, a VH CDR2 having an amino acid sequence of SEQ ID NO:706, and a VH CDR3 having an amino acid sequence of SEQ ID NO:707; and (ii) a VL comprising a VL CDR1 having an amino acid sequence of SEQ ID NO:289, a VL CDR2 having an amino acid sequence of SEQ ID NO:290, and a VL CDR3 having an amino acid sequence of SEQ ID NO:291. In some embodiments, the first binding domain that binds to TRGV9 comprises: (i) a VH comprising a VH CDR1 having an amino acid sequence of SEQ ID NO:292, a VH CDR2 having an amino acid sequence of SEQ ID NO:293, and a VH CDR3 having an amino acid sequence of SEQ ID NO:294; and (ii) a VL comprising a VL CDR1 having an amino acid sequence of SEQ ID NO:295, a VL CDR2 having an amino acid sequence of SEQ ID NO:296, and a VL CDR3 having an amino acid sequence of SEQ ID NO:297. In some embodiments, the first binding domain that binds to TRGV9 comprises: (i) a VH comprising a VH CDR1 having an amino acid sequence of SEQ ID NO:298, a VH CDR2 having an amino acid sequence of SEQ ID NO:299, and a VH CDR3 having an amino acid sequence of SEQ ID NO:300; and (ii) a VL comprising a VL CDR1 having an amino acid sequence of SEQ ID NO:301, a VL CDR2 having an amino acid sequence of SEQ ID NO:302, and a VL CDR3 having an amino acid sequence of SEQ ID NO:303. In some embodiments, the first binding domain that binds to TRGV9 comprises: (i) a VH comprising a VH CDR1 having an amino acid sequence of SEQ ID NO:304, a VH CDR2 having an amino acid sequence of SEQ ID NO:305, and a VH CDR3 having an amino acid sequence of SEQ ID NO:306; and (ii) a VL comprising a VL CDR1 having an amino acid sequence of SEQ ID NO:307, a VL CDR2 having an amino acid sequence of SEQ ID NO:308, and a VL CDR3 having an amino acid sequence of SEQ ID NO:309. In some embodiments, the first binding domain that binds to TRGV9 comprises: (i) a VH comprising a VH CDR1 having an amino acid sequence of SEQ ID NO:310, a VH CDR2 having an amino acid sequence of SEQ ID NO:311, and a VH CDR3 having an amino acid sequence of SEQ ID NO:312; and (ii) a VL comprising a VL CDR1 having an amino acid sequence of SEQ ID NO:313, a VL CDR2 having an amino acid sequence of SEQ ID NO:314, and a VL CDR3 having an amino acid sequence of SEQ ID NO:315. In some embodiments, the first binding domain that binds to TRGV9 comprises: (i) a VH comprising a VH CDR1 having an amino acid sequence of SEQ ID NO:316, a VH CDR2 having an amino acid sequence of SEQ ID NO:317, and a VH CDR3 having an amino acid sequence of SEQ ID NO:318; and (ii) a VL comprising a VL CDR1 having an amino acid sequence of SEQ ID NO:319, a VL CDR2 having an amino acid sequence of SEQ ID NO:320, and a VL CDR3 having an amino acid sequence of SEQ ID NO:321. In some embodiments, the first binding domain that binds to TRGV9 comprises: (i) a VH comprising a VH CDR1 having an amino acid sequence of SEQ ID NO:322, a VH CDR2 having an amino acid sequence of SEQ ID NO:323, and a VH CDR3 having an amino acid sequence of SEQ ID NO:324; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In some embodiments, the first binding domain that binds to TRGV9 comprises: (i) a VH comprising a VH CDR1 having an amino acid sequence of SEQ ID NO:322, a VH CDR2 having an amino acid sequence of SEQ ID NO:708, and a VH CDR3 having an amino acid sequence of SEQ ID NO:709; and (ii) a VL comprising a VL CDR1 having an amino acid sequence of SEQ ID NO:325, a VL CDR2 having an amino acid sequence of SEQ ID NO:326, and a VL CDR3 having an amino acid sequence of SEQ ID NO:327. In some embodiments, the first binding domain that binds to TRGV9 comprises: (i) a VH comprising a VH CDR1 having an amino acid sequence of SEQ ID NO:328, a VH CDR2 having an amino acid sequence of SEQ ID NO:329, and a VH CDR3 having an amino acid sequence of SEQ ID NO:330; and (ii) a VL comprising a VL CDR1 having an amino acid sequence of SEQ ID NO:331, a VL CDR2 having an amino acid sequence of SEQ ID NO:332, and a VL CDR3 having an amino acid sequence of SEQ ID NO:333. In some embodiments, the first binding domain that binds to TRGV9 comprises: (i) a VH comprising a VH CDR1 having an amino acid sequence of SEQ ID NO:334, a VH CDR2 having an amino acid sequence of SEQ ID NO:335, and a VH CDR3 having an amino acid sequence of SEQ ID NO:336; and (ii) a VL comprising a VL CDR1 having an amino acid sequence of SEQ ID NO:337, a VL CDR2 having an amino acid sequence of SEQ ID NO:338, and a VL CDR3 having an amino acid sequence of SEQ ID NO:339. In some embodiments, the first binding domain that binds to TRGV9 comprises: (i) a VH comprising a VH CDR1 having an amino acid sequence of SEQ ID NO:340, a VH CDR2 having an amino acid sequence of SEQ ID NO:341, and a VH CDR3 having an amino acid sequence of SEQ ID NO:342; and (ii) a VL comprising a VL CDR1 having an amino acid sequence of SEQ ID NO:343, a VL CDR2 having an amino acid sequence of SEQ ID NO:344, and a VL CDR3 having an amino acid sequence of SEQ ID NO:345. In some embodiments, the first binding domain that binds to TRGV9 comprises: (i) a VH comprising a VH CDR1 having an amino acid sequence of SEQ ID NO:346, a VH CDR2 having an amino acid sequence of SEQ ID NO:347, and a VH CDR3 having an amino acid sequence of SEQ ID NO:348; and (ii) a VL comprising a VL CDR1 having an amino acid sequence of SEQ ID NO:349, a VL CDR2 having an amino acid sequence of SEQ ID NO:350, and a VL CDR3 having an amino acid sequence of SEQ ID NO:351. In some embodiments, the first binding domain that binds to TRGV9 comprises: (i) a VH comprising a VH CDR1 having an amino acid sequence of SEQ ID NO:352, a VH CDR2 having an amino acid sequence of SEQ ID NO:353, and a VH CDR3 having an amino acid sequence of SEQ ID NO:354; and (ii) a VL comprising a VL CDR1 having an amino acid sequence of SEQ ID NO:355, a VL CDR2 having an amino acid sequence of SEQ ID NO:356, and a VL CDR3 having an amino acid sequence of SEQ ID NO:357. In some embodiments, the first binding domain that binds to TRGV9 comprises: (i) a VH comprising a VH CDR1 having an amino acid sequence of SEQ ID NO:358, a VH CDR2 having an amino acid sequence of SEQ ID NO:359, and a VH CDR3 having an amino acid sequence of SEQ ID NO:360; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In some embodiments, the first binding domain that binds to TRGV9 comprises: (i) a VH comprising a VH CDR1 having an amino acid sequence of SEQ ID NO:358, a VH CDR2 having an amino acid sequence of SEQ ID NO:710, and a VH CDR3 having an amino acid sequence of SEQ ID NO:711; and (ii) a VL comprising a VL CDR1 having an amino acid sequence of SEQ ID NO:361, a VL CDR2 having an amino acid sequence of SEQ ID NO:362, and a VL CDR3 having an amino acid sequence of SEQ ID NO:363. In some embodiments, the first binding domain that binds to TRGV9 comprises: (i) a VH comprising a VH CDR1 having an amino acid sequence of SEQ ID NO:364, a VH CDR2 having an amino acid sequence of SEQ ID NO:365, and a VH CDR3 having an amino acid sequence of SEQ ID NO:366; and (ii) a VL comprising a VL CDR1 having an amino acid sequence of SEQ ID NO:367, a VL CDR2 having an amino acid sequence of SEQ ID NO:368, and a VL CDR3 having an amino acid sequence of SEQ ID NO:369. In some embodiments, the first binding domain that binds to TRGV9 comprises: (i) a VH comprising a VH CDR1 having an amino acid sequence of SEQ ID NO:370, a VH CDR2 having an amino acid sequence of SEQ ID NO:371, and a VH CDR3 having an amino acid sequence of SEQ ID NO:372; and (ii) a VL comprising a VL CDR1 having an amino acid sequence of SEQ ID NO:373, a VL CDR2 having an amino acid sequence of SEQ ID NO:374, and a VL CDR3 having an amino acid sequence of SEQ ID NO:375. In some embodiments, the first binding domain that binds to TRGV9 comprises: (i) a VH comprising a VH CDR1 having an amino acid sequence of SEQ ID NO:376, a VH CDR2 having an amino acid sequence of SEQ ID NO:377, and a VH CDR3 having an amino acid sequence of SEQ ID NO:378; and (ii) a VL comprising a VL CDR1 having an amino acid sequence of SEQ ID NO:379, a VL CDR2 having an amino acid sequence of SEQ ID NO:380, and a VL CDR3 having an amino acid sequence of SEQ ID NO:381. In some embodiments, the first binding domain that binds to TRGV9 comprises: (i) a VH comprising a VH CDR1 having an amino acid sequence of SEQ ID NO:382, a VH CDR2 having an amino acid sequence of SEQ ID NO:383, and a VH CDR3 having an amino acid sequence of SEQ ID NO:384; and (ii) a VL comprising a VL CDR1 having an amino acid sequence of SEQ ID NO:385, a VL CDR2 having an amino acid sequence of SEQ ID NO:386, and a VL CDR3 having an amino acid sequence of SEQ ID NO:387. In some embodiments, the first binding domain that binds to TRGV9 comprises: (i) a VH comprising a VH CDR1 having an amino acid sequence of SEQ ID NO:388, a VH CDR2 having an amino acid sequence of SEQ ID NO:389, and a VH CDR3 having an amino acid sequence of SEQ ID NO:390; and (ii) a VL comprising a VL CDR1 having an amino acid sequence of SEQ ID NO:391, a VL CDR2 having an amino acid sequence of SEQ ID NO:392, and a VL CDR3 having an amino acid sequence of SEQ ID NO:393. In some embodiments, the first binding domain that binds to TRGV9 comprises: (i) a VH comprising a VH CDR1 having an amino acid sequence of SEQ ID NO:394, a VH CDR2 having an amino acid sequence of SEQ ID NO:395, and a VH CDR3 having an amino acid sequence of SEQ ID NO:396; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In some embodiments, the first binding domain that binds to TRGV9 comprises: (i) a VH comprising a VH CDR1 having an amino acid sequence of SEQ ID NO:394, a VH CDR2 having an amino acid sequence of SEQ ID NO:712, and a VH CDR3 having an amino acid sequence of SEQ ID NO:713; and (ii) a VL comprising a VL CDR1 having an amino acid sequence of SEQ ID NO:397, a VL CDR2 having an amino acid sequence of SEQ ID NO:398, and a VL CDR3 having an amino acid sequence of SEQ ID NO:399. In some embodiments, the first binding domain that binds to TRGV9 comprises: (i) a VH comprising a VH CDR1 having an amino acid sequence of SEQ ID NO:400, a VH CDR2 having an amino acid sequence of SEQ ID NO:401, and a VH CDR3 having an amino acid sequence of SEQ ID NO:402; and (ii) a VL comprising a VL CDR1 having an amino acid sequence of SEQ ID NO:403, a VL CDR2 having an amino acid sequence of SEQ ID NO:404, and a VL CDR3 having an amino acid sequence of SEQ ID NO:405. In some embodiments, the first binding domain that binds to TRGV9 comprises: (i) a VH comprising a VH CDR1 having an amino acid sequence of SEQ ID NO:406, a VH CDR2 having an amino acid sequence of SEQ ID NO:407, and a VH CDR3 having an amino acid sequence of SEQ ID NO:408; and (ii) a VL comprising a VL CDR1 having an amino acid sequence of SEQ ID NO:409, a VL CDR2 having an amino acid sequence of SEQ ID NO:410, and a VL CDR3 having an amino acid sequence of SEQ ID NO:411. In some embodiments, the first binding domain that binds to TRGV9 comprises: (i) a VH comprising a VH CDR1 having an amino acid sequence of SEQ ID NO:412, a VH CDR2 having an amino acid sequence of SEQ ID NO:413, and a VH CDR3 having an amino acid sequence of SEQ ID NO:414; and (ii) a VL comprising a VL CDR1 having an amino acid sequence of SEQ ID NO:415, a VL CDR2 having an amino acid sequence of SEQ ID NO:416, and a VL CDR3 having an amino acid sequence of SEQ ID NO:417. In some embodiments, the first binding domain that binds to TRGV9 comprises: (i) a VH comprising a VH CDR1 having an amino acid sequence of SEQ ID NO:418, a VH CDR2 having an amino acid sequence of SEQ ID NO:419, and a VH CDR3 having an amino acid sequence of SEQ ID NO:420; and (ii) a VL comprising a VL CDR1 having an amino acid sequence of SEQ ID NO:421, a VL CDR2 having an amino acid sequence of SEQ ID NO:422, and a VL CDR3 having an amino acid sequence of SEQ ID NO:423. In some embodiments, the first binding domain that binds to TRGV9 comprises: (i) a VH comprising a VH CDR1 having an amino acid sequence of SEQ ID NO:424, a VH CDR2 having an amino acid sequence of SEQ ID NO:425, and a VH CDR3 having an amino acid sequence of SEQ ID NO:426; and (ii) a VL comprising a VL CDR1 having an amino acid sequence of SEQ ID NO:427, a VL CDR2 having an amino acid sequence of SEQ ID NO:428, and a VL CDR3 having an amino acid sequence of SEQ ID NO:429. In some embodiments, the first binding domain that binds to TRGV9 comprises: (i) a VH comprising a VH CDR1 having an amino acid sequence of SEQ ID NO:430, a VH CDR2 having an amino acid sequence of SEQ ID NO:431, and a VH CDR3 having an amino acid sequence of SEQ ID NO:432; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In some embodiments, the first binding domain that binds to TRGV9 comprises: (i) a VH comprising a VH CDR1 having an amino acid sequence of SEQ ID NO:430, a VH CDR2 having an amino acid sequence of SEQ ID NO:714, and a VH CDR3 having an amino acid sequence of SEQ ID NO:715; and (ii) a VL comprising a VL CDR1 having an amino acid sequence of SEQ ID NO:433, a VL CDR2 having an amino acid sequence of SEQ ID NO:434, and a VL CDR3 having an amino acid sequence of SEQ ID NO:435. In some embodiments, the first binding domain that binds to TRGV9 comprises: (i) a VH comprising a VH CDR1 having an amino acid sequence of SEQ ID NO:436, a VH CDR2 having an amino acid sequence of SEQ ID NO:437, and a VH CDR3 having an amino acid sequence of SEQ ID NO:438; and (ii) a VL comprising a VL CDR1 having an amino acid sequence of SEQ ID NO:439, a VL CDR2 having an amino acid sequence of SEQ ID NO:440, and a VL CDR3 having an amino acid sequence of SEQ ID NO:441. In some embodiments, the first binding domain that binds to TRGV9 comprises: (i) a VH comprising a VH CDR1 having an amino acid sequence of SEQ ID NO:442, a VH CDR2 having an amino acid sequence of SEQ ID NO:443, and a VH CDR3 having an amino acid sequence of SEQ ID NO:444; and (ii) a VL comprising a VL CDR1 having an amino acid sequence of SEQ ID NO:445, a VL CDR2 having an amino acid sequence of SEQ ID NO:446, and a VL CDR3 having an amino acid sequence of SEQ ID NO:447. In some embodiments, the first binding domain that binds to TRGV9 comprises: (i) a VH comprising a VH CDR1 having an amino acid sequence of SEQ ID NO:448, a VH CDR2 having an amino acid sequence of SEQ ID NO:449, and a VH CDR3 having an amino acid sequence of SEQ ID NO:450; and (ii) a VL comprising a VL CDR1 having an amino acid sequence of SEQ ID NO:451, a VL CDR2 having an amino acid sequence of SEQ ID NO:452, and a VL CDR3 having an amino acid sequence of SEQ ID NO:453. In some embodiments, the first binding domain that binds to TRGV9 comprises: (i) a VH comprising a VH CDR1 having an amino acid sequence of SEQ ID NO:454, a VH CDR2 having an amino acid sequence of SEQ ID NO:455, and a VH CDR3 having an amino acid sequence of SEQ ID NO:456; and (ii) a VL comprising a VL CDR1 having an amino acid sequence of SEQ ID NO:457, a VL CDR2 having an amino acid sequence of SEQ ID NO:458, and a VL CDR3 having an amino acid sequence of SEQ ID NO:459. In some embodiments, the first binding domain that binds to TRGV9 comprises: (i) a VH comprising a VH CDR1 having an amino acid sequence of SEQ ID NO:460, a VH CDR2 having an amino acid sequence of SEQ ID NO:461, and a VH CDR3 having an amino acid sequence of SEQ ID NO:462; and (ii) a VL comprising a VL CDR1 having an amino acid sequence of SEQ ID NO:463, a VL CDR2 having an amino acid sequence of SEQ ID NO:464, and a VL CDR3 having an amino acid sequence of SEQ ID NO:465. In some embodiments, the first binding domain that binds to TRGV9 comprises: (i) a VH comprising a VH CDR1 having an amino acid sequence of SEQ ID NO:466, a VH CDR2 having an amino acid sequence of SEQ ID NO:467, and a VH CDR3 having an amino acid sequence of SEQ ID NO:468; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In some embodiments, the first binding domain that binds to TRGV9 comprises: (i) a VH comprising a VH CDR1 having an amino acid sequence of SEQ ID NO:466, a VH CDR2 having an amino acid sequence of SEQ ID NO:716, and a VH CDR3 having an amino acid sequence of SEQ ID NO:717; and (ii) a VL comprising a VL CDR1 having an amino acid sequence of SEQ ID NO:469, a VL CDR2 having an amino acid sequence of SEQ ID NO:470, and a VL CDR3 having an amino acid sequence of SEQ ID NO:471. In some embodiments, the first binding domain that binds to TRGV9 comprises: (i) a VH comprising a VH CDR1 having an amino acid sequence of SEQ ID NO:472, a VH CDR2 having an amino acid sequence of SEQ ID NO:473, and a VH CDR3 having an amino acid sequence of SEQ ID NO:474; and (ii) a VL comprising a VL CDR1 having an amino acid sequence of SEQ ID NO:475, a VL CDR2 having an amino acid sequence of SEQ ID NO:476, and a VL CDR3 having an amino acid sequence of SEQ ID NO:477. In some embodiments, the first binding domain that binds to TRGV9 comprises: (i) a VH comprising a VH CDR1 having an amino acid sequence of SEQ ID NO:478, a VH CDR2 having an amino acid sequence of SEQ ID NO:479, and a VH CDR3 having an amino acid sequence of SEQ ID NO:480; and (ii) a VL comprising a VL CDR1 having an amino acid sequence of SEQ ID NO:481, a VL CDR2 having an amino acid sequence of SEQ ID NO:482, and a VL CDR3 having an amino acid sequence of SEQ ID NO:483. In some embodiments, the first binding domain that binds to TRGV9 comprises: (i) a VH comprising a VH CDR1 having an amino acid sequence of SEQ ID NO:484, a VH CDR2 having an amino acid sequence of SEQ ID NO:485, and a VH CDR3 having an amino acid sequence of SEQ ID NO:486; and (ii) a VL comprising a VL CDR1 having an amino acid sequence of SEQ ID NO:487, a VL CDR2 having an amino acid sequence of SEQ ID NO:488, and a VL CDR3 having an amino acid sequence of SEQ ID NO:489. In some embodiments, the first binding domain that binds to TRGV9 comprises: (i) a VH comprising a VH CDR1 having an amino acid sequence of SEQ ID NO:490, a VH CDR2 having an amino acid sequence of SEQ ID NO:491, and a VH CDR3 having an amino acid sequence of SEQ ID NO:492; and (ii) a VL comprising a VL CDR1 having an amino acid sequence of SEQ ID NO:493, a VL CDR2 having an amino acid sequence of SEQ ID NO:494, and a VL CDR3 having an amino acid sequence of SEQ ID NO:495. In some embodiments, the first binding domain that binds to TRGV9 comprises: (i) a VH comprising a VH CDR1 having an amino acid sequence of SEQ ID NO:496, a VH CDR2 having an amino acid sequence of SEQ ID NO:497, and a VH CDR3 having an amino acid sequence of SEQ ID NO:498; and (ii) a VL comprising a VL CDR1 having an amino acid sequence of SEQ ID NO:499, a VL CDR2 having an amino acid sequence of SEQ ID NO:500, and a VL CDR3 having an amino acid sequence of SEQ ID NO:501. In some embodiments, the first binding domain that binds to TRGV9 comprises: (i) a VH comprising a VH CDR1 having an amino acid sequence of SEQ ID NO:502, a VH CDR2 having an amino acid sequence of SEQ ID NO:503, and a VH CDR3 having an amino acid sequence of SEQ ID NO:504; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In some embodiments, the first binding domain that binds to TRGV9 comprises: (i) a VH comprising a VH CDR1 having an amino acid sequence of SEQ ID NO:502, a VH CDR2 having an amino acid sequence of SEQ ID NO:718, and a VH CDR3 having an amino acid sequence of SEQ ID NO:719; and (ii) a VL comprising a VL CDR1 having an amino acid sequence of SEQ ID NO:505, a VL CDR2 having an amino acid sequence of SEQ ID NO:506, and a VL CDR3 having an amino acid sequence of SEQ ID NO:507. In some embodiments, the first binding domain that binds to TRGV9 comprises: (i) a VH comprising a VH CDR1 having an amino acid sequence of SEQ ID NO:508, a VH CDR2 having an amino acid sequence of SEQ ID NO:509, and a VH CDR3 having an amino acid sequence of SEQ ID NO:510; and (ii) a VL comprising a VL CDR1 having an amino acid sequence of SEQ ID NO:511, a VL CDR2 having an amino acid sequence of SEQ ID NO:512, and a VL CDR3 having an amino acid sequence of SEQ ID NO:513. In some embodiments, the first binding domain that binds to TRGV9 comprises: (i) a VH comprising a VH CDR1 having an amino acid sequence of SEQ ID NO:514, a VH CDR2 having an amino acid sequence of SEQ ID NO:515, and a VH CDR3 having an amino acid sequence of SEQ ID NO:516; and (ii) a VL comprising a VL CDR1 having an amino acid sequence of SEQ ID NO:517, a VL CDR2 having an amino acid sequence of SEQ ID NO:518, and a VL CDR3 having an amino acid sequence of SEQ ID NO:519. In some embodiments, the first binding domain that binds to TRGV9 comprises: (i) a VH comprising a VH CDR1 having an amino acid sequence of SEQ ID NO:520, a VH CDR2 having an amino acid sequence of SEQ ID NO:521, and a VH CDR3 having an amino acid sequence of SEQ ID NO:522; and (ii) a VL comprising a VL CDR1 having an amino acid sequence of SEQ ID NO:523, a VL CDR2 having an amino acid sequence of SEQ ID NO:524, and a VL CDR3 having an amino acid sequence of SEQ ID NO:525. In some embodiments, the first binding domain that binds to TRGV9 comprises: (i) a VH comprising a VH CDR1 having an amino acid sequence of SEQ ID NO:526, a VH CDR2 having an amino acid sequence of SEQ ID NO:527, and a VH CDR3 having an amino acid sequence of SEQ ID NO:528; and (ii) a VL comprising a VL CDR1 having an amino acid sequence of SEQ ID NO:529, a VL CDR2 having an amino acid sequence of SEQ ID NO:530, and a VL CDR3 having an amino acid sequence of SEQ ID NO:531. In some embodiments, the first binding domain that binds to TRGV9 comprises: (i) a VH comprising a VH CDR1 having an amino acid sequence of SEQ ID NO:532, a VH CDR2 having an amino acid sequence of SEQ ID NO:533, and a VH CDR3 having an amino acid sequence of SEQ ID NO:534; and (ii) a VL comprising a VL CDR1 having an amino acid sequence of SEQ ID NO:535, a VL CDR2 having an amino acid sequence of SEQ ID NO:536, and a VL CDR3 having an amino acid sequence of SEQ ID NO:537. In some embodiments, the first binding domain that binds to TRGV9 comprises: (i) a VH comprising a VH CDR1 having an amino acid sequence of SEQ ID NO:538, a VH CDR2 having an amino acid sequence of SEQ ID NO:539, and a VH CDR3 having an amino acid sequence of SEQ ID NO:540; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In some embodiments, the first binding domain that binds to TRGV9 comprises: (i) a VH comprising a VH CDR1 having an amino acid sequence of SEQ ID NO:538, a VH CDR2 having an amino acid sequence of SEQ ID NO:720, and a VH CDR3 having an amino acid sequence of SEQ ID NO:721; and (ii) a VL comprising a VL CDR1 having an amino acid sequence of SEQ ID NO:541, a VL CDR2 having an amino acid sequence of SEQ ID NO:542, and a VL CDR3 having an amino acid sequence of SEQ ID NO:543. In some embodiments, the first binding domain that binds to TRGV9 comprises: (i) a VH comprising a VH CDR1 having an amino acid sequence of SEQ ID NO:544, a VH CDR2 having an amino acid sequence of SEQ ID NO:545, and a VH CDR3 having an amino acid sequence of SEQ ID NO:546; and (ii) a VL comprising a VL CDR1 having an amino acid sequence of SEQ ID NO:547, a VL CDR2 having an amino acid sequence of SEQ ID NO:548, and a VL CDR3 having an amino acid sequence of SEQ ID NO:549. In some embodiments, the first binding domain that binds to TRGV9 comprises: (i) a VH comprising a VH CDR1 having an amino acid sequence of SEQ ID NO:550, a VH CDR2 having an amino acid sequence of SEQ ID NO:551, and a VH CDR3 having an amino acid sequence of SEQ ID NO:552; and (ii) a VL comprising a VL CDR1 having an amino acid sequence of SEQ ID NO:553, a VL CDR2 having an amino acid sequence of SEQ ID NO:554, and a VL CDR3 having an amino acid sequence of SEQ ID NO:555. In some embodiments, the second binding domain that binds CD123 comprises: (i) a VH comprising a VH CDR1 having an amino acid sequence of SEQ ID NO:556, a VH CDR2 having an amino acid sequence of SEQ ID NO:557, and a VH CDR3 having an amino acid sequence of SEQ ID NO:558; and (ii) a VL comprising a VL CDR1 having an amino acid sequence of SEQ ID NO:559, a VL CDR2 having an amino acid sequence of SEQ ID NO:560, and a VL CDR3 having an amino acid sequence of SEQ ID NO:561. In some embodiments, the second binding domain that binds CD123 comprises: (i) a VH comprising a VH CDR1 having an amino acid sequence of SEQ ID NO:562, a VH CDR2 having an amino acid sequence of SEQ ID NO:563, and a VH CDR3 having an amino acid sequence of SEQ ID NO:564; and (ii) a VL comprising a VL CDR1 having an amino acid sequence of SEQ ID NO:565, a VL CDR2 having an amino acid sequence of SEQ ID NO:566, and a VL CDR3 having an amino acid sequence of SEQ ID NO:567. In some embodiments, the second binding domain that binds CD123 comprises: (i) a VH comprising a VH CDR1 having an amino acid sequence of SEQ ID NO:568, a VH CDR2 having an amino acid sequence of SEQ ID NO:569, and a VH CDR3 having an amino acid sequence of SEQ ID NO:570; and (ii) a VL comprising a VL CDR1 having an amino acid sequence of SEQ ID NO:571, a VL CDR2 having an amino acid sequence of SEQ ID NO:572, and a VL CDR3 having an amino acid sequence of SEQ ID NO:573. In some embodiments, the second binding domain that binds CD123 comprises: (i) a VH comprising a VH CDR1 having an amino acid sequence of SEQ ID NO:574, a VH CDR2 having an amino acid sequence of SEQ ID NO:575, and a VH CDR3 having an amino acid sequence of SEQ ID NO:576; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In some embodiments, the second binding domain that binds CD123 comprises: (i) a VH comprising a VH CDR1 having an amino acid sequence of SEQ ID NO:574, a VH CDR2 having an amino acid sequence of SEQ ID NO:722, and a VH CDR3 having an amino acid sequence of SEQ ID NO:723; and (ii) a VL comprising a VL CDR1 having an amino acid sequence of SEQ ID NO:577, a VL CDR2 having an amino acid sequence of SEQ ID NO:578, and a VL CDR3 having an amino acid sequence of SEQ ID NO:579. In some embodiments, the second binding domain that binds CD123 comprises: (i) a VH comprising a VH CDR1 having an amino acid sequence of SEQ ID NO:580, a VH CDR2 having an amino acid sequence of SEQ ID NO:581, and a VH CDR3 having an amino acid sequence of SEQ ID NO:582; and (ii) a VL comprising a VL CDR1 having an amino acid sequence of SEQ ID NO:583, a VL CDR2 having an amino acid sequence of SEQ ID NO:584, and a VL CDR3 having an amino acid sequence of SEQ ID NO:585. In some embodiments, the second binding domain that binds CD123 comprises: (i) a VH comprising a VH CDR1 having an amino acid sequence of SEQ ID NO:586, a VH CDR2 having an amino acid sequence of SEQ ID NO:587, and a VH CDR3 having an amino acid sequence of SEQ ID NO:588; and (ii) a VL comprising a VL CDR1 having an amino acid sequence of SEQ ID NO:589, a VL CDR2 having an amino acid sequence of SEQ ID NO:590, and a VL CDR3 having an amino acid sequence of SEQ ID NO:591.

In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system.

In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is an antibody that binds to TRGV9, wherein the antibody comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system.

In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:7; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:34; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:35; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:36; and (ii) a VL comprising a VL CDR1, a VL CDR2, and a VL CDR3 having amino acid sequences of the VL CDR1, VL CDR2, and VL CDR3, respectively, of SEQ ID NO:8. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:65; and (ii) a VL comprising a VL CDR1, a VL CDR2, and a VL CDR3 having amino acid sequences of the VL CDR1, VL CDR2, and VL CDR3, respectively, of SEQ ID NO:66. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:67; and (ii) a VL comprising a VL CDR1, a VL CDR2, and a VL CDR3 having amino acid sequences of the VL CDR1, VL CDR2, and VL CDR3, respectively, of SEQ ID NO:68. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:95; and (ii) a VL comprising a VL CDR1, a VL CDR2, and a VL CDR3 having amino acid sequences of the VL CDR1, VL CDR2, and VL CDR3, respectively, of SEQ ID NO:96. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:104; and (ii) a VL comprising a VL CDR1, a VL CDR2, and a VL CDR3 having amino acid sequences of the VL CDR1, VL CDR2, and VL CDR3, respectively, of SEQ ID NO:105. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:113; and (ii) a VL comprising a VL CDR1, a VL CDR2, and a VL CDR3 having amino acid sequences of the VL CDR1, VL CDR2, and VL CDR3, respectively, of SEQ ID NO:114. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:123; and (ii) a VL comprising a VL CDR1, a VL CDR2, and a VL CDR3 having amino acid sequences of the VL CDR1, VL CDR2, and VL CDR3, respectively, of SEQ ID NO:124. In another aspect, provided herein is a bispecific antibody having a first binding domain that binds to TRGV9, wherein the first binding domain comprises: (i) a VH comprising a VH CDR1, a VH CDR2, and a VH CDR3 having amino acid sequences of the VH CDR1, VH CDR2, and VH CDR3, respectively, of SEQ ID NO:133; and (ii) a VL comprising a VL CDR1, a VL CDR2, and a VL CDR3 having amino acid sequences of the VL CDR1, VL CDR2, and VL CDR3, respectively, of SEQ ID NO:134. In certain embodiments, the bispecific antibody comprises a second binding domain that binds to tumor associated antigen. In certain embodiments, the bispecific antibody comprises a second binding domain that binds to CD123. In some embodiments, the second binding domain comprises: (i) a VH comprising a VH CDR1, a VH CDR2, and a VH CDR3 having amino acid sequences of the VH CDR1, VH CDR2, and VH CDR3, respectively, of SEQ ID NO:15; and (ii) a VL comprising a VL CDR1, a VL CDR2, and a VL CDR3 having amino acid sequences of the VL CDR1, VL CDR2, and VL CDR3, respectively, of SEQ ID NO:16. In some embodiments, the VH CDR1, VH CDR2, VH CDR3, VL CDR1, VL CDR2, and VL CDR3 sequences are according to the Kabat numbering system. In some embodiments, the VH CDR1, VH CDR2, VH CDR3, VL CDR1, VL CDR2, and VL CDR3 sequences are according to the Chothia numbering system. In some embodiments, the VH CDR1, VH CDR2, VH CDR3, VL CDR1, VL CDR2, and VL CDR3 sequences are according to the Exemplary numbering system. In some embodiments, the VH CDR1, VH CDR2, VH CDR3, VL CDR1, VL CDR2, and VL CDR3 sequences are according to the Contact numbering system. In some embodiments, the VH CDR1, VH CDR2, VH CDR3, VL CDR1, VL CDR2, and VL CDR3 sequences are according to the IMGT numbering system. In some embodiments, the VH CDR1, VH CDR2, VH CDR3, VL CDR1, VL CDR2, and VL CDR3 sequences are according to the AbM numbering system.

According to a particular aspect, provided herein is an isolated TRGV9 antibody or antigen-binding fragment thereof comprising (a) a first heavy chain (HC1); (b) a second heavy chain (HC2); (c) a first light chain (LC1); and (d) a second light chain (LC2). The HC1 can be associated with the LC1 and the HC2 can be associated with LC2. The HC1 can comprise a heavy chain complementarity determining region 1 (HCDR1), HCDR2, and HCDR3 comprising the amino acid sequences of:
 i. SEQ ID NO:1, SEQ ID NO:2, and SEQ ID NO:3, respectively,
 ii. SEQ ID NO:1, SEQ ID NO:2, and SEQ ID NO:31, respectively,
 iii. SEQ ID NO:1, SEQ ID NO:2, and SEQ ID NO:32, respectively, or
 iv. SEQ ID NO:1, SEQ ID NO:2, and SEQ ID NO:33, respectively,
and LC1 can comprise a light chain complementarity determining region 1 (LCDR1), LCDR2, and LCDR3 comprising the amino acid sequences of SEQ ID NO:4, SEQ ID NO:5, and SEQ ID NO:6, respectively. The HC1 and LC1 form a binding site for a first antigen, and the HC2 and LC2 form a binding site for a second antigen. The binding site for a first antigen can, for example, bind a TRGV9 on a γδ T cell. The binding site for a second antigen can, for example, bind a cancer antigen present on the surface of a cancer cell. The binding of the TRGV9 bispecific antibody to TRGV9 present on the surface of the γδ T cell, and the binding of the tumor associated antigen present on the surface of the cancer cell can, for example, result in the killing of the cancer cell.

According to another particular aspect, provided herein is an isolated TRGV9 antibody or antigen-binding fragment thereof comprising (a) a HC1; (b) a HC2; (c) a LC1; and (d) a LC2. The HC1 can be associated with the LC1 and the HC2 can be associated with LC2. In some embodiments, the HC1 comprises a HCDR1, HCDR2, and HCDR3 comprising the amino acid sequences of SEQ ID NO:1, SEQ ID NO:2, and SEQ ID NO:3, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:2, and SEQ ID NO:31, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:2, and SEQ ID NO:32, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:2, and SEQ ID NO:33, and LC1 comprises a LCDR1, LCDR2, and LCDR3 comprising the amino acid sequences of SEQ ID NO:4, SEQ ID NO:5, and SEQ ID NO:6, respectively. In some embodiments, the HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively. In some embodiments, the HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively. In some embodiments, the HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively. In some embodiments, the HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively. In some embodiments, the HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively. In some embodiments, the HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively. In some embodiments, the HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively. In some embodiments, the HC1 comprises a HCDR1, HCDR2, and HCDR3 comprising the amino acid sequences of SEQ ID NO:160, SEQ ID NO:161, and SEQ ID NO:162, respectively, and LC1 comprises a LCDR1, LCDR2, and LCDR3 comprising the amino acid sequences of SEQ ID NO:163, SEQ ID NO:164, and SEQ ID NO:165, respectively. In some embodiments, the HC1 comprises a HCDR1, HCDR2, and HCDR3 comprising the amino acid sequences of SEQ ID NO:166, SEQ ID NO:167, and SEQ ID NO:168, respectively, and LC1 comprises a LCDR1, LCDR2, and LCDR3 comprising the amino acid sequences of SEQ ID NO:169, SEQ ID NO:170, and SEQ ID NO:171, respectively. In some embodiments, the HC1 comprises a HCDR1, HCDR2, and HCDR3 comprising the amino acid sequences of SEQ ID NO:172, SEQ ID NO:173, and SEQ ID NO:174, respectively, and LC1 comprises a LCDR1, LCDR2, and LCDR3 comprising the amino acid sequences of SEQ ID NO:175, SEQ ID NO:176, and SEQ ID NO:177, respectively. In some embodiments, the HC1 comprises a HCDR1, HCDR2, and HCDR3 comprising the amino acid sequences of SEQ ID NO:178, SEQ ID NO:179, and SEQ ID NO:180, respectively, and LC1 comprises a LCDR1, LCDR2, and LCDR3 comprising the amino acid sequences of SEQ ID NO:181, SEQ ID NO:182, and SEQ ID NO:183, respectively. In some embodiments, the HC1 comprises a HCDR1, HCDR2, and HCDR3 comprising the amino acid sequences of SEQ ID NO:178, SEQ ID NO:700, and SEQ ID NO:701, respectively, and LC1 comprises a LCDR1, LCDR2, and LCDR3 comprising the amino acid sequences of SEQ ID NO:181, SEQ ID NO:182, and SEQ ID NO:183, respectively. In some embodiments, the HC1 comprises a HCDR1, HCDR2, and HCDR3 comprising the amino acid sequences of SEQ ID NO:184, SEQ ID NO:185, and SEQ ID NO:186, respectively, and LC1 comprises a LCDR1, LCDR2, and LCDR3 comprising the amino acid sequences of SEQ ID NO:187, SEQ ID NO:188, and SEQ ID NO:189, respectively. In some embodiments, the HC1 comprises a HCDR1, HCDR2, and HCDR3 comprising the amino acid sequences of SEQ ID NO:190, SEQ ID NO:191, and SEQ ID NO:192, respectively, and LC1 comprises a LCDR1, LCDR2, and LCDR3 comprising the amino acid sequences of SEQ ID NO:193, SEQ ID NO:194, and SEQ ID NO:195, respectively. In some embodiments, the HC1 comprises a HCDR1, HCDR2, and HCDR3 comprising the amino acid sequences of SEQ ID NO:196, SEQ ID NO:197, and SEQ ID NO:198, respectively, and LC1 comprises a LCDR1, LCDR2, and LCDR3 comprising the amino acid sequences of SEQ ID NO:199, SEQ ID NO:200, and SEQ ID NO:201, respectively. In some embodiments, the HC1 comprises a HCDR1, HCDR2, and HCDR3 comprising the amino acid sequences of SEQ ID NO:202, SEQ ID NO:203, and SEQ ID NO:204, respectively, and LC1 comprises a LCDR1, LCDR2, and LCDR3 comprising the amino acid sequences of SEQ ID NO:205, SEQ ID NO:206, and SEQ ID NO:207, respectively. In some embodiments, the HC1 comprises a HCDR1, HCDR2, and HCDR3 comprising the amino acid sequences of SEQ ID NO:208, SEQ ID NO:209, and SEQ ID NO:210, respectively, and LC1 comprises a LCDR1, LCDR2, and LCDR3 comprising the amino acid sequences of SEQ ID NO:211, SEQ ID NO:212, and SEQ ID NO:213, respectively. In some embodiments, the HC1 comprises a HCDR1, HCDR2, and HCDR3 comprising the amino acid sequences of SEQ ID NO:214, SEQ ID NO:215, and SEQ ID NO:216, respectively, and LC1 comprises a LCDR1, LCDR2, and LCDR3 comprising the amino acid sequences of SEQ ID NO:217, SEQ ID NO:218, and SEQ ID NO:219, respectively. In some embodiments, the HC1 comprises a HCDR1, HCDR2, and HCDR3 comprising the amino acid sequences of SEQ ID NO:214, SEQ ID NO:702, and SEQ ID NO:703, respectively, and LC1 comprises a LCDR1, LCDR2, and LCDR3 comprising the amino acid sequences of SEQ ID NO:217, SEQ ID NO:218, and SEQ ID NO:219, respectively. In some embodiments, the HC1 comprises a HCDR1, HCDR2, and HCDR3 comprising the amino acid sequences of SEQ ID NO:220, SEQ ID NO:221, and SEQ ID NO:222, respectively, and LC1 comprises a LCDR1, LCDR2, and LCDR3 comprising the amino acid sequences of SEQ ID NO:223, SEQ ID NO:224, and SEQ ID NO:225, respectively. In some embodiments, the HC1 comprises a HCDR1, HCDR2, and HCDR3 comprising the amino acid sequences of SEQ ID NO:226, SEQ ID NO:227, and SEQ ID NO:228, respectively, and LC1 comprises a LCDR1, LCDR2, and LCDR3 comprising the amino acid sequences of SEQ ID NO:229, SEQ ID NO:230, and SEQ ID NO:231, respectively. In some embodiments, the HC1 comprises a HCDR1, HCDR2, and HCDR3 comprising the amino acid sequences of SEQ ID NO:232, SEQ ID NO:233, and SEQ ID NO:234, respectively, and LC1 comprises a LCDR1, LCDR2, and LCDR3 comprising the amino acid sequences of SEQ ID NO:235, SEQ ID NO:236, and SEQ ID NO:237, respectively. In some embodiments, the HC1 comprises a HCDR1, HCDR2, and HCDR3 comprising the amino acid sequences of SEQ ID NO:238, SEQ ID NO:239, and SEQ ID NO:240, respectively, and LC1 comprises a LCDR1, LCDR2, and LCDR3 comprising the amino acid sequences of SEQ ID NO:241, SEQ ID NO:242, and SEQ ID NO:243, respectively. In some embodiments, the HC1 comprises a HCDR1, HCDR2, and HCDR3 comprising the amino acid sequences of SEQ ID NO:244, SEQ ID NO:245, and SEQ ID NO:246, respectively, and LC1 comprises a LCDR1, LCDR2, and LCDR3 comprising the amino acid sequences of SEQ ID NO:247, SEQ ID NO:248, and SEQ ID NO:249, respectively. In some embodiments, the HC1 comprises a HCDR1, HCDR2, and HCDR3 comprising the amino acid sequences of SEQ ID NO:250, SEQ ID NO:251, and SEQ ID NO:252, respectively, and LC1 comprises a LCDR1, LCDR2, and LCDR3 comprising the amino acid sequences of SEQ ID NO:253, SEQ ID NO:254, and SEQ ID NO:255, respectively. In some embodiments, the HC1 comprises a HCDR1, HCDR2, and HCDR3 comprising the amino acid sequences of SEQ ID NO:250, SEQ ID NO:704, and SEQ ID NO:705, respectively, and LC1 comprises a LCDR1, LCDR2, and LCDR3 comprising the amino acid sequences of SEQ ID NO:253, SEQ ID NO:254, and SEQ ID NO:255, respectively. In some embodiments, the HC1 comprises a HCDR1, HCDR2, and HCDR3 comprising the amino acid sequences of SEQ ID NO:256, SEQ ID NO:257, and SEQ ID NO:258, respectively, and LC1 comprises a LCDR1, LCDR2, and LCDR3 comprising the amino acid sequences of SEQ ID NO:259, SEQ ID NO:260, and SEQ ID NO:261, respectively. In some embodiments, the HC1 comprises a HCDR1, HCDR2, and HCDR3 comprising the amino acid sequences of SEQ ID NO:262, SEQ ID NO:263, and SEQ ID NO:264, respectively, and LC1 comprises a LCDR1, LCDR2, and LCDR3 comprising the amino acid sequences of SEQ ID NO:265, SEQ ID NO:266, and SEQ ID NO:267, respectively. In some embodiments, the HC1 comprises a HCDR1, HCDR2, and HCDR3 comprising the amino acid sequences of SEQ ID NO:268, SEQ ID NO:269, and SEQ ID NO:270, respectively, and LC1 comprises a LCDR1, LCDR2, and LCDR3 comprising the amino acid sequences of SEQ ID NO:271, SEQ ID NO:272, and SEQ ID NO:273, respectively. In some embodiments, the HC1 comprises a HCDR1, HCDR2, and HCDR3 comprising the amino acid sequences of SEQ ID NO:274, SEQ ID NO:275, and SEQ ID NO:276, respectively, and LC1 comprises a LCDR1, LCDR2, and LCDR3 comprising the amino acid sequences of SEQ ID NO:277, SEQ ID NO:278, and SEQ ID NO:279, respectively. In some embodiments, the HC1 comprises a HCDR1, HCDR2, and HCDR3 comprising the amino acid sequences of SEQ ID NO:280, SEQ ID NO:281, and SEQ ID NO:282, respectively, and LC1 comprises a LCDR1, LCDR2, and LCDR3 comprising the amino acid sequences of SEQ ID NO:283, SEQ ID NO:284, and SEQ ID NO:285, respectively. In some embodiments, the HC1 comprises a HCDR1, HCDR2, and HCDR3 comprising the amino acid sequences of SEQ ID NO:286, SEQ ID NO:287, and SEQ ID NO:288, respectively, and LC1 comprises a LCDR1, LCDR2, and LCDR3 comprising the amino acid sequences of SEQ ID NO:289, SEQ ID NO:290, and SEQ ID NO:291, respectively. In some embodiments, the HC1 comprises a HCDR1, HCDR2, and HCDR3 comprising the amino acid sequences of SEQ ID NO:286, SEQ ID NO:706, and SEQ ID NO:707, respectively, and LC1 comprises a LCDR1, LCDR2, and LCDR3 comprising the amino acid sequences of SEQ ID NO:289, SEQ ID NO:290, and SEQ ID NO:291, respectively. In some embodiments, the HC1 comprises a HCDR1, HCDR2, and HCDR3 comprising the amino acid sequences of SEQ ID NO:292, SEQ ID NO:293, and SEQ ID NO:294, respectively, and LC1 comprises a LCDR1, LCDR2, and LCDR3 comprising the amino acid sequences of SEQ ID NO:295, SEQ ID NO:296, and SEQ ID NO:297, respectively. In some embodiments, the HC1 comprises a HCDR1, HCDR2, and HCDR3 comprising the amino acid sequences of SEQ ID NO:298, SEQ ID NO:299, and SEQ ID NO:300, respectively, and LC1 comprises a LCDR1, LCDR2, and LCDR3 comprising the amino acid sequences of SEQ ID NO:301, SEQ ID NO:302, and SEQ ID NO:303, respectively. In some embodiments, the HC1 comprises a HCDR1, HCDR2, and HCDR3 comprising the amino acid sequences of SEQ ID NO:304, SEQ ID NO:305, and SEQ ID NO:306, respectively, and LC1 comprises a LCDR1, LCDR2, and LCDR3 comprising the amino acid sequences of SEQ ID NO:307, SEQ ID NO:308, and SEQ ID NO:309, respectively. In some embodiments, the HC1 comprises a HCDR1, HCDR2, and HCDR3 comprising the amino acid sequences of SEQ ID NO:310, SEQ ID NO:311, and SEQ ID NO:312, respectively, and LC1 comprises a LCDR1, LCDR2, and LCDR3 comprising the amino acid sequences of SEQ ID NO:313, SEQ ID NO:314, and SEQ ID NO:315, respectively. In some embodiments, the HC1 comprises a HCDR1, HCDR2, and HCDR3 comprising the amino acid sequences of SEQ ID NO:316, SEQ ID NO:317, and SEQ ID NO:318, respectively, and LC1 comprises a LCDR1, LCDR2, and LCDR3 comprising the amino acid sequences of SEQ ID NO:319, SEQ ID NO:320, and SEQ ID NO:321, respectively. In some embodiments, the HC1 comprises a HCDR1, HCDR2, and HCDR3 comprising the amino acid sequences of SEQ ID NO:322, SEQ ID NO:323, and SEQ ID NO:324, respectively, and LC1 comprises a LCDR1, LCDR2, and LCDR3 comprising the amino acid sequences of SEQ ID NO:325, SEQ ID NO:326, and SEQ ID NO:327, respectively. In some embodiments, the HC1 comprises a HCDR1, HCDR2, and HCDR3 comprising the amino acid sequences of SEQ ID NO:322, SEQ ID NO:708, and SEQ ID NO:709, respectively, and LC1 comprises a LCDR1, LCDR2, and LCDR3 comprising the amino acid sequences of SEQ ID NO:325, SEQ ID NO:326, and SEQ ID NO:327, respectively. In some embodiments, the HC1 comprises a HCDR1, HCDR2, and HCDR3 comprising the amino acid sequences of SEQ ID NO:328, SEQ ID NO:329, and SEQ ID NO:330, respectively, and LC1 comprises a LCDR1, LCDR2, and LCDR3 comprising the amino acid sequences of SEQ ID NO:331, SEQ ID NO:332, and SEQ ID NO:333, respectively. In some embodiments, the HC1 comprises a HCDR1, HCDR2, and HCDR3 comprising the amino acid sequences of SEQ ID NO:334, SEQ ID NO:335, and SEQ ID NO:336, respectively, and LC1 comprises a LCDR1, LCDR2, and LCDR3 comprising the amino acid sequences of SEQ ID NO:337, SEQ ID NO:338, and SEQ ID NO:339, respectively. In some embodiments, the HC1 comprises a HCDR1, HCDR2, and HCDR3 comprising the amino acid sequences of SEQ ID NO:340, SEQ ID NO:341, and SEQ ID NO:342, respectively, and LC1 comprises a LCDR1, LCDR2, and LCDR3 comprising the amino acid sequences of SEQ ID NO:343, SEQ ID NO:344, and SEQ ID NO:345, respectively. In some embodiments, the HC1 comprises a HCDR1, HCDR2, and HCDR3 comprising the amino acid sequences of SEQ ID NO:346, SEQ ID NO:347, and SEQ ID NO:348, respectively, and LC1 comprises a LCDR1, LCDR2, and LCDR3 comprising the amino acid sequences of SEQ ID NO:349, SEQ ID NO:350, and SEQ ID NO:351, respectively. In some embodiments, the HC1 comprises a HCDR1, HCDR2, and HCDR3 comprising the amino acid sequences of SEQ ID NO:352, SEQ ID NO:353, and SEQ ID NO:354, respectively, and LC1 comprises a LCDR1, LCDR2, and LCDR3 comprising the amino acid sequences of SEQ ID NO:355, SEQ ID NO:356, and SEQ ID NO:357, respectively. In some embodiments, the HC1 comprises a HCDR1, HCDR2, and HCDR3 comprising the amino acid sequences of SEQ ID NO:358, SEQ ID NO:359, and SEQ ID NO:360, respectively, and LC1 comprises a LCDR1, LCDR2, and LCDR3 comprising the amino acid sequences of SEQ ID NO:361, SEQ ID NO:362, and SEQ ID NO:363, respectively. In some embodiments, the HC1 comprises a HCDR1, HCDR2, and HCDR3 comprising the amino acid sequences of SEQ ID NO:358, SEQ ID NO:710, and SEQ ID NO:711, respectively, and LC1 comprises a LCDR1, LCDR2, and LCDR3 comprising the amino acid sequences of SEQ ID NO:361, SEQ ID NO:362, and SEQ ID NO:363, respectively. In some embodiments, the HC1 comprises a HCDR1, HCDR2, and HCDR3 comprising the amino acid sequences of SEQ ID NO:364, SEQ ID NO:365, and SEQ ID NO:366, respectively, and LC1 comprises a LCDR1, LCDR2, and LCDR3 comprising the amino acid sequences of SEQ ID NO:367, SEQ ID NO:368, and SEQ ID NO:369, respectively. In some embodiments, the HC1 comprises a HCDR1, HCDR2, and HCDR3 comprising the amino acid sequences of SEQ ID NO:370, SEQ ID NO:371, and SEQ ID NO:372, respectively, and LC1 comprises a LCDR1, LCDR2, and LCDR3 comprising the amino acid sequences of SEQ ID NO:373, SEQ ID NO:374, and SEQ ID NO:375, respectively. In some embodiments, the HC1 comprises a HCDR1, HCDR2, and HCDR3 comprising the amino acid sequences of SEQ ID NO:376, SEQ ID NO:377, and SEQ ID NO:378, respectively, and LC1 comprises a LCDR1, LCDR2, and LCDR3 comprising the amino acid sequences of SEQ ID NO:379, SEQ ID NO:380, and SEQ ID NO:381, respectively. In some embodiments, the HC1 comprises a HCDR1, HCDR2, and HCDR3 comprising the amino acid sequences of SEQ ID NO:382, SEQ ID NO:383, and SEQ ID NO:384, respectively, and LC1 comprises a LCDR1, LCDR2, and LCDR3 comprising the amino acid sequences of SEQ ID NO:385, SEQ ID NO:386, and SEQ ID NO:387, respectively. In some embodiments, the HC1 comprises a HCDR1, HCDR2, and HCDR3 comprising the amino acid sequences of SEQ ID NO:388, SEQ ID NO:389, and SEQ ID NO:390, respectively, and LC1 comprises a LCDR1, LCDR2, and LCDR3 comprising the amino acid sequences of SEQ ID NO:391, SEQ ID NO:392, and SEQ ID NO:393, respectively. In some embodiments, the HC1 comprises a HCDR1, HCDR2, and HCDR3 comprising the amino acid sequences of SEQ ID NO:394, SEQ ID NO:395, and SEQ ID NO:396, respectively, and LC1 comprises a LCDR1, LCDR2, and LCDR3 comprising the amino acid sequences of SEQ ID NO:397, SEQ ID NO:398, and SEQ ID NO:399, respectively. In some embodiments, the HC1 comprises a HCDR1, HCDR2, and HCDR3 comprising the amino acid sequences of SEQ ID NO:394, SEQ ID NO:712, and SEQ ID NO:713, respectively, and LC1 comprises a LCDR1, LCDR2, and LCDR3 comprising the amino acid sequences of SEQ ID NO:397, SEQ ID NO:398, and SEQ ID NO:399, respectively. In some embodiments, the HC1 comprises a HCDR1, HCDR2, and HCDR3 comprising the amino acid sequences of SEQ ID NO:400, SEQ ID NO:401, and SEQ ID NO:402, respectively, and LC1 comprises a LCDR1, LCDR2, and LCDR3 comprising the amino acid sequences of SEQ ID NO:403, SEQ ID NO:404, and SEQ ID NO:405, respectively. In some embodiments, the HC1 comprises a HCDR1, HCDR2, and HCDR3 comprising the amino acid sequences of SEQ ID NO:406, SEQ ID NO:407, and SEQ ID NO:408, respectively, and LC1 comprises a LCDR1, LCDR2, and LCDR3 comprising the amino acid sequences of SEQ ID NO:409, SEQ ID NO:410, and SEQ ID NO:411, respectively. In some embodiments, the HC1 comprises a HCDR1, HCDR2, and HCDR3 comprising the amino acid sequences of SEQ ID NO:412, SEQ ID NO:413, and SEQ ID NO:414, respectively, and LC1 comprises a LCDR1, LCDR2, and LCDR3 comprising the amino acid sequences of SEQ ID NO:415, SEQ ID NO:416, and SEQ ID NO:417, respectively. In some embodiments, the HC1 comprises a HCDR1, HCDR2, and HCDR3 comprising the amino acid sequences of SEQ ID NO:418, SEQ ID NO:419, and SEQ ID NO:420, respectively, and LC1 comprises a LCDR1, LCDR2, and LCDR3 comprising the amino acid sequences of SEQ ID NO:421, SEQ ID NO:422, and SEQ ID NO:423, respectively. In some embodiments, the HC1 comprises a HCDR1, HCDR2, and HCDR3 comprising the amino acid sequences of SEQ ID NO:424, SEQ ID NO:425, and SEQ ID NO:426, respectively, and LC1 comprises a LCDR1, LCDR2, and LCDR3 comprising the amino acid sequences of SEQ ID NO:427, SEQ ID NO:428, and SEQ ID NO:429, respectively. In some embodiments, the HC1 comprises a HCDR1, HCDR2, and HCDR3 comprising the amino acid sequences of SEQ ID NO:430, SEQ ID NO:431, and SEQ ID NO:432, respectively, and LC1 comprises a LCDR1, LCDR2, and LCDR3 comprising the amino acid sequences of SEQ ID NO:433, SEQ ID NO:434, and SEQ ID NO:435, respectively. In some embodiments, the HC1 comprises a HCDR1, HCDR2, and HCDR3 comprising the amino acid sequences of SEQ ID NO:430, SEQ ID NO:714, and SEQ ID NO:715, respectively, and LC1 comprises a LCDR1, LCDR2, and LCDR3 comprising the amino acid sequences of SEQ ID NO:433, SEQ ID NO:434, and SEQ ID NO:435, respectively. In some embodiments, the HC1 comprises a HCDR1, HCDR2, and HCDR3 comprising the amino acid sequences of SEQ ID NO:436, SEQ ID NO:437, and SEQ ID NO:438, respectively, and LC1 comprises a LCDR1, LCDR2, and LCDR3 comprising the amino acid sequences of SEQ ID NO:439, SEQ ID NO:440, and SEQ ID NO:441, respectively. In some embodiments, the HC1 comprises a HCDR1, HCDR2, and HCDR3 comprising the amino acid sequences of SEQ ID NO:442, SEQ ID NO:443, and SEQ ID NO:444, respectively, and LC1 comprises a LCDR1, LCDR2, and LCDR3 comprising the amino acid sequences of SEQ ID NO:445, SEQ ID NO:446, and SEQ ID NO:447, respectively. In some embodiments, the HC1 comprises a HCDR1, HCDR2, and HCDR3 comprising the amino acid sequences of SEQ ID NO:448, SEQ ID NO:449, and SEQ ID NO:450, respectively, and LC1 comprises a LCDR1, LCDR2, and LCDR3 comprising the amino acid sequences of SEQ ID NO:451, SEQ ID NO:452, and SEQ ID NO:453, respectively. In some embodiments, the HC1 comprises a HCDR1, HCDR2, and HCDR3 comprising the amino acid sequences of SEQ ID NO:454, SEQ ID NO:455, and SEQ ID NO:456, respectively, and LC1 comprises a LCDR1, LCDR2, and LCDR3 comprising the amino acid sequences of SEQ ID NO:457, SEQ ID NO:458, and SEQ ID NO:459, respectively. In some embodiments, the HC1 comprises a HCDR1, HCDR2, and HCDR3 comprising the amino acid sequences of SEQ ID NO:460, SEQ ID NO:461, and SEQ ID NO:462, respectively, and LC1 comprises a LCDR1, LCDR2, and LCDR3 comprising the amino acid sequences of SEQ ID NO:463, SEQ ID NO:464, and SEQ ID NO:465, respectively. In some embodiments, the HC1 comprises a HCDR1, HCDR2, and HCDR3 comprising the amino acid sequences of SEQ ID NO:466, SEQ ID NO:467, and SEQ ID NO:468, respectively, and LC1 comprises a LCDR1, LCDR2, and LCDR3 comprising the amino acid sequences of SEQ ID NO:469, SEQ ID NO:470, and SEQ ID NO:471, respectively. In some embodiments, the HC1 comprises a HCDR1, HCDR2, and HCDR3 comprising the amino acid sequences of SEQ ID NO:466, SEQ ID NO:716, and SEQ ID NO:717, respectively, and LC1 comprises a LCDR1, LCDR2, and LCDR3 comprising the amino acid sequences of SEQ ID NO:469, SEQ ID NO:470, and SEQ ID NO:471, respectively. In some embodiments, the HC1 comprises a HCDR1, HCDR2, and HCDR3 comprising the amino acid sequences of SEQ ID NO:472, SEQ ID NO:473, and SEQ ID NO:474, respectively, and LC1 comprises a LCDR1, LCDR2, and LCDR3 comprising the amino acid sequences of SEQ ID NO:475, SEQ ID NO:476, and SEQ ID NO:477, respectively. In some embodiments, the HC1 comprises a HCDR1, HCDR2, and HCDR3 comprising the amino acid sequences of SEQ ID NO:478, SEQ ID NO:479, and SEQ ID NO:480, respectively, and LC1 comprises a LCDR1, LCDR2, and LCDR3 comprising the amino acid sequences of SEQ ID NO:481, SEQ ID NO:482, and SEQ ID NO:483, respectively. In some embodiments, the HC1 comprises a HCDR1, HCDR2, and HCDR3 comprising the amino acid sequences of SEQ ID NO:484, SEQ ID NO:485, and SEQ ID NO:486, respectively, and LC1 comprises a LCDR1, LCDR2, and LCDR3 comprising the amino acid sequences of SEQ ID NO:487, SEQ ID NO:488, and SEQ ID NO:489, respectively. In some embodiments, the HC1 comprises a HCDR1, HCDR2, and HCDR3 comprising the amino acid sequences of SEQ ID NO:490, SEQ ID NO:491, and SEQ ID NO:492, respectively, and LC1 comprises a LCDR1, LCDR2, and LCDR3 comprising the amino acid sequences of SEQ ID NO:493, SEQ ID NO:494, and SEQ ID NO:495, respectively. In some embodiments, the HC1 comprises a HCDR1, HCDR2, and HCDR3 comprising the amino acid sequences of SEQ ID NO:496, SEQ ID NO:497, and SEQ ID NO:498, respectively, and LC1 comprises a LCDR1, LCDR2, and LCDR3 comprising the amino acid sequences of SEQ ID NO:499, SEQ ID NO:500, and SEQ ID NO:501, respectively. In some embodiments, the HC1 comprises a HCDR1, HCDR2, and HCDR3 comprising the amino acid sequences of SEQ ID NO:502, SEQ ID NO:503, and SEQ ID NO:504, respectively, and LC1 comprises a LCDR1, LCDR2, and LCDR3 comprising the amino acid sequences of SEQ ID NO:505, SEQ ID NO:506, and SEQ ID NO:507, respectively. In some embodiments, the HC1 comprises a HCDR1, HCDR2, and HCDR3 comprising the amino acid sequences of SEQ ID NO:502, SEQ ID NO:718, and SEQ ID NO:719, respectively, and LC1 comprises a LCDR1, LCDR2, and LCDR3 comprising the amino acid sequences of SEQ ID NO:505, SEQ ID NO:506, and SEQ ID NO:507, respectively. In some embodiments, the HC1 comprises a HCDR1, HCDR2, and HCDR3 comprising the amino acid sequences of SEQ ID NO:508, SEQ ID NO:509, and SEQ ID NO:510, respectively, and LC1 comprises a LCDR1, LCDR2, and LCDR3 comprising the amino acid sequences of SEQ ID NO:511, SEQ ID NO:512, and SEQ ID NO:513, respectively. In some embodiments, the HC1 comprises a HCDR1, HCDR2, and HCDR3 comprising the amino acid sequences of SEQ ID NO:514, SEQ ID NO:515, and SEQ ID NO:516, respectively, and LC1 comprises a LCDR1, LCDR2, and LCDR3 comprising the amino acid sequences of SEQ ID NO:517, SEQ ID NO:518, and SEQ ID NO:519, respectively. In some embodiments, the HC1 comprises a HCDR1, HCDR2, and HCDR3 comprising the amino acid sequences of SEQ ID NO:520, SEQ ID NO:521, and SEQ ID NO:522, respectively, and LC1 comprises a LCDR1, LCDR2, and LCDR3 comprising the amino acid sequences of SEQ ID NO:523, SEQ ID NO:524, and SEQ ID NO:525, respectively. In some embodiments, the HC1 comprises a HCDR1, HCDR2, and HCDR3 comprising the amino acid sequences of SEQ ID NO:526, SEQ ID NO:527, and SEQ ID NO:528, respectively, and LC1 comprises a LCDR1, LCDR2, and LCDR3 comprising the amino acid sequences of SEQ ID NO:529, SEQ ID NO:530, and SEQ ID NO:531, respectively. In some embodiments, the HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively. In some embodiments, the HC1 comprises a HCDR1, HCDR2, and HCDR3 comprising the amino acid sequences of SEQ ID NO:538, SEQ ID NO:539, and SEQ ID NO:540, respectively, and LC1 comprises a LCDR1, LCDR2, and LCDR3 comprising the amino acid sequences of SEQ ID NO:541, SEQ ID NO:542, and SEQ ID NO:543, respectively. In some embodiments, the HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively. In some embodiments, the HC1 comprises a HCDR1, HCDR2, and HCDR3 comprising the amino acid sequences of SEQ ID NO:538, SEQ ID NO:720, and SEQ ID NO:721, respectively, and LC1 comprises a LCDR1, LCDR2, and LCDR3 comprising the amino acid sequences of SEQ ID NO:541, SEQ ID NO:542, and SEQ ID NO:543, respectively. In some embodiments, the HC1 comprises a HCDR1, HCDR2, and HCDR3 comprising the amino acid sequences of SEQ ID NO:544, SEQ ID NO:545, and SEQ ID NO:546, respectively, and LC1 comprises a LCDR1, LCDR2, and LCDR3 comprising the amino acid sequences of SEQ ID NO:547, SEQ ID NO:548, and SEQ ID NO:549, respectively. In some embodiments, the HC1 comprises a HCDR1, HCDR2, and HCDR3 comprising the amino acid sequences of SEQ ID NO:550, SEQ ID NO:551, and SEQ ID NO:552, respectively, and LC1 comprises a LCDR1, LCDR2, and LCDR3 comprising the amino acid sequences of SEQ ID NO:553, SEQ ID NO:554, and SEQ ID NO:555, respectively. In specific embodiments, the HC1 and LC1 form a binding site for a first antigen, and the HC2 and LC2 form a binding site for a second antigen. In some embodiments, HC1 is associated with LC1 and HC2 is associated with LC2. In some embodiments, HC1 and LC1 form a binding site for a first antigen that specifically binds TRGV9. The binding site for a first antigen can, for example, bind a TRGV9 on a γδ T cell. The binding site for a second antigen can, for example, bind a cancer antigen present on the surface of a cancer cell. In some embodiments, the cancer antigen is CD123. The binding of the TRGV9 bispecific antibody to TRGV9 present on the surface of the γδ T cell, and the binding of the tumor associated antigen present on the surface of the cancer cell can, for example, result in the killing of the cancer cell.

In certain embodiments, the first binding domain of the bispecific antibody specifically binds TRGV9. In some embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody.

Also provided herein are anti-TRGV9/anti-CD123 bispecific antibodies or antigen-binding fragments thereof comprising an anti-TRGV9 antibody or an antigen-binding fragment thereof and an anti-CD123 antibody or antigen-binding fragment thereof. In certain embodiments the anti-TRGV9/anti-CD123 bispecific antibody or antigen binding fragment thereof comprises (a) a HC1; (b) a HC2; (c) a LC1; and a LC2. In some embodiments, HC1 is associated with LC1 and HC2 is associated with LC2. HC1 can, for example, comprise a HCDR1, HCDR2, and HCDR3 comprising the amino acid sequences of:
  i. SEQ ID NO:1, SEQ ID NO:2, and SEQ ID NO:3, respectively,
  ii. SEQ ID NO:1, SEQ ID NO:2, and SEQ ID NO:31, respectively,
  iii. SEQ ID NO:1, SEQ ID NO:2, and SEQ ID NO:32, respectively, or
  iv. SEQ ID NO:1, SEQ ID NO:2, and SEQ ID NO:33, respectively,
and LC1 can, for example, comprise a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. HC2 can, for example, comprise a HCDR1, HCDR2, and HCDR3 comprising the amino acid sequences of SEQ ID NO:9, SEQ ID NO:10, and SEQ ID NO:11, respectively, and LC2 can, for example, comprise a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In certain embodiments, the HC1 comprises the amino acid sequence of SEQ ID NO:7, SEQ ID NO:34, SEQ ID NO:35, or SEQ ID NO:36, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the TRGV9 is on the surface of a γδ T cell. In certain embodiments, the CD123 is on the surface of a cancer cell (e.g., a leukemia cell).

Also provided herein are anti-TRGV9/anti-CD123 bispecific antibodies or antigen-binding fragments thereof comprising an anti-TRGV9 antibody or an antigen-binding fragment thereof and an anti-CD123 antibody or antigen-binding fragment thereof. In certain embodiments the anti-TRGV9/anti-CD123 bispecific antibody or antigen binding fragment thereof comprises (a) a HC1; (b) a HC2; (c) a LC1; and a LC2. In some embodiments, HC1 is associated with LC1 and HC2 is associated with LC2. In some embodiments, HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a binding site for a first antigen that specifically binds TRGV9. In some embodiments, HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively, to form a binding site for a first antigen that specifically binds TRGV9. In some embodiments, the HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a binding site for a first antigen that specifically binds TRGV9. In some embodiments, the HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a binding site for a first antigen that specifically binds TRGV9. In some embodiments, the HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a binding site for a first antigen that specifically binds TRGV9. In some embodiments, the HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a binding site for a first antigen that specifically binds TRGV9. In some embodiments, the HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a binding site for a first antigen that specifically binds TRGV9. In some embodiments, the HC1 comprises a HCDR1, HCDR2, and HCDR3 comprising the amino acid sequences of SEQ ID NO:160, SEQ ID NO:161, and SEQ ID NO:162, respectively, and LC1 comprises a LCDR1, LCDR2, and LCDR3 comprising the amino acid sequences of SEQ ID NO:163, SEQ ID NO:164, and SEQ ID NO:165, respectively, to form a binding site for a first antigen that specifically binds TRGV9. In some embodiments, the HC1 comprises a HCDR1, HCDR2, and HCDR3 comprising the amino acid sequences of SEQ ID NO:166, SEQ ID NO:167, and SEQ ID NO:168, respectively, and LC1 comprises a LCDR1, LCDR2, and LCDR3 comprising the amino acid sequences of SEQ ID NO:169, SEQ ID NO:170, and SEQ ID NO:171, respectively, to form a binding site for a first antigen that specifically binds TRGV9. In some embodiments, the HC1 comprises a HCDR1, HCDR2, and HCDR3 comprising the amino acid sequences of SEQ ID NO:172, SEQ ID NO:173, and SEQ ID NO:174, respectively, and LC1 comprises a LCDR1, LCDR2, and LCDR3 comprising the amino acid sequences of SEQ ID NO:175, SEQ ID NO:176, and SEQ ID NO:177, respectively, to form a binding site for a first antigen that specifically binds TRGV9. In some embodiments, the HC1 comprises a HCDR1, HCDR2, and HCDR3 comprising the amino acid sequences of SEQ ID NO:178, SEQ ID NO:179, and SEQ ID NO:180, respectively, and LC1 comprises a LCDR1, LCDR2, and LCDR3 comprising the amino acid sequences of SEQ ID NO:181, SEQ ID NO:182, and SEQ ID NO:183, respectively, to form a binding site for a first antigen that specifically binds TRGV9. In some embodiments, the HC1 comprises a HCDR1, HCDR2, and HCDR3 comprising the amino acid sequences of SEQ ID NO:178, SEQ ID NO:700, and SEQ ID NO:701, respectively, and LC1 comprises a LCDR1, LCDR2, and LCDR3 comprising the amino acid sequences of SEQ ID NO:181, SEQ ID NO:182, and SEQ ID NO:183, respectively, to form a binding site for a first antigen that specifically binds TRGV9. In some embodiments, the HC1 comprises a HCDR1, HCDR2, and HCDR3 comprising the amino acid sequences of SEQ ID NO:184, SEQ ID NO:185, and SEQ ID NO:186, respectively, and LC1 comprises a LCDR1, LCDR2, and LCDR3 comprising the amino acid sequences of SEQ ID NO:187, SEQ ID NO:188, and SEQ ID NO:189, respectively, to form a binding site for a first antigen that specifically binds TRGV9. In some embodiments, the HC1 comprises a HCDR1, HCDR2, and HCDR3 comprising the amino acid sequences of SEQ ID NO:190, SEQ ID NO:191, and SEQ ID NO:192, respectively, and LC1 comprises a LCDR1, LCDR2, and LCDR3 comprising the amino acid sequences of SEQ ID NO:193, SEQ ID NO:194, and SEQ ID NO:195, respectively, to form a binding site for a first antigen that specifically binds TRGV9. In some embodiments, the HC1 comprises a HCDR1, HCDR2, and HCDR3 comprising the amino acid sequences of SEQ ID NO:196, SEQ ID NO:197, and SEQ ID NO:198, respectively, and LC1 comprises a LCDR1, LCDR2, and LCDR3 comprising the amino acid sequences of SEQ ID NO:199, SEQ ID NO:200, and SEQ ID NO:201, respectively, to form a binding site for a first antigen that specifically binds TRGV9. In some embodiments, the HC1 comprises a HCDR1, HCDR2, and HCDR3 comprising the amino acid sequences of SEQ ID NO:202, SEQ ID NO:203, and SEQ ID NO:204, respectively, and LC1 comprises a LCDR1, LCDR2, and LCDR3 comprising the amino acid sequences of SEQ ID NO:205, SEQ ID NO:206, and SEQ ID NO:207, respectively, to form a binding site for a first antigen that specifically binds TRGV9. In some embodiments, the HC1 comprises a HCDR1, HCDR2, and HCDR3 comprising the amino acid sequences of SEQ ID NO:208, SEQ ID NO:209, and SEQ ID NO:210, respectively, and LC1 comprises a LCDR1, LCDR2, and LCDR3 comprising the amino acid sequences of SEQ ID NO:211, SEQ ID NO:212, and SEQ ID NO:213, respectively, to form a binding site for a first antigen that specifically binds TRGV9. In some embodiments, the HC1 comprises a HCDR1, HCDR2, and HCDR3 comprising the amino acid sequences of SEQ ID NO:214, SEQ ID NO:215, and SEQ ID NO:216, respectively, and LC1 comprises a LCDR1, LCDR2, and LCDR3 comprising the amino acid sequences of SEQ ID NO:217, SEQ ID NO:218, and SEQ ID NO:219, respectively, to form a binding site for a first antigen that specifically binds TRGV9. In some embodiments, the HC1 comprises a HCDR1, HCDR2, and HCDR3 comprising the amino acid sequences of SEQ ID NO:214, SEQ ID NO:702, and SEQ ID NO:703, respectively, and LC1 comprises a LCDR1, LCDR2, and LCDR3 comprising the amino acid sequences of SEQ ID NO:217, SEQ ID NO:218, and SEQ ID NO:219, respectively, to form a binding site for a first antigen that specifically binds TRGV9. In some embodiments, the HC1 comprises a HCDR1, HCDR2, and HCDR3 comprising the amino acid sequences of SEQ ID NO:220, SEQ ID NO:221, and SEQ ID NO:222, respectively, and LC1 comprises a LCDR1, LCDR2, and LCDR3 comprising the amino acid sequences of SEQ ID NO:223, SEQ ID NO:224, and SEQ ID NO:225, respectively, to form a binding site for a first antigen that specifically binds TRGV9. In some embodiments, the HC1 comprises a HCDR1, HCDR2, and HCDR3 comprising the amino acid sequences of SEQ ID NO:226, SEQ ID NO:227, and SEQ ID NO:228, respectively, and LC1 comprises a LCDR1, LCDR2, and LCDR3 comprising the amino acid sequences of SEQ ID NO:229, SEQ ID NO:230, and SEQ ID NO:231, respectively, to form a binding site for a first antigen that specifically binds TRGV9. In some embodiments, the HC1 comprises a HCDR1, HCDR2, and HCDR3 comprising the amino acid sequences of SEQ ID NO:232, SEQ ID NO:233, and SEQ ID NO:234, respectively, and LC1 comprises a LCDR1, LCDR2, and LCDR3 comprising the amino acid sequences of SEQ ID NO:235, SEQ ID NO:236, and SEQ ID NO:237, respectively, to form a binding site for a first antigen that specifically binds TRGV9. In some embodiments, the HC1 comprises a HCDR1, HCDR2, and HCDR3 comprising the amino acid sequences of SEQ ID NO:238, SEQ ID NO:239, and SEQ ID NO:240, respectively, and LC1 comprises a LCDR1, LCDR2, and LCDR3 comprising the amino acid sequences of SEQ ID NO:241, SEQ ID NO:242, and SEQ ID NO:243, respectively, to form a binding site for a first antigen that specifically binds TRGV9. In some embodiments, the HC1 comprises a HCDR1, HCDR2, and HCDR3 comprising the amino acid sequences of SEQ ID NO:244, SEQ ID NO:245, and SEQ ID NO:246, respectively, and LC1 comprises a LCDR1, LCDR2, and LCDR3 comprising the amino acid sequences of SEQ ID NO:247, SEQ ID NO:248, and SEQ ID NO:249, respectively, to form a binding site for a first antigen that specifically binds TRGV9. In some embodiments, the HC1 comprises a HCDR1, HCDR2, and HCDR3 comprising the amino acid sequences of SEQ ID NO:250, SEQ ID NO:251, and SEQ ID NO:252, respectively, and LC1 comprises a LCDR1, LCDR2, and LCDR3 comprising the amino acid sequences of SEQ ID NO:253, SEQ ID NO:254, and SEQ ID NO:255, respectively, to form a binding site for a first antigen that specifically binds TRGV9. In some embodiments, the HC1 comprises a HCDR1, HCDR2, and HCDR3 comprising the amino acid sequences of SEQ ID NO:250, SEQ ID NO:704, and SEQ ID NO:705, respectively, and LC1 comprises a LCDR1, LCDR2, and LCDR3 comprising the amino acid sequences of SEQ ID NO:253, SEQ ID NO:254, and SEQ ID NO:255, respectively, to form a binding site for a first antigen that specifically binds TRGV9. In some embodiments, the HC1 comprises a HCDR1, HCDR2, and HCDR3 comprising the amino acid sequences of SEQ ID NO:256, SEQ ID NO:257, and SEQ ID NO:258, respectively, and LC1 comprises a LCDR1, LCDR2, and LCDR3 comprising the amino acid sequences of SEQ ID NO:259, SEQ ID NO:260, and SEQ ID NO:261, respectively, to form a binding site for a first antigen that specifically binds TRGV9. In some embodiments, the HC1 comprises a HCDR1, HCDR2, and HCDR3 comprising the amino acid sequences of SEQ ID NO:262, SEQ ID NO:263, and SEQ ID NO:264, respectively, and LC1 comprises a LCDR1, LCDR2, and LCDR3 comprising the amino acid sequences of SEQ ID NO:265, SEQ ID NO:266, and SEQ ID NO:267, respectively, to form a binding site for a first antigen that specifically binds TRGV9. In some embodiments, the HC1 comprises a HCDR1, HCDR2, and HCDR3 comprising the amino acid sequences of SEQ ID NO:268, SEQ ID NO:269, and SEQ ID NO:270, respectively, and LC1 comprises a LCDR1, LCDR2, and LCDR3 comprising the amino acid sequences of SEQ ID NO:271, SEQ ID NO:272, and SEQ ID NO:273, respectively, to form a binding site for a first antigen that specifically binds TRGV9. In some embodiments, the HC1 comprises a HCDR1, HCDR2, and HCDR3 comprising the amino acid sequences of SEQ ID NO:274, SEQ ID NO:275, and SEQ ID NO:276, respectively, and LC1 comprises a LCDR1, LCDR2, and LCDR3 comprising the amino acid sequences of SEQ ID NO:277, SEQ ID NO:278, and SEQ ID NO:279, respectively, to form a binding site for a first antigen that specifically binds TRGV9. In some embodiments, the HC1 comprises a HCDR1, HCDR2, and HCDR3 comprising the amino acid sequences of SEQ ID NO:280, SEQ ID NO:281, and SEQ ID NO:282, respectively, and LC1 comprises a LCDR1, LCDR2, and LCDR3 comprising the amino acid sequences of SEQ ID NO:283, SEQ ID NO:284, and SEQ ID NO:285, respectively, to form a binding site for a first antigen that specifically binds TRGV9. In some embodiments, the HC1 comprises a HCDR1, HCDR2, and HCDR3 comprising the amino acid sequences of SEQ ID NO:286, SEQ ID NO:287, and SEQ ID NO:288, respectively, and LC1 comprises a LCDR1, LCDR2, and LCDR3 comprising the amino acid sequences of SEQ ID NO:289, SEQ ID NO:290, and SEQ ID NO:291, respectively, to form a binding site for a first antigen that specifically binds TRGV9. In some embodiments, the HC1 comprises a HCDR1, HCDR2, and HCDR3 comprising the amino acid sequences of SEQ ID NO:286, SEQ ID NO:706, and SEQ ID NO:707, respectively, and LC1 comprises a LCDR1, LCDR2, and LCDR3 comprising the amino acid sequences of SEQ ID NO:289, SEQ ID NO:290, and SEQ ID NO:291, respectively, to form a binding site for a first antigen that specifically binds TRGV9. In some embodiments, the HC1 comprises a HCDR1, HCDR2, and HCDR3 comprising the amino acid sequences of SEQ ID NO:292, SEQ ID NO:293, and SEQ ID NO:294, respectively, and LC1 comprises a LCDR1, LCDR2, and LCDR3 comprising the amino acid sequences of SEQ ID NO:295, SEQ ID NO:296, and SEQ ID NO:297, respectively, to form a binding site for a first antigen that specifically binds TRGV9. In some embodiments, the HC1 comprises a HCDR1, HCDR2, and HCDR3 comprising the amino acid sequences of SEQ ID NO:298, SEQ ID NO:299, and SEQ ID NO:300, respectively, and LC1 comprises a LCDR1, LCDR2, and LCDR3 comprising the amino acid sequences of SEQ ID NO:301, SEQ ID NO:302, and SEQ ID NO:303, respectively, to form a binding site for a first antigen that specifically binds TRGV9. In some embodiments, the HC1 comprises a HCDR1, HCDR2, and HCDR3 comprising the amino acid sequences of SEQ ID NO:304, SEQ ID NO:305, and SEQ ID NO:306, respectively, and LC1 comprises a LCDR1, LCDR2, and LCDR3 comprising the amino acid sequences of SEQ ID NO:307, SEQ ID NO:308, and SEQ ID NO:309, respectively, to form a binding site for a first antigen that specifically binds TRGV9. In some embodiments, the HC1 comprises a HCDR1, HCDR2, and HCDR3 comprising the amino acid sequences of SEQ ID NO:310, SEQ ID NO:311, and SEQ ID NO:312, respectively, and LC1 comprises a LCDR1, LCDR2, and LCDR3 comprising the amino acid sequences of SEQ ID NO:313, SEQ ID NO:314, and SEQ ID NO:315, respectively, to form a binding site for a first antigen that specifically binds TRGV9. In some embodiments, the HC1 comprises a HCDR1, HCDR2, and HCDR3 comprising the amino acid sequences of SEQ ID NO:316, SEQ ID NO:317, and SEQ ID NO:318, respectively, and LC1 comprises a LCDR1, LCDR2, and LCDR3 comprising the amino acid sequences of SEQ ID NO:319, SEQ ID NO:320, and SEQ ID NO:321, respectively, to form a binding site for a first antigen that specifically binds TRGV9. In some embodiments, the HC1 comprises a HCDR1, HCDR2, and HCDR3 comprising the amino acid sequences of SEQ ID NO:322, SEQ ID NO:323, and SEQ ID NO:324, respectively, and LC1 comprises a LCDR1, LCDR2, and LCDR3 comprising the amino acid sequences of SEQ ID NO:325, SEQ ID NO:326, and SEQ ID NO:327, respectively, to form a binding site for a first antigen that specifically binds TRGV9. In some embodiments, the HC1 comprises a HCDR1, HCDR2, and HCDR3 comprising the amino acid sequences of SEQ ID NO:322, SEQ ID NO:708, and SEQ ID NO:709, respectively, and LC1 comprises a LCDR1, LCDR2, and LCDR3 comprising the amino acid sequences of SEQ ID NO:325, SEQ ID NO:326, and SEQ ID NO:327, respectively, to form a binding site for a first antigen that specifically binds TRGV9. In some embodiments, the HC1 comprises a HCDR1, HCDR2, and HCDR3 comprising the amino acid sequences of SEQ ID NO:328, SEQ ID NO:329, and SEQ ID NO:330, respectively, and LC1 comprises a LCDR1, LCDR2, and LCDR3 comprising the amino acid sequences of SEQ ID NO:331, SEQ ID NO:332, and SEQ ID NO:333, respectively, to form a binding site for a first antigen that specifically binds TRGV9. In some embodiments, the HC1 comprises a HCDR1, HCDR2, and HCDR3 comprising the amino acid sequences of SEQ ID NO:334, SEQ ID NO:335, and SEQ ID NO:336, respectively, and LC1 comprises a LCDR1, LCDR2, and LCDR3 comprising the amino acid sequences of SEQ ID NO:337, SEQ ID NO:338, and SEQ ID NO:339, respectively, to form a binding site for a first antigen that specifically binds TRGV9. In some embodiments, the HC1 comprises a HCDR1, HCDR2, and HCDR3 comprising the amino acid sequences of SEQ ID NO:340, SEQ ID NO:341, and SEQ ID NO:342, respectively, and LC1 comprises a LCDR1, LCDR2, and LCDR3 comprising the amino acid sequences of SEQ ID NO:343, SEQ ID NO:344, and SEQ ID NO:345, respectively, to form a binding site for a first antigen that specifically binds TRGV9. In some embodiments, the HC1 comprises a HCDR1, HCDR2, and HCDR3 comprising the amino acid sequences of SEQ ID NO:346, SEQ ID NO:347, and SEQ ID NO:348, respectively, and LC1 comprises a LCDR1, LCDR2, and LCDR3 comprising the amino acid sequences of SEQ ID NO:349, SEQ ID NO:350, and SEQ ID NO:351, respectively, to form a binding site for a first antigen that specifically binds TRGV9. In some embodiments, the HC1 comprises a HCDR1, HCDR2, and HCDR3 comprising the amino acid sequences of SEQ ID NO:352, SEQ ID NO:353, and SEQ ID NO:354, respectively, and LC1 comprises a LCDR1, LCDR2, and LCDR3 comprising the amino acid sequences of SEQ ID NO:355, SEQ ID NO:356, and SEQ ID NO:357, respectively, to form a binding site for a first antigen that specifically binds TRGV9. In some embodiments, the HC1 comprises a HCDR1, HCDR2, and HCDR3 comprising the amino acid sequences of SEQ ID NO:358, SEQ ID NO:359, and SEQ ID NO:360, respectively, and LC1 comprises a LCDR1, LCDR2, and LCDR3 comprising the amino acid sequences of SEQ ID NO:361, SEQ ID NO:362, and SEQ ID NO:363, respectively, to form a binding site for a first antigen that specifically binds TRGV9. In some embodiments, the HC1 comprises a HCDR1, HCDR2, and HCDR3 comprising the amino acid sequences of SEQ ID NO:358, SEQ ID NO:710, and SEQ ID NO:711, respectively, and LC1 comprises a LCDR1, LCDR2, and LCDR3 comprising the amino acid sequences of SEQ ID NO:361, SEQ ID NO:362, and SEQ ID NO:363, respectively, to form a binding site for a first antigen that specifically binds TRGV9. In some embodiments, the HC1 comprises a HCDR1, HCDR2, and HCDR3 comprising the amino acid sequences of SEQ ID NO:364, SEQ ID NO:365, and SEQ ID NO:366, respectively, and LC1 comprises a LCDR1, LCDR2, and LCDR3 comprising the amino acid sequences of SEQ ID NO:367, SEQ ID NO:368, and SEQ ID NO:369, respectively, to form a binding site for a first antigen that specifically binds TRGV9. In some embodiments, the HC1 comprises a HCDR1, HCDR2, and HCDR3 comprising the amino acid sequences of SEQ ID NO:370, SEQ ID NO:371, and SEQ ID NO:372, respectively, and LC1 comprises a LCDR1, LCDR2, and LCDR3 comprising the amino acid sequences of SEQ ID NO:373, SEQ ID NO:374, and SEQ ID NO:375, respectively, to form a binding site for a first antigen that specifically binds TRGV9. In some embodiments, the HC1 comprises a HCDR1, HCDR2, and HCDR3 comprising the amino acid sequences of SEQ ID NO:376, SEQ ID NO:377, and SEQ ID NO:378, respectively, and LC1 comprises a LCDR1, LCDR2, and LCDR3 comprising the amino acid sequences of SEQ ID NO:379, SEQ ID NO:380, and SEQ ID NO:381, respectively, to form a binding site for a first antigen that specifically binds TRGV9. In some embodiments, the HC1 comprises a HCDR1, HCDR2, and HCDR3 comprising the amino acid sequences of SEQ ID NO:382, SEQ ID NO:383, and SEQ ID NO:384, respectively, and LC1 comprises a LCDR1, LCDR2, and LCDR3 comprising the amino acid sequences of SEQ ID NO:385, SEQ ID NO:386, and SEQ ID NO:387, respectively, to form a binding site for a first antigen that specifically binds TRGV9. In some embodiments, the HC1 comprises a HCDR1, HCDR2, and HCDR3 comprising the amino acid sequences of SEQ ID NO:388, SEQ ID NO:389, and SEQ ID NO:390, respectively, and LC1 comprises a LCDR1, LCDR2, and LCDR3 comprising the amino acid sequences of SEQ ID NO:391, SEQ ID NO:392, and SEQ ID NO:393, respectively, to form a binding site for a first antigen that specifically binds TRGV9. In some embodiments, the HC1 comprises a HCDR1, HCDR2, and HCDR3 comprising the amino acid sequences of SEQ ID NO:394, SEQ ID NO:395, and SEQ ID NO:396, respectively, and LC1 comprises a LCDR1, LCDR2, and LCDR3 comprising the amino acid sequences of SEQ ID NO:397, SEQ ID NO:398, and SEQ ID NO:399, respectively, to form a binding site for a first antigen that specifically binds TRGV9. In some embodiments, the HC1 comprises a HCDR1, HCDR2, and HCDR3 comprising the amino acid sequences of SEQ ID NO:394, SEQ ID NO:712, and SEQ ID NO:713, respectively, and LC1 comprises a LCDR1, LCDR2, and LCDR3 comprising the amino acid sequences of SEQ ID NO:397, SEQ ID NO:398, and SEQ ID NO:399, respectively, to form a binding site for a first antigen that specifically binds TRGV9. In some embodiments, the HC1 comprises a HCDR1, HCDR2, and HCDR3 comprising the amino acid sequences of SEQ ID NO:400, SEQ ID NO:401, and SEQ ID NO:402, respectively, and LC1 comprises a LCDR1, LCDR2, and LCDR3 comprising the amino acid sequences of SEQ ID NO:403, SEQ ID NO:404, and SEQ ID NO:405, respectively, to form a binding site for a first antigen that specifically binds TRGV9. In some embodiments, the HC1 comprises a HCDR1, HCDR2, and HCDR3 comprising the amino acid sequences of SEQ ID NO:406, SEQ ID NO:407, and SEQ ID NO:408, respectively, and LC1 comprises a LCDR1, LCDR2, and LCDR3 comprising the amino acid sequences of SEQ ID NO:409, SEQ ID NO:410, and SEQ ID NO:411, respectively, to form a binding site for a first antigen that specifically binds TRGV9. In some embodiments, the HC1 comprises a HCDR1, HCDR2, and HCDR3 comprising the amino acid sequences of SEQ ID NO:412, SEQ ID NO:413, and SEQ ID NO:414, respectively, and LC1 comprises a LCDR1, LCDR2, and LCDR3 comprising the amino acid sequences of SEQ ID NO:415, SEQ ID NO:416, and SEQ ID NO:417, respectively, to form a binding site for a first antigen that specifically binds TRGV9. In some embodiments, the HC1 comprises a HCDR1, HCDR2, and HCDR3 comprising the amino acid sequences of SEQ ID NO:418, SEQ ID NO:419, and SEQ ID NO:420, respectively, and LC1 comprises a LCDR1, LCDR2, and LCDR3 comprising the amino acid sequences of SEQ ID NO:421, SEQ ID NO:422, and SEQ ID NO:423, respectively, to form a binding site for a first antigen that specifically binds TRGV9. In some embodiments, the HC1 comprises a HCDR1, HCDR2, and HCDR3 comprising the amino acid sequences of SEQ ID NO:424, SEQ ID NO:425, and SEQ ID NO:426, respectively, and LC1 comprises a LCDR1, LCDR2, and LCDR3 comprising the amino acid sequences of SEQ ID NO:427, SEQ ID NO:428, and SEQ ID NO:429, respectively, to form a binding site for a first antigen that specifically binds TRGV9. In some embodiments, the HC1 comprises a HCDR1, HCDR2, and HCDR3 comprising the amino acid sequences of SEQ ID NO:430, SEQ ID NO:431, and SEQ ID NO:432, respectively, and LC1 comprises a LCDR1, LCDR2, and LCDR3 comprising the amino acid sequences of SEQ ID NO:433, SEQ ID NO:434, and SEQ ID NO:435, respectively, to form a binding site for a first antigen that specifically binds TRGV9. In some embodiments, the HC1 comprises a HCDR1, HCDR2, and HCDR3 comprising the amino acid sequences of SEQ ID NO:430, SEQ ID NO:714, and SEQ ID NO:715, respectively, and LC1 comprises a LCDR1, LCDR2, and LCDR3 comprising the amino acid sequences of SEQ ID NO:433, SEQ ID NO:434, and SEQ ID NO:435, respectively, to form a binding site for a first antigen that specifically binds TRGV9. In some embodiments, the HC1 comprises a HCDR1, HCDR2, and HCDR3 comprising the amino acid sequences of SEQ ID NO:436, SEQ ID NO:437, and SEQ ID NO:438, respectively, and LC1 comprises a LCDR1, LCDR2, and LCDR3 comprising the amino acid sequences of SEQ ID NO:439, SEQ ID NO:440, and SEQ ID NO:441, respectively, to form a binding site for a first antigen that specifically binds TRGV9. In some embodiments, the HC1 comprises a HCDR1, HCDR2, and HCDR3 comprising the amino acid sequences of SEQ ID NO:442, SEQ ID NO:443, and SEQ ID NO:444, respectively, and LC1 comprises a LCDR1, LCDR2, and LCDR3 comprising the amino acid sequences of SEQ ID NO:445, SEQ ID NO:446, and SEQ ID NO:447, respectively, to form a binding site for a first antigen that specifically binds TRGV9. In some embodiments, the HC1 comprises a HCDR1, HCDR2, and HCDR3 comprising the amino acid sequences of SEQ ID NO:448, SEQ ID NO:449, and SEQ ID NO:450, respectively, and LC1 comprises a LCDR1, LCDR2, and LCDR3 comprising the amino acid sequences of SEQ ID NO:451, SEQ ID NO:452, and SEQ ID NO:453, respectively, to form a binding site for a first antigen that specifically binds TRGV9. In some embodiments, the HC1 comprises a HCDR1, HCDR2, and HCDR3 comprising the amino acid sequences of SEQ ID NO:454, SEQ ID NO:455, and SEQ ID NO:456, respectively, and LC1 comprises a LCDR1, LCDR2, and LCDR3 comprising the amino acid sequences of SEQ ID NO:457, SEQ ID NO:458, and SEQ ID NO:459, respectively, to form a binding site for a first antigen that specifically binds TRGV9. In some embodiments, the HC1 comprises a HCDR1, HCDR2, and HCDR3 comprising the amino acid sequences of SEQ ID NO:460, SEQ ID NO:461, and SEQ ID NO:462, respectively, and LC1 comprises a LCDR1, LCDR2, and LCDR3 comprising the amino acid sequences of SEQ ID NO:463, SEQ ID NO:464, and SEQ ID NO:465, respectively, to form a binding site for a first antigen that specifically binds TRGV9. In some embodiments, the HC1 comprises a HCDR1, HCDR2, and HCDR3 comprising the amino acid sequences of SEQ ID NO:466, SEQ ID NO:467, and SEQ ID NO:468, respectively, and LC1 comprises a LCDR1, LCDR2, and LCDR3 comprising the amino acid sequences of SEQ ID NO:469, SEQ ID NO:470, and SEQ ID NO:471, respectively, to form a binding site for a first antigen that specifically binds TRGV9. In some embodiments, the HC1 comprises a HCDR1, HCDR2, and HCDR3 comprising the amino acid sequences of SEQ ID NO:466, SEQ ID NO:716, and SEQ ID NO:717, respectively, and LC1 comprises a LCDR1, LCDR2, and LCDR3 comprising the amino acid sequences of SEQ ID NO:469, SEQ ID NO:470, and SEQ ID NO:471, respectively, to form a binding site for a first antigen that specifically binds TRGV9. In some embodiments, the HC1 comprises a HCDR1, HCDR2, and HCDR3 comprising the amino acid sequences of SEQ ID NO:472, SEQ ID NO:473, and SEQ ID NO:474, respectively, and LC1 comprises a LCDR1, LCDR2, and LCDR3 comprising the amino acid sequences of SEQ ID NO:475, SEQ ID NO:476, and SEQ ID NO:477, respectively, to form a binding site for a first antigen that specifically binds TRGV9. In some embodiments, the HC1 comprises a HCDR1, HCDR2, and HCDR3 comprising the amino acid sequences of SEQ ID NO:478, SEQ ID NO:479, and SEQ ID NO:480, respectively, and LC1 comprises a LCDR1, LCDR2, and LCDR3 comprising the amino acid sequences of SEQ ID NO:481, SEQ ID NO:482, and SEQ ID NO:483, respectively, to form a binding site for a first antigen that specifically binds TRGV9. In some embodiments, the HC1 comprises a HCDR1, HCDR2, and HCDR3 comprising the amino acid sequences of SEQ ID NO:484, SEQ ID NO:485, and SEQ ID NO:486, respectively, and LC1 comprises a LCDR1, LCDR2, and LCDR3 comprising the amino acid sequences of SEQ ID NO:487, SEQ ID NO:488, and SEQ ID NO:489, respectively, to form a binding site for a first antigen that specifically binds TRGV9. In some embodiments, the HC1 comprises a HCDR1, HCDR2, and HCDR3 comprising the amino acid sequences of SEQ ID NO:490, SEQ ID NO:491, and SEQ ID NO:492, respectively, and LC1 comprises a LCDR1, LCDR2, and LCDR3 comprising the amino acid sequences of SEQ ID NO:493, SEQ ID NO:494, and SEQ ID NO:495, respectively, to form a binding site for a first antigen that specifically binds TRGV9. In some embodiments, the HC1 comprises a HCDR1, HCDR2, and HCDR3 comprising the amino acid sequences of SEQ ID NO:496, SEQ ID NO:497, and SEQ ID NO:498, respectively, and LC1 comprises a LCDR1, LCDR2, and LCDR3 comprising the amino acid sequences of SEQ ID NO:499, SEQ ID NO:500, and SEQ ID NO:501, respectively, to form a binding site for a first antigen that specifically binds TRGV9. In some embodiments, the HC1 comprises a HCDR1, HCDR2, and HCDR3 comprising the amino acid sequences of SEQ ID NO:502, SEQ ID NO:503, and SEQ ID NO:504, respectively, and LC1 comprises a LCDR1, LCDR2, and LCDR3 comprising the amino acid sequences of SEQ ID NO:505, SEQ ID NO:506, and SEQ ID NO:507, respectively, to form a binding site for a first antigen that specifically binds TRGV9. In some embodiments, the HC1 comprises a HCDR1, HCDR2, and HCDR3 comprising the amino acid sequences of SEQ ID NO:502, SEQ ID NO:718, and SEQ ID NO:719, respectively, and LC1 comprises a LCDR1, LCDR2, and LCDR3 comprising the amino acid sequences of SEQ ID NO:505, SEQ ID NO:506, and SEQ ID NO:507, respectively, to form a binding site for a first antigen that specifically binds TRGV9. In some embodiments, the HC1 comprises a HCDR1, HCDR2, and HCDR3 comprising the amino acid sequences of SEQ ID NO:508, SEQ ID NO:509, and SEQ ID NO:510, respectively, and LC1 comprises a LCDR1, LCDR2, and LCDR3 comprising the amino acid sequences of SEQ ID NO:511, SEQ ID NO:512, and SEQ ID NO:513, respectively, to form a binding site for a first antigen that specifically binds TRGV9. In some embodiments, the HC1 comprises a HCDR1, HCDR2, and HCDR3 comprising the amino acid sequences of SEQ ID NO:514, SEQ ID NO:515, and SEQ ID NO:516, respectively, and LC1 comprises a LCDR1, LCDR2, and LCDR3 comprising the amino acid sequences of SEQ ID NO:517, SEQ ID NO:518, and SEQ ID NO:519, respectively, to form a binding site for a first antigen that specifically binds TRGV9. In some embodiments, the HC1 comprises a HCDR1, HCDR2, and HCDR3 comprising the amino acid sequences of SEQ ID NO:520, SEQ ID NO:521, and SEQ ID NO:522, respectively, and LC1 comprises a LCDR1, LCDR2, and LCDR3 comprising the amino acid sequences of SEQ ID NO:523, SEQ ID NO:524, and SEQ ID NO:525, respectively, to form a binding site for a first antigen that specifically binds TRGV9. In some embodiments, the HC1 comprises a HCDR1, HCDR2, and HCDR3 comprising the amino acid sequences of SEQ ID NO:526, SEQ ID NO:527, and SEQ ID NO:528, respectively, and LC1 comprises a LCDR1, LCDR2, and LCDR3 comprising the amino acid sequences of SEQ ID NO:529, SEQ ID NO:530, and SEQ ID NO:531, respectively, to form a binding site for a first antigen that specifically binds TRGV9. In some embodiments, the HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively, to form a binding site for a first antigen that specifically binds TRGV9. In some embodiments, the HC1 comprises a HCDR1, HCDR2, and HCDR3 comprising the amino acid sequences of SEQ ID NO:538, SEQ ID NO:539, and SEQ ID NO:540, respectively, and LC1 comprises a LCDR1, LCDR2, and LCDR3 comprising the amino acid sequences of SEQ ID NO:541, SEQ ID NO:542, and SEQ ID NO:543, respectively, to form a binding site for a first antigen that specifically binds TRGV9. In some embodiments, the HC1 comprises a HCDR1, HCDR2, and HCDR3 comprising the amino acid sequences of SEQ ID NO:538, SEQ ID NO:720, and SEQ ID NO:721, respectively, and LC1 comprises a LCDR1, LCDR2, and LCDR3 comprising the amino acid sequences of SEQ ID NO:541, SEQ ID NO:542, and SEQ ID NO:543, respectively, to form a binding site for a first antigen that specifically binds TRGV9. In some embodiments, the HC1 comprises a HCDR1, HCDR2, and HCDR3 comprising the amino acid sequences of SEQ ID NO:544, SEQ ID NO:545, and SEQ ID NO:546, respectively, and LC1 comprises a LCDR1, LCDR2, and LCDR3 comprising the amino acid sequences of SEQ ID NO:547, SEQ ID NO:548, and SEQ ID NO:549, respectively, to form a binding site for a first antigen that specifically binds TRGV9. In some embodiments, the HC1 comprises a HCDR1, HCDR2, and HCDR3 comprising the amino acid sequences of SEQ ID NO:550, SEQ ID NO:551, and SEQ ID NO:552, respectively, and LC1 comprises a LCDR1, LCDR2, and LCDR3 comprising the amino acid sequences of SEQ ID NO:553, SEQ ID NO:554, and SEQ ID NO:555, respectively, to form a binding site for a first antigen that specifically binds TRGV9. The HC2 can, for example, comprise a HCDR1, HCDR2, and HCDR3 comprising the amino acid sequences of SEQ ID NO:9, SEQ ID NO:10, and SEQ ID NO:11, respectively, and LC2 can, for example, comprise a LCDR1, LCDR2, and LCDR3 comprising the amino acid sequences of SEQ ID NO:12, SEQ ID NO:13, and SEQ ID NO:14, respectively, to form a binding site for a second antigen that specifically binds CD123. In some embodiments, the HC2 comprises a HCDR1, HCDR2, and HCDR3 comprising the amino acid sequence of SEQ ID NO:556, SEQ ID NO:557, and SEQ ID NO:558, respectively, and a LCDR1, LCDR2, and LCDR3 comprising the amino acid sequence of SEQ ID NO:559, SEQ ID NO:560, and SEQ ID NO:561, respectively, to form a binding site for a second antigen that specifically binds CD123. In some embodiments, the HC2 comprises a HCDR1, HCDR2, and HCDR3 comprising the amino acid sequence of SEQ ID NO:562, SEQ ID NO:563, and SEQ ID NO:564, respectively, and a LCDR1, LCDR2, and LCDR3 comprising the amino acid sequence of SEQ ID NO:565, SEQ ID NO:566, and SEQ ID NO:567, respectively, to form a binding site for a second antigen that specifically binds CD123. In some embodiments, the HC2 comprises a HCDR1, HCDR2, and HCDR3 comprising the amino acid sequence of SEQ ID NO:568, SEQ ID NO:569, and SEQ ID NO:570, respectively, and a LCDR1, LCDR2, and LCDR3 comprising the amino acid sequence of SEQ ID NO:571, SEQ ID NO:572, and SEQ ID NO:573, respectively, to form a binding site for a second antigen that specifically binds CD123. In some embodiments, the HC2 comprises a HCDR1, HCDR2, and HCDR3 comprising the amino acid sequence of SEQ ID NO:574, SEQ ID NO:575, and SEQ ID NO:576, respectively, and a LCDR1, LCDR2, and LCDR3 comprising the amino acid sequence of SEQ ID NO:577, SEQ ID NO:578, and SEQ ID NO:579, respectively, to form a binding site for a second antigen that specifically binds CD123. In some embodiments, the HC2 comprises a HCDR1, HCDR2, and HCDR3 comprising the amino acid sequence of SEQ ID NO:574, SEQ ID NO:722, and SEQ ID NO:723, respectively, and a LCDR1, LCDR2, and LCDR3 comprising the amino acid sequence of SEQ ID NO:577, SEQ ID NO:578, and SEQ ID NO:579, respectively, to form a binding site for a second antigen that specifically binds CD123. In some embodiments, the HC2 comprises a HCDR1, HCDR2, and HCDR3 comprising the amino acid sequence of SEQ ID NO:580, SEQ ID NO:581, and SEQ ID NO:582, respectively, and a LCDR1, LCDR2, and LCDR3 comprising the amino acid sequence of SEQ ID NO:583, SEQ ID NO:584, and SEQ ID NO:585, respectively, to form a binding site for a second antigen that specifically binds CD123. In some embodiments, the HC2 comprises a HCDR1, HCDR2, and HCDR3 comprising the amino acid sequence of SEQ ID NO:586, SEQ ID NO:587, and SEQ ID NO:588; and (ii) a VL comprising a VL CDR1 having an amino acid sequence of SEQ ID NO:589, SEQ ID NO:590, and SEQ ID NO:591, respectively, to form a binding site for a second antigen that specifically binds CD123. In certain embodiments, the HC1 comprises the amino acid sequence of SEQ ID NO:7, SEQ ID NO:34, SEQ ID NO:35, or SEQ ID NO:36, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:7, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:34, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:35, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:36, and LC1 comprises the amino acid sequence of SEQ ID NO:8, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:65, and LC1 comprises the amino acid sequence of SEQ ID NO:66, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:67, and LC1 comprises the amino acid sequence of SEQ ID NO:68, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:95, and LC1 comprises the amino acid sequence of SEQ ID NO:96, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:104, and LC1 comprises the amino acid sequence of SEQ ID NO:105, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:113, and LC1 comprises the amino acid sequence of SEQ ID NO:114, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:123, and LC1 comprises the amino acid sequence of SEQ ID NO:124, and the HC2 comprises the amino acid sequence of SEQ ID NO:15 and LC2 comprises the amino acid sequence of SEQ ID NO:16. In certain embodiments, the HC1 comprises the amino acid sequence of SEQ ID NO:133, and LC1 comprises the amino acid sequence of SEQ ID NO:134, and the HC2 comprises the amino acid sequence of SEQ ID NO:15 and LC2 comprises the amino acid sequence of SEQ ID NO:16. In certain embodiments, the TRGV9 is on the surface of a γδ T cell. In certain embodiments, the CD123 is on the surface of a cancer cell (e.g., a leukemia cell).

In some embodiments, the antibody specifically binds TRGV9. In other embodiments, the TRGV9 is present on the surface of a γδ T cell. In some embodiments, the antibody is a humanized antibody. In certain embodiments, the antibody is an IgG antibody. In other embodiments, the IgG antibody is an IgG1, IgG2, IgG3, or IgG4 antibody. In some embodiments, the antibody is a bispecific antibody. In certain embodiments, the antibody is multivalent. In other embodiments, the antibody is capable of binding at least three antigens. In some embodiments, the antibody is capable of binding at least five antigens.

In some embodiments, the bispecific antibody provided herein is a diabody, a cross-body, or a bispecific antibody obtained via a controlled Fab arm exchange as those described herein.

In some embodiments, the bispecific antibodies include IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) In some embodiments, different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus) and the DuoBody (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules can include ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine—China).

In some embodiments, Fab fusion bispecific antibodies include F(ab)$_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length bispecific antibodies provided herein can be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms can be engineered to favor heterodimerization over homodimerization. The resulting product is a bispecific antibody having two Fab arms or half molecules which each binding a distinct epitope, i.e. an epitope on TRGV9 and an epitope on a tumor antigen.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Publ. No. WO2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob." Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface can be used, as described in US Pat. Publ. No. US2010/0015133; US Pat. Publ. No. US2009/0182127; US Pat. Publ. No. US2010/028637; or US Pat. Publ. No. US2011/0123532. In other strategies, heterodimerization can be promoted by the following substitutions (expressed as modified position in the first CH3 domain of the first heavy chain/modified position in the second CH3 domain of the second heavy chain): L351Y_F405AY407V/T394W, T366I_K392M T394W/F405A_Y407V, T366L_K392M T394W/F405A_Y407V, L351Y_Y407A/T366A_K409F, L351Y_Y407A/T366V K409F Y407A/T366A_K409F, or T350V_L351Y_F405A Y407V/T350V_T366L_K392L_T394W as described in U.S. Pat. Publ. No. US2012/0149876 or U.S. Pat. Publ. No. US2013/0195849.

In addition to methods described above, bispecific antibodies provided herein can be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in PCT Pat. Publ. No. WO2011/131746. In the methods, the first monospecific bivalent antibody (e.g., anti-CD33 antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions can optionally be restored to non-reducing conditions. Exemplary reducing agents that can be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, or a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 can be used.

In some embodiments, the anti-TRGV9 antibody is a multispecific antibody. In other embodiments, the anti-TRGV9 antibody is a bispecific antibody. In other embodiments, the bispecific antibody comprises an antigen binding fragment of an anti-TRGV9 antibody provided herein.

In some embodiments, the anti-TRGV9 bispecific antibody does not comprise a single chain antibody. In some embodiments, the anti-TRGV9 bispecific antibody does not comprise a single domain antibody. In certain embodiments, the anti-TRGV9 bispecific antibody does not comprise a nanobody. In certain embodiments, the anti-TRGV9 bispecific antibody does not comprise a VHH antibody. In certain embodiments, the anti-TRGV9 bispecific antibody does not comprise a llama antibody.

Also provided herein is a bispecific antibody comprising an anti-TRGV9 antibody or antigen-binding fragment thereof, and an anti-CD123 antibody or antigen-binding fragment thereof. In certain embodiments, the bispecific antibody comprises an anti-TRGV9 antibody, and an anti-CD123 antibody. In certain embodiments, the bispecific antibody comprises an antigen binding fragment of an anti-TRGV9 antibody, and an anti-CD123 antibody. In certain embodiments, the bispecific antibody comprises an anti-TRGV9 antibody, and an antigen-binding fragment of an anti-CD123 antibody. In certain embodiments, the bispecific antibody comprises an antigen-binding fragment of an anti-TRGV9 antibody, and an antigen binding fragment of an anti-CD123 antibody.

In some embodiments, an anti-TRGV9 bispecific antibody provided herein does not comprise a VH CDR1, VH CDR2, and VH CDR3 having the amino acid sequence of SEQ ID NOs:730, 731, and 732, respectively. In some embodiments, an anti-TRGV9 bispecific antibody provided herein does not comprise a VH CDR1, VH CDR2, and VH CDR3 having the amino acid sequence of SEQ ID NOs:733, 734, and 735, respectively. In some embodiments, an anti-TRGV9 bispecific antibody provided herein does not comprise a VH CDR1, VH CDR2, and VH CDR3 having the amino acid sequence of SEQ ID NOs:736, 737, and 738, respectively. In some embodiments, an anti-TRGV9 bispecific antibody provided herein does not comprise a VH CDR1, VH CDR2, and VH CDR3 having the amino acid sequence of SEQ ID NOs:739, 740, and 741, respectively. In some embodiments, an anti-TRGV9 bispecific antibody provided herein does not comprise a VH CDR1, VH CDR2, and VH CDR3 having the amino acid sequence of SEQ ID NOs:742, 743, and 744, respectively. In some embodiments, an anti-TRGV9 bispecific antibody provided herein does not comprise a VH CDR1, VH CDR2, and VH CDR3 having the amino acid sequence of SEQ ID NOs:745, 746, and 747, respectively. In some embodiments, an anti-TRGV9 bispecific antibody provided herein does not comprise a VH CDR1, VH CDR2, and VH CDR3 having the amino acid sequence of SEQ ID NOs:748, 749, and 750, respectively. In some embodiments, an anti-TRGV9 bispecific antibody provided herein does not comprise a VH domain having the amino acid sequence of SEQ ID NO:751. In some embodiments, an anti-TRGV9 bispecific antibody provided herein does not comprise a VH domain having the amino acid sequence of SEQ ID NO:752. In some embodiments, an anti-TRGV9 bispecific antibody provided herein does not comprise a VH domain having the amino acid sequence of SEQ ID NO:753. In some embodiments, an anti-TRGV9 bispecific antibody provided herein does not comprise a VH domain having the amino acid sequence of SEQ ID NO:754. In some embodiments, an anti-TRGV9 bispecific antibody provided herein does not comprise a VH domain having the amino acid sequence of SEQ ID NO:755. In some embodiments, an anti-TRGV9 bispecific antibody provided herein does not comprise a VH domain having the amino acid sequence of SEQ ID NO:756. In some embodiments, an anti-TRGV9 bispecific antibody provided herein does not comprise a VH domain having the amino acid sequence of SEQ ID NO:757.

In certain embodiments, the anti-TRGV9 antibody or antigen-binding fragment thereof comprises a HCDR1, HCDR2, HCDR3, a LCDR1, LCDR2, and LCDR3, having the polypeptide sequence of:
  i. SEQ ID NOs:1, 2, 3, 4, 5, and 6, respectively;
  ii. SEQ ID NOs:1, 2, 31, 4, 5, and 6, respectively;
  iii. SEQ ID NOs:1, 2, 32, 4, 5, and 6, respectively; or
  iv. SEQ ID NOs:1, 2, 33, 4, 5, and 6, respectively;
and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively.

In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 3, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 31, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 32, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 2, 33, 4, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:1, 76, 3, 77, 5, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:60, 61, 62, 63, 64, and 6, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:89, 90, 91, 92, 93, and 94, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:98, 99, 100, 101, 102, and 103, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs: 107, 108, 109, 110, 111, and 112, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs:117, 118, 119, 120, 121, and 122, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In certain embodiments, the anti-TRGV9 antibody or antigen-binding fragment thereof comprises a HCDR1, HCDR2, HCDR3, a LCDR1, LCDR2, and LCDR3, having the polypeptide sequence of SEQ ID NOs: 127, 128, 129, 130, 131, and 132, respectively; and the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively.

In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:160, 161, 162, 163, 164, and 165, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:166, 167, 168, 169, 170, and 171, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:172, 173, 174, 175, 176, and 177, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs: 178, 179, 180, 181, 182, and 183, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:178, 700, 701, 181, 182, and 183, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:184, 185, 186, 187, 188, and 189, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:190, 191, 192, 193, 194, and 195, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:196, 197, 198, 199, 200, and 201, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:202, 203, 204, 205, 206, and 207, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:208, 209, 210, 211, 212, and 213, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:214, 215, 216, 217, 218, and 219, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:214, 702, 703, 217, 218, and 219, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:220, 221, 222, 223, 224, and 225, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:226, 227, 228, 229, 230, and 231, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:232, 233, 234, 235, 236, and 237, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:238, 239, 240, 241, 242, and 243, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:244, 245, 246, 247, 248, and 249, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:250, 251, 252, 253, 254, and 255, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:250, 704, 705, 253, 254, and 255, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:256, 257, 258, 259, 260, and 261, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:262, 263, 264, 265, 266, and 267, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:268, 269, 270, 271, 272, and 273, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:274, 275, 276, 277, 278, and 279, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:280, 281, 282, 283, 284, and 285, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:286, 287, 288, 289, 290, and 291, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:286, 706, 707, 289, 290, and 291, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:292, 293, 294, 295, 296, and 297, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:298, 299, 300, 301, 302, and 303, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:304, 305, 306, 307, 308, and 309, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:310, 311, 312, 313, 314, and 315, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:316, 317, 318, 319, 320, and 321, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:322, 323, 324, 325, 326, and 327, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:322, 708, 709, 325, 326, and 327, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:328, 329, 330, 331, 332, and 333, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:334, 335, 336, 337, 338, and 339, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:340, 341, 342, 343, 344, and 345, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:346, 347, 348, 349, 350, and 351, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:352, 353, 354, 355, 356, and 357, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:358, 359, 360, 361, 362, and 363, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:358, 710, 711, 361, 362, and 363, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:364, 365, 366, 367, 368, and 369, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:370, 371, 372, 373, 374, and 375, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:376, 377, 378, 379, 380, and 381, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:382, 383, 384, 385, 386, and 387, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:388, 389, 390, 391, 392, and 393, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:394, 395, 396, 397, 398, and 399, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:394, 712, 713, 397, 398, and 399, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:400, 401, 402, 403, 404, and 405, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:406, 407, 408, 409, 410, and 411, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:412, 413, 414, 415, 416, and 417, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:418, 419, 420, 421, 422, and 423, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:424, 425, 426, 427, 428, and 429, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:430, 431, 432, 433, 434, and 435, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:430, 714, 715, 433, 434, and 435, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:436, 437, 438, 439, 440, and 441, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:442, 443, 444, 445, 446, and 447, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:448, 449, 450, 451, 452, and 453, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:454, 455, 456, 457, 458, and 459, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:460, 461, 462, 463, 464, and 465, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:466, 467, 468, 469, 470, and 471, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:466, 716, 717, 469, 470, and 471, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:472, 473, 474, 475, 476, and 477, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:478, 479, 480, 481, 482, and 483, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:484, 485, 486, 487, 488, and 489, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:490, 491, 492, 493, 494, and 495, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:496, 497, 498, 499, 500, and 501, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:502, 503, 504, 505, 506, and 507, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:502, 718, 719, 505, 506, and 507, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:508, 509, 510, 511, 512, and 513, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:514, 515, 516, 517, 518, and 519, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:520, 521, 522, 523, 524, and 525, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:526, 527, 528, 529, 530, and 531, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:532, 533, 534, 535, 536, and 537, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:538, 539, 540, 541, 542, and 543, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:538, 720, 721, 541, 542, and 543, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:544, 545, 546, 547, 548, and 549, respectively. In certain embodiments, the anti-TRGV9 antibody or antigen-binding fragment thereof comprises a HCDR1, HCDR2, HCDR3, LCDR1, LCDR2, and LCDR3, having the polypeptide sequence of SEQ ID NOs:550, 551, 552, 553, 554, and 555, respectively.

In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:9, 10, 11, 12, 13, and 14, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:556, 557, 558, 559, 560, and 561, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:562, 563, 564, 565, 566, and 567, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:568, 569, 570, 571, 572, and 573, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs: 574, 575, 576, 577, 578, and 579, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:574, 722, 723, 577, 578, and 579, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:580, 581, 582, 583, 584, and 585, respectively. In some embodiments, the anti-CD123 antibody or antigen-binding fragment thereof comprises a HCDR1, HCDR2, HCDR3, LCDR1, LCDR2, and LCDR3, having the polypeptide sequence of SEQ ID NOs:586, 587, 588, 589, 590, and 591, respectively.

In certain embodiments, the bispecific antibody comprises any of the anti-TRGV9 antibodies provided herein. In some embodiments, the bispecific antibody comprises an antigen binding fragment of any of the anti-TRGV9 antibodies provided herein. In certain embodiments, the bispecific antibody comprises any of the anti-CD123 antibodies provided herein. In some embodiments, the bispecific antibody comprises an antigen binding fragment of any of the anti-CD123 antibodies provided herein. In other embodiments, the bispecific antibody comprises any of the anti-TRGV9 antibodies provided herein, and any of the CD123 antibodies provided herein. In some embodiments, the bispecific antibody comprises any of the anti-TRGV9 antibodies provided herein, and an antigen binding fragment of any of the CD123 antibodies provided herein. In other embodiments, the bispecific antibody comprises an antigen binding fragment any of the anti-TRGV9 antibodies provided herein, and any of the CD123 antibodies provided herein. In yet other embodiments, the bispecific antibody comprises an antigen binding fragment of any of the anti-TRGV9 antibodies provided herein, and an antigen binding fragment of any of the CD123 antibodies provided herein.

According to another particular aspect, provided herein is an isolated anti-TRGV9/anti-CD123 bispecific antibody or antigen-binding fragment thereof that induces antibody-dependent cell-mediated cytotoxicity (ADCC). The bispecific antibody or antigen-binding fragment thereof can, for example, induce ADCC in vitro.

In certain embodiments, the bispecific antibody or antigen-binding fragment thereof induces γδ T cell dependent cytotoxicity of a cancer cell in vitro with an $EC_{50}$ of less than about 160 pM, when assessed in vitro at an effector to target cell ratio of 1:1. In one such embodiment, the bispecific antibody is an isolated anti-TRGV9/anti-CD123 bispecific antibody or antigen-binding fragment thereof that exhibits an $EC_{50}$ of less than about 160 pM, when assessed in vitro with a mixture of γδ T effector cells and Kasumi3 AML, target cells, where such cells are present in an effector to target cell ratio of about 1:1 and the bispecific antibody or antigen-binding fragment thereof is present at a concentration of about 30 ng/mL.

In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein, HC1 comprises a HCDR1, HCDR2, and HCDR3 comprising the amino acid sequences of (i) SEQ ID NO:1, SEQ ID NO:2, and SEQ ID NO:3, respectively, (ii) SEQ ID NO:1, SEQ ID NO:2, and SEQ ID NO:31, respectively, (iii) SEQ ID NO:1, SEQ ID NO:2, and SEQ ID NO:32, respectively, or (iv) SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein, HC1 comprises a HCDR1, HCDR2, and HCDR3 comprising the amino acid sequences of SEQ ID NO:1, SEQ ID NO:2, and SEQ ID NO:3, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:31, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:32, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:2, and SEQ ID NO:33, respectively, and LC1 comprises a LCDR1, LCDR2, and LCDR3 comprising the amino acid sequences of SEQ ID NO:4, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:1, SEQ ID NO:76, and SEQ ID NO:3, respectively, and LC1 comprises a LCDR1, LCDR2, and LCDR3 comprising the amino acid sequences of SEQ ID NO:77, SEQ ID NO:5, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:60, SEQ ID NO:61, and SEQ ID NO:62, respectively, and LC1 comprises a LCDR1, LCDR2, and LCDR3 comprising the amino acid sequences of SEQ ID NO:63, SEQ ID NO:64, and SEQ ID NO:6, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:89, SEQ ID NO:90, and SEQ ID NO:91, respectively, and LC1 comprises a LCDR1, LCDR2, and LCDR3 comprising the amino acid sequences of SEQ ID NO:92, SEQ ID NO:93, and SEQ ID NO:94, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:98, SEQ ID NO:99, and SEQ ID NO:100, respectively, and LC1 comprises a LCDR1, LCDR2, and LCDR3 comprising the amino acid sequences of SEQ ID NO:101, SEQ ID NO:102, and SEQ ID NO:103, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:107, SEQ ID NO:108, and SEQ ID NO:109, respectively, and LC1 comprises a LCDR1, LCDR2, and LCDR3 comprising the amino acid sequences of SEQ ID NO:110, SEQ ID NO:111, and SEQ ID NO:112, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:117, SEQ ID NO:118, and SEQ ID NO:119, respectively, and LC1 comprises a LCDR1, LCDR2, and LCDR3 comprising the amino acid sequences of SEQ ID NO:120, SEQ ID NO:121, and SEQ ID NO:122, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:127, SEQ ID NO:128, and SEQ ID NO:129, respectively, and LC1 comprises a LCDR1, LCDR2, and LCDR3 comprising the amino acid sequences of SEQ ID NO:130, SEQ ID NO:131, and SEQ ID NO:132, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:160, SEQ ID NO:161, and SEQ ID NO:162, respectively, and LC1 comprises a LCDR1, LCDR2, and LCDR3 comprising the amino acid sequences of SEQ ID NO:163, SEQ ID NO:164, and SEQ ID NO:165, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:166, SEQ ID NO:167, and SEQ ID NO:168, respectively, and LC1 comprises a LCDR1, LCDR2, and LCDR3 comprising the amino acid sequences of SEQ ID NO:169, SEQ ID NO:170, and SEQ ID NO:171, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:172, SEQ ID NO:173, and SEQ ID NO:174, respectively, and LC1 comprises a LCDR1, LCDR2, and LCDR3 comprising the amino acid sequences of SEQ ID NO:175, SEQ ID NO:176, and SEQ ID NO:177, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:178, SEQ ID NO:179, and SEQ ID NO:180, respectively, and LC1 comprises a LCDR1, LCDR2, and LCDR3 comprising the amino acid sequences of SEQ ID NO:181, SEQ ID NO:182, and SEQ ID NO:183, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:178, SEQ ID NO:700, and SEQ ID NO:701, respectively, and LC1 comprises a LCDR1, LCDR2, and LCDR3 comprising the amino acid sequences of SEQ ID NO:181, SEQ ID NO:182, and SEQ ID NO:183, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:184, SEQ ID NO:185, and SEQ ID NO:186, respectively, and LC1 comprises a LCDR1, LCDR2, and LCDR3 comprising the amino acid sequences of SEQ ID NO:187, SEQ ID NO:188, and SEQ ID NO:189, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:190, SEQ ID NO:191, and SEQ ID NO:192, respectively, and LC1 comprises a LCDR1, LCDR2, and LCDR3 comprising the amino acid sequences of SEQ ID NO:193, SEQ ID NO:194, and SEQ ID NO:195, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:196, SEQ ID NO:197, and SEQ ID NO:198, respectively, and LC1 comprises a LCDR1, LCDR2, and LCDR3 comprising the amino acid sequences of SEQ ID NO:199, SEQ ID NO:200, and SEQ ID NO:201, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:202, SEQ ID NO:203, and SEQ ID NO:204, respectively, and LC1 comprises a LCDR1, LCDR2, and LCDR3 comprising the amino acid sequences of SEQ ID NO:205, SEQ ID NO:206, and SEQ ID NO:207, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:208, SEQ ID NO:209, and SEQ ID NO:210, respectively, and LC1 comprises a LCDR1, LCDR2, and LCDR3 comprising the amino acid sequences of SEQ ID NO:211, SEQ ID NO:212, and SEQ ID NO:213, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:214, SEQ ID NO:215, and SEQ ID NO:216, respectively, and LC1 comprises a LCDR1, LCDR2, and LCDR3 comprising the amino acid sequences of SEQ ID NO:217, SEQ ID NO:218, and SEQ ID NO:219, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:214, SEQ ID NO:702, and SEQ ID NO:703, respectively, and LC1 comprises a LCDR1, LCDR2, and LCDR3 comprising the amino acid sequences of SEQ ID NO:217, SEQ ID NO:218, and SEQ ID NO:219, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:220, SEQ ID NO:221, and SEQ ID NO:222, respectively, and LC1 comprises a LCDR1, LCDR2, and LCDR3 comprising the amino acid sequences of SEQ ID NO:223, SEQ ID NO:224, and SEQ ID NO:225, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:226, SEQ ID NO:227, and SEQ ID NO:228, respectively, and LC1 comprises a LCDR1, LCDR2, and LCDR3 comprising the amino acid sequences of SEQ ID NO:229, SEQ ID NO:230, and SEQ ID NO:231, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:232, SEQ ID NO:233, and SEQ ID NO:234, respectively, and LC1 comprises a LCDR1, LCDR2, and LCDR3 comprising the amino acid sequences of SEQ ID NO:235, SEQ ID NO:236, and SEQ ID NO:237, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:238, SEQ ID NO:239, and SEQ ID NO:240, respectively, and LC1 comprises a LCDR1, LCDR2, and LCDR3 comprising the amino acid sequences of SEQ ID NO:241, SEQ ID NO:242, and SEQ ID NO:243, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:244, SEQ ID NO:245, and SEQ ID NO:246, respectively, and LC1 comprises a LCDR1, LCDR2, and LCDR3 comprising the amino acid sequences of SEQ ID NO:247, SEQ ID NO:248, and SEQ ID NO:249, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:250, SEQ ID NO:251, and SEQ ID NO:252, respectively, and LC1 comprises a LCDR1, LCDR2, and LCDR3 comprising the amino acid sequences of SEQ ID NO:253, SEQ ID NO:254, and SEQ ID NO:255, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:250, SEQ ID NO:704, and SEQ ID NO:705, respectively, and LC1 comprises a LCDR1, LCDR2, and LCDR3 comprising the amino acid sequences of SEQ ID NO:253, SEQ ID NO:254, and SEQ ID NO:255, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:256, SEQ ID NO:257, and SEQ ID NO:258, respectively, and LC1 comprises a LCDR1, LCDR2, and LCDR3 comprising the amino acid sequences of SEQ ID NO:259, SEQ ID NO:260, and SEQ ID NO:261, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:262, SEQ ID NO:263, and SEQ ID NO:264, respectively, and LC1 comprises a LCDR1, LCDR2, and LCDR3 comprising the amino acid sequences of SEQ ID NO:265, SEQ ID NO:266, and SEQ ID NO:267, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:268, SEQ ID NO:269, and SEQ ID NO:270, respectively, and LC1 comprises a LCDR1, LCDR2, and LCDR3 comprising the amino acid sequences of SEQ ID NO:271, SEQ ID NO:272, and SEQ ID NO:273, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:274, SEQ ID NO:275, and SEQ ID NO:276, respectively, and LC1 comprises a LCDR1, LCDR2, and LCDR3 comprising the amino acid sequences of SEQ ID NO:277, SEQ ID NO:278, and SEQ ID NO:279, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:280, SEQ ID NO:281, and SEQ ID NO:282, respectively, and LC1 comprises a LCDR1, LCDR2, and LCDR3 comprising the amino acid sequences of SEQ ID NO:283, SEQ ID NO:284, and SEQ ID NO:285, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:286, SEQ ID NO:287, and SEQ ID NO:288, respectively, and LC1 comprises a LCDR1, LCDR2, and LCDR3 comprising the amino acid sequences of SEQ ID NO:289, SEQ ID NO:290, and SEQ ID NO:291, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:286, SEQ ID NO:706, and SEQ ID NO:707, respectively, and LC1 comprises a LCDR1, LCDR2, and LCDR3 comprising the amino acid sequences of SEQ ID NO:289, SEQ ID NO:290, and SEQ ID NO:291, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:292, SEQ ID NO:293, and SEQ ID NO:294, respectively, and LC1 comprises a LCDR1, LCDR2, and LCDR3 comprising the amino acid sequences of SEQ ID NO:295, SEQ ID NO:296, and SEQ ID NO:297, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:298, SEQ ID NO:299, and SEQ ID NO:300, respectively, and LC1 comprises a LCDR1, LCDR2, and LCDR3 comprising the amino acid sequences of SEQ ID NO:301, SEQ ID NO:302, and SEQ ID NO:303, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:304, SEQ ID NO:305, and SEQ ID NO:306, respectively, and LC1 comprises a LCDR1, LCDR2, and LCDR3 comprising the amino acid sequences of SEQ ID NO:307, SEQ ID NO:308, and SEQ ID NO:309, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:310, SEQ ID NO:311, and SEQ ID NO:312, respectively, and LC1 comprises a LCDR1, LCDR2, and LCDR3 comprising the amino acid sequences of SEQ ID NO:313, SEQ ID NO:314, and SEQ ID NO:315, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:316, SEQ ID NO:317, and SEQ ID NO:318, respectively, and LC1 comprises a LCDR1, LCDR2, and LCDR3 comprising the amino acid sequences of SEQ ID NO:319, SEQ ID NO:320, and SEQ ID NO:321, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:322, SEQ ID NO:323, and SEQ ID NO:324, respectively, and LC1 comprises a LCDR1, LCDR2, and LCDR3 comprising the amino acid sequences of SEQ ID NO:325, SEQ ID NO:326, and SEQ ID NO:327, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:322, SEQ ID NO:708, and SEQ ID NO:709, respectively, and LC1 comprises a LCDR1, LCDR2, and LCDR3 comprising the amino acid sequences of SEQ ID NO:325, SEQ ID NO:326, and SEQ ID NO:327, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:328, SEQ ID NO:329, and SEQ ID NO:330, respectively, and LC1 comprises a LCDR1, LCDR2, and LCDR3 comprising the amino acid sequences of SEQ ID NO:331, SEQ ID NO:332, and SEQ ID NO:333, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:334, SEQ ID NO:335, and SEQ ID NO:336, respectively, and LC1 comprises a LCDR1, LCDR2, and LCDR3 comprising the amino acid sequences of SEQ ID NO:337, SEQ ID NO:338, and SEQ ID NO:339, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:340, SEQ ID NO:341, and SEQ ID NO:342, respectively, and LC1 comprises a LCDR1, LCDR2, and LCDR3 comprising the amino acid sequences of SEQ ID NO:343, SEQ ID NO:344, and SEQ ID NO:345, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:346, SEQ ID NO:347, and SEQ ID NO:348, respectively, and LC1 comprises a LCDR1, LCDR2, and LCDR3 comprising the amino acid sequences of SEQ ID NO:349, SEQ ID NO:350, and SEQ ID NO:351, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:352, SEQ ID NO:353, and SEQ ID NO:354, respectively, and LC1 comprises a LCDR1, LCDR2, and LCDR3 comprising the amino acid sequences of SEQ ID NO:355, SEQ ID NO:356, and SEQ ID NO:357, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:358, SEQ ID NO:359, and SEQ ID NO:360, respectively, and LC1 comprises a LCDR1, LCDR2, and LCDR3 comprising the amino acid sequences of SEQ ID NO:361, SEQ ID NO:362, and SEQ ID NO:363, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:358, SEQ ID NO:710, and SEQ ID NO:711, respectively, and LC1 comprises a LCDR1, LCDR2, and LCDR3 comprising the amino acid sequences of SEQ ID NO:361, SEQ ID NO:362, and SEQ ID NO:363, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:364, SEQ ID NO:365, and SEQ ID NO:366, respectively, and LC1 comprises a LCDR1, LCDR2, and LCDR3 comprising the amino acid sequences of SEQ ID NO:367, SEQ ID NO:368, and SEQ ID NO:369, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:370, SEQ ID NO:371, and SEQ ID NO:372, respectively, and LC1 comprises a LCDR1, LCDR2, and LCDR3 comprising the amino acid sequences of SEQ ID NO:373, SEQ ID NO:374, and SEQ ID NO:375, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:376, SEQ ID NO:377, and SEQ ID NO:378, respectively, and LC1 comprises a LCDR1, LCDR2, and LCDR3 comprising the amino acid sequences of SEQ ID NO:379, SEQ ID NO:380, and SEQ ID NO:381, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:382, SEQ ID NO:383, and SEQ ID NO:384, respectively, and LC1 comprises a LCDR1, LCDR2, and LCDR3 comprising the amino acid sequences of SEQ ID NO:385, SEQ ID NO:386, and SEQ ID NO:387, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:388, SEQ ID NO:389, and SEQ ID NO:390, respectively, and LC1 comprises a LCDR1, LCDR2, and LCDR3 comprising the amino acid sequences of SEQ ID NO:391, SEQ ID NO:392, and SEQ ID NO:393, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:394, SEQ ID NO:395, and SEQ ID NO:396, respectively, and LC1 comprises a LCDR1, LCDR2, and LCDR3 comprising the amino acid sequences of SEQ ID NO:397, SEQ ID NO:398, and SEQ ID NO:399, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:394, SEQ ID NO:712, and SEQ ID NO:713, respectively, and LC1 comprises a LCDR1, LCDR2, and LCDR3 comprising the amino acid sequences of SEQ ID NO:397, SEQ ID NO:398, and SEQ ID NO:399, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:400, SEQ ID NO:401, and SEQ ID NO:402, respectively, and LC1 comprises a LCDR1, LCDR2, and LCDR3 comprising the amino acid sequences of SEQ ID NO:403, SEQ ID NO:404, and SEQ ID NO:405, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:406, SEQ ID NO:407, and SEQ ID NO:408, respectively, and LC1 comprises a LCDR1, LCDR2, and LCDR3 comprising the amino acid sequences of SEQ ID NO:409, SEQ ID NO:410, and SEQ ID NO:411, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:412, SEQ ID NO:413, and SEQ ID NO:414, respectively, and LC1 comprises a LCDR1, LCDR2, and LCDR3 comprising the amino acid sequences of SEQ ID NO:415, SEQ ID NO:416, and SEQ ID NO:417, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:418, SEQ ID NO:419, and SEQ ID NO:420, respectively, and LC1 comprises a LCDR1, LCDR2, and LCDR3 comprising the amino acid sequences of SEQ ID NO:421, SEQ ID NO:422, and SEQ ID NO:423, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:424, SEQ ID NO:425, and SEQ ID NO:426, respectively, and LC1 comprises a LCDR1, LCDR2, and LCDR3 comprising the amino acid sequences of SEQ ID NO:427, SEQ ID NO:428, and SEQ ID NO:429, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:430, SEQ ID NO:431, and SEQ ID NO:432, respectively, and LC1 comprises a LCDR1, LCDR2, and LCDR3 comprising the amino acid sequences of SEQ ID NO:433, SEQ ID NO:434, and SEQ ID NO:435, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:430, SEQ ID NO:714, and SEQ ID NO:715, respectively, and LC1 comprises a LCDR1, LCDR2, and LCDR3 comprising the amino acid sequences of SEQ ID NO:433, SEQ ID NO:434, and SEQ ID NO:435, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:436, SEQ ID NO:437, and SEQ ID NO:438, respectively, and LC1 comprises a LCDR1, LCDR2, and LCDR3 comprising the amino acid sequences of SEQ ID NO:439, SEQ ID NO:440, and SEQ ID NO:441, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:442, SEQ ID NO:443, and SEQ ID NO:444, respectively, and LC1 comprises a LCDR1, LCDR2, and LCDR3 comprising the amino acid sequences of SEQ ID NO:445, SEQ ID NO:446, and SEQ ID NO:447, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:448, SEQ ID NO:449, and SEQ ID NO:450, respectively, and LC1 comprises a LCDR1, LCDR2, and LCDR3 comprising the amino acid sequences of SEQ ID NO:451, SEQ ID NO:452, and SEQ ID NO:453, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:454, SEQ ID NO:455, and SEQ ID NO:456, respectively, and LC1 comprises a LCDR1, LCDR2, and LCDR3 comprising the amino acid sequences of SEQ ID NO:457, SEQ ID NO:458, and SEQ ID NO:459, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:460, SEQ ID NO:461, and SEQ ID NO:462, respectively, and LC1 comprises a LCDR1, LCDR2, and LCDR3 comprising the amino acid sequences of SEQ ID NO:463, SEQ ID NO:464, and SEQ ID NO:465, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:466, SEQ ID NO:467, and SEQ ID NO:468, respectively, and LC1 comprises a LCDR1, LCDR2, and LCDR3 comprising the amino acid sequences of SEQ ID NO:469, SEQ ID NO:470, and SEQ ID NO:471, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:466, SEQ ID NO:716, and SEQ ID NO:717, respectively, and LC1 comprises a LCDR1, LCDR2, and LCDR3 comprising the amino acid sequences of SEQ ID NO:469, SEQ ID NO:470, and SEQ ID NO:471, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:472, SEQ ID NO:473, and SEQ ID NO:474, respectively, and LC1 comprises a LCDR1, LCDR2, and LCDR3 comprising the amino acid sequences of SEQ ID NO:475, SEQ ID NO:476, and SEQ ID NO:477, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:478, SEQ ID NO:479, and SEQ ID NO:480, respectively, and LC1 comprises a LCDR1, LCDR2, and LCDR3 comprising the amino acid sequences of SEQ ID NO:481, SEQ ID NO:482, and SEQ ID NO:483, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:484, SEQ ID NO:485, and SEQ ID NO:486, respectively, and LC1 comprises a LCDR1, LCDR2, and LCDR3 comprising the amino acid sequences of SEQ ID NO:487, SEQ ID NO:488, and SEQ ID NO:489, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:490, SEQ ID NO:491, and SEQ ID NO:492, respectively, and LC1 comprises a LCDR1, LCDR2, and LCDR3 comprising the amino acid sequences of SEQ ID NO:493, SEQ ID NO:494, and SEQ ID NO:495, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:496, SEQ ID NO:497, and SEQ ID NO:498, respectively, and LC1 comprises a LCDR1, LCDR2, and LCDR3 comprising the amino acid sequences of SEQ ID NO:499, SEQ ID NO:500, and SEQ ID NO:501, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:502, SEQ ID NO:503, and SEQ ID NO:504, respectively, and LC1 comprises a LCDR1, LCDR2, and LCDR3 comprising the amino acid sequences of SEQ ID NO:505, SEQ ID NO:506, and SEQ ID NO:507, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:502, SEQ ID NO:503, and SEQ ID NO:719, respectively, and LC1 comprises a LCDR1, LCDR2, and LCDR3 comprising the amino acid sequences of SEQ ID NO:505, SEQ ID NO:506, and SEQ ID NO:507, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:508, SEQ ID NO:509, and SEQ ID NO:510, respectively, and LC1 comprises a LCDR1, LCDR2, and LCDR3 comprising the amino acid sequences of SEQ ID NO:511, SEQ ID NO:512, and SEQ ID NO:513, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:514, SEQ ID NO:515, and SEQ ID NO:516, respectively, and LC1 comprises a LCDR1, LCDR2, and LCDR3 comprising the amino acid sequences of SEQ ID NO:517, SEQ ID NO:518, and SEQ ID NO:519, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:520, SEQ ID NO:521, and SEQ ID NO:522, respectively, and LC1 comprises a LCDR1, LCDR2, and LCDR3 comprising the amino acid sequences of SEQ ID NO:523, SEQ ID NO:524, and SEQ ID NO:525, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:526, SEQ ID NO:527, and SEQ ID NO:528, respectively, and LC1 comprises a LCDR1, LCDR2, and LCDR3 comprising the amino acid sequences of SEQ ID NO:529, SEQ ID NO:530, and SEQ ID NO:531, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:532, SEQ ID NO:533, and SEQ ID NO:534, respectively, and LC1 comprises a LCDR1, LCDR2, and LCDR3 comprising the amino acid sequences of SEQ ID NO:535, SEQ ID NO:536, and SEQ ID NO:537, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:538, SEQ ID NO:539, and SEQ ID NO:540, respectively, and LC1 comprises a LCDR1, LCDR2, and LCDR3 comprising the amino acid sequences of SEQ ID NO:541, SEQ ID NO:542, and SEQ ID NO:543, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:538, SEQ ID NO:720, and SEQ ID NO:721, respectively, and LC1 comprises a LCDR1, LCDR2, and LCDR3 comprising the amino acid sequences of SEQ ID NO:541, SEQ ID NO:542, and SEQ ID NO:543, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:544, SEQ ID NO:545, and SEQ ID NO:546, respectively, and LC1 comprises a LCDR1, LCDR2, and LCDR3 comprising the amino acid sequences of SEQ ID NO:547, SEQ ID NO:548, and SEQ ID NO:549, respectively, to form a first antigen-binding site that specifically binds TRGV9. In another embodiment, the bispecific antibody is an isolated anti-TRGV9/anti-CD123 bispecific antibody or antigen-binding fragment thereof comprising (a) a HC1; (b) a HC2; (c) a LC1; and (d) a LC2, wherein HC1 is associated with LC1 and HC2 is associated with LC2, and wherein HC1 comprises a HCDR1, HCDR2, and HCDR3 comprising the amino acid sequences of SEQ ID NO:550, SEQ ID NO:551, and SEQ ID NO:552, respectively, and LC1 comprises a LCDR1, LCDR2, and LCDR3 comprising the amino acid sequences of SEQ ID NO:553, SEQ ID NO:554, and SEQ ID NO:555, respectively, to form a first antigen-binding site that specifically binds TRGV9. In some embodiments, HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14 respectively, to form a second antigen-binding site that specifically binds CD123, wherein the anti-TRGV9/anti-CD123 bispecific antibody or antigen-binding fragment thereof exhibits an $EC_{50}$ of less than about 160 pM, when assessed in vitro with a mixture of γδ T effector cells and Kasumi3 AML target cells, where such cells are present in an effector to target cell ratio of about 1:1 and the bispecific antibody or antigen-binding fragment thereof is present at a concentration of about 30 ng/mL. In some embodiments, HC2 comprises a HCDR1, HCDR2, and HCDR3 comprising the amino acid sequences of SEQ ID NO:9, SEQ ID NO:10, and SEQ ID NO:11, respectively, and LC2 comprises a LCDR1, LCDR2, and LCDR3 comprising the amino acid sequences of SEQ ID NO:12, SEQ ID NO:13, and SEQ ID NO:14 respectively, to form a second antigen-binding site that specifically binds CD123. In some embodiments, the HC2 comprises a HCDR1, HCDR2, and HCDR3 comprising the amino acid sequence of SEQ ID NO:556, SEQ ID NO:557, and SEQ ID NO:558, respectively, and a LCDR1, LCDR2, and LCDR3 comprising the amino acid sequence of SEQ ID NO:559, SEQ ID NO:560, and SEQ ID NO:561, respectively, to form a second antigen-binding site that specifically binds CD123. In some embodiments, the HC2 comprises a HCDR1, HCDR2, and HCDR3 comprising the amino acid sequence of SEQ ID NO:562, SEQ ID NO:563, and SEQ ID NO:564, respectively, and a LCDR1, LCDR2, and LCDR3 comprising the amino acid sequence of SEQ ID NO:565, SEQ ID NO:566, and SEQ ID NO:567, respectively, to form a second antigen-binding site that specifically binds CD123. In some embodiments, the HC2 comprises a HCDR1, HCDR2, and HCDR3 comprising the amino acid sequence of SEQ ID NO:568, SEQ ID NO:569, and SEQ ID NO:570, respectively, and a LCDR1, LCDR2, and LCDR3 comprising the amino acid sequence of SEQ ID NO:571, SEQ ID NO:572, and SEQ ID NO:573, respectively, to form a second antigen-binding site that specifically binds CD123. In some embodiments, the HC2 comprises a HCDR1, HCDR2, and HCDR3 comprising the amino acid sequence of SEQ ID NO:574, SEQ ID NO:575, and SEQ ID NO:576, respectively, and a LCDR1, LCDR2, and LCDR3 comprising the amino acid sequence of SEQ ID NO:577, SEQ ID NO:578, and SEQ ID NO:579, respectively, to form a second antigen-binding site that specifically binds CD123. In some embodiments, the HC2 comprises a HCDR1, HCDR2, and HCDR3 comprising the amino acid sequence of SEQ ID NO:574, SEQ ID NO:722, and SEQ ID NO:723, respectively, and a LCDR1, LCDR2, and LCDR3 comprising the amino acid sequence of SEQ ID NO:577, SEQ ID NO:578, and SEQ ID NO:579, respectively, to form a second antigen-binding site that specifically binds CD123. In some embodiments, the HC2 comprises a HCDR1, HCDR2, and HCDR3 comprising the amino acid sequence of SEQ ID NO:580, SEQ ID NO:581, and SEQ ID NO:582, respectively, and a LCDR1, LCDR2, and LCDR3 comprising the amino acid sequence of SEQ ID NO:583, SEQ ID NO:584, and SEQ ID NO:585, respectively, to form a second antigen-binding site that specifically binds CD123. In some embodiments, the HC2 comprises a HCDR1, HCDR2, and HCDR3 comprising the amino acid sequence of SEQ ID NO:586, SEQ ID NO:587, and SEQ ID NO:588; and (ii) a VL comprising a VL CDR1 having an amino acid sequence of SEQ ID NO:589, SEQ ID NO:590, and SEQ ID NO:591, respectively, to form a second antigen-binding site that specifically binds CD123. In certain embodiments, the anti-TRGV9/anti-CD123 bispecific antibody or antigen-binding fragment thereof exhibits an $EC_{50}$ of less than about 160 pM, when assessed in vitro with a mixture of γδ T effector cells and Kasumi3 AML target cells, where such cells are present in an effector to target cell ratio of about 1:1 and the bispecific antibody or antigen-binding fragment thereof is present at a concentration of about 30 ng/mL.

In certain embodiments, the $EC_{50}$ is less than about 1000 pM, less than about 900 pM, less than about 800 pM, less than about 700 pM, less than about 600 pM, less than about 500 pM, less than about 400 pM, less than about 300 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM.

In certain embodiments, the effector to target cell ratio can, for example, be 0.01:1, 0.02:1, 0.03:1, 0.04:1, 0.05:1, 0.06:1, 0.07:1, 0.08:1, 0.09:1, 1:1, 2:1, 3:1, 4:1, 5:1, 6:1, 7:1, 8:1, 9:1, or 10:1.

In certain embodiments, the concentration of the bispecific antibody or antigen-binding fragment thereof is about 0.000005 ng/mL, about 0.00005 ng/mL, about 0.0005, about 0.005 ng/mL, about 0.01 ng/mL, about 0.02 ng/mL, about 0.03 ng/mL, about 0.04 ng/mL, about 0.05 ng/mL, about 0.06 ng/mL, about 0.07 ng/mL, about 0.08 ng/mL, about 0.09 ng/mL, about 0.1 ng/mL, about 0.5 ng/mL, about 1.0 ng/mL, about 10 ng/mL, about 20 ng/mL about, about 30 ng/mL about 40 ng/mL, about 50 ng/mL, about 60 ng/mL, about 70 ng/mL, about 80 ng/mL, about 90 ng/mL, about 100 ng/mL, or about 1000 ng/mL.

In some embodiments described herein, immune effector properties of the anti-TRGV9/anti-CD123 bispecific antibodies can be enhanced or silenced through Fc modifications by techniques known to those skilled in the art. For example, Fc effector functions such as Clq binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. can be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such Abs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α-1,6-fucosyltrasferase (FUT8) gene (Mori et al., Biotechnol Bioeng 88:901-908, 2004), or coexpression of β-1,4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the anti-TRGV9/anti-CD123 bispecific antibodies can also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

According to another particular aspect, provided herein is an isolated anti-TRGV9/anti-CD123 bispecific antibody or antigen-binding fragment thereof. In some embodiments, the anti-TRGV9/anti-CD123 bispecific antibody or antigen-binding fragment thereof is chimeric.

According to another particular aspect, provided herein is an isolated anti-TRGV9/anti-CD123 bispecific antibody or antigen-binding fragment thereof. In some embodiments, the anti-TRGV9/anti-CD123 bispecific antibody or antigen-binding fragment thereof is human or humanized.

Also provided is a nucleic acid encoding an antibody that binds to a TRGV9 provided herein. Also provided is a vector comprising a nucleic acid encoding an antibody that binds to a TRGV9 provided herein. Also provided is a host cell comprising a vector comprising a nucleic acid encoding an antibody that binds to a TRGV9 provided herein. Also provided is a kit comprising the vector comprising a nucleic acid encoding an antibody that binds to a TRGV9 provided herein, and packaging for the same.

Also provided is a nucleic acid encoding a bispecific antibody comprising: (a) a first binding domain that binds to TRGV9, and (b) a second binding domain that binds to a second target that is not TRGV9, as provided herein. Also provided is a vector comprising a nucleic acid encoding a bispecific antibody that binds to a TRGV9 provided herein. Also provided is a host cell comprising a vector comprising a nucleic acid encoding a bispecific antibody that binds to a TRGV9 provided herein. Also provided is a kit comprising the vector comprising a nucleic acid encoding a bispecific antibody that binds to a TRGV9 provided herein, and packaging for the same.

In another general aspect, provided is an isolated nucleic acid encoding an antibody or antigen-binding fragment thereof provided herein. In some embodiments, the antibody is a TRGV9 antibody provided herein. In certain embodiments, the antibody is a monoclonal antibody. In another general aspect, provided is an isolated nucleic acid encoding a bispecific antibody or antigen-binding fragment thereof provided herein. In some embodiments, the antibody is a TRGV bispecific antibody provided herein. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies and/or bispecific antibodies provided herein can be altered without changing the amino acid sequences of the proteins.

In another general aspect, provided is a vector comprising an isolated nucleic acid encoding an antibody or antigen-binding fragment thereof provided herein. In some embodiments, the antibody is a TRGV antibody provided herein. In certain embodiments, the antibody is a monoclonal antibody. In some embodiments, the antibody is a TRGV bispecific antibody provided herein. In another general aspect, provided is a vector comprising an isolated nucleic acid encoding a bispecific antibody or antigen-binding fragment thereof provided herein. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to certain embodiments. Such techniques are well known to those skilled in the art in view of the present disclosure.

In another general aspect, provided is a host cell comprising an isolated nucleic acid encoding an antibody or antigen-binding fragment thereof provided herein. In some embodiments, the antibody is a TRGV antibody provided herein. In certain embodiments, the antibody is a monoclonal antibody. In some embodiments, the antibody is a TRGV bispecific antibody provided herein. Any host cell known to those skilled in the art in view of the present disclosure can be used for recombinant expression of antibodies or antigen-binding fragments thereof provided herein. In some embodiments, the host cells are E. coli TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, provided is a method of producing an antibody or antigen-binding fragment thereof disclosed herein. The methods comprise culturing a cell comprising a nucleic acid encoding the antibody or antigen-binding fragment thereof under conditions to produce an antibody or antigen-binding fragment thereof disclosed herein and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

In another general aspect, provided is a method of producing a bispecific antibody or antigen-binding fragment thereof disclosed herein. The methods comprise culturing a cell comprising a nucleic acid encoding the bispecific antibody or antigen-binding fragment thereof under conditions to produce a bispecific antibody or antigen-binding fragment thereof disclosed herein and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, provided is a pharmaceutical composition comprising an isolated bispecific antibody or antigen-binding fragment thereof provided herein and a pharmaceutically acceptable carrier. Also provided is a pharmaceutical composition comprising an antibody that binds to a TRGV9 provided herein, and a pharmaceutically acceptable carrier. Also provided is a method of producing the pharmaceutical composition, comprising combining the antibody with a pharmaceutically acceptable carrier to obtain the pharmaceutical composition. In another aspect, provided herein is a pharmaceutical composition comprising a comprising: (a) a first binding domain that binds to TRGV9, and (b) a second binding domain that binds to a second target that is not TRGV9, and a pharmaceutically acceptable carrier. Any of the bispecific antibodies provided herein are contemplated in the pharmaceutical compositions. In certain embodiments, the second binding domain binds to CD123. The term "pharmaceutical composition" as used herein means a product comprising an antibody provided herein together with a pharmaceutically acceptable carrier. Antibodies provided herein and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness or biological activity of a composition provided herein. According to particular embodiments, in view of the present disclosure, any pharmaceutically acceptable carrier suitable for use in an antibody pharmaceutical composition can be used herein.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carriers can be used in formulating the pharmaceutical compositions provided herein.

In one embodiment, the pharmaceutical composition is a liquid formulation. One example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment, the pH of the formulation is from about 7.0 to about 9.5. In another embodiment, the pH of the formulation is from about 3.0 to about 7.0.

In another embodiment, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments.

In another embodiment, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments.

In another embodiment, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can include mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethyl-cellulose. Another example of an isotonic agent is a sugar alcohol. In some embodiments, the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments.

In another embodiment, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments.

In another embodiment, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment, the pharmaceutical composition comprises a stabilizer. In some embodiments, said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments.

In further embodiments, the pharmaceutical composition comprises one or more surfactants, such as a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments.

In a further embodiment, the pharmaceutical composition comprises one or more protease inhibitors, such as, e.g., EDTA, and/or benzamidine hydrochloric acid (HC1). The protease inhibitor can be present individually or in the aggregate, in a concentration from about 0.1 mg/ml to about 20 mg/ml. Pharmaceutical compositions comprising each one of these specific protease inhibitors constitute alternative embodiments.

In another general aspect, provided is a method of producing a pharmaceutical composition comprising a bispecific antibody or antigen-binding fragment thereof provided herein, comprising combining a bispecific antibody or antigen-binding fragment thereof with a pharmaceutically acceptable carrier to obtain the pharmaceutical composition.

Methods of Use

In one general aspect, provided is a method of activating a γδ T cell expressing TRGV9, comprising contacting the γδ T cell with an antibody that binds to a TRGV9 provided herein. In another aspect, provided herein is a method of activating a γδ T cell expressing TRGV9, comprising contacting the γδ T cell with the bispecific antibody, as provided herein. In some embodiments, the contacting results in an increase in CD69, CD25, and/or Granzyme B expression, as compared to a control γδ T cell expressing TRGV9.

In another general aspect, provided is a method of inactivating a γδ T cell expressing TRGV9, comprising contacting the γδ T cell with an antibody that binds to a TRGV9 provided herein. In another aspect, provided herein is a method of inactivating a γδ T cell expressing TRGV9, comprising contacting the γδ T cell with the bispecific antibody, as provided herein.

In another general aspect, provided is a method of blocking activation of a γδ T cell expressing TRGV9, comprising contacting the γδ T cell with an antibody that binds to a TRGV9 provided herein. In another aspect, provided herein is a method of blocking activation of a γδ T cell expressing TRGV9, comprising contacting the γδ T cell with the bispecific antibody, as provided herein.

In another general aspect, provided is a method of modulating the activation of a γδ T cell expressing TRGV9, comprising contacting the γδ T cell with an antibody that binds to a TRGV9 provided herein. In another aspect, provided herein is a method of modulating the activation of a γδ T cell expressing TRGV9, comprising contacting the γδ T cell with the bispecific antibody, as provided herein.

In another aspect, provided herein is a method of directing a γδ T cell expressing TRGV9 to a cancer cell, the method comprising contacting the γδ T cell with a bispecific antibody provided herein. In some embodiments, the contacting directs the γδ T cell to the cancer cell.

In another general aspect, provided is a method of targeting CD123 on the surface of a cancer cell, the method comprising exposing the cancer cell to an anti-TRGV9/anti-CD123 bispecific antibody or antigen binding fragment thereof or a pharmaceutical composition provided herein.

The functional activity of bispecific antibodies and antigen-binding fragments thereof that bind TRGV9 and/or CD123 can be characterized by methods known in the art and as described herein. Methods for characterizing antibodies and antigen-binding fragments thereof that bind TRGV9 and/or CD123 include, but are not limited to, affinity and specificity assays including Biacore, ELISA, and OctetRed analysis; binding assays to detect the binding of antibodies to CD123 on cancer cells by FACS; binding assays to detect the binding of antibodies to TRGV9 on γδ T cells. According to particular embodiments, the methods for characterizing antibodies and antigen-binding fragments thereof that bind TRGV9 and/or CD123 include those described below.

In another general aspect, provided herein is a method of directing Vγ9-expressing γδ T cells to a cancer cell. The methods comprise contacting the Vγ9-expressing γδ T cell with an anti-TRGV9/anti-CD123 bispecific antibody or antigen binding fragment thereof. In some embodiments, the anti-TRGV9/anti-CD123 bispecific antibody or antigen binding fragment thereof directs the Vγ9-expressing γδ T cell to a cancer cell having CD123 on its surface.

In another general aspect, provided herein is a method for inhibiting growth or proliferation of cancer cells. The methods comprise contacting the Vγ9-expressing γδ T cells with an anti-TRGV9/anti-CD123 bispecific antibody or antigen binding fragment thereof. In some embodiments, contacting the cancer cells with the anti-TRGV9/anti-CD123 bispecific antibody or antigen binding fragment thereof composition inhibits the growth or proliferation of the cancer cells.

In another aspect, provided herein is a method of inhibiting growth or proliferation of cancer cells expressing a cancer antigen on the cell surface, the method comprising contacting the cancer cells with a bispecific antibody provided herein. In some embodiments, contacting the cancer cells with the pharmaceutical composition inhibits growth or proliferation of the cancer cells. In some embodiments, the cancer cells are in the presence of a γδ T cell expressing TRGV9 while in contact with the bispecific antibody.

In another aspect, provided herein is a method for eliminating cancer cells in a subject, comprising administering an effective amount of a bispecific antibody, as provided herein, to the subject. In another general aspect, provided is a method of treating a cancer in a subject in need thereof, comprising administering to the subject an isolated bispecific antibody or antigen binding fragment thereof that specifically binds TRGV9 and a tumor-associated antigen presented on the surface of a tumor cell (e.g., CD123) or a pharmaceutical composition disclosed herein. The cancer can, for example, be a CD123-expressing cancer. The cancer can, for example, be a CD123-expressing cancer. The cancer can, for example, be a hematologic cancer. The hematologic cancer can, for example, be a leukemia, a lymphoma, and a myeloma. The leukemia can be an acute myeloid leukemia (AML) or an acute lymphocytic leukemia (ALL). In some embodiments, the subject is a human. In some embodiments, the subject is a subject in need thereof.

According to certain embodiments, the pharmaceutical composition comprises an effective amount of an anti-TRGV9/anti-CD123 bispecific antibody or antigen-binding fragment thereof. As used herein, the term "effective amount" refers to an amount of an active ingredient or component that elicits the desired biological or medicinal response in a subject.

According to particular embodiments, an effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, provided are compositions used in the treatment of a cancer. For cancer therapy, the compositions can be used in combination with another treatment including, but not limited to, a chemotherapy, an anti-CD20 mAb, an anti-TIM-3 mAb, an anti-CTLA-4 antibody, an anti-PD-L1 antibody, an anti-PD-1 antibody, a PD-1/PD-L1 therapy, IDO, an anti-OX40 antibody, an anti-GITR antibody, an anti-CD40 antibody, an anti-CD38 antibody, cytokines, oncolytic viruses, TLR agonists, STING agonist, other immuno-oncology drugs, an antiangiogenic agent, a radiation therapy, an antibody-drug conjugate (ADC), a targeted therapy, or other anticancer drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Anti-TRGV9 antibodies provided herein may also be used as agents to detect Vγ9-expressing cells. Thus, in another methods, provided is a method of detecting a cell expressing Vγ9, comprising contacting a cell with a TRGV9 antibody provided herein. In certain embodiments, the detecting is by ELISA. In some embodiments, the detecting is by FACS analysis. Also provided are kits comprising a TRGV9 antibody provided herein, and instructions for use.

EMBODIMENTS

This invention provides the following non-limiting embodiments.

In one set of embodiments, provided are:
1. An antibody that binds to T Cell Receptor Gamma Variable 9 (TRGV9).
2. The antibody of embodiment 1, wherein the antibody comprises:
   (i) a VH comprising a VH complementarity determining region (CDR) 1 having an amino acid sequence of SEQ ID NO:1, a VH CDR2 having an amino acid sequence of SEQ ID NO:2, and a VH CDR3 having an amino acid sequence of SEQ ID NO:31; and
   (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.
3. The antibody of embodiment 2, wherein the antibody comprises a VH having an amino acid sequence of SEQ ID NO:34.
4. The antibody of embodiment 2, wherein the antibody comprises a VL having an amino acid sequence of SEQ ID NO:8.
5. The antibody of embodiment 2, wherein the antibody comprises a VH having an amino acid sequence of SEQ ID NO:34, and a VL having an amino acid sequence of SEQ ID NO:8.
6. The antibody of embodiment 1, wherein the antibody comprises:
   (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and
   (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.
7. The antibody of embodiment 6, wherein the antibody comprises a VH having an amino acid sequence of SEQ ID NO:35.
8. The antibody of embodiment 6, wherein the antibody comprises a VL having an amino acid sequence of SEQ ID NO:8.
9. The antibody of embodiment 6, wherein the antibody comprises a VH having an amino acid sequence of SEQ ID NO:35, and a VL having an amino acid sequence of SEQ ID NO:8.
10. The antibody of embodiment 1, wherein the antibody comprises:
    (i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and
    (ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.
11. The antibody of embodiment 10, wherein the antibody comprises a VH having an amino acid sequence of SEQ ID NO:36.
12. The antibody of embodiment 10, wherein the antibody comprises a VL having an amino acid sequence of SEQ ID NO:8.
13. The antibody of embodiment 10, wherein the antibody comprises a VH having an amino acid sequence of SEQ ID NO:36, and a VL having an amino acid sequence of SEQ ID NO:8.
14. The antibody of embodiment 1, wherein the antibody comprises:
    (i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and
    (ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6.
15. The antibody of embodiment 1, wherein the antibody comprises:
    (i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and
    (ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6.
16. The antibody of embodiment 14 or 15, wherein the antibody comprises a VH having an amino acid sequence of SEQ ID NO:65.
17. The antibody of embodiment 14 or 15, wherein the antibody comprises a VL having an amino acid sequence of SEQ ID NO:66.

18. The antibody of embodiment 14 or 15, wherein the antibody comprises a VH having an amino acid sequence of SEQ ID NO:65, and a VL having an amino acid sequence of SEQ ID NO:66.
19. The antibody of embodiment 14 or 15, wherein the antibody comprises a VH having an amino acid sequence of SEQ ID NO:67.
20. The antibody of embodiment 14 or 15, wherein the antibody comprises a VL having an amino acid sequence of SEQ ID NO:68.
21. The antibody of embodiment 14 or 15, wherein the antibody comprises a VH having an amino acid sequence of SEQ ID NO:67, and a VL having an amino acid sequence of SEQ ID NO:68.
22. The antibody of embodiment 1, wherein the antibody comprises:
   (i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100; and
   (ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103.
23. The antibody of embodiment 22, wherein the antibody comprises a VH having an amino acid sequence of SEQ ID NO:104.
24. The antibody of embodiment 22, wherein the antibody comprises a VL having an amino acid sequence of SEQ ID NO:105.
25. The antibody of embodiment 22, wherein the antibody comprises a VH having an amino acid sequence of SEQ ID NO:104, and a VL having an amino acid sequence of SEQ ID NO:105.
26. The antibody of embodiment 1, wherein the antibody comprises:
   (i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109; and
   (ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112.
27. The antibody of embodiment 26, wherein the antibody comprises a VH having an amino acid sequence of SEQ ID NO:113.
28. The antibody of embodiment 26, wherein the antibody comprises a VL having an amino acid sequence of SEQ ID NO:114.
29. The antibody of embodiment 26, wherein the antibody comprises a VH having an amino acid sequence of SEQ ID NO:113, and a VL having an amino acid sequence of SEQ ID NO:114.
30. The antibody of embodiment 1, wherein the antibody comprises:
   (i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119; and
   (ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122.
31. The antibody of embodiment 30, wherein the antibody comprises a VH having an amino acid sequence of SEQ ID NO:123.
32. The antibody of embodiment 30, wherein the antibody comprises a VL having an amino acid sequence of SEQ ID NO:124.
33. The antibody of embodiment 30, wherein the antibody comprises a VH having an amino acid sequence of SEQ ID NO:123, and a VL having an amino acid sequence of SEQ ID NO:124.
34. The antibody of embodiment 1, wherein the antibody comprises:
   (i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129; and
   (ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132.
35. The antibody of embodiment 34, wherein the antibody comprises a VH having an amino acid sequence of SEQ ID NO:133.
36. The antibody of embodiment 34, wherein the antibody comprises a VL having an amino acid sequence of SEQ ID NO:134.
37. The antibody of embodiment 34, wherein the antibody comprises a VH having an amino acid sequence of SEQ ID NO:133, and a VL having an amino acid sequence of SEQ ID NO:134.
38. The antibody of any one of embodiments 1 to 37, wherein the TRGV9 is present on the surface of a γδ T cell.
39. The antibody of any one of embodiments 1 to 38, wherein the antibody is a humanized antibody.
40. The antibody of any one of embodiments 1 to 39, wherein the antibody is an IgG antibody.
41. The antibody of embodiment 40, wherein the IgG antibody is an IgG1, IgG2, IgG3, or IgG4 antibody.
42. The antibody of any one of embodiments 1 to 41, wherein the antibody is multivalent.
43. The antibody of embodiment 42, wherein the antibody is capable of binding at least three antigens.
44. The antibody of embodiment 42, wherein the antibody is capable of binding at least five antigens.
45. A nucleic acid encoding the antibody of any one of embodiments 1 to 44.
46. A vector comprising the nucleic acid of embodiment 45.
47. A host cell comprising the vector of embodiment 45.
48. A kit comprising the vector of embodiment 45 and packaging for the same.
49. A pharmaceutical composition comprising the antibody of any one of embodiments 1 to 44, and a pharmaceutically acceptable carrier.
50. A method of producing the pharmaceutical composition of embodiment 49, comprising combining the antibody with a pharmaceutically acceptable carrier to obtain the pharmaceutical composition.
51. A method of activating a γδ T cell expressing TRGV9, comprising contacting the γδ T cell with the antibody of any one of embodiments 1 to 44.

52. The method of embodiment 51, wherein the contacting results in an increase in CD69, CD25, and/or Granzyme B expression, as compared to a control γδ T cell expressing TRGV9.

53. A bispecific antibody comprising:
(a) a first binding domain that binds to TRGV9, and
(b) a second binding domain that binds to a second target that is not TRGV9.

54. The bispecific antibody of embodiment 53, wherein the first binding domain comprises:
(i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:3; and
(ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

55. The bispecific antibody of embodiment 54, wherein the first binding domain comprises a VH having an amino acid sequence of SEQ ID NO:7.

56. The bispecific antibody of embodiment 54, wherein the first binding domain comprises a VL having an amino acid sequence of SEQ ID NO:8.

57. The bispecific antibody of embodiment 54, wherein the first binding domain comprises a VH having an amino acid sequence of SEQ ID NO:7, and a VL having an amino acid sequence of SEQ ID NO:8.

58. The bispecific antibody of embodiment 53, wherein the first binding domain comprises:
(i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:31; and
(ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

59. The bispecific antibody of embodiment 58, wherein the first binding domain comprises a VH having an amino acid sequence of SEQ ID NO:34.

60. The bispecific antibody of embodiment 58, wherein the first binding domain comprises a VL having an amino acid sequence of SEQ ID NO:8.

61. The bispecific antibody of embodiment 58, wherein the first binding domain comprises a VH having an amino acid sequence of SEQ ID NO:34, and a VL having an amino acid sequence of SEQ ID NO:8.

62. The bispecific antibody of embodiment 53, wherein the first binding domain comprises:
(i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:32; and
(ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

63. The bispecific antibody of embodiment 62, wherein the first binding domain comprises a VH having an amino acid sequence of SEQ ID NO:35.

64. The bispecific antibody of embodiment 62, wherein the first binding domain comprises a VL having an amino acid sequence of SEQ ID NO:8.

65. The bispecific antibody of embodiment 62, wherein the first binding domain comprises a VH having an amino acid sequence of SEQ ID NO:35, and a VL having an amino acid sequence of SEQ ID NO:8.

66. The bispecific antibody of embodiment 53, wherein the first binding domain comprises:
(i) a VH comprising a VH CDR1 having an amino acid sequence of SEQ ID NO:1, a VH CDR2 having an amino acid sequence of SEQ ID NO:2, and a VH CDR3 having an amino acid sequence of SEQ ID NO:33; and
(ii) a VL comprising a VL CDR1 having an amino acid sequence of SEQ ID NO:4, a VL CDR2 having an amino acid sequence of SEQ ID NO:5, and a VL CDR3 having an amino acid sequence of SEQ ID NO:6.

67. The bispecific antibody of embodiment 66, wherein the first binding domain comprises a VH having an amino acid sequence of SEQ ID NO:36.

68. The bispecific antibody of embodiment 66, wherein the first binding domain comprises a VL having an amino acid sequence of SEQ ID NO:8.

69. The bispecific antibody of embodiment 66, wherein the first binding domain comprises a VH having an amino acid sequence of SEQ ID NO:36, and a VL having an amino acid sequence of SEQ ID NO:8.

70. The bispecific antibody of embodiment 53, wherein the first binding domain comprises:
(i) a VH comprising a VH CDR1 having an amino acid sequence of SEQ ID NO:1, a VH CDR2 having an amino acid sequence of SEQ ID NO:76, and a VH CDR3 having an amino acid sequence of SEQ ID NO:3; and
(ii) a VL comprising a VL CDR1 having an amino acid sequence of SEQ ID NO:77, a VL CDR2 having an amino acid sequence of SEQ ID NO:5, and a VL CDR3 having an amino acid sequence of SEQ ID NO:6.

71. The bispecific antibody of embodiment 53, wherein the first binding domain comprises:
(i) a VH comprising a VH CDR1 having an amino acid sequence of SEQ ID NO:60, a VH CDR2 having an amino acid sequence of SEQ ID NO:61, and a VH CDR3 having an amino acid sequence of SEQ ID NO:62; and
(ii) a VL comprising a VL CDR1 having an amino acid sequence of SEQ ID NO:63, a VL CDR2 having an amino acid sequence of SEQ ID NO:64, and a VL CDR3 having an amino acid sequence of SEQ ID NO:6.

72. The bispecific antibody of embodiment 70 or 71, wherein the first binding domain comprises a VH having an amino acid sequence of SEQ ID NO:65.

73. The bispecific antibody of embodiment 70 or 71, wherein the first binding domain comprises a VL having an amino acid sequence of SEQ ID NO:66.

74. The bispecific antibody of embodiment 70 or 71, wherein the first binding domain comprises a VH having an amino acid sequence of SEQ ID NO:65, and a VL having an amino acid sequence of SEQ ID NO:66.

75. The bispecific antibody of embodiment 70 or 71, wherein the first binding domain comprises a VH having an amino acid sequence of SEQ ID NO:67.

76. The bispecific antibody of embodiment 70 or 71, wherein the first binding domain comprises a VL having an amino acid sequence of SEQ ID NO:68.

77. The bispecific antibody of embodiment 70 or 71, wherein the first binding domain a VH having an amino acid sequence of SEQ ID NO:67, and a VL having an amino acid sequence of SEQ ID NO:68.

78. The bispecific antibody of embodiment 53, wherein the first binding domain comprises:

(i) a VH comprising a VH CDR1 having an amino acid sequence of SEQ ID NO:89, a VH CDR2 having an amino acid sequence of SEQ ID NO:90, and a VH CDR3 having an amino acid sequence of SEQ ID NO:91; and
(ii) a VL comprising a VL CDR1 having an amino acid sequence of SEQ ID NO:92, a VL CDR2 having an amino acid sequence of SEQ ID NO:93, and a VL CDR3 having an amino acid sequence of SEQ ID NO:94.

79. The bispecific antibody of embodiment 78, wherein the first binding domain comprises a VH having an amino acid sequence of SEQ ID NO:95.

80. The bispecific antibody of embodiment 78, wherein the first binding domain comprises a VL having an amino acid sequence of SEQ ID NO:96.

81. The bispecific antibody of embodiment 78, wherein the first binding domain comprises a VH having an amino acid sequence of SEQ ID NO:95, and a VL having an amino acid sequence of SEQ ID NO:96.

82. The bispecific antibody of embodiment 53, wherein the first binding domain comprises:
(i) a VH comprising a VH CDR1 having an amino acid sequence of SEQ ID NO:98, a VH CDR2 having an amino acid sequence of SEQ ID NO:99, and a VH CDR3 having an amino acid sequence of SEQ ID NO:100, and
(ii) a VL comprising a VL CDR1 having an amino acid sequence of SEQ ID NO:101, a VL CDR2 having an amino acid sequence of SEQ ID NO:102, and a VL CDR3 having an amino acid sequence of SEQ ID NO:103.

83. The bispecific antibody of embodiment 82, wherein the first binding domain comprises a VH having an amino acid sequence of SEQ ID NO:104.

84. The bispecific antibody of embodiment 82, wherein the first binding domain comprises a VL having an amino acid sequence of SEQ ID NO:105.

85. The bispecific antibody of embodiment 82, wherein the first binding domain comprises a VH having an amino acid sequence of SEQ ID NO:104, and a VL having an amino acid sequence of SEQ ID NO:105.

86. The bispecific antibody of embodiment 53, wherein the first binding domain comprises:
(i) a VH comprising a VH CDR1 having an amino acid sequence of SEQ ID NO:107, a VH CDR2 having an amino acid sequence of SEQ ID NO:108, and a VH CDR3 having an amino acid sequence of SEQ ID NO:109, and
(ii) a VL comprising a VL CDR1 having an amino acid sequence of SEQ ID NO:110, a VL CDR2 having an amino acid sequence of SEQ ID NO:111, and a VL CDR3 having an amino acid sequence of SEQ ID NO:112.

87. The bispecific antibody of embodiment 86, wherein the first binding domain comprises a VH having an amino acid sequence of SEQ ID NO:113.

88. The bispecific antibody of embodiment 86, wherein the first binding domain comprises a VL having an amino acid sequence of SEQ ID NO:114.

89. The bispecific antibody of embodiment 86, wherein the first binding domain comprises a VH having an amino acid sequence of SEQ ID NO:113, and a VL having an amino acid sequence of SEQ ID NO:114.

90. The bispecific antibody of embodiment 53, wherein the first binding domain comprises:
(i) a VH comprising a VH CDR1 having an amino acid sequence of SEQ ID NO:117, a VH CDR2 having an amino acid sequence of SEQ ID NO:118, and a VH CDR3 having an amino acid sequence of SEQ ID NO:119, and
(ii) a VL comprising a VL CDR1 having an amino acid sequence of SEQ ID NO:120, a VL CDR2 having an amino acid sequence of SEQ ID NO:121, and a VL CDR3 having an amino acid sequence of SEQ ID NO:122.

91. The bispecific antibody of embodiment 90, wherein the first binding domain comprises a VH having an amino acid sequence of SEQ ID NO:123.

92. The bispecific antibody of embodiment 90, wherein the first binding domain comprises a VL having an amino acid sequence of SEQ ID NO:124.

93. The bispecific antibody of embodiment 90, wherein the first binding domain comprises a VH having an amino acid sequence of SEQ ID NO:123, and a VL having an amino acid sequence of SEQ ID NO:124.

94. The bispecific antibody of embodiment 53, wherein the first binding domain comprises:
(i) a VH comprising a VH CDR1 having an amino acid sequence of SEQ ID NO:127, a VH CDR2 having an amino acid sequence of SEQ ID NO:128, and a VH CDR3 having an amino acid sequence of SEQ ID NO:129, and
(ii) a VL comprising a VL CDR1 having an amino acid sequence of SEQ ID NO:130, a VL CDR2 having an amino acid sequence of SEQ ID NO:131, and a VL CDR3 having an amino acid sequence of SEQ ID NO:132.

95. The bispecific antibody of embodiment 94, wherein the first binding domain comprises a VH having an amino acid sequence of SEQ ID NO:133.

96. The bispecific antibody of embodiment 94, wherein the first binding domain comprises a VL having an amino acid sequence of SEQ ID NO:134.

97. The bispecific antibody of embodiment 94, wherein the first binding domain comprises a VH having an amino acid sequence of SEQ ID NO:133, and a VL having an amino acid sequence of SEQ ID NO:134.

98. The bispecific antibody of any one of embodiments 53 to 97, wherein the second target is a cancer antigen present on the surface of a cancer cell.

99. The bispecific antibody of embodiment 98, wherein the antigen on the surface of the cancer cell is a tumor-specific antigen, a tumor associated antigen, or a neoantigen.

100. The bispecific antibody of any one of embodiments 53 to 99, wherein the second target is CD123.

101. The bispecific antibody of embodiment 100, wherein the second binding domain comprises:
(i) a VH comprising a VH CDR1 having an amino acid sequence of SEQ ID NO:9, a VH CDR2 having an amino acid sequence of SEQ ID NO:10, and a VH CDR3 having an amino acid sequence of SEQ ID NO:11, and
(ii) a VL comprising a VL CDR1 having an amino acid sequence of SEQ ID NO:12, a VL CDR2 having an amino acid sequence of SEQ ID NO:13, and a VL CDR3 having an amino acid sequence of SEQ ID NO:14.

102. The bispecific antibody of embodiment 101, wherein the second binding domain comprises a VH having an amino acid sequence of SEQ ID NO:15.

103. The bispecific antibody of embodiment 101, wherein the second binding domain comprises a VL having an amino acid sequence of SEQ ID NO:16.
104. The bispecific antibody of embodiment 101, wherein the second binding domain comprises a VH having an amino acid sequence of SEQ ID NO:15, and a VL having an amino acid sequence of SEQ ID NO:16.
105. The bispecific antibody of any one of embodiments 53 to 104, wherein the TRGV9 is present on the surface of a γδ T cell.
106. The bispecific antibody of any one of embodiments 53 to 104, wherein the TRGV9 is present on the surface of a γδ T cell, and the second target is a cancer antigen expressed on the surface of the cancer cell.
107. The bispecific antibody of embodiment 106, wherein the cancer cell is killed when the bispecific antibody binds to the TRGV9 on the surface of the γδ T cell and the antigen on the surface of the cancer cell.
108. The bispecific antibody of any one of embodiments 53 to 107, wherein the first binding domain is humanized, the second binding domain is humanized, or both the first binding domain and the second binding domain are humanized.
109. The bispecific antibody of any one of embodiments 53 to 108, wherein the bispecific antibody is an IgG antibody.
110. The bispecific antibody of embodiment 109, wherein the IgG antibody is an IgG1, IgG2, IgG3, or IgG4 antibody.
111. A pharmaceutical composition comprising the bispecific antibody of any one of embodiments 53 to 110, and a pharmaceutically acceptable carrier.
112. A method of directing a γδ T cell expressing TRGV9 to a cancer cell, the method comprising contacting the γδ T cell with the bispecific antibody of any one of embodiments 53 to 110, wherein the contacting directs the γδ T cell to the cancer cell.
113. A method of inhibiting growth or proliferation of cancer cells expressing a cancer antigen on the cell surface, the method comprising contacting the cancer cells with the bispecific antibody of any one of embodiments 53 to 110, wherein contacting the cancer cells with the pharmaceutical composition inhibits growth or proliferation of the cancer cells.
114. The method of embodiment 113, wherein the cancer cells are in the presence of a γδ T cell expressing TRGV9 while in contact with the bispecific antibody.
115. A method for eliminating cancer cells in a subject, comprising administering an effective amount of the bispecific antibody of any one of embodiments 53 to 110 to the subject.
116. The method of embodiment 115, wherein the subject is a subject in need thereof.
117. The method of embodiments 115 or 116, wherein the subject is a human.
118. A method of activating a γδ T cell expressing TRGV9, comprising contacting the γδ T cell with the bispecific antibody of any one of embodiments 53 to 110.

In another set of embodiments, provided are:
1. An isolated TRGV9 bispecific antibody or antigen binding fragment thereof, the isolated TRGV9 bispecific antibody or antigen binding fragment thereof comprising:
   a. a first heavy chain (HC1);
   b. a second heavy chain (HC2);
   c. a first light chain (LC1); and
   d. a second light chain (LC2),
   wherein HC1 is associated with LC1 and HC2 is associated with LC2, and
   wherein HC1 comprises a heavy chain complementarity determining region 1 (HCDR1), HCDR2, and HCDR3 comprising the amino acid sequences of:
   i. SEQ ID NO:1, SEQ ID NO:2, and SEQ ID NO:3, respectively,
   ii. SEQ ID NO:1, SEQ ID NO:2, and SEQ ID NO:31, respectively,
   iii. SEQ ID NO:1, SEQ ID NO:2, and SEQ ID NO:32, respectively, or
   iv. SEQ ID NO:1, SEQ ID NO:2, and SEQ ID NO:33, respectively,
   and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen.
2. The isolated TRGV9 bispecific antibody or antigen binding fragment thereof of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.
3. The isolated TRGV9 bispecific antibody or antigen binding fragment thereof of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.
4. The isolated TRGV9 bispecific antibody or antigen binding fragment thereof any one of embodiments 1 to 3, wherein the binding site for a first antigen binds to TRGV9 on a γδ T cell.
5. The isolated TRGV9 bispecific antibody or antigen binding fragment thereof any one of embodiments 1 to 4, wherein the binding site for a second antigen binds to a cancer antigen present on the surface of a cancer cell.
6. The isolated TRGV9 bispecific antibody or antigen binding fragment of embodiment 5, wherein the binding of the bispecific antibody to TRGV9 present on the surface of the γδ T cell and the binding of the cancer antigen present on the surface of the cancer cell results in the killing of the cancer cell.
7. The isolated TRGV9 bispecific antibody or antigen binding fragment of any one of embodiments 1 to 6, wherein HC1 and LC1 are humanized.
8. The isolated TRGV9 bispecific antibody or antigen binding fragment thereof any one of embodiments 1 to 7, wherein HC2 and LC2 bind to CD123.
9. The isolated TRGV9 bispecific antibody or antigen binding fragment thereof any one of embodiments 1 to 8, wherein the bispecific antibody or antigen binding fragment thereof is an IgG1, an IgG2, an IgG3, or an IgG4 isotype.
10. The isolated TRGV9 bispecific antibody or antigen binding fragment thereof any one of embodiments 1 to 9, wherein the bispecific antibody or antigen binding fragment thereof is an IgG4 isotype.
11. The isolated TRGV9 bispecific antibody or antigen binding fragment thereof any one of embodiments 1 to 10, wherein the bispecific antibody or antigen binding fragment thereof induces γδ T cell dependent cytotoxicity of a cancer cell in vitro with an $EC_{50}$ of less than about 500 pM.

12. The isolated TRGV9 bispecific antibody or antigen binding fragment thereof of embodiment 11, wherein the bispecific antibody or antigen binding fragment thereof induces γδ T cell dependent cytotoxicity of a cancer cell in vitro with an $EC_{50}$ of less than about 300 pM.
13. The isolated TRGV9 bispecific antibody or antigen binding fragment thereof of embodiment 11, wherein the bispecific antibody or antigen binding fragment thereof induces γδ T cell dependent cytotoxicity of a cancer cell in vitro with an $EC_{50}$ of less than about 160 pM.
14. The isolated TRGV9 bispecific antibody or antigen binding fragment thereof any one of embodiments 11 to 13, wherein the $EC_{50}$ is assessed with a mixture of γδ T effector cells and Kasumi3 AML target cells.
15. The isolated TRGV9 bispecific antibody or antigen binding fragment thereof of embodiment 14, wherein the effector cell to target cell ratio is about 0.01 to 1 to about 5 to 1.
16. The isolated TRGV9 bispecific antibody or antigen binding fragment thereof of embodiment 15, wherein the effector cell to target cell ratio is about 0.1 to 1 to about 2 to 1.
17. The isolated TRGV9 bispecific antibody or antigen binding fragment thereof of embodiment 16, wherein the effector cell to target cell ratio is about 1:1.
18. The isolated TRGV9 bispecific antibody or antigen binding fragment thereof any one of embodiments 1 to 17, wherein the bispecific antibody or antigen binding fragment thereof is multivalent.
19. The isolated TRGV9 bispecific antibody or antigen binding fragment thereof of embodiment 18, wherein the bispecific antibody or antigen binding fragment thereof is capable of binding at least three antigens.
20. The isolated TRGV9 bispecific antibody or antigen binding fragment thereof of embodiment 18, wherein the bispecific antibody or antigen binding fragment thereof is capable of binding at least five antigens.
21. An isolated γδ T cell bispecific antibody or antigen binding fragment thereof, the isolated γδ T cell bispecific antibody or antigen binding fragment thereof comprising:
   a. a first heavy chain (HC1);
   b. a second heavy chain (HC2);
   c. a first light chain (LC1); and
   d. a second light chain (LC2),
   wherein HC1 is associated with LC1 and HC2 is associated with LC2,
   wherein HC1 and LC1 form a binding site for a first antigen on a γδ T cell, and
   wherein HC2 and LC2 form a binding site for a second antigen.
22. A bispecific antibody comprising: a first means capable of specifically binding a T cell receptor gamma chain; and a second means capable of specifically binding a target molecule that is not a T cell receptor gamma chain.
23. A process for making a molecule capable of specifically binding to more than one target molecule, the molecule comprising: a step for performing a function of obtaining an oligopeptide or polypeptide capable of binding to a T cell receptor gamma chain; a step for performing a function of obtaining an oligopeptide or polypeptide capable of binding to a target; and a step for performing a function of providing a molecule capable of specifically binding to a T cell receptor gamma chain and a target molecule.
24. The process of embodiment 23, wherein the step for performing a function of obtaining an oligopeptide or polypeptide capable of binding to a target is repeated n times and further comprising n steps for performing a function of providing a molecule capable of specifically binding to a T cell receptor gamma chain and n number of target molecules, wherein n is at least 2.

In another set of embodiments, provided are:
1. An isolated anti-TRGV9/anti-CD123 bispecific antibody or antigen binding fragment thereof comprising:
   a. a first heavy chain (HC1);
   b. a second heavy chain (HC2)
   c. a first light chain (LC1); and
   d. a second light chain (LC2),
   wherein HC1 is associated with LC1 and HC2 is associated with LC2, and
   wherein HC1 comprises a heavy chain complementarity determining region 1 (HCDR1), HCDR2, and HCDR3 comprising the amino acid sequences of:
   i. SEQ ID NO:1, SEQ ID NO:2, and SEQ ID NO:3, respectively,
   ii. SEQ ID NO:1, SEQ ID NO:2, and SEQ ID NO:31, respectively,
   iii. SEQ ID NO:1, SEQ ID NO:2, and SEQ ID NO:32, respectively, or
   iv. SEQ ID NO:1, SEQ ID NO:2, and SEQ ID NO:33, respectively,
   and LC1 comprises a light chain complementarity determining region 1 (LCDR1), LCDR2, and LCDR3 comprising the amino acid sequences of SEQ ID NO:4, SEQ ID NO:5, and SEQ ID NO:6, respectively, to form a binding site for a first antigen that specifically binds Vγ9, and wherein HC2 comprises a heavy chain complementarity determining region 1 (HCDR1), HCDR2, and HCDR3 comprising the amino acid sequences of SEQ ID NO:9, SEQ ID NO:10, and SEQ ID NO:11, respectively, and LC2 comprises a light chain complementarity determining region 1 (LCDR1), LCDR2, and LCDR3 comprising the amino acid sequences of SEQ ID NO:12, SEQ ID NO:13, and SEQ ID NO:14, respectively, to form a binding site for a second antigen that specifically binds CD123.
2. The isolated anti-TRGV9/anti-CD123 bispecific antibody or antigen binding fragment thereof of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.
3. The isolated anti-TRGV9/anti-CD123 bispecific antibody or antigen binding fragment thereof of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.
4. The isolated anti-TRGV9/anti-CD123 bispecific antibody or antigen binding fragment thereof any one of embodiments 1 to 3, wherein HC2 comprises an amino acid sequence having at least 95% identity to the amino acid sequence of SEQ ID NO:15 and LC2 comprises an amino acid sequence having at least 95% identity to the amino acid sequence of SEQ ID NO:16.
5. The isolated anti-TRGV9/anti-CD123 bispecific antibody or antigen binding fragment thereof of embodiment 4, wherein HC2 comprises the amino acid sequence of SEQ ID NO:15 and LC2 comprises the amino acid sequence of SEQ ID NO:16.

6. The isolated anti-TRGV9/anti-CD123 bispecific antibody or antigen binding fragment thereof any one of embodiments 1 to 5, wherein the TRGV9 is on the surface of a γδ T cell.
7. The isolated anti-TRGV9/anti-CD123 bispecific antibody or antigen binding fragment thereof any one of embodiments 1 to 6, wherein the CD123 is on the surface of a tumor cell or a CD34+ stem cell.
8. The isolated anti-TRGV9/anti-CD123 bispecific antibody or antigen binding fragment thereof any one of embodiments 1 to 7, wherein the binding of the bispecific antibody to TRGV9 present on the surface of the γδ T cell and the binding of the CD123 on the surface of the cancer cell results in the killing of the cancer cell.
9. The isolated anti-TRGV9/anti-CD123 bispecific antibody or antigen binding fragment thereof any one of embodiments 1 to 8, wherein HC1 and LC1 are humanized.
10. The isolated anti-TRGV9/anti-CD123 bispecific antibody or antigen binding fragment thereof any one of embodiments 1 to 9, wherein HC2 and LC2 are humanized.
11. The isolated anti-TRGV9/anti-CD123 bispecific antibody or antigen binding fragment thereof any one of embodiments 1 to 10, wherein the bispecific antibody or antigen binding fragment thereof is an IgG1, an IgG2, an IgG3, or an IgG4 isotype.
12. The isolated anti-TRGV9/anti-CD123 bispecific antibody or antigen binding fragment thereof any one of embodiments 1 to 11, wherein the bispecific antibody or antigen binding fragment thereof is an IgG4 isotype.
13. The isolated anti-TRGV9/anti-CD123 bispecific antibody or antigen binding fragment thereof any one of embodiments 1 to 12, wherein the bispecific antibody or antigen binding fragment thereof induces γδ T cell dependent cytotoxicity of a cancer cell in vitro with an $EC_{50}$ of less than about 500 pM.
14. The isolated anti-TRGV9/anti-CD123 bispecific antibody or antigen binding fragment thereof of embodiment 13, wherein the bispecific antibody or antigen binding fragment thereof induces γδ T cell dependent cytotoxicity of a cancer cell in vitro with an $EC_{50}$ of less than about 300 pM.
15. The isolated anti-TRGV9/anti-CD123 bispecific antibody or antigen binding fragment thereof of embodiment 13, wherein the bispecific antibody or antigen binding fragment thereof induces γδ T cell dependent cytotoxicity of a cancer cell in vitro with an $EC_{50}$ of less than about 160 pM.
16. The isolated anti-TRGV9/anti-CD123 bispecific antibody or antigen binding fragment thereof any one of embodiments 13 to 15, wherein the $EC_{50}$ is assessed with a mixture of γδ T effector cells and Kasumi3 AML target cells.
17. The isolated anti-TRGV9/anti-CD123 bispecific antibody or antigen binding fragment thereof of embodiment 16, wherein the effector cell to target cell ratio is about 0.01 to 1 to about 5 to 1.
18. The isolated anti-TRGV9/anti-CD123 bispecific antibody or antigen binding fragment thereof of embodiment 17, wherein the effector cell to target cell ratio is about 0.1 to 1 to about 2 to 1.
19. The isolated anti-TRGV9/anti-CD123 bispecific antibody or antigen binding fragment thereof of embodiment 18, wherein the effector cell to target cell ratio is about 1:1.
20. A method of making the isolated anti-TRGV9/anti-CD123 bispecific antibody or antigen binding fragment thereof any one of embodiments 1 to 19, the method comprising culturing a cell comprising a nucleic acid encoding the anti-TRGV9/anti-CD123 bispecific antibody or antigen binding fragment thereof under conditions to produce the bispecific antibody or antigen binding fragment thereof and recovering the bispecific antibody or antigen binding fragment thereof.

In another set of embodiments, provided are:

1. An isolated TRGV9 bispecific antibody or antigen epitope binding fragment thereof, wherein the isolated TRGV9 bispecific antibody or antigen epitope binding fragment thereof comprises a binding site for a first antigen and a binding site for a second antigen, wherein the binding site for the first antigen binds a TRGV9 epitope on a γδ T cell and the binding site for the second antigen binds an epitope of the second antigen on a surface of a target cell, and the binding of the TRGV9 epitope on the γδ T cell and the binding of the second antigen epitope on the target cell results in the killing of the target cell.
2. The isolated TRGV9 bispecific antibody or antigen binding fragment thereof, wherein the isolated TRGV9 bispecific antibody or antigen binding fragment thereof comprises:
   a. a first heavy chain (HC1);
   b. a second heavy chain (HC2);
   c. a first light chain (LC1); and
   d. a second light chain (LC2),
   wherein HC1 is associated with LC1 and HC2 is associated with LC2, and
   wherein HC1 comprises a heavy chain complementarity determining region 1 (HCDR1), HCDR2, and HCDR3 comprising the amino acid sequences of:
   i. SEQ ID NO:1, SEQ ID NO:2, and SEQ ID NO:3, respectively,
   ii. SEQ ID NO:1, SEQ ID NO:2, and SEQ ID NO:31, respectively,
   iii. SEQ ID NO:1, SEQ ID NO:2, and SEQ ID NO:32, respectively, or
   iv. SEQ ID NO:1, SEQ ID NO:2, and SEQ ID NO:33, respectively,
   and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form the binding site for the first antigen, and wherein HC2 and LC2 form the binding site for the second antigen epitope.
3. The isolated TRGV9 bispecific antibody or antigen binding fragment thereof of embodiment 2, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.
4. The isolated TRGV9 bispecific antibody or antigen binding fragment thereof of embodiment 3, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.
5. The isolated TRGV9 bispecific antibody or antigen binding fragment of any one of embodiments 2 to 4, wherein HC1 and LC1 are humanized.
6. The isolated TRGV9 bispecific antibody or antigen binding fragment thereof any one of embodiments 2 to 5, wherein HC2 and LC2 bind to a CD123 epitope.

7. The isolated TRGV9 bispecific antibody or antigen binding fragment thereof of embodiment 6, wherein HC2 comprises an amino acid sequence having at least 95% identity to the amino acid sequence of SEQ ID NO:15 and LC2 comprises an amino acid sequence having at least 95% identity to the amino acid sequence of SEQ ID NO:16.
8. The isolated TRGV9 bispecific antibody or antigen binding fragment thereof of embodiment 7, wherein HC2 comprises the amino acid sequence of SEQ ID NO:15 and LC2 comprises the amino acid sequence of SEQ ID NO:16.
9. The isolated TRGV9 bispecific antibody or antigen binding fragment thereof any one of embodiments 1 to 8, wherein the bispecific antibody or antigen binding fragment thereof is an IgG1, an IgG2, an IgG3, or an IgG4 isotype.
10. The isolated TRGV9 bispecific antibody or antigen binding fragment thereof any one of embodiments 1 to 9, wherein the bispecific antibody or antigen binding fragment thereof is an IgG4 isotype.
11. The isolated TRGV9 bispecific antibody or antigen binding fragment thereof any one of embodiments 1 to 10, wherein the bispecific antibody or antigen binding fragment thereof induces γδ T cell dependent cytotoxicity of a cancer cell in vitro with an $EC_{50}$ of less than about 500 pM.
12. The isolated TRGV9 bispecific antibody or antigen binding fragment thereof of embodiment 11, wherein the bispecific antibody or antigen binding fragment thereof induces γδ T cell dependent cytotoxicity of a cancer cell in vitro with an $EC_{50}$ of less than about 300 pM.
13. The isolated TRGV9 bispecific antibody or antigen binding fragment thereof of embodiment 12, wherein the bispecific antibody or antigen binding fragment thereof induces γδ T cell dependent cytotoxicity of a cancer cell in vitro with an $EC_{50}$ of less than about 160 pM.
14. The isolated TRGV9 bispecific antibody or antigen binding fragment thereof any one of embodiments 11 to 13, wherein the $EC_{50}$ is assessed with a mixture of γδ T effector cells and Kasumi3 AML target cells.
15. The isolated TRGV9 bispecific antibody or antigen binding fragment thereof of embodiment 14, wherein the effector cell to target cell ratio is about 0.01 to 1 to about 5 to 1.
16. The isolated TRGV9 bispecific antibody or antigen binding fragment thereof of embodiment 15, wherein the effector cell to target cell ratio is about 0.1 to 1 to about 2 to 1.
17. The isolated TRGV9 bispecific antibody or antigen binding fragment thereof of embodiment 16, wherein the effector cell to target cell ratio is about 1:1.
18. An isolated γδ T cell bispecific antibody or antigen binding fragment thereof, wherein the isolated γδ T cell bispecific antibody or antigen binding fragment thereof comprises a binding site for a first antigen epitope and a binding site for a second antigen epitope, wherein the binding site for the first antigen epitope binds a first antigen on a γδ T cell and the binding site for the second antigen epitope binds the second antigen epitope on a surface of a target cell, and the binding of the first antigen epitope on the γδ T cell and the binding of the second antigen epitope on the target cell results in the killing of the target cell.

In another set of embodiments, provided are:
1. An isolated nucleic acid encoding a TRGV9 bispecific antibody or antigen binding fragment thereof, the isolated TRGV9 bispecific antibody or antigen binding fragment thereof comprising:
   a. a first heavy chain (HC1);
   b. a second heavy chain (HC2);
   c. a first light chain (LC1); and
   d. a second light chain (LC2),
      wherein HC1 is associated with LC1 and HC2 is associated with LC2, and wherein HC1 comprises a heavy chain complementarity determining region 1 (HCDR1), HCDR2, and HCDR3 comprising the amino acid sequences of:
      i. SEQ ID NO:1, SEQ ID NO:2, and SEQ ID NO:3, respectively,
      ii. SEQ ID NO:1, SEQ ID NO:2, and SEQ ID NO:31, respectively,
      iii. SEQ ID NO:1, SEQ ID NO:2, and SEQ ID NO:32, respectively, or
      iv. SEQ ID NO:1, SEQ ID NO:2, and SEQ ID NO:33, respectively,
      and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen.
2. The isolated nucleic acid of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.
3. The isolated nucleic acid of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.
4. The isolated nucleic acid of any one of embodiments 1 to 3, wherein the binding site for a first antigen binds to TRGV9 on a γδ T cell.
5. The isolated nucleic acid of any one of embodiments 1 to 4, wherein the binding site for a second antigen binds to a cancer antigen present on the surface of a cancer cell.
6. The isolated nucleic acid of embodiment 5, wherein the binding of the bispecific antibody to TRGV9 present on the surface of the γδ T cell and the binding of the cancer antigen present on the surface of the cancer cell results in the killing of the cancer cell.
7. The isolated nucleic acid of any one of embodiments 1 to 6, wherein HC1 and LC1 are humanized.
8. The isolated nucleic acid of any one of embodiments 1 to 7, wherein HC2 and LC2 bind to CD123.
9. The isolated nucleic acid of any one of embodiments 1 to 8, wherein the bispecific antibody or antigen binding fragment thereof is an IgG1, an IgG2, an IgG3, or an IgG4 isotype.
10. The isolated nucleic acid of any one of embodiments 1 to 9, wherein the bispecific antibody or antigen binding fragment thereof is an IgG4 isotype.
11. The isolated nucleic acid of any one of embodiments 1 to 10, wherein the bispecific antibody or antigen binding fragment thereof induces γδ T cell dependent cytotoxicity of a cancer cell in vitro with an $EC_{50}$ of less than about 500 pM.

12. The isolated nucleic acid of embodiment 11, wherein the bispecific antibody or antigen binding fragment thereof induces γδ T cell dependent cytotoxicity of a cancer cell in vitro with an $EC_{50}$ of less than about 300 pM.
13. The isolated nucleic acid of embodiment 11, wherein the bispecific antibody or antigen binding fragment thereof induces γδ T cell dependent cytotoxicity of a cancer cell in vitro with an $EC_{50}$ of less than about 160 pM.
14. The isolated nucleic acid of any one of embodiments 11 to 13, wherein the $EC_{50}$ is assessed with a mixture of γδ T effector cells and Kasumi3 AML target cells.
15. The isolated nucleic acid of embodiment 14, wherein the effector cell to target cell ratio is about 0.01 to 1 to about 5 to 1.
16. The isolated nucleic acid of embodiment 15, wherein the effector cell to target cell ratio is about 0.1 to 1 to about 2 to 1.
17. The isolated nucleic acid of embodiment 16, wherein the effector cell to target cell ratio is about 1:1.
18. The isolated nucleic acid of any one of embodiments 1 to 17, wherein the bispecific antibody or antigen binding fragment thereof is multivalent.
19. The isolated nucleic acid of embodiment 18, wherein the bispecific antibody or antigen binding fragment thereof is capable of binding at least three antigens.
20. The isolated nucleic acid of embodiment 18, wherein the bispecific antibody or antigen binding fragment thereof is capable of binding at least five antigens.
21. A vector comprising the isolated nucleic acid of any one of embodiments 1 to 20.
22. A host cell comprising the vector of embodiment 21.
23. A kit comprising the vector of embodiment 21 and packaging for the same.

In another set of embodiments, provided are:
1. A pharmaceutical composition comprising an isolated TRGV9 bispecific antibody or antigen binding fragment thereof, the isolated TRGV9 bispecific antibody or antigen binding fragment thereof comprising:
    a. a first heavy chain (HC1);
    b. a second heavy chain (HC2);
    c. a first light chain (LC1); and
    d. a second light chain (LC2),
    wherein HC1 is associated with LC1 and HC2 is associated with LC2, and
    wherein HC1 comprises a heavy chain complementarity determining region 1 (HCDR1), HCDR2, and HCDR3 comprising the amino acid sequences of:
        i. SEQ ID NO:1, SEQ ID NO:2, and SEQ ID NO:3, respectively,
        ii. SEQ ID NO:1, SEQ ID NO:2, and SEQ ID NO:31, respectively,
        iii. SEQ ID NO:1, SEQ ID NO:2, and SEQ ID NO:32, respectively, or
        iv. SEQ ID NO:1, SEQ ID NO:2, and SEQ ID NO:33, respectively,
    and LC1 comprises a light chain complementarity determining region 1 (LCDR1), LCDR2, and LCDR2 comprising the amino acid sequences of SEQ ID NO:4, SEQ ID NO:5, and SEQ ID NO:6, respectively, to form a binding site for a first antigen, and wherein HC2 and LC2 form a binding site for a second antigen,
    and a pharmaceutically acceptable carrier.
2. The pharmaceutical composition of embodiment 1, wherein HC1 comprises an amino acid sequence having at least 95% identity to an amino acid sequence selected from SEQ ID NO:7, SEQ ID NO:34, SEQ ID NO:35, or SEQ ID NO:36, and LC1 comprises an amino acid sequence having at least 95% identity to the amino acid sequence of SEQ ID NO:8.
3. The pharmaceutical composition of embodiment 2, wherein HC1 comprises the amino acid sequence selected from SEQ ID NO:7, SEQ ID NO:34, SEQ ID NO:35, or SEQ ID NO:36, and LC1 comprises the amino acid sequence of SEQ ID NO:8.
4. The pharmaceutical composition of any one of embodiments 1 to 3, wherein the binding site for a first antigen binds to TRGV9 on a γδ T cell.
5. The pharmaceutical composition of any one of embodiments 1 to 4, wherein the binding site for a second antigen binds to a cancer antigen present on the surface of a cancer cell.
6. The pharmaceutical composition of embodiment 5, wherein the binding of the bispecific antibody to TRGV9 present on the surface of the γδ T cell and the binding of the cancer antigen present on the surface of the cancer cell results in the killing of the cancer cell.
7. The pharmaceutical composition of any one of embodiments 1 to 6, wherein HC1 and LC1 are humanized.
8. The pharmaceutical composition of any one of embodiments 1 to 7, wherein HC2 and LC2 bind to CD123.
9. The pharmaceutical composition of any one of embodiments 1 to 8, wherein the bispecific antibody or antigen binding fragment thereof is an IgG1, an IgG2, an IgG3, or an IgG4 isotype.
10. A method of directing a Vγ9-expressing γδ T cell to a cancer cell, the method comprising contacting a Vγ9-expressing γδ T cell with the pharmaceutical composition of any one of embodiments 1 to 9, wherein contacting the Vγ9-expressing γδ T cell with the pharmaceutical composition directs the Vγ9-expressing γδ T cell to a cancer cell.
11. A method of inhibiting growth or proliferation of cancer cells expressing a cancer antigen on the cell surface, the method comprising contacting the cancer cells with the pharmaceutical composition of any one of embodiments 1 to 9, wherein contacting the cancer cells with the pharmaceutical composition inhibits growth or proliferation of the cancer cells.
12. The method of embodiment 11, wherein the cancer cell is in the presence of a Vγ9-expressing γδ T cell while in contact with anti-TRGV9 bispecific antibody or antigen binding fragment thereof
13. A method for treating a cancer in a subject in need thereof, the method comprising:
    a. identifying a subject in need of cancer treatment; and
    b. administering to the subject in need thereof the pharmaceutical composition of any one of embodiments 1 to 9,
    wherein administering the pharmaceutical composition to the subject in need thereof treats the cancer in the subject.
14. A method of activating a Vγ9-expressing γδ T cell, the method comprising contacting the Vγ9-expressing γδ T cell with the pharmaceutical composition of any one of embodiments 1 to 9, wherein contacting the Vγ9-expressing γδ T cell with the pharmaceutical composition results in an increase in CD69, CD25, and/or Granzyme B expression as compared to a control Vγ9-expressing γδ T cell.
15. A method of producing the pharmaceutical composition of any one of embodiments 1 to 9, the method comprising combining the bispecific antibody or antigen binding fragment thereof with a pharmaceutically acceptable carrier to obtain the pharmaceutical composition.

Provided in the Examples herein are exemplary multispecific (bispecific) antibodies that bind to TRGV9 and CD123 (also known as IL3RA). CD123 is expressed on a variety of cell types in various tissues, including adipose tissue, adrenal gland, appendix, bone marrow, breast, bronchus, caudate, cerebellum, cerebral cortex, cervix, uterine, colon, duodenum, endometrium, epididymis, esophagus, fallopian tube, gallbladder, heart muscle, hippocampus, kidney, liver, lung, lymph node, nasopharynx, oral mucosa, ovary, pancreas, parathyroid gland, placenta, prostate, rectum, salivary gland, seminal vesicle, skeletal muscle, skin, small intestine, smooth muscle, soft tissue, spleen, stomach, testis, thyroid gland, tonsil, urinary bladder, and vagina (see, e.g., proteinatlas.org). Thus, these Examples are illustrative of exemplary bispecific antibodies that can effectively target a wide variety of cells and tissues in a subject.

In some embodiments, provided herein is a bispecific antibody comprising: (a) a first binding domain that binds to a TRGV9 antigen, and (b) a second binding domain that binds to a second target antigen. In some embodiments, provided herein is a bispecific antibody comprising: (a) a first binding domain that specifically binds to a TRGV9 antigen, and (b) a second binding domain that specifically binds to a second target antigen. In some embodiments, provided herein is a bispecific antibody comprising: (a) a first binding domain that binds to a first epitope on a TRGV9 antigen, and (b) a second binding domain that binds to a second epitope on a second target antigen. In some embodiments, provided herein is a bispecific antibody comprising: (a) a first binding domain that specifically binds to a first epitope on a TRGV9 antigen, and (b) a second binding domain that specifically binds to a second epitope on a second target antigen. In certain embodiments, the second target antigen is a cancer antigen on the surface of a cancer cell. In certain embodiments, the second target antigen is CD123.

Exemplary binding agents that bind to TRGV9, as well as exemplary binding agents that bind to CD123 are provided elsewhere herein, for example in the Examples, as well as in Tables 1-31.

Particular embodiments of this invention are described herein. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. A number of embodiments of the invention have been described. Nevertheless, it will be understood that various modifications may be made without departing from the spirit and scope of the invention. Accordingly, the descriptions in the Examples section are intended to illustrate but not limit the scope of invention described in the claims.

EXAMPLES

Example 1: Production of Multispecific Antibodies that Bind γδ T Cells 1.1: Production of MABs that Bind γδ T Cell Antigens Antigens or portions of antigens specific for γδ T cells are used to immunize an animal (e.g., a mouse or a rabbit). To generate the γδ T cell monoclonal antibodies, peripheral blood mononuclear cells are isolated from the whole blood of the immunized animal, and antigen specific B cells are grown. B cells secreting reactive antibodies for the γδ T cell antigens are identified by an antigen-binding ELISA screening of the B cell culture supernatants. High binding ELISA plates are coated with the γδ T cell antigen overnight. The ELISA plates are blocked, and diluted B cell culture supernatants are added to the plates. The plates are incubated at room temperature and following incubation, a secondary antibody specific for recognizing the γδ T cell antigen antibody is added to the plate to determine if the γδ T cell antigen antibody bound the γδ T cell antigen. Binding of the antibody is determined by reaction of a substrate on the secondary antibody.

After the identification of monoclonal antibodies that are capable of binding γδ T cell antigens, the variable regions of the heavy and light chains of the γδ T cell antibody are sequenced. Constructs are created for the expression of the heavy and light chain of the γδ T cell antibody. The constructs are transfected into a host cell to express the heavy and light chains, and the γδ T cell antibody is isolated from the supernatant.

1.2: Production of γδ T Cell Bispecific Antibodies

The variable region sequence of the γδ T cell monoclonal antibody and a second monoclonal antibody capable of binding a target antigen on a target cell of interest are used to generate a bispecific antibody to be tested for γδ T cell re-directed killing of the target cells. Target antigens of interest can be selected from, but not limited, antigens described in Zhang et al., Nucleic Acids Research 47(D1): D721-D728 (2019). γδ T cell bispecific antibodies are produced as full-length antibodies in the knob-into-hole format as human IgG4, as previously described (Atwell et al., J. Mol. Biol. 270:26-35 (1997)). Nucleic acid sequences encoding variable regions are sub-cloned into custom mammalian expression vectors containing the constant region of IgG4 expression cassettes using standard PCR restriction enzyme based cloning techniques. The bispecific antibodies are expressed by transient transfection in Chinese hamster ovary cell line. The antibodies are initially purified by MAB SELECT SURE Protein A column (GE Healthcare, Piscataway, N.J.) (Brown, Bottomley et al. Biochem Soc Trans. 1998 August; 26(3):5249.). The column is equilibrated with Phosphate Buffer Saline (PBS), pH 7.2 and is loaded with fermentation supernatant at a flow rate of 2 mL/min. After loading, the column is washed with PBS (4 column volumes (CV)) followed by elution in 30 mM sodium acetate, pH 3.5. Fractions containing protein peaks as monitored by absorbance at 280 nm in Akta Explorer (GE healthcare) are pooled together and are neutralized to pH 5.0 by adding 1% of 3M sodium acetate, pH 9.0. As a polishing step, the antibodies are purified on a preparative size exclusion chromatography (SEC) using a SUPERDEX 200 column (GE healthcare). The integrity of sample is assessed by endotoxin measurement and SDS polyacrylamide gel electrophoresis under reducing and non-reducing conditions. The final protein concentrations are determined.

1.3: Production of ANTI-TRGV9 Bispecific Antibodies

Variable region sequences of exemplary anti-TRGV9 monoclonal antibodies are provided below in Table 1 and Table 2.

TABLE 1

Anti-TRGV9 mAb CDR Sequences

| Antibody | VH CDR1 | VH CDR2 | VH CDR3 | VL CDR1 | VL CDR2 | VL CDR3 |
|---|---|---|---|---|---|---|
| TRGV9Ab_1 (LP7A5_1) | DHYIN (SEQ ID NO: 1) | QIYPGDGNT YYNQKFKG (SEQ ID NO: 2) | NYGDYTIDF (SEQ ID NO: 3) | KSSQSLLYS SNQKNYLA (SEQ ID NO: 4) | WASTRES (SEQ ID NO: 5) | QQYYRYHT (SEQ ID NO: 6) |
| TRGV9Ab_2 (LP7A5_2) | DHYIN (SEQ ID NO: 1) | QIYPGDGNT YYNQKFKG (SEQ ID NO: 2) | NMGMYTIDF (SEQ ID NO: 31) | KSSQSLLYS SNQKNYLA (SEQ ID NO: 4) | WASTRES (SEQ ID NO: 5) | QQYYRYHT (SEQ ID NO: 6) |
| TRGV9Ab_3 (LP7A5_3) | DHYIN (SEQ ID NO: 1) | QIYPGDGNT YYNQKFKG (SEQ ID NO: 2) | NMGMYTLDF (SEQ ID NO: 32) | KSSQSLLYS SNQKNYLA (SEQ ID NO: 4) | WASTRES (SEQ ID NO: 5) | QQYYRYHT (SEQ ID NO: 6) |
| TRGV9Ab_4 (LP7A5_4) | DHYIN (SEQ ID NO: 1) | QIYPGDGNT YYNQKFKG (SEQ ID NO: 2) | NYGDYTLDF (SEQ ID NO: 33) | KSSQSLLYS SNQKNYLA (SEQ ID NO: 4) | WASTRES (SEQ ID NO: 5) | QQYYRYHT (SEQ ID NO: 6) |

TABLE 2

Anti-TRGV9 mAb VH and VL Domain Sequences

| Antibody | VH | VL |
|---|---|---|
| TRGV9Ab_1 (LP7A5_1) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NYGDYTIDFWGQGTSVTVSS (SEQ ID NO: 7) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |
| TRGV9Ab_2 (LP7A5_2) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NMGMYTIDFWGQGTSVTVSS (SEQ ID NO: 34) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |
| TRGV9Ab_3 (LP7A5_3) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NMGMYTLDFWGQGTSVTVSS (SEQ ID NO: 35) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |
| TRGV9Ab_4 (LP7A5_4) | EVQLQQSGAELARPGASVKLSCKASGFTFTDHY INWVKQRTGQGLEWIGQIYPGDGNTYYNQKFKG KATLTADKSSSTAYMQLSSLTSEDSAVYFCAP NYGDYTLDFWGQGTSVTVSS (SEQ ID NO: 36) | DIVMSQSPSSLAVSVGEKVTMSCKSSQSLLYSSN QKNYLAWYQQKPGQSPKLLIYWASTRESGVPDRF TGSGSGTDFTLTISSVKAEDLAVYYCQQYYRY HTFGTGTKLEIK (SEQ ID NO: 8) |

Variable region sequences of an anti-TRGV9 monoclonal antibody and a second monoclonal antibody capable of binding a target antigen on a target cell of interest are used to generate a bispecific antibody to be tested for γδ T cell re-directed killing of the target cells. Target antigens of interest can be selected from, but not limited to, antigens described in Zhang et al., Nucleic Acids Research 47(D1): D721-D728 (2019). Anti-TRGV9 bispecific antibodies are produced as full-length antibodies in the knob-into-hole format as human IgG4, as previously described (Atwell et al., J. Mol. Biol. 270:26-35 (1997)). Nucleic acid sequences encoding variable regions are sub-cloned into custom mammalian expression vectors containing the constant region of IgG4 expression cassettes using standard PCR restriction enzyme based cloning techniques. The bispecific antibodies are expressed by transient transfection in Chinese hamster ovary cell line. The antibodies are initially purified by MAB SELECT SURE Protein A column (GE Healthcare, Piscataway, N.J.) (Brown, Bottomley et al. Biochem Soc Trans. 1998 August; 26(3):5249). The column is equilibrated with Phosphate Buffer Saline (PBS), pH 7.2 and is loaded with fermentation supernatant at a flow rate of 2 mL/min. After loading, the column is washed with PBS (4 column volumes (CV)) followed by elution in 30 mM sodium acetate, pH 3.5. Fractions containing protein peaks as monitored by Absorbance at 280 nm in Akta Explorer (GE healthcare) are pooled together and are neutralized to pH 5.0 by adding 1% of 3M sodium acetate, pH 9.0. As a polishing step, the antibodies are purified on a preparative size exclusion chromatography (SEC) using a SUPERDEX 200 column (GE healthcare). The integrity of sample is assessed by endotoxin measurement and SDS polyacrylamide gel electrophoresis under reducing and non-reducing conditions. The final protein concentrations are determined.

Example 2—Bispecific Antibodies that Bind TRGV9 and a Cancer Antigen

Examples 2.1-2.4 are based on the premise that γδ T cells, which mainly express heterodimers of TRGV9 and Vδ2 chains demonstrate potent anti-tumor functions. These cells express TCR-TRGV9 and the majority, if not all, of these cells exhibit efficient cytotoxicity of tumor target cells. This ability is then harnessed using bispecific antibodies constructed such that one arm binds to the TRGV9 structure and the other arm binds to a tumor-associated antigen expressed by the tumor cells. Thus, the bispecific antibody bridges the effector and target cells together-resulting in tumor cell killing. This mechanism of action is described in the schematic outlined in FIG. 1.

The subsequent examples can be divided into the following categories: (1) Generation and characterization of bispecific antibodies capable of binding to the TRGV9 arm expressed on γδ T cells and a cancer antigen (e.g., CD123) on cancer cells (Examples 2.1, 2.2, and 2.3); and (2) Evidence for bispecific antibody-enabled target cell killing by γδ T cells expanded in vitro (Example 2.4).

Example 2.1: Production of ANTI-TRGV9 MAB

The mouse IgG1 anti-human T cell receptor TRGV9 clone 7A5 was sourced commercially. Sample preparation and LC/MSMS analysis were performed by Lake Pharma. (San Carlos, Calif.). The sample was reduced and alkylated, divided into seven aliquots, and proteolytically digested with Trypsin/LysC, Chymotrypsin, LysC, Pepsin, and AspN, Elastase, and Proteinase K enzymes. Resulting peptides were desalted using a ZIPTIP C18 Pipette Tips and separated on-line using reverse phase chromatography. Mass spectrometry was performed on THERMO Q-EXACTIVE spectrometer using HCD fragmentation. MS data sets were analyzed using PEAKS software by matching de novo sequence tags to an IMGT-based antibody sequences database. Gaps in the sequence were assigned using Contig sequence assembly of de novo identified peptides. All CDRs and hyper-mutations were confirmed by inspecting the MS/MS spectra The sequences obtained are shown in Tables 3-7.

TABLE 3

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_1 | DHYIN | 1 | QIYPGDGNT YYNQKFKG | 2 | NYGDYTIDF | 3 |

| Antibody | LCDR1 | SEQ ID NO: | LCDR2 | SEQ ID NO: | LCDR3 | SEQ ID NO: |
|---|---|---|---|---|---|---|
| LP7A5_1 | KSSQSLLYS SNQKNYLA | 4 | WASTRES | 5 | QQYYRYHT | 6 |

TABLE 4

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_2 | DHYIN | 1 | QIYPGDGNT YYNQKFKG | 2 | NMGMYTIDF | 31 |

| Antibody | LCDR1 | SEQ ID NO: | LCDR2 | SEQ ID NO: | LCDR3 | SEQ ID NO: |
|---|---|---|---|---|---|---|
| LP7A5_2 | KSSQSLLYS SNQKNYLA | 4 | WASTRES | 5 | QQYYRYHT | 6 |

TABLE 5

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_3 | DHYIN | 1 | QIYPGDGNT YYNQKFKG | 2 | NMGMYTLDF | 32 |

| Antibody | LCDR1 | SEQ ID NO: | LCDR2 | SEQ ID NO: | LCDR3 | SEQ ID NO: |
|---|---|---|---|---|---|---|
| LP7A5_3 | KSSQSLLYS SNQKNYLA | 4 | WASTRES | 5 | QQYYRYHT | 6 |

TABLE 6

CDR Sequences of anti-TRGV9 mAb.

| Antibody | HCDR1 | SEQ ID NO: | HCDR2 | SEQ ID NO: | HCDR3 | SEQ ID NO: |
|---|---|---|---|---|---|---|
| LP7A5_4 | DHYIN | 1 | QIYPGDGNT YYNQKFKG | 2 | NYGDYTLDF | 33 |

| Antibody | LCDR1 | SEQ ID NO: | LCDR2 | SEQ ID NO: | LCDR3 | SEQ ID NO: |
|---|---|---|---|---|---|---|
| LP7A5_4 | KSSQSLLYS SNQKNYLA | 4 | WASTRES | 5 | QQYYRYHT | 6 |

TABLE 7

Heavy chain and light chain sequences of anti-TRGV9 mAb.

| mAb | Heavy Chain Amino Acid Sequence | SEQ ID NO: |
|---|---|---|
| LP7A5_1 | EVQLQQSGAELARPGASVKLSCKASGFTFT<u>DHY INWVKQRTGQGLEWIG<u>QIYPGDGNTYYNQKFKG</u> KATLTADKSSSTAYMQLSSLTSEDSAVYFCAP<u>N YGDYTID</u>FWGQGTSVTVSS | 7 |
| LP7A5_2 | EVQLQQSGAELARPGASVKLSCKASGFTFT<u>DHY INWVKQRTGQGLEWIG<u>QIYPGDGNTYYNQKFKG</u> KATLTADKSSSTAYMQLSSLTSEDSAVYFCAP<u>N MGMYTID</u>FWGQGTSVTVSS | 34 |
| LP7A5_3 | EVQLQQSGAELARPGASVKLSCKASGFTFT<u>DHY INWVKQRTGQGLEWIG<u>QIYPGDGNTYYNQKFKG</u> KATLTADKSSSTAYMQLSSLTSEDSAVYFCAPN MGMY<u>TLD</u>FWGQGTSVTVSS | 35 |
| LP7A5_4 | EVQLQQSGAELARPGASVKLSCKASGFTFT<u>DHY INWVKQRTGQGLEWIG<u>QIYPGDGNTYYNQKFKG</u> KATLTADKSSSTAYMQLSSLTSEDSAVYFCAP<u>N YGDYTLD</u>FWGQGTSVTVSS | 36 |

| | Light Chain Amino Acid Sequence | SEQ ID NO: |
|---|---|---|
| LP7A5_1 | DIVMSQSPSSLAVSVGEKVTMSC<u>KSSQSLLYSS NQKNYLA</u>WYQQKPGQSPKLLIY<u>WASTRES</u>GVPD RFTGSGSGTDFTLTISSVKAEDLAVYYC<u>QQYYR YHT</u>FGTGTKLEIK | 8 |

Example 2.2: Preparation of ANTI-TRGV9/Anti-CD123 Bispecific Antibodies

The variable region sequence of LP7A5 (anti-TRGV9) and I3RB217 (anti-CD123 antibody) (HCDRs and LCDRs in Table 8, HC and LC in Table 9) were used to generate a bispecific antibody to be tested for T cell re-directed killing of acute myeloid leukemia (AML) cells. VG1 (anti-TRGV9×CD123) and VG3 (anti-TRGV9×Null) bispecific antibodies were produced as full-length antibodies in the knob-into-hole format as human IgG4, as previously described (Atwell et al. J. Mol. Biol. 270: 26-35, 1997). Nucleic acid sequences encoding variable regions were sub-cloned into a custom mammalian expression vectors containing constant region of IgG4 expression cassettes using standard PCR restriction enzyme based cloning techniques. The bispecific antibodies were expressed by transient transfection in Chinese hamster ovary cell line. The antibodies were initially purified by MAB SELECT SURE Protein A column (GE Healthcare, Piscataway, N.J.) (Brown, Bottomley et al. Biochem Soc Trans. 1998 August; 26(3):5249.). The column was equilibrated with Phosphate Buffer Saline (PBS), pH 7.2 and loaded with fermentation supernatant at a flow rate of 2 mL/min. After loading, the column was washed with PBS (4 column volumes (CV)) followed by elution in 30 mM sodium acetate, pH 3.5. Fractions containing protein peaks as monitored by Absorbance at 280 nm in AKTA EXPLORER (GE healthcare) were pooled together and were neutralized to pH 5.0 by adding 1% of 3M sodium acetate, pH 9.0. As a polishing step, the antibodies were purified on a preparative size exclusion chromatography (SEC) using a SUPERDEX 200 column (GE healthcare). The integrity of sample was assessed by endotoxin measurement and SDS polyacrylamide gel electrophoresis under reducing and non-reducing conditions. The final protein concentrations were 1.0 mg/ml for anti-TRGV9/anti-CD123 and 1.0 mg/mL for anti-TRGV9/Null. The final EU levels of anti-TRGV9/anti-CD123 and anti-TRGV9/Null based on these were <3.0 EU/mg.

TABLE 8

CDR Sequences of anti-CD123 mAb.

| Antibody | HCDR1 | SEQ ID NO: | HCDR2 | SEQ ID NO: | HCDR3 | SEQ ID NO: |
|---|---|---|---|---|---|---|
| I3RB217 | SYWIS | 9 | IIDPSDSDT RYSPSFQG | 10 | GDGSTDLDY | 11 |

| Antibody | LCDR1 | SEQ ID NO: | LCDR2 | SEQ ID NO: | LCDR3 | SEQ ID NO: |
|---|---|---|---|---|---|---|
| I3RB217 | RASQSV SSSYL | 12 | GASSRAT | 13 | QQDYGFPWT | 14 |

TABLE 9

Heavy chain and light chain sequences of anti-CD123 mAb.

| mAb ID | Heavy Chain Amino Acid Sequence | SEQ ID NO: |
|---|---|---|
| I3RB217 | EVQLVQSGAEVKKPGESLKISCKGSGYSFTS YWISWVRQMPGKGLEWMGIIDPSDSDTRYSP SFQGQVTISADKSISTAYLQWSSLKASDTAM YYCARGDGSTDLDYWGQGTLVTVSS | 15 |

TABLE 9-continued

Heavy chain and light chain sequences of anti-CD123 mAb.

| mAb ID | Light Chain Amino Acid Sequence | SEQ ID NO: |
|---|---|---|
| I3RB217 | EIVLTQSPGTLSLSPGERATLSCRASQSVSS SYLAWYQQKPGQAPRLLIYGASSRATGIPDR FSGSGSGTDFTLTISRLEPEDFAVYYCQQDY GFPWTFGQGTKVEIK | 16 |

TABLE 10

Sequences of half antibodies expressed in CHO cells.

| mAb ID | 'Knob' arm and 'hole' arm amino acid sequence | SEQ ID NO: |
|---|---|---|
| VG1 (ANTI-TRGV9 half antibody) | MAWVWTLLFLMAAAQSIQADIVMSQSPSSLAVSVGEKVTMSCKSSQSLLYS SNQKNYLAWYQQKPGQSPKLLIYWASTRESGVPDRFTGSGSGTDFTLTISSV KAEDLAVYYCQQYYRYHTFGTGTKLEIKRTVAAPSVFIFPPSDEQLKSGTAS VVCLLNNFYPREAKVQWKVDNALQSGNSQESVTEQDSKDSTYSLSSTLTLS KADYEKHKVYACEVTHQGLSSPVTKSFNRGECGGSEGKSSGSGSESKSTEG KSSGSGSESKSTGGSEVQLQQSGAELARPGASVKLSCKASGFTFTDHYINWV KQRTGQGLEWIGQIYPGDGNTYYNQKFKGKATLTADKSSSTAYMQLSSLTS EDSAVYFCAPNYGDYTIDFWGQGTSVTVSSASTKGPSVFPLAPCSRSTSEST AALGCLVKDYFPEPVTVSWNSGALTSGVHTFPAVLQSSGLYSLSSVVTVPSS SLGTKTYTCNVDHKPSNTKVDKRVESKYGPPCPPCPAPEAAGGPSVFLFPPK PKDTLMISRTPEVTCVVVDVSQEDPEVQFNWYVDGVEVHNAKTKPREEQF NSTYRVVSVLTVLHQDWLNGKEYKCKVSNKGLPSSIEKTISKAKGQPREPQ VYTLPPSQEEMTKNQVSLSCAVKGFYPSDIAVEWESNGQPENNYKTTPPVL DSDGSFFLVSRLTVDKSRWQEGNVFSCSVMHEALHNRFTQKSLSLSLGK | 17 |
| VG1 (anti-CD123 half Ab) | MAWVWTLLFLMAAAQSIQAEIVLTQSPGTLSLSPGERATLSCRASQSVSSSY LAWYQQKPGQAPRLLIYGASSRATGIPDRFSGSGSGTDFTLTISRLEPEDFAV YYCQQDYGFPWTFGQGTKVEIKRTVAAPSVFIFPPSDEQLKSGTASVVCLLN NFYPREAKVQWKVDNALQSGNSQESVTEQDSKDSTYSLSSTLTLSKADYEK HKVYACEVTHQGLSSPVTKSFNRGECGGSEGKSSGSGSESKSTEGKSSGSGS ESKSTGGSEVQLVQSGAEVKKPGESLKISCKGSGYSFTSYWISWVRQMPGK GLEWMGIIDPSDSDTRYSPSFQGQVTISADKSISTAYLQWSSLKASDTAMYY CARGDGSTDLDYWGQGTLVTVSSASTKGPSVFPLAPCSRSTSESTAALGCLV KDYFPEPVTVSWNSGALTSGVHTFPAVLQSSGLYSLSSVVTVPSSSLGTKTY TCNVDHKPSNTKVDKRVESKYGPPCPPCPAPEAAGGPSVFLFPPKPKDTLMI SRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQ EEMTKNQVSLWCLVKGFYPSDIAVEWESNGQPENNYKTTPPVLDSD GSFFL YSRLTVDKSRWQEGNVFSCSVMHEALHNHYTQKSLSLSLGK | 18 |
| VG3 (B23B49 Null half Ab) | MAWVWTLLFLMAAAQSIQAEIVLTQSPGTLSLSPGERATLSCRASQSVSSSY LAWYQQKPGQAPRLLIYGASSRATGIPDRFSGSGSGTDFTLTISRLEPEDFAV YYCQQDYGFPWTFGQGTKVEIKRTVAAPSVFIFPPSDEQLKSGTASVVCLLN NFYPREAKVQWKVDNALQSGNSQESVTEQDSKDSTYSLSSTLTLSKADYEK HKVYACEVTHQGLSSPVTKSFNRGECGGSEGKSSGSGSESKSTEGKSSGSGS ESKSTGGSEVQLVQSGAEVKKPGESLKISCKGSGYSFTSYWISWVRQMPGK GLEWMGIIDPSDSDTRYSPSFQGQVTISADKSISTAYLQWSSLKASDTAMYY CARGDGSTDLDYWGQGTLVTVSSASTKGPSVFPLAPCSRSTSESTAALGCLV KDYFPEPVTVSWNSGALTSGVHTFPAVLQSSGLYSLSSVVTVPSSSLGTKTY TCNVDHKPSNTKVDKRVESKYGPPCPPCPAPEAAGGPSVFLFPPKPKDTLMI SRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQ EEMTKNQVSLWCLVKGFYPSDIAVEWESNGQPENNYKTTPPVLDSDGSFFL YSRLTVDKSRWQEGNVFSCSVMHEALHNHYTQKSLSLSLGK | 19 |

Half Antibody DNA sequence

| | | |
|---|---|---|
| VG1 (ANTI-TRGV9 half Ab) | ATGGCCTGGGTGTGGACCCTGCTGTTCCTGATGGCCGCCGCCCAGAGCAT CCAGGCCGACATCGTGATGAGCCAGAGCCCAAGCAGCCTGGCCGTGAGC GTGGGCGAGAAGGTGACCATGAGCTGCAAGAGCAGCCAGAGCCTGCTGT ACAGCAGCAACCAGAAGAACTACCTGGCCTGGTACCAGCAGAAGCCAG GCCAGAGCCCAAAGCTGCTGATCTACTGGGCCAGCACCCGCGAGAGCGG CGTGCCAGACCGCTTCACCGGCAGCGGCAGCGGCACCGACTTCACCCTG ACCATCAGCAGCGTGAAGGCCGAGGACCTGGCCGTGTACTACTGCCAGC AGTACTACCGCTACCACACCTTCGGCACCGGCACCAAGCTGGAGATCAA GCGCACCGTGGCCGCCCCAAGCGTGTTCATCTTCCCACCAAGCGACGAG CAGCTGAAGAGCGGCACCGCCAGCGTGGTGTGCCTGCTGAACAACTTCT | 20 |

TABLE 10-continued

Sequences of half antibodies expressed in CHO cells.

| | | |
|---|---|---|
| | ACCCACGCGAGGCCAAGGTGCAGTGGAAGGTGGACAACGCCCTGCAGA<br>GCGGCAACAGCCAGGAGAGCGTGACCGAGCAGGACAGCAAGGACAGCA<br>CCTACAGCCTGAGCAGCACCCTGACCCTGAGCAAGGCCGACTACGAGAA<br>GCACAAGGTGTACGCCTGCGAGGTGACCCACCAGGGCCTGAGCAGCCCA<br>GTGACCAAGAGCTTCAACCGCGGCGAGTGCggcggcagcgagggcaaga<br>gcagcggcagcggcagcgagagcaagagcaccgagggcaagagcagcgg<br>cagcggcagcggcgagagcaagagcaccggcggca<br>gcGAGGTGCAGCTGCAGCAGAGCGGCGCCGAGCTGGCCCGCCCAGGCGC<br>CAGCGTGAAGCTGAGCTGCAAGGCCAGCGGCTTCACCTTCACCGACCAC<br>TACATCAACTGGGTGAAGCAGCGCACCGGCCAGGGCCTGGAGTGGATCG<br>GCCAGATCTACCCAGGCGACGGCAACACCTACTACAACCAGAAGTTCAA<br>GGGCAAGGCCACCCTGACCGCCGACAAGAGCAGCAGCACCGCCTACATG<br>CAGCTGAGCAGCCTGACCAGCGAGGACAGCGCCGTGTACTTCTGCGCCC<br>CAAACTACGGCGACTACACCATCGACTTCTGGGGCCAGGGCACCAGCGT<br>GACCGTGAGCAGCGCCAGCACCAAGGGCCCAAGCGTGTTCCCACTGGCC<br>CCATGCAGCCGCAGCACCAGCGAGAGCACCGCCGCCCTGGGCTGCCTGG<br>TGAAGGACTACTTCCCAGAGCCAGTGACCGTGAGCTGGAACAGCGGCGC<br>CCTGACCAGCGGCGTGCACACCTTCCCAGCCGTGCTGCAGAGCAGCGGC<br>CTGTACAGCCTGAGCAGCGTGGTGACCGTGCCAAGCAGCAGCCTGGGCA<br>CCAAGACCTACACCTGCAACGTGGACCACAAGCCAAGCAACACCAAGGT<br>GGACAAGCGCGTGGAGAGCAAGTACGGCCCACCATGCCCACCATGCCCA<br>GCCCCAGAGGCCGCCGGCGGCCCAAGCGTGTTCCTGTTCCCACCAAAGC<br>CAAAGGACACCCTGATGATCAGCCGCACCCCAGAGGTGACCTGCGTGGT<br>GGTGGACGTGAGCCAGGAGGACCCAGAGGTGCAGTTCAACTGGTACGTG<br>GACGGCGTGGAGGTGCACAACGCCAAGACCAAGCCACGCGAGGAGCAG<br>TTCAACAGCACCTACCGCGTGGTGAGCGTGCTGACCGTGCTGCACCAGG<br>ACTGGCTGAACGGCAAGGAGTACAAGTGCAAGGTGAGCAACAAGGGCC<br>TGCCAAGCAGCATCGAGAAGACCATCAGCAAGGCCAAGGGCCAGCCAC<br>GCGAGCCACAGGTGTACACCCTGCCACCAAGCCAGGAGGAGATGACCA<br>AGAACCAGGTGAGCCTGTGGTGCCTGGTGAAGGGCTTCTACCCAAGCGA<br>CATCGCCGTGGAGTGGGAGAGCAACGGCCAGCCAGAGAACAACTACAA<br>GACCACCCCACCAGTGCTGGACAGCGACGGCAGCTTCTTCCTGTACAGC<br>CGCCTGACCGTGGACAAGAGCCGCTGGCAGGAGGGCAACGTGTTCAGCT<br>GCAGCGTGATGCACGAGGCCCTGCACAACCACTACACCCAGAAGAGCCT<br>GAGCCTGAGCCTGGGCAAG | |
| VG1<br>(anti-<br>CD123<br>half Ab) | ATGGCCTGGGTGTGGACCCTGCTGTTCCTGATGGCCGCCGCCCAGAGCAT<br>CCAGGCCGAGATCGTGCTGACCCAGAGCCCAGGCACCCTGAGCCTGAGC<br>CCAGGCGAGCGCGCCACCCTGAGCTGCCGCGCCAGCCAGAGCGTGAGCA<br>GCAGCTACCTGGCCTGGTACCAGCAGAAGCCAGGCCAGGCCCCACGCCT<br>GCTGATCTACGGCGCCAGCAGCCGCGCCACCGGCATCCCAGACCGCTTC<br>AGCGGCAGCGGCAGCGGCACCGACTTCACCCTGACCATCAGCCGCCTGG<br>AGCCAGAGGACTTCGCCGTGTACTACTGCCAGCAGGACTACGGCTTCCC<br>ATGGACCTTCGGCCAGGGCACCAAGGTGGAGATCAAGCGCACCGTGGCC<br>GCCCCAAGCGTGTTCATCTTCCCACCAAGCGACGAGCAGCTGAAGAGCG<br>GCACCGCCAGCGTGGTGTGCCTGCTGAACAACTTCTACCCACGCGAGGC<br>CAAGGTGCAGTGGAAGGTGGACAACGCCCTGCAGAGCGGCAACAGCCA<br>GGAGAGCGTGACCGAGCAGGACAGCAAGGACAGCACCTACAGCCTGAG<br>CAGCACCCTGACCCTGAGCAAGGCCGACTACGAGAAGCACAAGGTGTAC<br>GCCTGCGAGGTGACCCACCAGGGCCTGAGCAGCCCAGTGACCAAGAGCT<br>TCAACCGCGGCGAGTGCggcggcagcgagggcaagagcagcggcagcgg<br>cagcgagagcaagagcaccgagggcaagagcagcggcagcggcagcgag<br>agcaagagcaccggcggcagcGAGGTGCAGCT<br>GGTGCAGAGCGGCGCCGAGGTGAAGAAGCCAGGCGAGAGCCTGAAGAT<br>CAGCTGCAAGGGCAGCGGCTACAGCTTCACCAGCTACTGGATCAGCTGG<br>GTGCGCCAGATGCCAGGCAAGGGCCTGGAGTGGATGGGCATCATCGACC<br>CAAGCGACAGCGACACCCGCTACAGCCCAAGCTTCCAGGGCCAGGTGAC<br>CATCAGCGCCGACAAGAGCATCAGCACCGCCTACCTGCAGTGGAGCAGC<br>CTGAAGGCCAGCGACACCGCCATGTACTACTGCGCCCGCGGCGACGGCA<br>GCACCGACCTGGACTACTGGGGCCAGGGCACCCTGGTGACCGTGAGCAG<br>CGCCAGCACCAAGGGCCCAAGCGTGTTCCCACTGGCCCCATGCAGCCGC<br>AGCACCAGCGAGAGCACCGCCGCCCTGGGCTGCCTGGTGAAGGACTACT<br>TCCCAGAGCCAGTGACCGTGAGCTGGAACAGCGGCGCCCTGACCAGCGG<br>CGTGCACACCTTCCCAGCCGTGCTGCAGAGCAGCGGCCTGTACAGCCTG<br>AGCAGCGTGGTGACCGTGCCAAGCAGCAGCCTGGGCACCAAGACCTACA<br>CCTGCAACGTGGACCACAAGCCAAGCAACACCAAGGTGGACAAGCGCG<br>TGGAGAGCAAGTACGGCCCACCATGCCCACCATGCCCAGCCCCAGAGGC<br>CGCCGGCGCCCAAGCGTGTTCCTGTTCCCACCAAAGCCAAAGGACACC<br>CTGATGATCAGCCGCACCCCAGAGGTGACCTGCGTGGTGGTGGACGTGA<br>GCCAGGAGGACCCAGAGGTGCAGTTCAACTGGTACGTGGACGGCGTGGA<br>GGTGCACAACGCCAAGACCAAGCCACGCGAGGAGCAGTTCAACAGCAC<br>CTACCGCGTGGTGAGCGTGCTGACCGTGCTGCACCAGGACTGGCTGAAC<br>GGCAAGGAGTACAAGTGCAAGGTGAGCAACAAGGGCCTGCCAAGCAGC<br>ATCGAGAAGACCATCAGCAAGGCCAAGGGCCAGCCACGCGAGCCACAG<br>GTGTACACCCTGCCACCAAGCCAGGAGGAGATGACCAAGAACCAGGTG<br>AGCCTGTGGTGCCTGGTGAAGGGCTTCTACCCAAGCGACATCGCCGTGG<br>AGTGGGAGAGCAACGGCCAGCCAGAGAACAACTACAAGACCACCCCAC<br>CAGTGCTGGACAGCGACGGCAGCTTCTTCCTGTACAGCCGCCTGACCGT | 21 |

TABLE 10-continued

Sequences of half antibodies expressed in CHO cells.

|  |  |  |
|---|---|---|
|  | GGACAAGAGCCGCTGGCAGGAGGGCAACGTGTTCAGCTGCAGCGTGATG CACGAGGCCCTGCACAACCACTACACCCAGAAGAGCCTGAGCCTGAGCC TGGGCAAG |  |
| VG3 (Null half Ab) | ATGGCCTGGGTGTGGACCCTGCTGTTCCTGATGGCCGCCGCCCAGAGCAT CCAGGCCGACATCGTGATGACCCAGAGCCCAGACAGCCTGGCCGTGAGC CTGGGCGAGCGCGCCACCATCAACTGCCGCGCCAGCCAGAGCGTGGACT ACAACGGCATCAGCTACATGCACTGGTACCAGCAGAAGCCAGGCCAGCC ACCAAAGCTGCTGATCTACGCCGCCAGCAACCCAGAGAGCGGCGTGCCA GACCGCTTCAGCGGCAGCGGCAGCGGCACCGACTTCACCCTGACCATCA GCAGCCTGCAGGCCGAGGACGTGGCCGTGTACTACTGCCAGCAGATCAT CGAGGACCCATGGACCTTCGGCCAGGGCACCAAGGTGGAGATCAAGCGC ACCGTGGCCGCCCCAAGCGTGTTCATCTTCCCACCAAGCGACGAGCAGC TGAAGAGCGGCACCGCCAGCGTGGTGTGCCTGCTGAACAACTTCTACCC ACGCGAGGCCAAGGTGCAGTGGAAGGTGGACAACGCCCTGCAGAGCGG CAACAGCCAGGAGAGCGTGACCGAGCAGGACAGCAAGGACAGCACCTA CAGCCTGAGCAGCACCCTGACCCTGAGCAAGGCCGACTACGAGAAGCAC AAGGTGTACGCCTGCGAGGTGACCCACCAGGGCCTGAGCAGCCCAGTGA CCAAGAGCTTCAACCGCGGCGAGTGCGGCGGCAGCGAGGGCAAGAGCA GCGGCAGCGGCAGCGAGAGCAAGAGCACCGAGGGCAAGAGCAGCGGCA GCGGCAGCGAGAGCAAGAGCACCGGCGGCAGCCAGATCACCCTGAAGG AGAGCGGCCCAACCCTGGTGAAGCCAACCCAGACCCTGACCCTGACCTG CACCTTCAGCGGCTTCAGCCTGAGCACCAGCGGCATGGGCGTGAGCTGG ATCCGCCAGCCACCAGGCAAGGCCCTGGAGTGGCTGGCCCACATCTACT GGGACGACGACAAGCGCTACAACCCAAGCCTGAAGAGCCGCCTGACCAT CACCAAGGACACCAGCAAGAACCAGGTGGTGCTGACCATGACCAACATG GACCCAGTGGACACCGCCACCTACTACTGCGCCCGCCTGTACGGCTTCAC CTACGGCTTCGCCTACTGGGGCCAGGGCACCCTGGTGACCGTGAGCAGC GCCAGCACCAAGGGCCCAAGCGTGTTCCCACTGGCCCCATGCAGCCGCA GCACCAGCGAGAGCACCGCCGCCCTGGGCTGCCTGGTGAAGGACTACTT CCCAGAGCCAGTGACCGTGAGCTGGAACAGCGGCGCCCTGACCAGCGGC GTGCACACCTTCCCAGCCGTGCTGCAGAGCAGCGGCCTGTACAGCCTGA GCAGCGTGGTGACCGTGCCAAGCAGCAGCCTGGGCACCAAGACCTACAC CTGCAACGTGGACCACAAGCCAAGCAACACCAAGGTGGACAAGCGCGT GGGAGAGCAAGTACGGCCCCACCATGCCCACCATGCCCAGCCCCAGAGGCC GCCGGCGGCCCAAGCGTGTTCCTGTTCCCACCAAAGCCAAAGGACACCC TGATGATCAGCCGCACCCCAGAGGTGACCTGCGTGGTGGTGGACGTGAG CCAGGAGGACCCAGAGGTGCAGTTCAACTGGTACGTGGACGGCGTGGAG GTGCACAACGCCAAGACCAAGCCACGCGAGGAGCAGTTCAACAGCACCT ACCGCGTGGTGAGCGTGCTGACCGTGCTGCACCAGGACTGGCTGAACGG CAAGGAGTACAAGTGCAAGGTGAGCAACAAGGGCCTGCCAAGCAGCAT CGAGAAGACCATCAGCAAGGCCAAGGGCCAGCCACGCGAGCCACAGGT GTACACCCTGCCACCAAGCCAGGAGGAGATGACCAAGAACCAGGTGAG CCTGTGGTGCCTGGTGAAGGGCTTCTACCCAAGCGACATCGCCGTGGAG TGGGAGAGCAACGGCCAGCCAGAGAACAACTACAAGACCACCCCACCA GTGCTGGACAGCGACGGCAGCTTCTTCCTGTACAGCCGCCTGACCGTGG ACAAGAGCCGCTGGCAGGAGGGCAACGTGTTCAGCTGCAGCGTGATGCA CGAGGCCCTGCACAACCACTACACCCAGAAGAGCCTGAGCCTGAGCCTG GGCAAG | 22 |

TABLE 11

Heavy and Light Chain Sequences for TRGV9 bispecific antibodies

| Bispecific Antibody | | Amino Acid Sequence |
|---|---|---|
| VG1 (ANTI-TRGV9/anti-CD123) | Heavy chain VG1 (SEQ ID NO: 23) | 1 EVQLQQSGAELARPGASVKLSCKASGFTFTDHYINWVKQRT GQGLEWIGQIYPGDGNTYYNQKFKGKATLTADKSSSTAYM QLSSLTSEDSAVYFCAPNYGDYTIDFWGQGTSVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEAAGGPSVFLFPPKPKDT LMISRTPEVTCVVVDVSQEDPEVQFNWYVDGVEVHNAKTK PREEQFNSTYRVVSVLTVLHQDWLNGKEYKCKVSNKGLPS SIEKTISKAKGQPREPQVYTLPPSQEEMTKNQVSLSCAVKGF YPSDIAVEWESNGQPENNYKTTPPVLDSDGSFFLVSRLTVD KSRWQEGNVFSCSVMHEALHNRFTQKSLSLSLGK |
| | Light Chain VG1 (SEQ ID NO: 24) | 1 DIVMSQSPSSLAVSVGEKVTMSCKSSQSLLYSSNQKNYLAW YQQKPGQSPKLLIYWASTRESGVPDRFTGSGSGTDFTLTISS VKAEDLAVYYCQQYYRYHTFGTGTKLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQG LSSPVTKSFNRGEC |

TABLE 11-continued

Heavy and Light Chain Sequences for TRGV9 bispecific antibodies

| Bispecific Antibody | | Amino Acid Sequence |
|---|---|---|
| | Heavy chain 2 VG1 (SEQ ID NO: 25) | EVQLVQSGAEVKKPGESLKISCKGSGYSFTSYWISWVRQMPGKGLEWMGIIDPSDSDTRYSPSFQGQVTISADKSISTAYLQWSSLKASDTAMYYCARGDGSTDLDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLGK |
| | Light Chain 2 VG1 (SEQ ID NO: 26) | EIVLTQSPGTLSLSPGERATLSCRASQSVSSSYLAWYQQKPGQAPRLLIYGASSRATGIPDRFSGSGSGTDFTLTISRLEPEDFAVYYCQQDYGFPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| ANTI-TRGV9 x Null | Heavy chain 1 VG3 (SEQ ID NO: 27) | QVQLQESGPGLVKPSETLSLTCTVSGYSITSGYFWNWIRQPPGKGLEWIGYISYDGSNNYNPSLKSRVTISRDTSKNQFSLKLSSVTAADTAVYYCASPSPGTGYAVDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVMHEALHNRFTQKSLSLSLGK |
| | Light Chain 1 VG3 (SEQ ID NO: 28) | DIQMTQSPSSLSASVGDRVTITCRSSQSLVHSNGNTYLHWYQQKPGKAPKFLIYKVSNRFSGVPSRFSGSGSGTDFTLTISSLQPEDFATYYCSQSTHVPFTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Heavy chain 2 VG3 (SEQ ID NO: 29) | QITLKESGPTLVKPTQTLTLTCTFSGFSLSTSGMGVSWIRQPPGKALEWLAHIYWDDDKRYNPSLKSRLTITKDTSKNQVVLTMTNMDPVDTATYYCARLYGFTYGFAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLGK |
| | Light Chain 2 VG3 (SEQ ID NO: 30) | DIVMTQSPDSLAVSLGERATINCRASQSVDYNGISYMHWYQQKPGQPPKLLIYAASNPESGVPDRFSGSGSGTDFTLTISSLQAEDVAVYYCQQIIEDPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

Example 2.3: Characterization of Vγ9+ (γδ) T Cells and Pan T Cells

Figure 2:
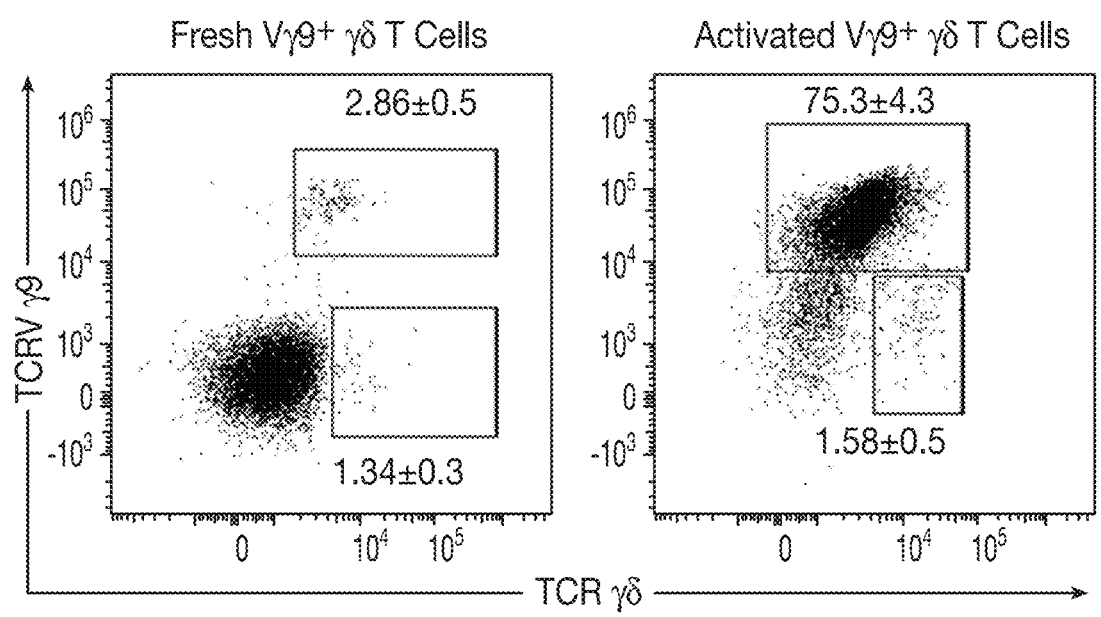
FIG. 2 shows a graph demonstrating that Zoledronic acid selectively expands Vγ9Vδ2 T cells from whole peripheral blood mononuclear cells (PBMCs).

Zoledronic acid selectively expands Vγ9+ γδ T cells from whole PBMCs. PBMCs were isolated from whole fresh PBMCs using EASYSEP Human γδ T cell isolation kit (Stem cell Technologies; Vancouver, Calif.) according to manufacturer instructions. Isolated PBMCs were cultured in RPMI-10 (RPMI supplemented with 10% FBS, 1× Pen/Strep) medium with recombinant human IL-2 (rhIL-2) to a final concentration of 1000 IU/mL and recombinant human IL-15 (rhIL-15) to a final concentration of 10 ng/mL and Zoledronic acid to a final concentration of 5 μM. for 14 days. Numbers in representative dot plots show the frequency (mean±SEM) of Vγ9+ and Vγ9− TCR γδ T cells among total PBMCs on day 0 (left) and day 14 of PBMCs cultured with Zoledronic acid+IL-2+IL-15 (right). Represented data is mean (±SEM) of five donors (n=5) from a single experiment (FIG. 2).

Figure 3A:
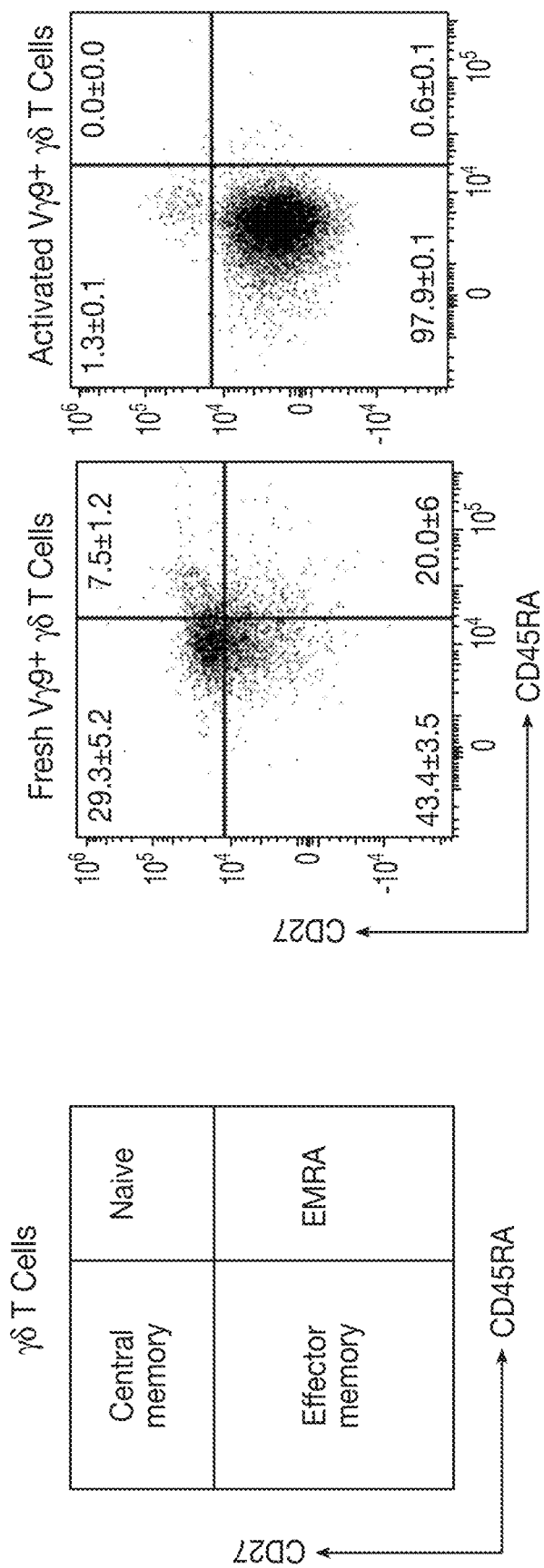
FIGS. 3A-3E show phenotypic characterization of Vγ9+ γδ T cells.
Figure 3B:
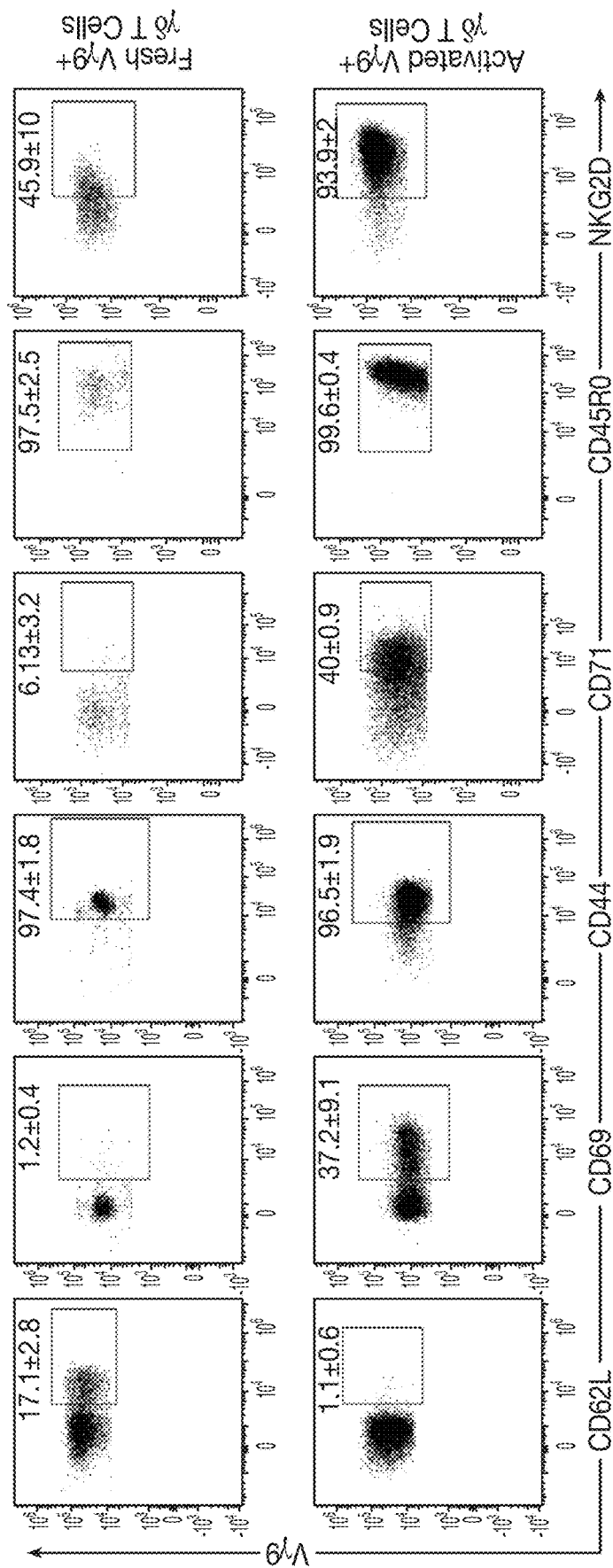
Figure 3C:
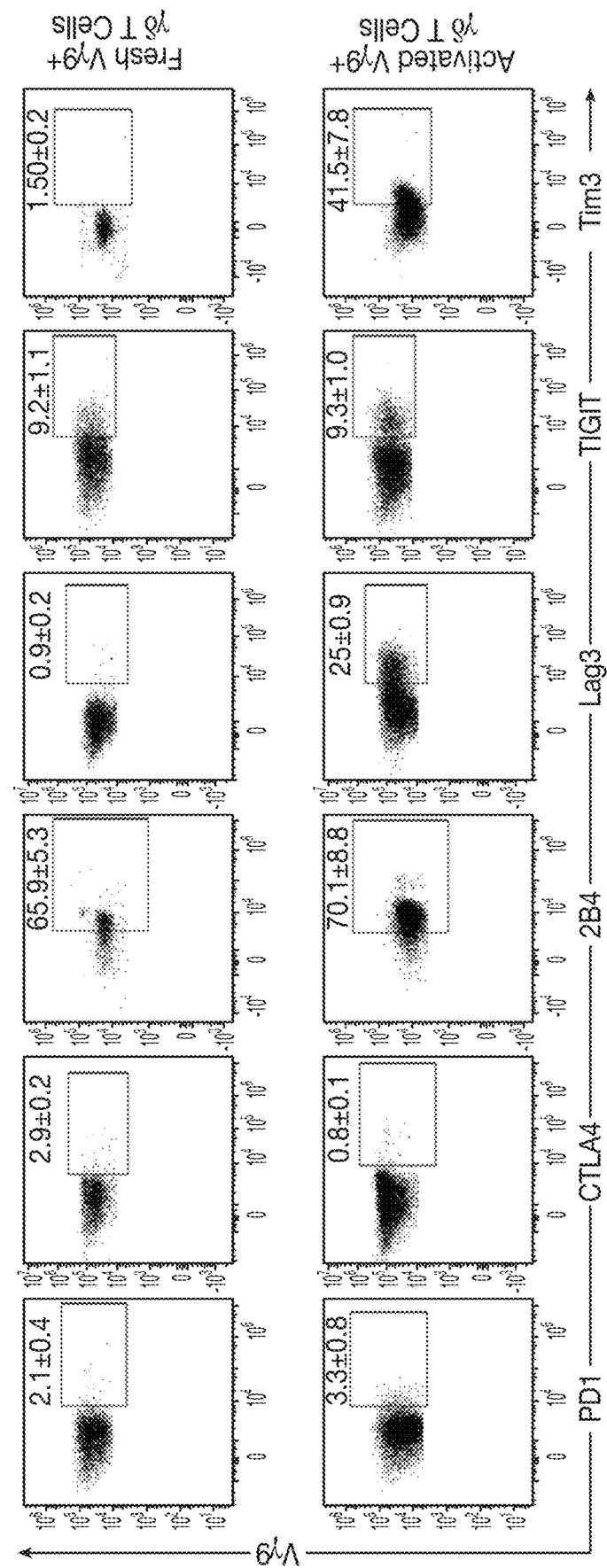
Figure 3D:
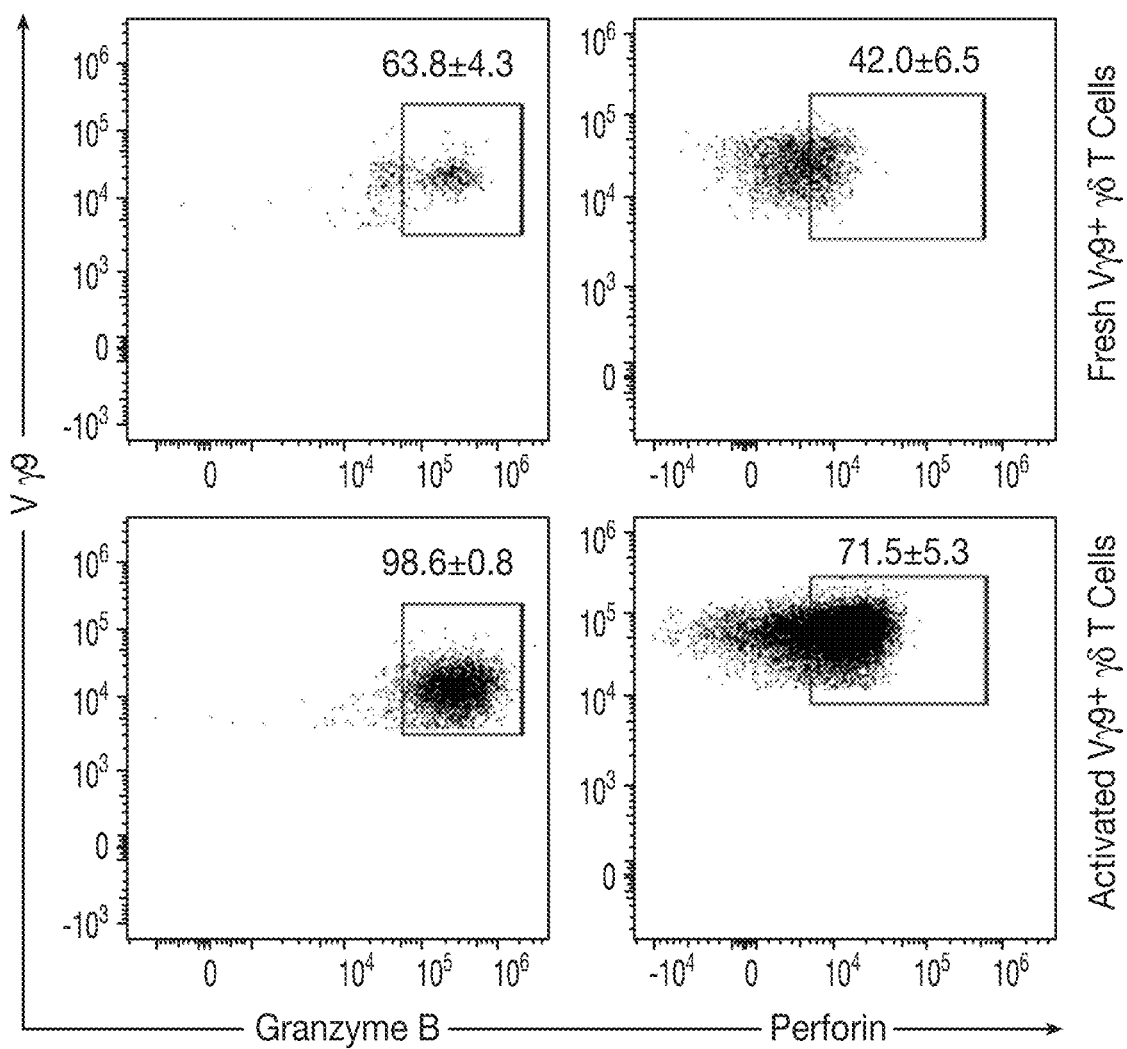
Figure 3E:
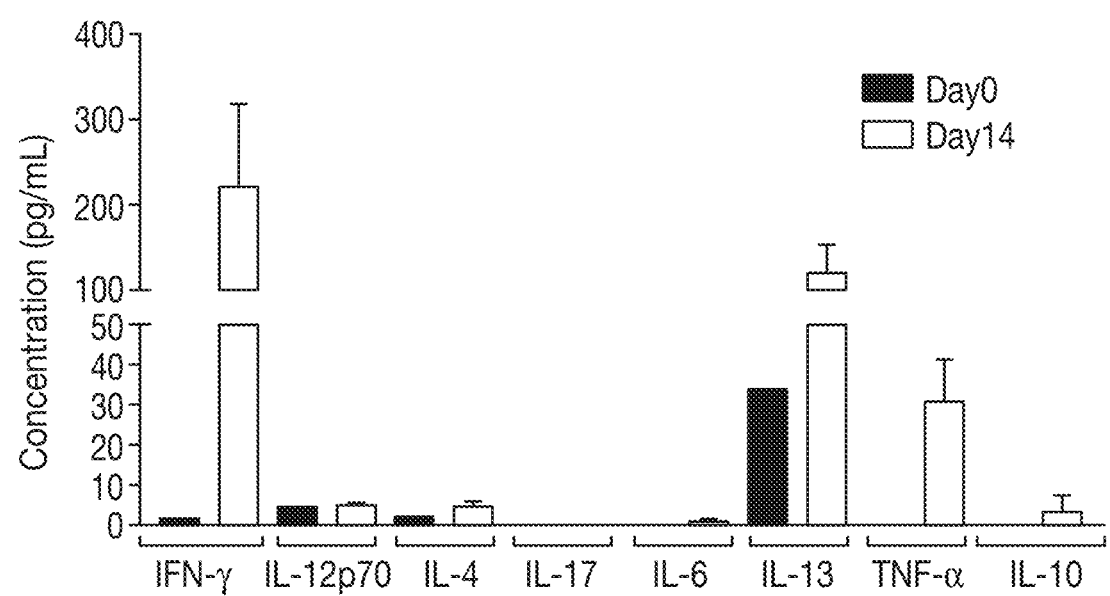

FIGS. 3A to 3E demonstrate the phenotypic characterization of Vγ9+ γδ T cells. FIG. 3A shows a schematic depiction of gates used to describe the differentiation of γδ T cells (left). Representative FACS-dot plots show the differentiation profile of Vγ9+ γδ T cells from fresh PBMCs (left) and PBMCs cultured ex vivo with Zoledronic acid+IL-2+IL-15 for 14 days (right). Numbers in quadrants mirror the frequency (mean±SEM) of the respective population among fresh and activated Vγ9+ γδ T cells. Represented data is mean (±SEM) of five donors (n=5) from a single experiment. FIG. 3B shows numbers in representative dot plots mirroring the frequency (mean±SEM) of Vγ9+ γδ T cells positive for respective activation marker either from fresh PBMCs (upper row) or PBMCs cultured with Zoledronic acid+IL-2+IL-15 for 14 days (lower row). Represented data is mean (±SEM) of seven donors (n=7) for CD62L, CD69, CD44 expression data from two independent experiments. n=5 donors for NKG2D and 2 donors for CD45RO and CD71 expression data respectively from a single experiment. FIG. 3C shows numbers above gates in dot plots depicting the frequency (mean±SEM) of Vγ9+ γδ T cells positive for respective inhibitory receptor surface expression either from fresh PBMCs (upper row) or PBMCs cultured with Zoledronic acid+IL-2+IL-15 for day 14 days (lower row). Data shown here is mean (±SEM) of five donors (n=5) for PD1, CTLA4, TIGIT and LAG3 surface expression and seven donors (n=7) for 2B4 and TIM3 surface expression data from two independent experiments. FIG. 3D shows representative FACS dot plots demonstrating the frequency (mean±SEM) of Vγ9+ γδ T cells expressing intracellular Granzyme B (left column) and Perforin (right column) from fresh PBMCs (upper row) and PBMCs cultured ex vivo with Zoledronic acid+IL-2+IL-15 for 14 days (lower row). Depicted data is mean (±SEM) of four (n=4) and seven (n=7) donors for Granzyme B and Perforin data respectively from two independent experiments. FIG. 3E shows bars representing the mean (±SEM) concentration (pg/mL) of cytokine in the cell culture supernatant on day 0 and day 14 of PBMCs culture with Zoledronic acid+IL-2+IL-15. Represented data is mean (±SEM) of four wells (n=4) from a single donor.

Figure 4:
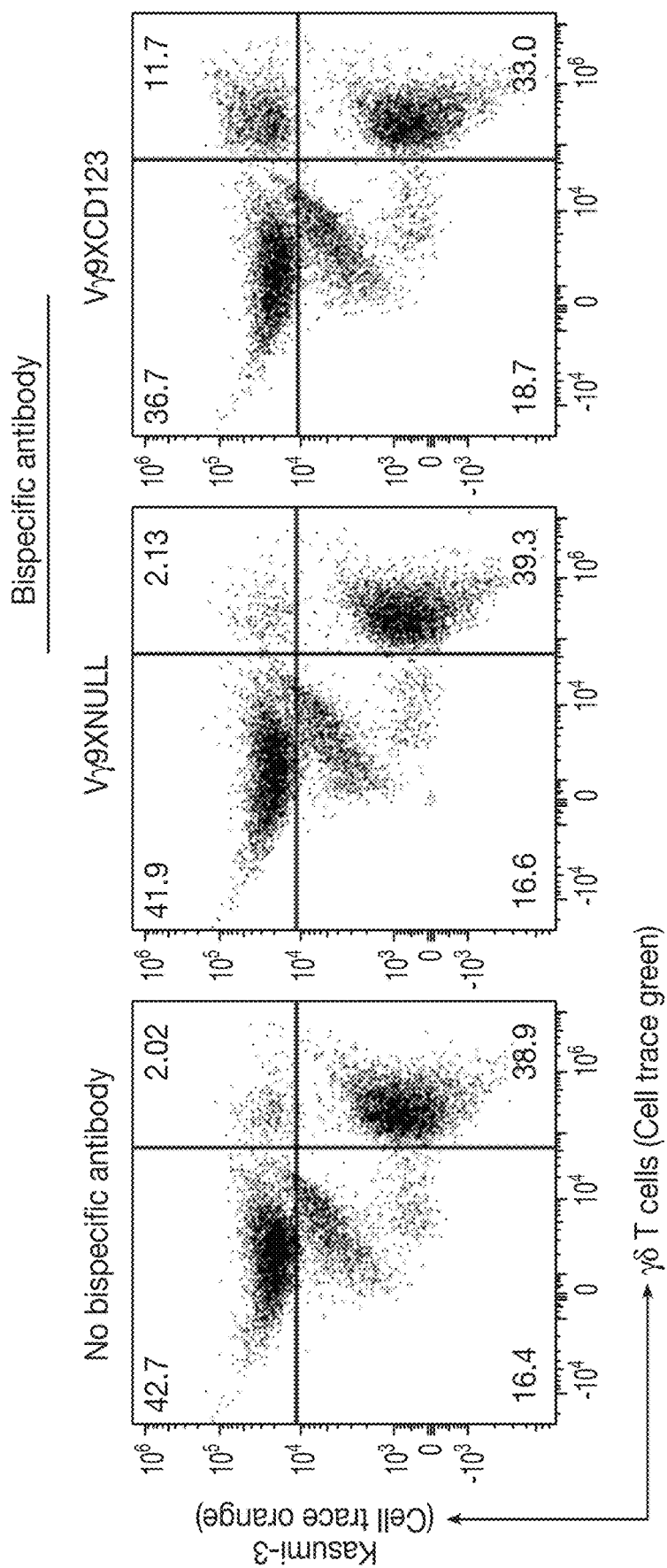
FIG. 4 shows a histogram demonstrating that VG1 (an anti-TRGV9/anti-CD123 bispecific antibody) recruits Vγ9+ T cells as demonstrated by conjugate formation between γδ T cells and Kasumi-3 cells.

FIG. 4 shows that the anti-TRGV9/anti-CD123 bispecific antibody recruits γδ T cells into biphasic cell-cell conjugate. γδ T cells (effector cells) were isolated from whole fresh PBMCs using EASYSEP Human γδ T cell isolation kit (Stem cell Technologies) according to manufacturer instructions. γδ T cells were labelled with 0.25 μM CELL-TRACKER™ Green CMFDA Dye for 30 min. and Kasumi-3 (Targets) cells were labelled with 1 μM CELL-TRACKER™ Orange CMRA Dye in RPMI medium for 30 minutes at 37° C. Both labeled γδ T cells and Kasumi-3 were co-cultured. Labeled Effector (E) and Target (T) cells at an E:T ratio of 1:1 (50,000 cells of each cell type/well) with 1 microgram per ML of bispecific antibody (anti-TRGV9/anti-CD123, anti-TRGV9/anti-NULL) and incubated at 37° C. for 1 hour. At the end of the incubation, cells were spun down at 1200 rpm for 5 minutes and resuspended in FACS buffer. Cells were acquired utilizing the flow cytometer and analysis was performed using FLOWJO analysis software. Numbers in quadrants of representative FACS plots show the frequency of recruited or non-recruited cells to the cell-cell conjugate either in the absence (left dot plot) or presence of anti-TRGV9/anti-NULL (middle dot plot) and anti-TRGV9/anti-CD123 (right dot plot) bispecific antibody. Data shown here is from a single experiment.

Figure 5A:
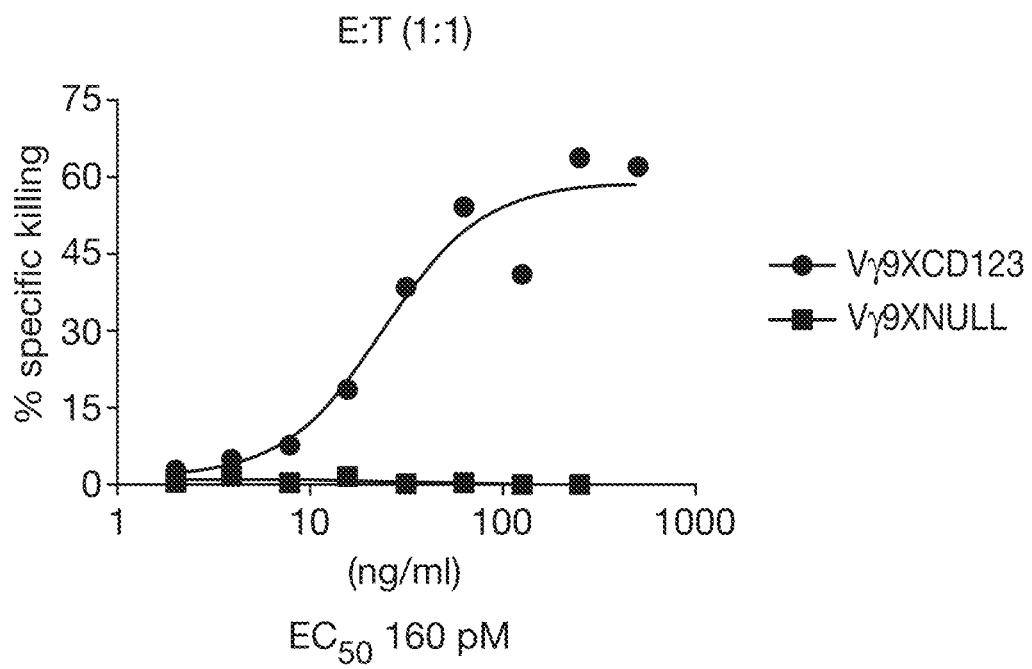
FIGS. 5A-5C show graphs demonstrating VG1 (anti-TRGV9/anti-CD123 bispecific antibody) bispecific mediated γδ T cell cytotoxicity against Kasumi-3 cells at different effector to target cell ratios (1:1 for FIG. 5A; 5:1 for FIG. 5B; and 10:1 for FIG. 5C).
Figure 5B:
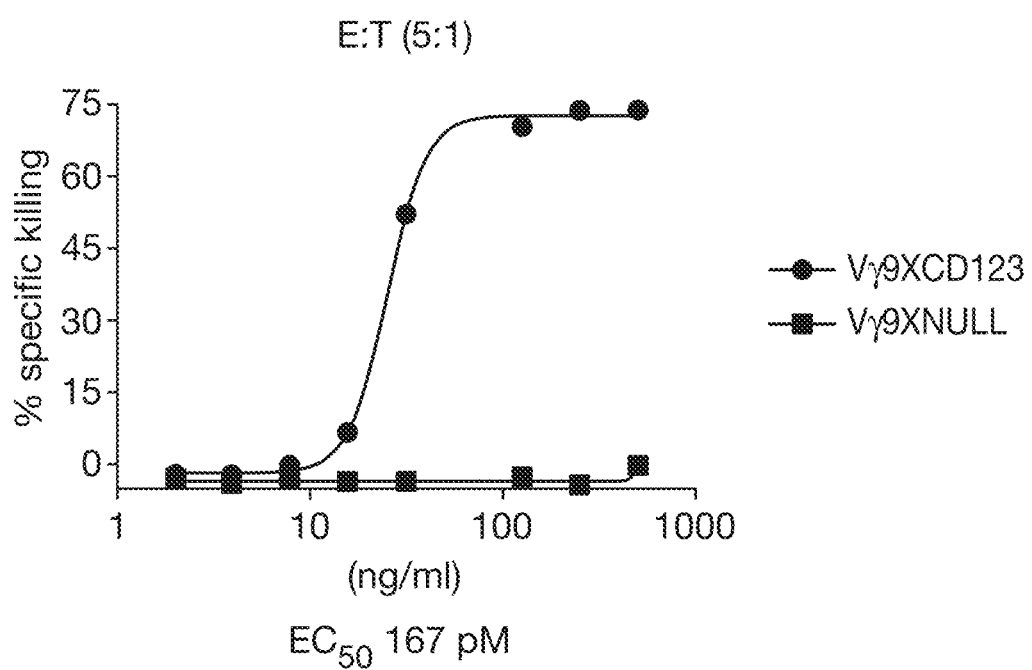
Figure 5C:
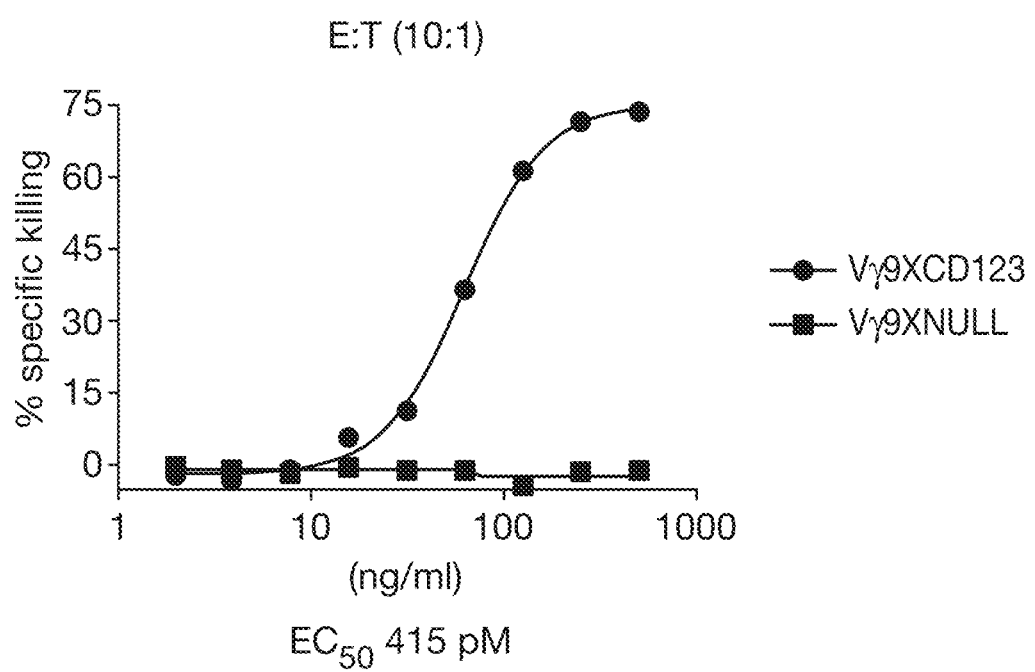

Example 2.4: Evaluation of Binding and Cytotoxic Properties of the ANTI-TRGV9/Anti-CD123 Bispecific Antibody Using Kasumi-3 Cells and Human γδ T Cells FIG. 5 shows that the anti-TRGV9/anti-CD123 bispecific antibody mediates γδ T cell cytotoxicity against CD123 expressing Kasumi-3 cells in vitro. Enriched γδ T cells (Effectors), isolated from PBMCs cultured with Zoledronic acid+IL-2+IL-15 for 12 days, were co-cultured with CF SE labelled Kasumi-3 cells (Targets) at 1:1, 5:1 and 10:1 E:T ratios in the presence of various concentrations of the bispecific antibody for 24 hours. Dose response curves show anti-TRGV9/anti-CD123 and anti-TRGV9/anti-NULL bispecific mediated γδ T cell cytotoxicity against CD123 expressing Kasumi-3 cells in a dose dependent manner at 1:1 (FIG. 5A) 5:1 (FIG. 5B) and 10:1 (FIG. 5C) E:T ratios. Cytotoxicity values represented here were subtracted of basal cytotoxicity value observed in the absence of bispecific antibody. $EC_{50}$ values were calculated as described in methods. Representative data shown here are from a single experiment.

Figure 6A:
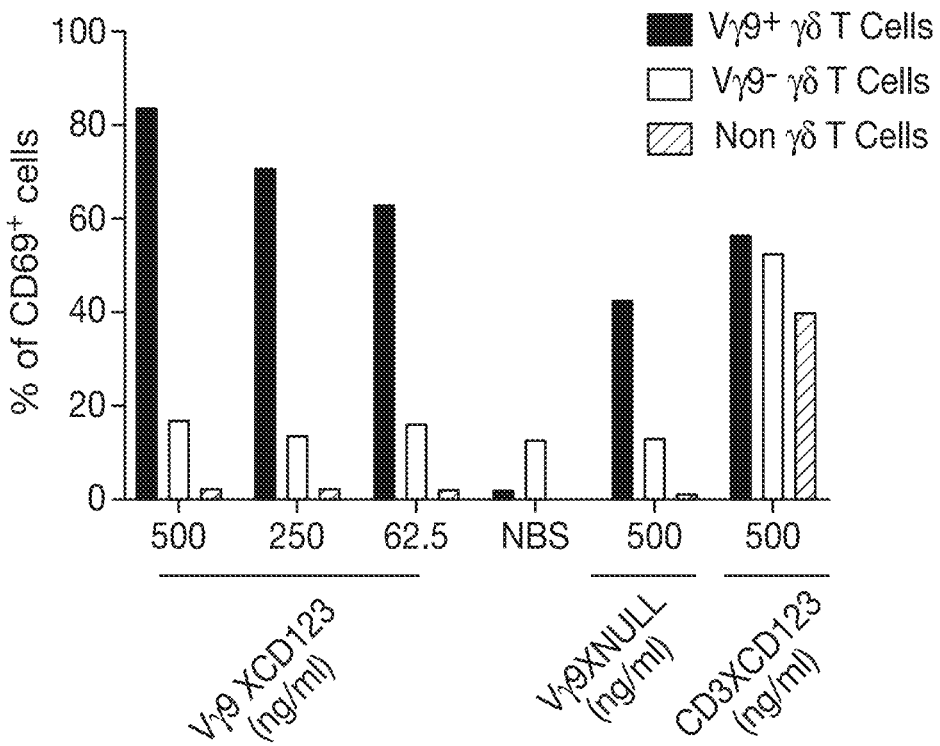
FIGS. 6A-6C show graphs demonstrating CD69 (FIG. 6A), CD25 (FIG. 6B), or Granzyme B (FIG. 6C) expression on Vγ9+ γδ T cells, non-Vγ9+ γδ T cells, and Pan-T cells (non γδ T cells) co-cultured with Kasumi-3 cells and VG1, VG3, or no bispecific antibody.
Figure 6B:
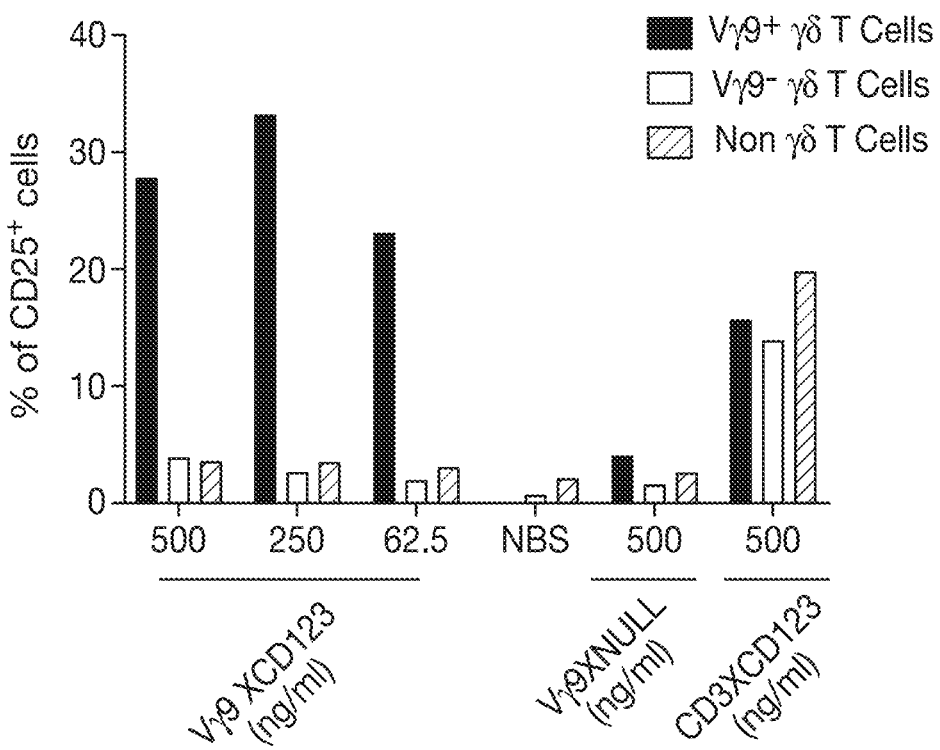
Figure 6C:
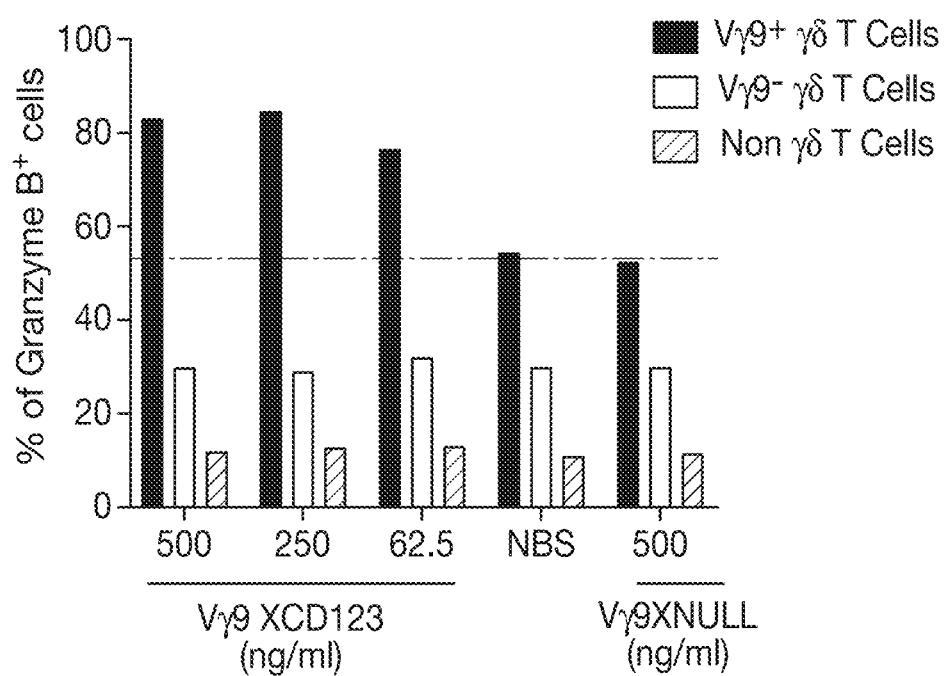

FIG. 6 shows that the anti-TRGV9/anti-CD123 bispecific selectively activates Vγ9+ γδ T cells. Whole fresh PBMCs were co-cultured with Kasumi-3 cells in the presence of various concentrations of the anti-TRGV9/anti-CD123 bispecific antibody for 72 hours at 37° C. As a positive and negative control, co-cultured cells were stimulated with anti-CD3/anti-CD123 and anti-TRGV9/anti-NULL bispecifics for 72 hours at 37° C. Bars represent the frequency of Vγ9+, Vγ9− γδ T cells and non-γδ T cells positive for CD69 (FIG. 6A, left), CD25 (FIG. 6A, right) surface expression, and intracellular Granzyme B (FIG. 6B) expression. The dotted line in FIG. 6B indicates the basal levels of Granzyme B expression in Vγ9+ γδ T cells. NBS denotes no bispecific antibody added to the co-cultured cells. Data shown here are from a single experiment.

Example 3: Humanization of Anti-TRGV9 Clone 7A5

Mouse anti-human Vγ9 clone LP7A5 (7A5) binds to the antigen (Vγ9-Vδ2 fused to human Fc) with a KD of 1.9 nM. Humanization of murine 7A5 was performed following the approach outlined by Singh et al., mAbs J, 2015. Based on sequence conservation, the heavy chain germline IGHV1-8*01 was chosen for framework adaption. Three somatic hypermutation sites in the heavy chain were chosen for binary library design. A potential Iso-Asp isomerization site (DG motif) in the CDR-H2 was also included in the design to mitigate this potential liability. For light chain frame adaption, IGKV4-1*01 was chosen as the closest homologous human germline. Owing to high sequence homology, only one position (Asn22) was included in the library design. The variants were cloned and expressed in E. coli. The supernatants were screened in single point ELISA and the periplasmic preparation was used for dose response. A mouse/human chimeric 7A5 Fab was used as parental control. Clone 7A5_17 (7A5_var17) maintained the binding activity similar to murine 7A5 and was converted to IgG for additional profiling. The $EC_{50}$ for primary cell binding for clone 7A5_17 and 7A5 were 200 pM and 159 pM.

The sequences obtained are shown in Tables 12-15. The three VH CDR and three VL CDR sequences of the humanized anti-human TRGV9 clone 7A5_var17 are shown in Table 12 (two versions, depending on CDR type, are provided); and the VH and VL sequences of the humanized anti-human TRGV9 clone 7A5_var17 are shown in Table 14 (SEQ ID NOs:65 and 66, respectively). The three VH CDR and three VL CDR sequences of the humanized anti-human TRGV9 clone 7A5_var29 are shown in Table 13 (two versions, depending on CDR type, are provided); and the VH and VL sequences of the humanized anti-human TRGV9 clone 7A5_var29 are shown in Table 15 (SEQ ID NOs:67 and 68, respectively).

TABLE 12

CDR sequences of humanized anti-human TRGV9 clone 7A5_var 17.

| mAb ID | HCDR1 | SEQ ID NO: | HCDR2 | SEQ ID NO: | HCDR3 | SEQ ID NO: |
|---|---|---|---|---|---|---|
| 7A5_var17 (CDR v.1) | GFTFTDHY | 60 | IYPGSGNT | 61 | ARNYGDYTIDF | 62 |
| 7A5_var17 (CDR v.2) | DHYIN | 1 | QIYPGSGNTYYNQKFKG | 76 | NYGDYTIDF | 3 |

| mAb ID | LCDR1 | SEQ ID NO: | LCDR2 | SEQ ID NO: | LCDR3 | SEQ ID NO: |
|---|---|---|---|---|---|---|
| 7A5_var17 (CDR v.1) | QSVLYSSNNKNY | 63 | WAS | 64 | QQYYRYHT | 6 |
| 7A5_var17 (CDR v.2) | KSSQSVLYSSNNKNYLA | 77 | WASTRES | 5 | QQYYRYHT | 6 |

TABLE 13

CDR sequences of humanized anti-human TRGV9 clone 7A5_var 29.

| mAb ID | HCDR1 | SEQ ID NO: | HCDR2 | SEQ ID NO: | HCDR3 | SEQ ID NO: |
|---|---|---|---|---|---|---|
| 7A5_var29 (CDR v.1) | GFTFTDHY | 60 | IYPGSGNT | 61 | ARNYGDYTIDF | 62 |
| 7A5_var29 (CDR v.2) | DHYIN | 1 | QIYPGSGNTYYNQKFKG | 76 | NYGDYTIDF | 3 |

| mAb ID | LCDR1 | SEQ ID NO: | LCDR2 | SEQ ID NO: | LCDR3 | SEQ ID NO: |
|---|---|---|---|---|---|---|
| 7A5_var29 (CDR v.1) | QSVLYSSNNKNY | 63 | WAS | 64 | QQYYRYHT | 6 |
| 7A5_var29 (CDR v.2) | KSSQSVLYSSNNKNYLA | 77 | WASTRES | 5 | QQYYRYHT | 6 |

TABLE 14

Heavy chain and light chain V-region sequences of humanized anti-human TRGV9 clone 7A5_var17.

| mAb ID | Heavy Chain V-region Amino Acid Sequence | SEQ ID NO: |
|---|---|---|
| 7A5_var17 | QVQLVQSGAE VKKPGASVKV SCKASGFTFT DHYINWVRQA TGQGLEWMGQ IYPGSGNTYY NQKFKGRVTM TRDTSISTAY MELSSLRSED TAVYYCARNY GDYTIDFWGQ GTSVTVSS | 65 |

| mAb ID | Light Chain V-region Amino Acid Sequence | SEQ ID NO: |
|---|---|---|
| 7A5_var17 | DIVMTQSPDS LAVSLGERAT INCKSSQSVL YSSNNKNYLA WYQQKPGQPP KLLIYWASTR ESGVPDRFSG SGSGTDFTLT ISSLQAEDVA VYYCQQYYRY HTFGTGTKLE IK | 66 |

TABLE 15

Heavy chain and light chain V-region sequences of humanized anti-human TRGV9 clone 7A5_var29.

| mAb ID | Heavy Chain V-region Amino Acid Sequence | SEQ ID NO: |
|---|---|---|
| 7A5_var29 | QVQLVQSGAE VKKPGASVKV SCKASGFTFT DHYINWVRQA TGQGLEWMGQ IYPGSGNTYY NQKFKGRVTM TRNTSISTAY MELSSLRSED TAVYYCARNY GDYTIDFWGQ GTSVTVSS | 67 |

| mAb ID | Light Chain V-region Amino Acid Sequence | SEQ ID NO: |
|---|---|---|
| 7A5_var29 | DIVMTQSPDS LAVSLGERAT ISCKSSQSVL YSSNNKNYLA WYQQKPGQPP KLLIYWASTR ESGVPDRFSG SGSGTDFTLT ISSLQAEDVA VYYCQQYYRY HTFGTGTKLE IK | 68 |

Example 4—Multispecific Antibodies that Bind TRGV9 and TAA1

T cell acute lymphoblastic leukemia (T-ALL) are aggressive neoplasms characterized by the proliferation and accumulation in blood, bone marrow and lymphoid organs of T cell precursors abnormally arrested in differentiation. Current first-line chemotherapy regimens provide overall survival rates of approximately 85-90% in children and about 50% in adults (Pui et al. *J. Clin. Oncol. Off. J. Am. Soc. Clin. Oncol.* 2015; 33(27):2938-2948; Litzow et al. *Blood.* 2015; 126(7):833-841). T-ALL represent a heterogeneous group of malignancies classified into different molecular subtypes on the basis of aberrant expression of specific driver oncogenic transcription factors and global transcriptomic signatures (Belver et al. *Nat. Rev. Cancer.* 2016; 16(8):494-507; *Nat. Genet.* 2017; 49(8):1211-1218). T-cells are the most abundant (~75% of blood lymphocytes) and potent immune killer cells. The role of effector T-cells in the anti-cancer immune response is strongly supported by in vitro studies and the observation that a high infiltration of CD8+ T cells in several types of cancers correlates with a favorable clinical prognostic.

Vγ9Vδ2 T lymphocytes, a major γ/δ T cell subset in humans, recognize phosphoantigens, certain tumor cells, and cells treated with aminobisphosphonates. This cell population displays cytolytic activity against various tumor cells. The γ/δ TCR is a heterodimeric TCR complex composed of covalently bound γ and δ chains involved in antigen recognition and the non-covalently associated monomorphic proteins CD3δ, γ, ε, and ζ chains. The Vγ9 TCR is a variant of the TCR γ chain expressed on a subset of γ/δ T cells.

Examples 4.1-4.6 are based on the premise that γδ T cells, which mainly express heterodimers of TRGV9 and Vδ2 chains demonstrate potent anti-tumor functions. These cells express TCR-TRGV9 and the majority, if not all, of these cells exhibit efficient cytotoxicity of tumor target cells. This ability is then harnessed using bispecific antibodies constructed such that one arm binds to the TRGV9 structure and the other arm binds to a T-cell Tumor-Associated Antigen (TAA1) expressed by the tumor cells (e.g., T cell lymphomas). Thus, the bispecific antibody bridges the effector and target cells together, resulting in tumor cell killing. This mechanism of action is described in the schematic outlined in FIG. 1.

The subsequent examples can be divided into the following categories: (1) Generation and characterization of bispecific antibodies capable of binding to the TRGV9 arm expressed on γδ T cells and TAA1 on αβ T cells (Examples 4.1, 4.2, and 4.3); and (2) Evidence for bispecific antibody binding and bispecific antibody-enabled target cell killing by γδ T cells expanded in vitro (Example 4.4 and 4.5).

γδ T cell stimulation and expansion was performed. Expansion of Vγ9-Vδ2 T cells was carried out by treating PBMCs in complete RPMI media containing rhIL-2 (1000 IU/mL), rhIL-15 (10 ng/mL) and zoledronic acid (5 µM) for 14 days.

Example 4.1: Production and De Novo Sequencing of Anti-TRGV9 MAB

The mouse IgG1 anti-human T cell receptor anti-TRGV9 clone 7A5 was sourced commercially. Sample preparation and LC-MS/MS analysis were performed by Lake Pharma (San Carlos, Calif.). The sample was reduced and alkylated, divided into seven aliquots, and proteolytically digested with Trypsin/LysC, Chymotrypsin, LysC, Pepsin, and AspN, Elastase, and Proteinase K enzymes. Resulting peptides were desalted using a ZIPTIP C18 Pipette Tips and separated on-line using reverse phase chromatography. Mass spectrometry was performed on THERMO Q-EXACTIVE spectrometer using HCD fragmentation. MS data sets were analyzed using PEAKS software by matching de novo sequence tags to an IMGT-based antibody sequences database. Gaps in the sequence were assigned using Contig sequence assembly of de novo identified peptides. All CDRs and hyper-mutations were confirmed by inspecting the MS/MS spectra.

The three VH CDR and three VL CDR sequences of the mouse anti-human TRGV9 clone 7A5 (LP7A5_1) are previously shown in Table 3 (SEQ ID NOs:1-6, respectively); and the VH and VL sequences of the mouse anti-human TRGV9 clone 7A5 (LP7A5_1) are previously shown in Table 7 (SEQ ID NOs:7 and 8, respectively).

Example 4.2: Production and De Novo Sequencing of Anti-TAA1 MAB

The mouse IgG2a monoclonal anti-human TAA1 clone was commercially sourced. The VH CDR1-3, VL CDR1-3, VH and VL sequences of this clone (data not shown) were obtained using a similar procedure as described above for the anti-TRGV9 clone 7A5.

Example 4.3: Preparation of ANTI-TRGV9/ANTI-TAA1 Bispecific Antibodies

The variable region sequence of clone 7A5 (anti-TRGV9 antibody) and the TAA1 clone (anti-TAA1 antibody) were used to generate a bispecific antibody to be tested for T cell re-directed killing of acute myeloid leukemia (AML) cells. The bispecific antibodies VG4 (anti-TRGV9×TAA1) and VG3 (anti-TRGV9×Null) were produced as full-length antibodies in the knob-into-hole format as human IgG4. Nucleic acid sequences encoding variable regions were sub-cloned into a custom mammalian expression vectors containing constant region of human IgG4 expression cassettes using standard PCR restriction enzyme based standard cloning techniques, and sequenced verified. The bispecific antibodies were expressed by transient transfection in a Chinese hamster ovary (CHO) cell line. Sequences of certain bispecific antibodies expressed in the CHO cells are shown in Table 16 below. Certain individual heavy and light chain antibody sequences are shown in Table 17 below

TABLE 16

Sequences of antibodies expressed in CHO cells

| mAb ID | 'Knob' arm and 'hole' arm amino acid sequence | SEQ ID NO: |
|---|---|---|
| Anti-TRGV9_7A5_1 (half-mAb) | Heavy Chain A | 78 |
| | MAWVWTLLFLMAAAQSIQAEVQLQQSGAELARPGA | |
| | SVKLSCKASGFTFTDHYINWVKQRTGQGLEWIGQI | |
| | YPGDGNTYYNQKFKGKATLTADKSSSTAYMQLSSL | |
| | TSEDSAVYFCAPNYGDYTIDFWGQGTSVTVSSAST | |
| | KGPSVFPLAPSSKSTSGGTAALGCLVKDYFPEPVT | |
| | VSWNSGALTSGVHTFPAVLQSSGLYSLSSVVTVPS | |
| | SSLGTQTYICNVNHKPSNTKVDKKVEPKSCDKTHT | |
| | CPPCPAPEAAGGPSVFLFPPKPKDTLMISRTPEVT | |
| | CVVVSVSHEDPEVKFNWYVDGVEVHNAKTKPREEQ | |
| | YNSTYRVVSVLTVLHQDWLNGKEYKCKVSNKALPA | |
| | PIEKTISKAKGQPREPQVYVYPPSREEMTKNQVSL | |
| | TCLVKGFYPSDIAVEWESNGQPENNYKTTPPVLDS | |
| | DGSFALVSKLTVDKSRWQQGNVFSCSVMHEALHNR | |
| | FTQKSLSLSPGK | |

TABLE 16-continued

Sequences of antibodies expressed in CHO cells

| mAb ID | 'Knob' arm and 'hole' arm amino acid sequence | SEQ ID NO: |
|---|---|---|
| | Light Chain MAWVWTLLFLMAAAQSIQADIVMSQSPSSLAVSVG EKVTMSCKSSQSLLYSSNQKNYLAWYQQKPGQSPK LLIYWASTRESGVPDRFTGSGSGTDFTLTISSVKA EDLAVYYCQQYYRYHTFGTGTKLEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 79 |
| Anti-TRGV9_7A5_var 17 | Heavy Chain A MAWVWTLLFLMAAAQSIQAVQLVQSGAEVKKPGA SVKVSCKASGFTFTDHYINWVRQATGQGLEWMGQI YPGSGNTYYNQKFKGRVTMTRDTSISTAYMELSSL RSEDTAVYYCARNYGDYTIDFWGQGTSVTVSSAST KGPSVFPLAPSSKSTSGGTAALGCLVKDYFPEPVT VSWNSGALTSGVHTFPAVLQSSGLYSLSSVVTVPS SSLGTQTYICNVNHKPSNTKVDKKVEPKSCDKTHT CPPCPAPEAAGGPSVFLFPPKPKDTLMISRTPEVT CVVVSVSHEDPEVKFNWYVDGVEVHNAKTKPREEQ YNSTYRVVSVLTVLHQDWLNGKEYKCKVSNKALPA PIEKTISKAKGQPREPQVYVYPPSREEMTKNQVSL TCLVKGFYPSDIAVEWESNGQPENNYKTTPPVLDS DGSFALVSKLTVDKSRWQQGNVFSCSVMHEALHNR FTQKSLSLSPGK | 80 |
| | Light Chain MAWVWTLLFLMAAAQSIQADIVMTQSPDSLAVSLG ERATINCKSSQSVLYSSNNKNYLAWYQQKPGQPPK LLIYWASTRESGVPDRFSGSGSGTDFTLTISSLQA EDVAVYYCQQYYRHTFGTGTKLEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 81 |
| Anti-TRGV9_7A5_var 29 | Heavy Chain A MAWVWTLLFLMAAAQSIQAVQLVQSGAEVKKPGA SVKVSCKASGFTFTDHYINWVRQATGQGLEWMGQI YPGSGNTYYNQKFKGRVTMTRNTSISTAYMELSSL RSEDTAVYYCARNYGDYTIDFWGQGTSVTVSSAST KGPSVFPLAPSSKSTSGGTAALGCLVKDYFPEPVT VSWNSGALTSGVHTFPAVLQSSGLYSLSSVVTVPS SSLGTQTYICNVNHKPSNTKVDKKVEPKSCDKTHT CPPCPAPEAAGGPSVFLFPPKPKDTLMISRTPEVT CVVVSVSHEDPEVKFNWYVDGVEVHNAKTKPREEQ YNSTYRVVSVLTVLHQDWLNGKEYKCKVSNKALPA PIEKTISKAKGQPREPQVYVYPPSREEMTKNQVSL TCLVKGFYPSDIAVEWESNGQPENNYKTTPPVLDS DGSFALVSKLTVDKSRWQQGNVFSCSVMHEALHNR FTQKSLSLSPGK | 82 |
| | Light Chain MAWVWTLLFLMAAAQSIQADIVMTQSPDSLAVSLG ERATISCKSSQSVLYSSNNKNYLAWYQQKPGQPPK LLIYWASTRESGVPDRFSGSGSGTDFTLTISSLQA EDVAVYYCQQYYRHTFGTGTKLEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | 83 |
| Anti-TAA1 (half-mAb) | Heavy Chain B SEQUENCE NOT SHOWN | — |
| | Light Chain SEQUENCE NOT SHOWN | — |
| Anti-RSV (half-mAb) | Heavy Chain B MAWVWTLLFLMAAAQSIQAQITLKESGPTLVKPTQ TLTLTCTFSGESLSTSGMGVSWIRQPPGKALEWLA HIYWDDDKRYNPSLKSRLTITKDTSKNQVVLTMTN MDPVDTATYYCARLYGFTYGFAYWGQGTLVTVSSA STKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPEAAGGPSVFLEPPKPKDTLMISRTPE VTCVVVSVSHEDPEVKFNWYVDGVEVHNAKTKPRE EQYNSTYRVVSVLTVLHQDWLNGKEYKCKVSNKAL PAPIEKTISKAKGQPREPQVYVLPPSREEMTKNQV SLLCLVKGFYPSDIAVEWESNGQPENNYLTWPPVL DSDGSFFLYSKLTVDKSRWQQGNVFSCSVMHEALH NHYTQKSLSLSPGK | 86 |
| | Light Chain METHSQVFVYMLLWLSGVEGDIVMSPVSLAVSL GERATINCRASQSVDYNGISYMHWYQQKPGQPPKL | 87 |

TABLE 16-continued

Sequences of antibodies expressed in CHO cells

| mAb ID | 'Knob' arm and 'hole' arm amino acid sequence | SEQ ID NO: |
|---|---|---|
| | LIYAASNPESGVPDRFSGSGSGTDFTLTISSLQAE DVAVYYCQQIIEDPWTEGQGTKVEIKRTVAAPSVF IFPPSDEQLKSGTASVVCLLNNFYPREAKVQWKVD NALQSGNSQESVTEQDSKDSTYSLSSTLTLSKADY EKHKVYACEVTHQGLSSPVTKSFNRGEC | | scFv Sequences

| Anti-TRGV9_7A5_var 17-scFv | Heavy Chain A MAWVWTLLFLMAAAQSIQADIVMTQSPDSLAVSLG ERATINCKSSQSVLYSSNNKNYLAWYQQKPGQPPK LLIYWASTRESGVPDRFSGSGSGTDFTLTISSLQA EDVAVYYCQQYYRHTFGTGTKLEIKGGSEGKSSG SGSESKSTGGSQVQLVQSGAEVKKPGASVKVSCKA SGFTFTDHYINWVRQATGQGLEWMGQIYPGSGNTY YNQKFKGRVTMTRDTSISTAYMELSSLRSEDTAVY YCARNYGDYTIDFWGQGTSVTVSSEPKSSDKTHTC PPCPAPEAAGGPSVFLFPPKPKDTLMISRTPEVTC VVVSVSHEDPEVKFNWYVDGVEVHNAKTKPREEQY NSTYRVVSVLTVLHQDWLNGKEYKCKVSNKALPAP IEKTISKAKGQPREPQVYVYPPSREEMTKNQVSLT CLVKGFYPSDIAVEWESNGQPENNYKTTPPVLDSD GSFALVSKLTVDKSRWQQGNVFSCSVMHEALHNHY TQKSLSLSPGK | 70 |
| Anti-TRGV9_7A5_var 29-scFv | Heavy Chain A MAWVWTLLFLMAAAQSIQADIVMTQSPDSLAVSLG ERATISCKSSQSVLYSSNNKNYLAWYQQKPGQPPK LLIYWASTRESGVPDRFSGSGSGTDFTLTISSLQA EDVAVYYCQQYYRHTFGTGTKLEIKGGSEGKSSG SGSESKSTGGSQVQLVQSGAEVKKPGASVKVSCKA SGFTFTDHYINWVRQATGQGLEWMGQIYPGSGNTY YNQKFKGRVTMTRNTSISTAYMELSSLRSEDTAVY YCARNYGDYTIDFWGQGTSVTVSSEPKSSDKTHTC PPCPAPEAAGGPSVFLFPPKPKDTLMISRTPEVTC VVVSVSHEDPEVKFNWYVDGVEVHNAKTKPREEQY NSTYRVVSVLTVLHQDWLNGKEYKCKVSNKALPAP IEKTISKAKGQPREPQVYVYPPSREEMTKNQVSLT CLVKGFYPSDIAVEWESNGQPENNYKTTPPVLDSD GSFALVSKLTVDKSRWQQGNVFSCSVMHEALHNHY TQKSLSLSPGK | 73 |
| Anti-TAA1-scFv | Heavy Chain B SEQUENCE NOT SHOWN | — |
| Anti-Null-scFv | Heavy Chain B MAWVWTLLFLMAAAQSIQADIQMTQSPSSLSASVG DRVTITCRASQSISSYLNWYQQKPGCAPKLLIYAA SSLQSGVPSRFSGSGSGTDFTLTISSLQPEDFATY YCQQSYSTPLTFGQGTKVEIKGGGSGGSGGCPPCG GSGGEVQLLESGGGLVQPGGSLRLSCAASGFTFSS YAMSWVRQAPGKGLEWVSAISGSGGSTYYADSVKG RFTISRDNSKNTLYLQMNSLRAEDTAVYYCAKYDG IYGELDFWGCGTLVTVSSEPKSSDKTHTCPPCPAP EAAGGPSVFLFPPKPKDTLMISRTPEVTCVVVSVS HEDPEVKFNWYVDGVEVHNAKTKPREEQYNSTYRV VSVLTVLHQDWLNGKEYKCKVSNKALPAPIEKTIS KAKGQPREPQVYVLPPSREEMTKNQVSLLCLVKGF YPSDIAVEWESNGQPENNYLTWPPVLDSDGSFFLY SKLTVDKSRWQQGNVFSCSVMHEALHNHYTQKSLS LSPGK | 88 |

TABLE 17

Anti-TRGV9 Heavy and Light Chain Sequences

| Antibody | Heavy Chain | Light Chain |
|---|---|---|
| TRGV9_7A5_1 | EVQLQQSGAELARPGASVKLSCKASGF TFTDHYINWVKQRTGQGLEWIGQIYPG DGNTYYNQKFKGKATLTADKSSSTAYM QLSSLTSEDSAVYFCAPNYGDYTIDFW | DIVMSQSPSSLAVSVG EKVTMSCKSSQSLLYS SNQKNYLAWYQQKPGQ SPKLLIYWASTRESGV |

TABLE 17-continued

Anti-TRGV9 Heavy and Light Chain Sequences

| Antibody | Heavy Chain | Light Chain |
|---|---|---|
| | GQGTSVTVSSASTKGPSVFPLAPSSKS<br>TSGGTAALGCLVKDYFPEPVTVSWNSG<br>ALTSGVHTFPAVLQSSGLYSLSSVVTV<br>PSSSLGTQTYICNVNHKPSNTKVDKKV<br>EPKSCDKTHTCPPCPAPEAAGGPSVFL<br>FPPKPKDTLMISRTPEVTCVVVSVSHE<br>NSTYRVVSVLTVLHQDWLNGKEYKCKV<br>SNKALPAPIEKTISKAKGQPREPQVYV<br>YPPSREEMTKNQVSLTCLVKGFYPSDI<br>AVEWESNGQPENNYKTTPPVLDSDGSF<br>ALVSKLTVDKSRWQQGNVFSCSVMHEA<br>LHNRFTQKSLSLSPGK<br>(SEQ ID NO: 69) | PDRFTGSGSGTDFTLT<br>ISSVKAEDLAVYYCQQ<br>YYRYHTFGTGTKLEIK<br>RTVAAPSVFIFPPSDE<br>QLKSGTASVVCLLNNF<br>YPREAKDPEVKFNWYV<br>DGVEVHNAKTKPREEQ<br>YVQWKVDNALQSGNSQ<br>ESVTEQDSKDSTYSLS<br>STLTLSKADYEKHKVY<br>ACEVTHQGLSSPVTKS<br>FNRGEC<br>(SEQ ID NO: 24) |
| TRGV9_<br>var17 | QVQLVQSGAEVKKPGASVKVSCKASGF<br>TFTDHYINWVRQATGQGLEWMGQIYPG<br>SGNTYYNQKFKGRVTMTRDTSISTAYM<br>ELSSLRSEDTAVYYCARNYGDYTIDFW<br>GQGTSVTVSSASTKGPSVFPLAPSSKS<br>TSGGTAALGCLVKDYFPEPVTVSWNSG<br>ALTSGVHTFPAVLQSSGLYSLSSVVTV<br>PSSSLGTQTYICNVNHKPSNTKVDKKV<br>EPKSCDKTHTCPPCPAPEAAGGPSVFL<br>FPPKPKDTLMISRTPEVTCVVVSVSHE<br>DPEVKFNWYVDGVEVHNAKTKPREEQY<br>NSTYRVVSVLTVLHQDWLNGKEYKCKV<br>SNKALPAPIEKTISKAKGQPREPQVYV<br>YPPSREEMTKNQVSLTCLVKGFYPSDI<br>AVEWESNGQPENNYKTTPPVLDSDGSF<br>ALVSKLTVDKSRWQQGNVFSCSVMHEA<br>LHNRFTQKSLSLSPGK<br>(SEQ ID NO: 71) | DIVMTQSPDSLAVSLG<br>ERATINCKSSQSVLYS<br>SNNKNYLAWYQQKPGQ<br>PPKLLIYWASTRESGV<br>PDRFSGSGSGTDFTLT<br>ISSLQAEDVAVYYCQQ<br>YYRYHTFGTGTKLEIK<br>RTVAAPSVFIFPPSDE<br>QLKSGTASVVCLLNNF<br>YPREAKVQWKVDNALQ<br>SGNSQESVTEQDSKDS<br>TYSLSSTLTLSKADYE<br>KHKVYACEVTHQGLSS<br>PVTKSFNRGEC<br>(SEQ ID NO: 72) |
| TRGV9_<br>var29 | QVQLVQSGAEVKKPGASVKVSCKASGF<br>TFTDHYINWVRQATGQGLEWMGQIYPG<br>SGNTYYNQKFKGRVTMTRNTSISTAYM<br>ELSSLRSEDTAVYYCARNYGDYTIDFW<br>GQGTSVTVSSASTKGPSVFPLAPSSKS<br>TSGGTAALGCLVKDYFPEPVTVSWNSG<br>ALTSGVHTFPAVLQSSGLYSLSSVVTV<br>PSSSLGTQTYICNVNHKPSNTKVDKKV<br>EPKSCDKTHTCPPCPAPEAAGGPSVFL<br>FPPKPKDTLMISRTPEVTCVVVSVSHE<br>DPEVKFNWYVDGVEVHNAKTKPREEQY<br>NSTYRVVSVLTVLHQDWLNGKEYKCKV<br>SNKALPAPIEKTISKAKGQPREPQVYV<br>YPPSREEMTKNQVSLTCLVKGFYPSDI<br>AVEWESNGQPENNYKTTPPVLDSDGSF<br>ALVSKLTVDKSRWQQGNVFSCSVMHEA<br>LHNRFTQKSLSLSPGK<br>(SEQ ID NO: 74) | DIVMTQSPDSLAVSLG<br>ERATISCKSSQSVLYS<br>SNNKNYLAWYQQKPGQ<br>PPKLLIYWASTRESGV<br>PDRFSGSGSGTDFTLT<br>ISSLQAEDVAVYYCQQ<br>YYRYHTFGTGTKLEIK<br>RTVAAPSVFIFPPSDE<br>QLKSGTASVVCLLNNF<br>YPREAKVQWKVDNALQ<br>SGNSQESVTEQDSKDS<br>TYSLSSTLTLSKADYE<br>KHKVYACEVTHQGLSS<br>PVTKSFNRGEC<br>(SEQ ID NO: 75) |
| TAA1 | SEQUENCE NOT SHOWN | SEQUENCE NOT SHOWN |

The antibodies were initially purified by MAB SELECT SURE Protein A column (GE Healthcare). The column was equilibrated with PBS pH 7.2 and loaded with fermentation supernatant at a flow rate of 2 mL/min. After loading, the column was washed with 4 column volumes of PBS followed by elution in 30 mM sodium acetate, pH 3.5. Fractions containing protein peaks as monitored by absorbance at 280 nm were pooled and neutralized to pH 5.0 by adding 1% 3 M sodium acetate pH 9.0. The bispecific mAbs were further purified on a preparative SUPERDEX 200 10/300 GL (GE healthcare) size exclusion chromatography (SEC) column equilibrated with PBS buffer. The integrity of the sample was assessed by endotoxin measurement and SDS-PAGE under reducing and non-reducing conditions. The final protein concentrations were 1.0 mg/ml for anti-TRGV9/anti-TAA1 and 1.0 mg/mL for ANTI-TRGV9/Null. The final EU levels of ANTI-TRGV9/anti-TAA1 and ANTI-TRGV9/Null based on these were <3.0 EU/mg.

Example 4.4: Binding Activity of ANTI-TAA1 and ANTI-TRGV9 Antibodies on Target Cell Lines Binding of antibodies to TAA1 expressing cell line and γδ T cells was carried out by flow cytometry. Briefly, 50,000 target cells or γδ T cells were incubated at 4° C. for 45 minutes with serial dilutions of various antibodies. After washing with wash buffer (PBS+2% FBS), antibody bound to cell surface was detected by incubating the cells with PE labelled mouse anti human IgG1 secondary antibody (Southern Biotech, Birmingham, Ala.) for 30 minutes at 4° C. Cells were washed with wash buffer (PBS+2% FBS) and the fluorescence of stained cells was measured on Novocyte flow cytometer. Cells were visualized on forward and sideward scatter and doublets were excluded. No secondary antibody control was used to establish background fluorescence and to gate on specific population. Background value was subtracted from main samples to get specific binding value.

Figure 7:
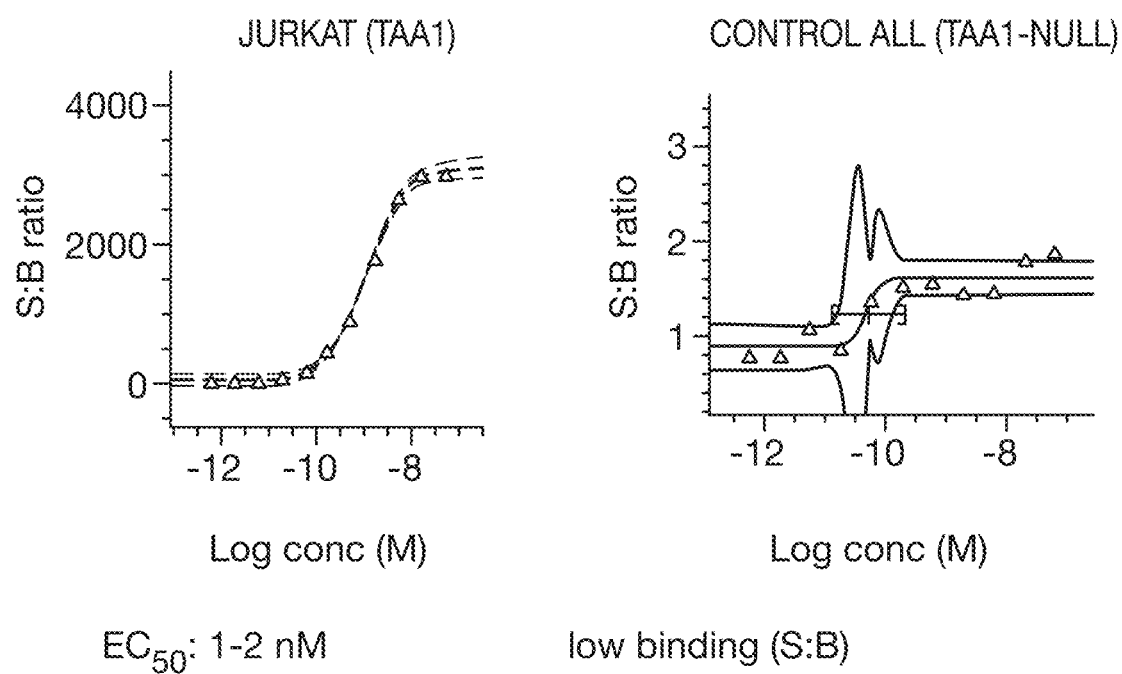
FIG. 7 shows selective cell binding of anti-TAA1 (TAA mIgG2a, TAA1B1) to transfected Jurkat cells. The $EC_{50}$ for binding was ~1 to 2 nM. TAA1B1 did not show any significant binding to a control ALL cell line that endogenously expresses an unrelated protein (TAA1-NULL), but does not express TAA1.

As shown in FIG. 7, the EC50 for binding of anti-TAA1 antibodies (TAA1 mIgG2a, TAA1B1) to TAA1 expressing Jurkat cell lines was ~1 to 2 nM. TAA1B1 did not show any significant binding to a control ALL cell line that endogenously expresses an unrelated protein (TAA1-NULL), but does not express TAA1.

Figure 8:
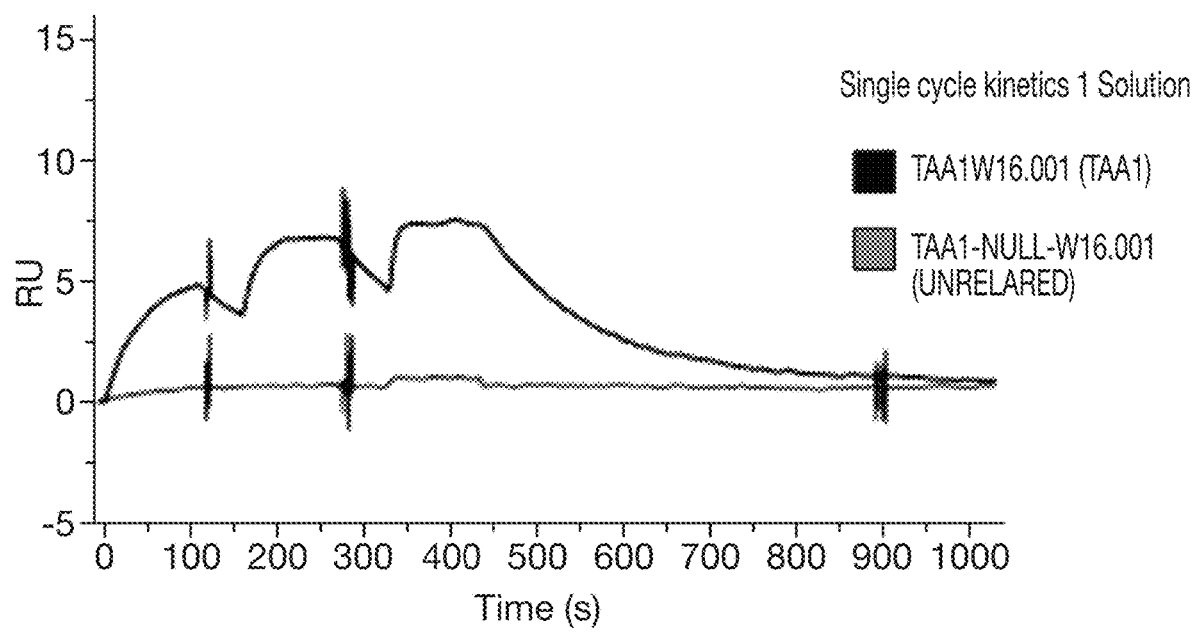
FIG. 8 shows selective protein binding of anti-TAA1 (TAA1 mIgG2a, TAA1B1) to a recombinant TAA1 protein (TAA1W16). TAA1B1 did not show any significant binding to the unrelated protein (TAA1-NULL-W16).

Additional surface plasmon resonance (SPR) experiments were used to determine specific binding of anti-TAA1 mAb to TAA1. Briefly, SPR experiments were carried out in HBSP buffer at 25° C. The experimental set up was following: Goat anti-murine Fc surface was immobilized on a sensor chip, and binding was tested by capturing the mouse anti-human TAA1 clone mAb at different densities. The recombinant TAA1 protein (TAA1W16) and an unrelated protein (TAA1-NULL-W16) were used as analyte to bind in solution in a single cycle kinetics. Raw binding data were processed by double referencing, e.g., interspot on an empty chip surface. As shown in FIG. 8, the anti-TAA1 antibodies (TAA1 mIgG2a, TAA1B1) specifically bound to recombinant TAA1 (TAA1W16). TAA1B1 did not show any significant binding to the unrelated protein (TAA1-NULL-W16).

Figure 9:
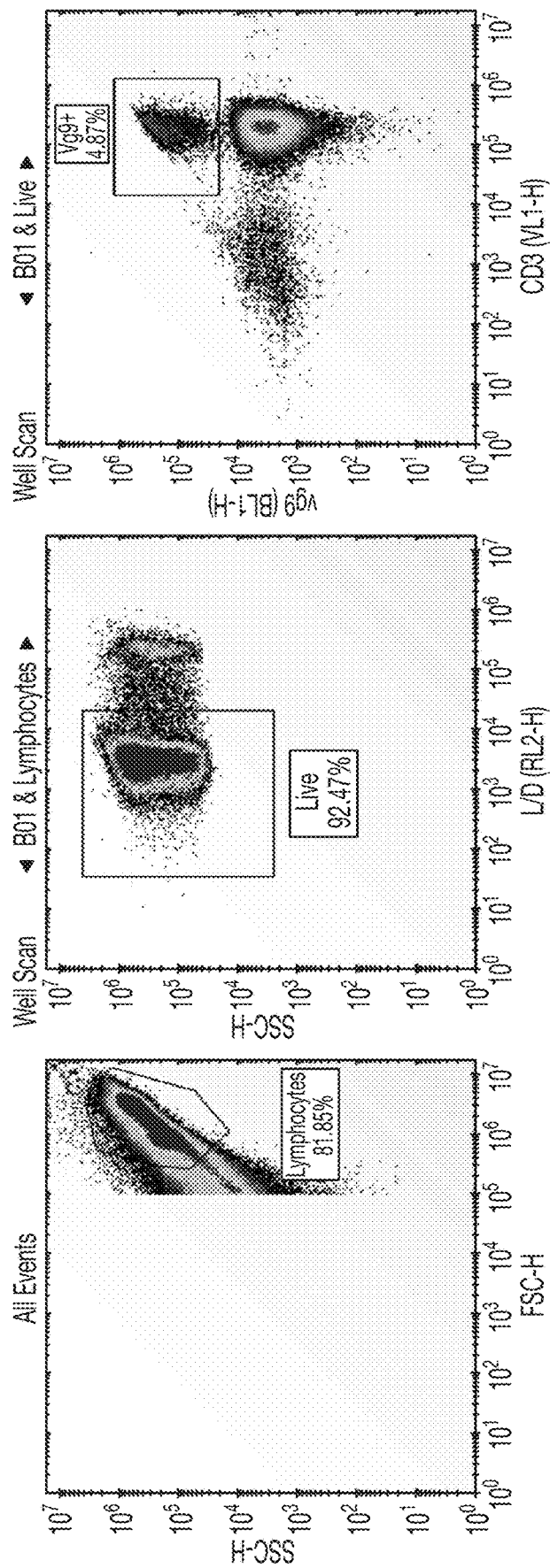
FIG. 9 shows phenotyping of Vg9+ cells used for cytotoxicity studies of a TAA1×Vγ9 bispecific (TAA1B50) from a healthy donor.
Figure 10:
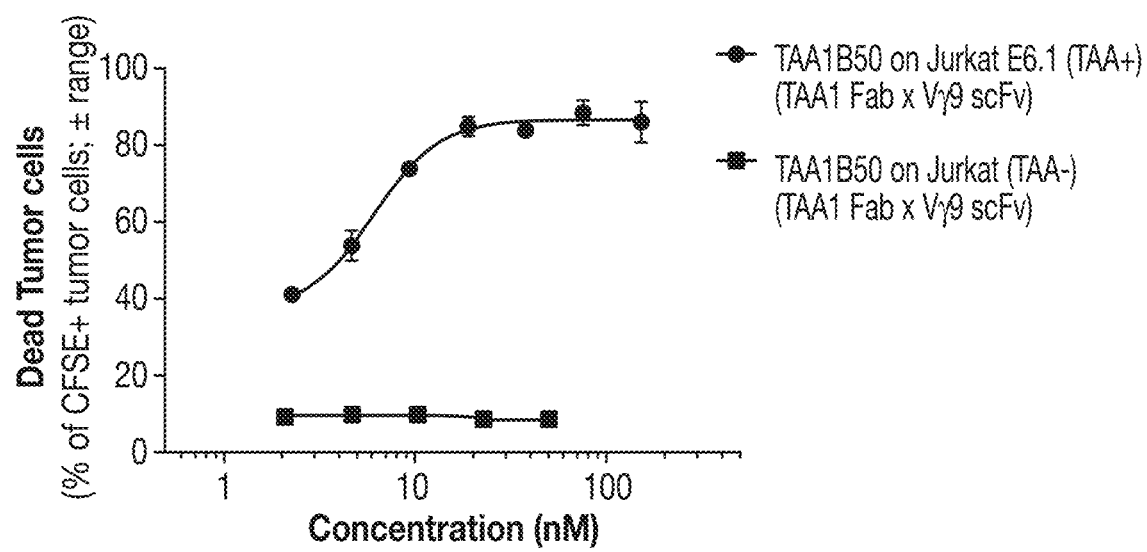
FIG. 10 shows that the anti-TRGV9/anti-TAA1 bispecific antibody mediates γδ T cell cytotoxicity against TAA1 expressing Jurkat cells in vitro. Cytotoxicity values represented here were subtracted of basal cytotoxicity value observed in the absence of bispecific antibody. $EC_{50}$ values were calculated as described in methods. Representative data shown here are from a single experiment.

Example 4.5: Evaluation of Binding and Cytotoxic Properties of the ANTI-TRGV9/ANTI-TAA1 Bispecific Antibody Using Jurkat Cells and Human γδ T Cells FIG. 9 shows the phenotyping of Vγ9+ cells (TAA1B50) from a healthy donor of used for cytotoxicity studies of an anti-TAA1×Vγ9 bispecific. FIG. 10 shows that the anti-TRGV9/anti-TAA1 bispecific antibody mediates γδ T cell (TAA1B50) cytotoxicity against TAA1-expressing Jurkat cells in vitro. Enriched γδ T cells (Effectors), isolated from PBMCs cultured with Zoledronic acid+IL-2+IL-15 for 12 days, were co-cultured with CFSE labelled Jurkat cells (Targets) at 0.5:1 to 10:1 E:T ratios in the presence of various concentrations of the bispecific antibody for 24 to 72 hours. Dose response curves show an anti-TRGV9/anti-TAA1 (TAA1 Fab×Vγ9 scFv) bispecific mediated γδ T cell cytotoxicity against TAA1-expressing Jurkat cells in a dose dependent manner, as compared to Jurkat cells that do not endogenously express TAA1. Cytotoxicity values represented here were subtracted of basal cytotoxicity value observed in the absence of bispecific antibody. $EC_{50}$ values were calculated as described above. Representative data shown are from a single experiment.

To additionally study the ability of a Vγ9×TAA1 bispecific to mediate γδ T cell cytotoxicity against Jurkat cells with γδ T cells from different donors, γδ T cells were enriched. In particular, Vγ9Vδ2 T cells from 5 different donors (328337, 328676, 327587, 328630, 326287) were expanded from total PBMC population for 13 days. Briefly, PBMC were cultured in the presence of zoledronic acid (Sigma, SML0223) (350 nM, days 0 to 13), rhIL-2 (Miltenyi, 130-097-748) (1000 U/mL days 0-2, 800 U/mL days 2-5, 100 U/mL days 5-13) and rhIL-15 (Miltenyi, 130-095-765) (10 ng/mL days 0-13) in complete growth media (RPMI, 10% HI FBS, 1% Pen/strep). At day 13 of expansion, cells were harvested and enriched with EASYSEP™ Human Gamma/Delta T Cell Isolation Kit (Stem Cell Technologies, 19255) according to manufacturer's instructions. Following enrichment procedure, cells were seeded at 1×10⁶/mL in complete growth media with addition of 350 nM zoledronic acid, 100 U/mL IL-2 and 10 ng/mL IL-15 and rested overnight.

Figure 11:
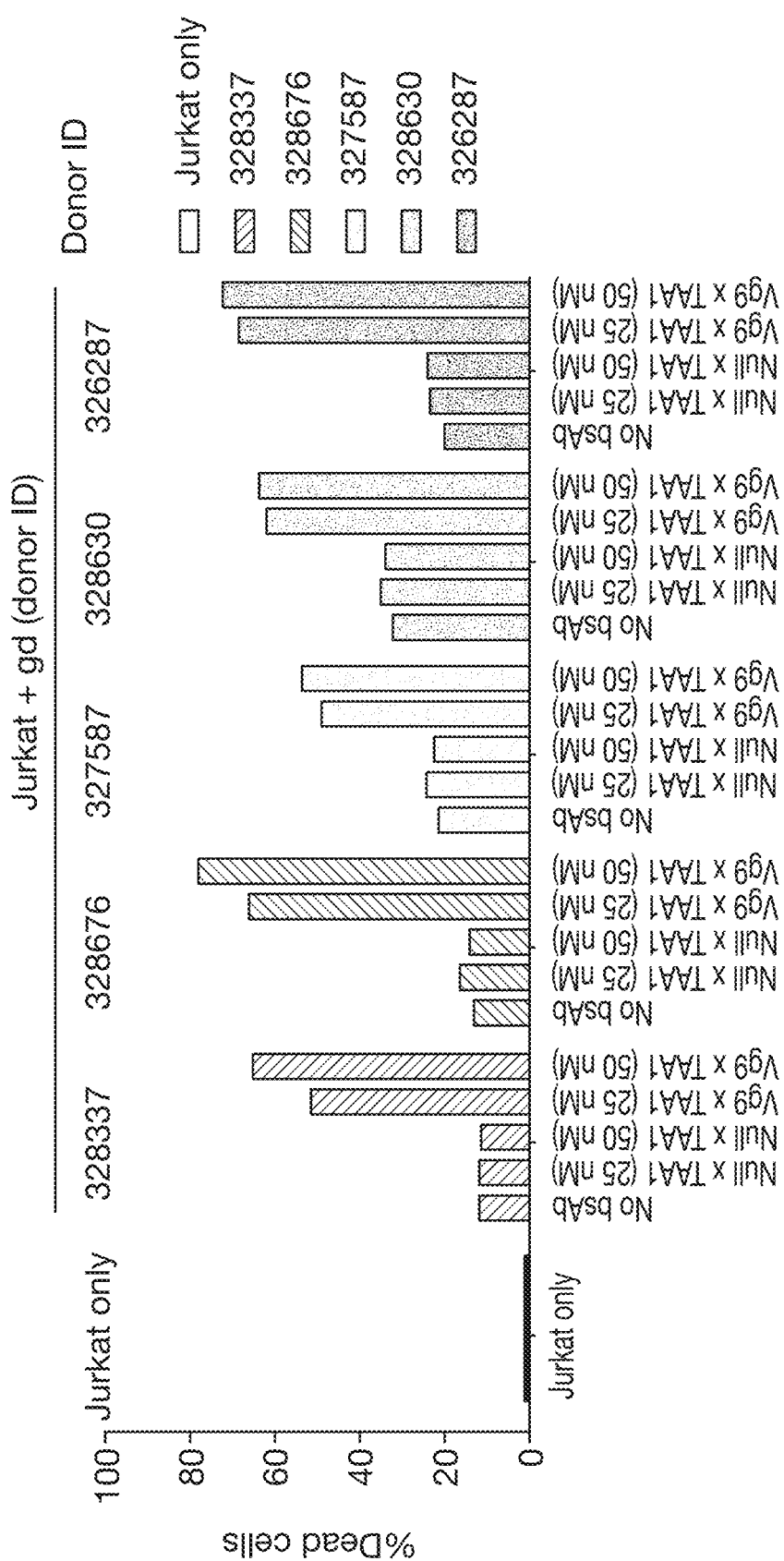
FIG. 11 shows bispecific antibody mediated cytotoxicity. Expanded and enriched Vγ9Vδ2 T cells from various donors were used to induce cytotoxicity to Jurkat cell line (E:T ratio 1:1) in presence of Vγ9×TAA1 at indicated concentrations. Assay was conducted for 16 hrs. Percent dead target cells for various conditions are given in the figure.

For the killing assay, rested γδ T cells were harvested, and cell number and viability were determined. Target cells (Jurkat cells expressing TAA1) were labelled with 0.25 µM CFSE (Thermo, C34554) for 5 min. at room temperature. Cells were washed 3 times and cell number and viability were determined. Killing assay at an E:T ratio of 1:1 ($10^5$ effector cells: $10^5$ target cells) was set up for 16 hours in 96 well plate in complete growth media in the absence on zoledronic acid and cytokines. Vγ9×TAA1 bispecific molecules were adjusted in concentration by limiting dilution to yield final concentration 25 nM and 50 nM in final volume 150 µL/well. After 16 hours, cells were harvested and stained with cocktail containing antibodies against: CD3 (Biolegend, 300424), Vγ9 (Biolegend, 331310), CD25 (Biolegend, 356142), CD69 (Biolegend, 310930), as well as Near-IR (Thermo, L34975) and Fc block (BD, 546219). Cells were washed 3 times, fixed and analysed by flow cytometry. FIG. 11 depicts anti-TRGV9/anti-TAA1 bispecific antibody mediated cytotoxicity. Vγ9×TAA1 bispecific antibodies at both concentrations tested resulted in greater killing in all five of the donor Vγ9Vδ2 T cell populations as compared to the addition of a NULL/TAA1 bispecific or no bispecific antibody. The additional of Vγ9×TAA1 bispecific antibodies also failed to kill Jurkat cells when donor γδ T cells were not present.

Example 5—Multispecific Antibodies that Bind TRGV9 and TAA2

Example 5 is based on the premise that γδ T cells, which mainly express heterodimers of TRGV9 and Vδ2 chains demonstrate potent anti-tumor functions. These cells express TCR-TRGV9 and the majority, if not all, of these cells exhibit efficient cytotoxicity of tumor target cells. This ability is then harnessed using bispecific antibodies constructed such that one arm binds to the TRGV9 structure and the other arm binds to a second T cell Tumor-Associated Antigen (TAA2) expressed by the tumor cells (e.g., certain leukemias and lymphomas). Thus, the bispecific antibody bridges the effector and target cells together, resulting in tumor cell killing. This mechanism of action is described in the schematic outlined in FIG. 1.

The subsequent examples can be divided into the following categories: (1) Generation and characterization of bispecific antibodies capable of binding to the TRGV9 arm expressed on γδ T cells and a certain tumor associated antigen (TAA2) (Examples 5.1, 5.2, 5.3 and 5.4); and (2) Evidence for bispecific antibody-enabled target cell killing by γδ T cells expanded in vitro (Example 5.5).

Example 5.1: Anti-Vg9 Antibody Generation

Immunogen.

A recombinant human TCR Vγ9×Vδ2 fused to a human Fc was used as an immunogen, and the sequence is listed in Table 18.

TABLE 18

Amino acid sequence of recombinant human TCR Vγ9 × Vδ2 heterodimeric protein fused to human Fc

| Name | Protein ID | Sequence |
| --- | --- | --- |
| Recombinant human [TCR Vg9 × Vd2]-hFc | Vg9 chain | MAWVWTLLFLMAAAQSIQAAGHLEQPQISST KTLSKTARLECVVSGITISATSVYWYRERPG EVIQPLVSISYDGTVRKESGIPSGKFEVDRI PETSTSTLTIHNVEKQDIATYYCALWEAQQE LGKKIKVFGPGTKLIITDKQLDADVSPKPTI FLPSIAETKLQKAGTYLCLLEKFFPDVIKIH WEEKKSNTILGSQEGNTMKTNDTYMKFSWLT VPEKSLDKEHRCIVRHENNKNGVDQEIIFPP IKTDVITMDPKDNEPKSCDKTHTCPPCPAPE LLGGPSVFLFPPKPKDTLMISRIPEVTCVVV DVSHEDPEVKFNWYVDGVEVHNAKTKPREEQ YNSTYRVVSVLTVLHQDWLNGKEYKCKVSNK ALPAPIEKTISKAKGQPREPQVYVYPPSREE MTKNQVSLTCLVKGFYPSDIAVEWESNGQPE NNYKTTPPVLDSDGSFALVSKLTVDKSRWQQ GNVFSCSVMHEALHNHYTQKSLSLSPGK | SEQ ID NO: 156 |
| | Vd2 chain | MAWVWTLLFLMAAAQSIQAAIELVPEHQTVP VSIGVPATLRCSMKGEAIGNYYINWYRKTQG NTMTFIYREKDIYGPGFKDNFQGDIDIAKNL AVLKILAPSERDEGSYYCACDTLGMGGEYTD KLIFGKGTRVIVEPRSQPHTKPSVFVMKNGT NVACLVKEFYPKDIRINLVSSKKITEFDPAI VISPSGKYNAVKLGKYEDSNSVTCSVQHDNK TVHSTDFEVKTDSTDHVKPKETENTKQPSKS EPKSCDKTHTCPPCPAPELLGGPSVFLFPPK PKDTLMISRTPEVTCVVVDVSHEDPEVKFNW YVDGVEVHNAKTKPREEQYNSTYRVVSVLTV LHQDWLNGKEYKCKVSNKALPAPIEKTISKA KGQPREPQVYVLPPSREEMTKNQVSLLCLVK GFYPSDIAVEWESNGQPENNYLTWPPVLDSD GSFFLYSKLTVDKSRWQQGNVFSCSVMHEAL HNHYTQKSLSLSPGK | SEQ ID NO: 157 |

Protein Production of the Immunogen.

Expression plasmids encoding the immunogen (see Table 18) were transfected into CHO cell at a DNA ratio of 1:1. Total amount of DNA for a 750 mL expression scale was 750 µg. Final expression volume was 1 L after two feedings and enhancer additions. Using an ÄKTAPRIME plus instrument (GE Healthcare Life Sciences), supernatant (1 L) after 7 days was applied with a flow-rate of 5 mL/min to a MAB SELECT SURE (GE Life Sciences) with a column volume (CV) of 10 mL pre-equilibrated with phosphate buffered saline (PBS), pH 6.8. Non-specific proteins binding to the column material was washed off with PBS supplemented with 500 mM NaCl, pH 6.8 (5 CV). The Fc-containing immunogen was eluted stepwise with 40 mM sodium acetate pH 5.0 (5 CV), pH 4.5 (5 CV), pH 4.0 (10 CV), pH 3.5 (5 CV), and pH 3.0 (5 CV). Fractions were pooled, and applied (5 mL) at a flow-rate of 0.2 mL/min on to a HiLoad 16/600 SUPERDEX (GE Healthcare) column pre-equilibrated with PBS (pH 6.8). Target protein was eluted, pooled, and analyzed by SDS-PAGE, analytic SEC, and intact mass by mass spectrometry. Purity was estimated to >99%.

Antibodies were generated using ALIVAMAB transgenic mice technology (Ablexis). ALIVAMAB mice were immunized with recombinant human Vγ9/Vδ2 TCR protein. Lymphocytes were extracted from secondary lymphoid organs and either fused with FO mouse myeloma cell line for hybridoma generation or subjected to single cell sorting via FACS. Hybridoma supernatants were screened by MSD electrochemiluminescence or by FACS for binding to γδ T cells. Confirmed cell binders were light chain isotyped via ELISA. Single cell sorting supernatants were screened by MSD electrochemiluminescence for binding to recombinant human Vγ9/Vδ2 protein. Several hits with the desired binding profile were selected and sequenced, as provided below.

The CDR sequences of certain VG9 antibodies are provided in Tables 19-22, and the respective VH and VL regions are provided in Tables 23-26, respectively.

TABLE 19

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9B420-LH | GFTFSNYD | 98 | ISSSSSYI | 99 | ARDVGVTDYYYYGMDV | 100 |

| Antibody | LCDR1 | SEQ ID NO: | LCDR2 | SEQ ID NO: | LCDR3 | SEQ ID NO: |
|---|---|---|---|---|---|---|
| VG9B420-LH | QSVASSY | 101 | GAS | 102 | QQYGSSPPYT | 103 |

TABLE 20

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9SB10SC1087 P18_D08 | GDTFNNYA | 107 | IIPFFGTP | 108 | ARPGSGSPDYYYYDMDV | 109 |

| Antibody | LCDR1 | SEQ ID NO: | LCDR2 | SEQ ID NO: | LCDR3 | SEQ ID NO: |
|---|---|---|---|---|---|---|
| VG9SB10SC1087 P18_D08 | QSLVHSDGNTY | 110 | KIS | 111 | MQATQFPLT | 112 |

TABLE 21

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9SB10SC1087 P18_C12 | GGTFSSYA | 117 | NIPIFNTA | 118 | VREGTGYSYGLDY | 119 |

| Antibody | LCDR1 | SEQ ID NO: | LCDR2 | SEQ ID NO: | LCDR3 | SEQ ID NO: |
|---|---|---|---|---|---|---|
| VG9SB10SC1087 P18_C12 | QSLIHSDGNTY | 120 | KIS | 121 | MQAKQFPIT | 122 |

TABLE 22

CDR Sequences of anti-TRGV9 antibody (Vγ9 clone).

| Antibody | HCDR1 | SEQ ID NO: | HCDR2 | SEQ ID NO: | HCDR3 | SEQ ID NO: |
|---|---|---|---|---|---|---|
| VG9SB10SC1087 P19_C03 | GGSISSGGSY | 127 | IYNSGST | 128 | ARDSNYEWFFDL | 129 |

| Antibody | LCDR1 | SEQ ID NO: | LCDR2 | SEQ ID NO: | LCDR3 | SEQ ID NO: |
|---|---|---|---|---|---|---|
| VG9SB1-SC1087 P19_C03 | QSVSSY | 130 | DAS | 131 | QQRSNWPLT | 132 |

TABLE 23

Heavy chain and light chain V-region sequences of anti-TRGV9 antibody (Vγ9 clone).

| mAb ID | | SEQ ID NO: |
|---|---|---|
| | Heavy Chain V-region Amino Acid Sequence | |
| VG9B420-LH | EVQLVESGGGLVKPGGSLRLSCSASGFTFSNYDMNW VRQAPGKGLEWVSSISSSSSYIYYADSVKGRFTISR DNAKNSLYLQMNSLRAEDTAVYHCARDVGVTTDYYY YGMDVWGQGTMVTVSS | 104 |
| | Light Chain V-region Amino Acid Sequence | |
| VG9B420-LH | EIVMTQSPGTLSLSPGDRATLSCRASQSVASSYLAW YQQKPGQSPRLLIYGASSRATGIPDRFSGSGSGTDF TLTISRLEPEDFAVYYCQQYGSSPPYTFGQGTRLEI K | 105 |

TABLE 24

Heavy chain and light chain V-region sequences of anti-TRGV9 antibody (Vγ9 clone).

| mAb ID | | SEQ ID NO: |
|---|---|---|
| | Heavy Chain V-region Amino Acid Sequence | |
| VG9SB10SC1 087_P18_D08 | EVQLVQSGAEVKKPGSSVKVSCKASGDTFNNYA ISWVRQAPGQGLEWMGGIIPFFGTPDYAQKFQG RVTITADKSTSTAYMELSGLRSEDTAVYYCARP GSGSPDYYYYDMDVWGQGTTVTVSS | 113 |
| | Light Chain V-region Amino Acid Sequence | |
| VG9SB10SC1 087_P18_D08 | DIVMTQTPLSSPVTLGQPASISCRSSQSLVHSD GNTYLSWLQQRPGQPPRLLIYKISNRFSGVPDR FSGSGAGTDFTLKINRVEAEDVGVYYCMQATQF PLTFGGGTKVEIK | 114 |

TABLE 25

Heavy chain and light chain V-region sequences of anti-TRGV9 antibody (Vγ9 clone).

| mAb ID | | SEQ ID NO: |
|---|---|---|
| | Heavy Chain V-region Amino Acid Sequence | |
| VG9SB10SC1 087_P18_C12 | EVQLVQSGAEVKKPGSSVKVSCKASGGTFSSYA ISWVRQAPGQGLEWMGGNIPIFNTANYAQKFQD RVTITADKSTSTAYMELSSLRSEDTAVYYCVRE GTGYSYGLDYWGQGTPVTVSS | 123 |
| | Light Chain V-region Amino Acid Sequence | |
| VG9SB10SC1 087_P18_C12 | EIVMTQSPLSSPVTLGQPASISCRSSQSLIHSD GNTYLSWLQQRPGQPPRLLIYKISNRFSGVPDR F4SGSGAGTDFTLKISRVEAEDVGIYYCMQAKQ FPITFGQGTKVDIK | 124 |

TABLE 26

Heavy chain and light chain V-region sequences of anti-TRGV9 antibody (Vγ9 clone).

| mAb ID | | SEQ ID NO: |
|---|---|---|
| | Heavy Chain V-region Amino Acid Sequence | |
| VG9SB10SC1 087_P19_C03 | QVQLQESGPGLVKPSQTLSLTCTVSGGSISSGG SYWSWIRQHPGKGLEWIGYIYNSGSTYYNPSLK SRVSMSVDTSKNQFSLKLSSVTAADTAVYYCAR DSNYEWFFDLWGPGTLVTVSS | 133 |
| | Light Chain V-region Amino Acid Sequence | |
| VG9SB10SC1 087_P19_C03 | EIVMTQSPATLSLSPGERATLSCRASQSVSSYL AWYQQKPGQAPRLLIYDASNRATGIPARFSGSG SGTDFTLTISSLEPEDFAVYYCQQRSNWPLTFG GGTKVEIK | 134 |

Variable Region Cloning.

Both RNA purified by QIAGEN kit (RNEASY Plus Mini Kit) and B cells lysate were used for cDNA synthesis using the Smarter cDNA synthesis kit (Clontech, Mount View, Calif.). To facilitate cDNA synthesis, oligodT was used to prime reverse transcription of all messenger RNAs followed by "5' capping" with a SMARTER IIA oligonucleotide. Subsequent amplification of the VH and VL fragments was performed using a two-step PCR amplification using 5' primers targeting the Smarter IIA cap and 3' primers targeting consensus regions in CH1. Briefly, each 50 μl PCR reaction consists of 20 μM of forward and reverse primer mixes, 25 μl of PRIMESTAR MAX DNA polymerase premix (Clontech), 2 μl of unpurified cDNA, and 21 μl of double-distilled H₂O. The cycling program started at 94° C. for 3 min, followed by 35 cycles (94° C. for 30 Sec, 55° C. for 1 min, 68° C. for 1 min), and ended at 72° C. for 7 min. The second round PCR was performed with VL and VH 2nd round primers containing 15 bp complementary extensions that "overlap" respective regions in their respective Lonza mother vector (VH and VL). Second round PCR was performed with the following program: 94° C. for 3 min; 35 cycles (94° C. for 30 Sec, 55° C. for 1 min, 68° C. for 1 min), and ended at 72° C. for 7 min. IN-FUSION® HD Cloning Kit (Clonetech, U.S.A.) was used for directional cloning of VL gene into Lonza huIgK or Lambda vector and VH gene into Lonza huIgG1 vector. To facilitate IN-FUSION® HD Cloning, PCR products were treated with Cloning Enhancer before IN-FUSION HD Cloning. Cloning and transformation were performed according to manufacturer's protocol (Clonetech, U.S.A.). Mini-prep DNAs were subjected to Sanger sequencing to confirm that complete V-gene fragments were obtained.

Example 5.2: Production and De Novo Sequencing of Anti-TRGV9 MAB

The mouse IgG1 anti-human T cell receptor anti-TRGV9 clone B3 was sourced commercially. Sample preparation and LC-MS/MS analysis were performed by RAPID NOVOR (ON, Canada). Twenty-one in-solution and in-gel digestions were prepared using six different enzymes (Pepsin, Trypsin, Chymotrypsin, Asp N, Lys C, Glu C). The in-solution digestions for the sample was processed with disulfide reduction, alkylation, and then enzyme digestion. Each digestion contains peptides from all immunoglobulin chains. The in-gel digestions were prepared for immunoglobulin chains after gel separation. The sample was processed with disulfide reduction, gel separation, deglycosylation, disulfide reduction a second time, alkylation and then digestion. Digestions were analyzed by LC-MS/MS using THERMO-FISHER Q EXACTIVE™, ORBITRAP FUSION™ mass spectrometers. Peptides were characterized from LC-MS/MS data using de novo peptide sequencing and then assembled into antibody sequences.

The three VH CDR and three VL CDR sequences of anti-human T cell receptor Vγ9 clone B3 are shown in Table 27 (SEQ ID NOs:89-94, respectively); and the VH and VL sequences of the anti-human T cell receptor anti-human T cell receptor Vγ9 clone B3 are shown in Table 28 (SEQ ID NOs:95 and 96, respectively).

TABLE 27

CDR sequences of mouse anti-human TCR Vγ9 clone B3.

| Antibody | HCDR1 | SEQ ID NO: | HCDR2 | SEQ ID NO: | HCDR3 | SEQ ID NO: |
|---|---|---|---|---|---|---|
| Vg9_B3_RN | GFTFSSNY | 89 | IHGGTGGI | 90 | ARRGYGAWFAY | 91 |

| Antibody | LCDR1 | SEQ ID NO: | LCDR2 | SEQ ID NO: | LCDR3 | SEQ ID NO: |
|---|---|---|---|---|---|---|
| Vg9_B3_RN | ENIHNY | 92 | NAK | 93 | QHFWSYPLT | 94 |

TABLE 28

Heavy chain and light chain sequences of mouse anti-human TCR Vγ9 clone B3.

| mAb ID | | SEQ ID NO: |
|---|---|---|
| | Heavy Chain Amino Acid Sequence (from VG9B2) | |
| Vg9_B3_RN | QGQMQQSGAELVKPGASVKLSCKTSGFTFSSNY ISWLKQKPGQSLEWIAWIHGGTGGIGYNQKFTG KAQLTVDTSSTTAYMQFSSLTTEDSAIYYCARR GYGAWFAYWGQGTLVTVSA | 95 |
| | Light Chain Amino Acid Sequence (from VG9B2) | |
| Vg9_B3_RN | DIQMTQSPASLSASVGETVTITCRASENIHNYL AWYQQKQGKSPQLLVYNAKTLADGVPSRFSGSG SGTQYSLKINSLQPEDFGNYYCQHFWSYPLTFG AGTKLELK | 96 |

Figure 12:
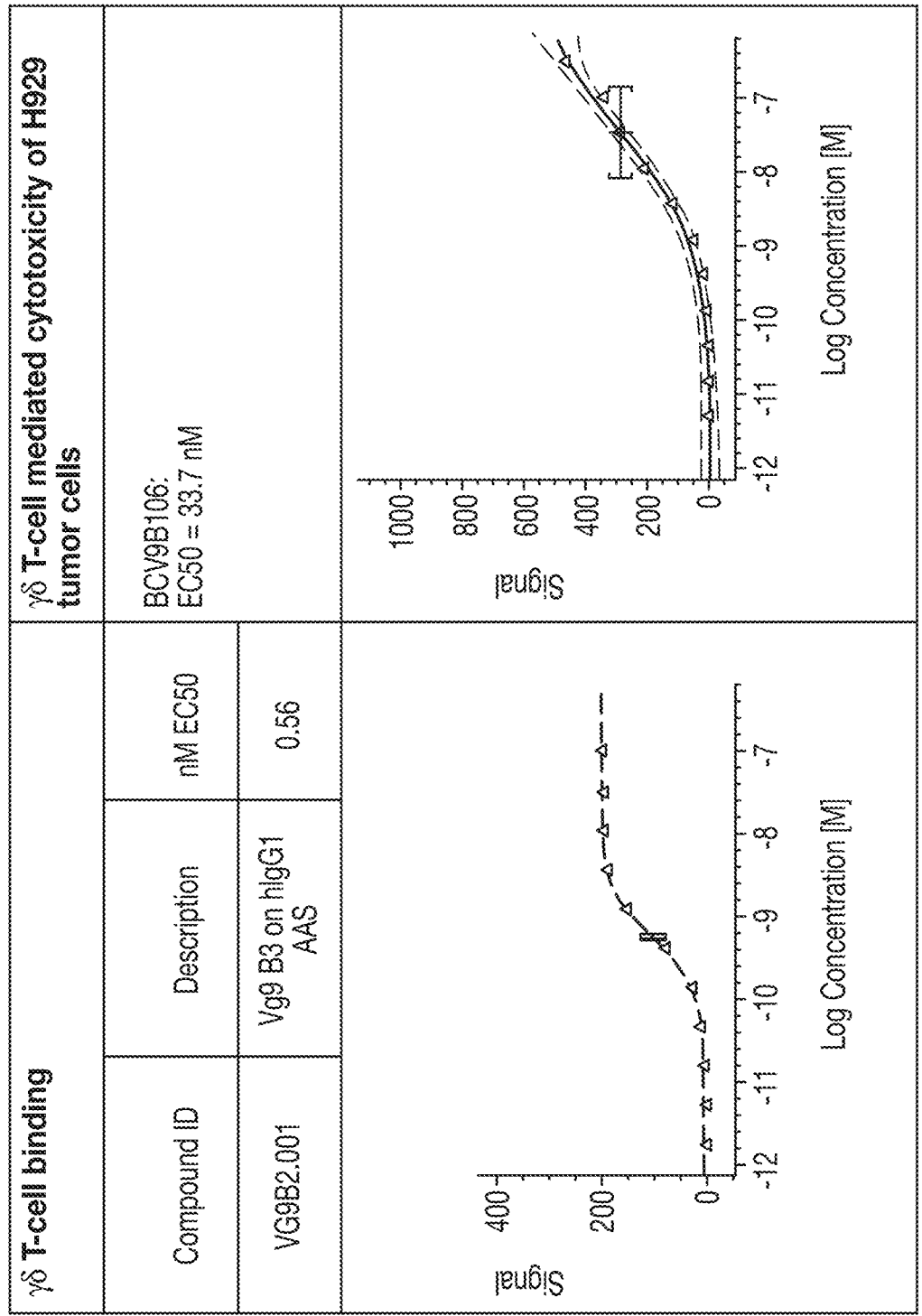
FIG. 12 shows that the anti-TRGV9/anti-TAA2 bispecific antibody (TAA2V9B106 (B3)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.
Figure 13:
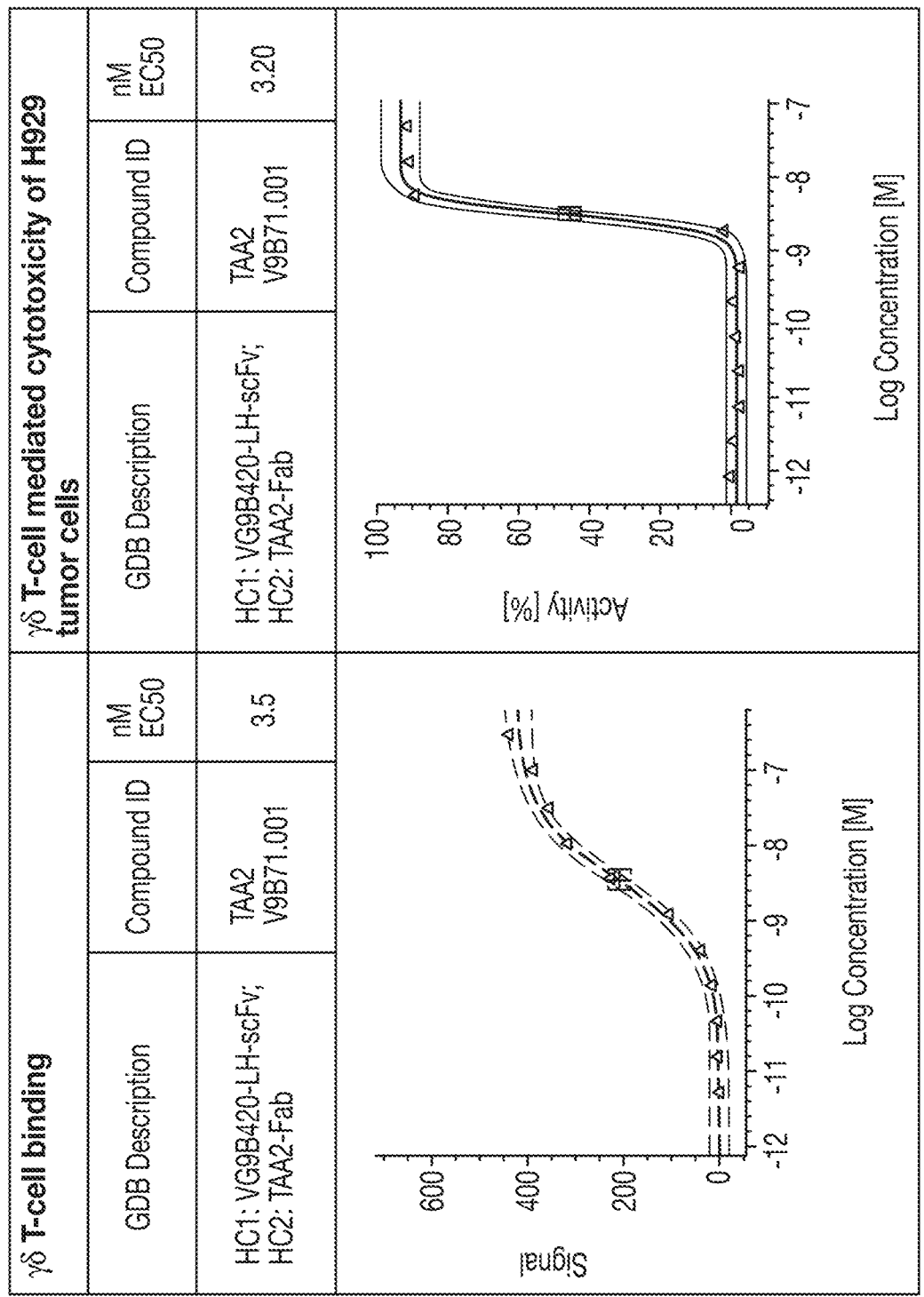
FIG. 13 shows that the anti-TRGV9/anti-TAA2 bispecific antibody (HC1: VG9B420-LH-scFv; HC2: TAA2-Fab (TAA2V9B71.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.
Figure 14:
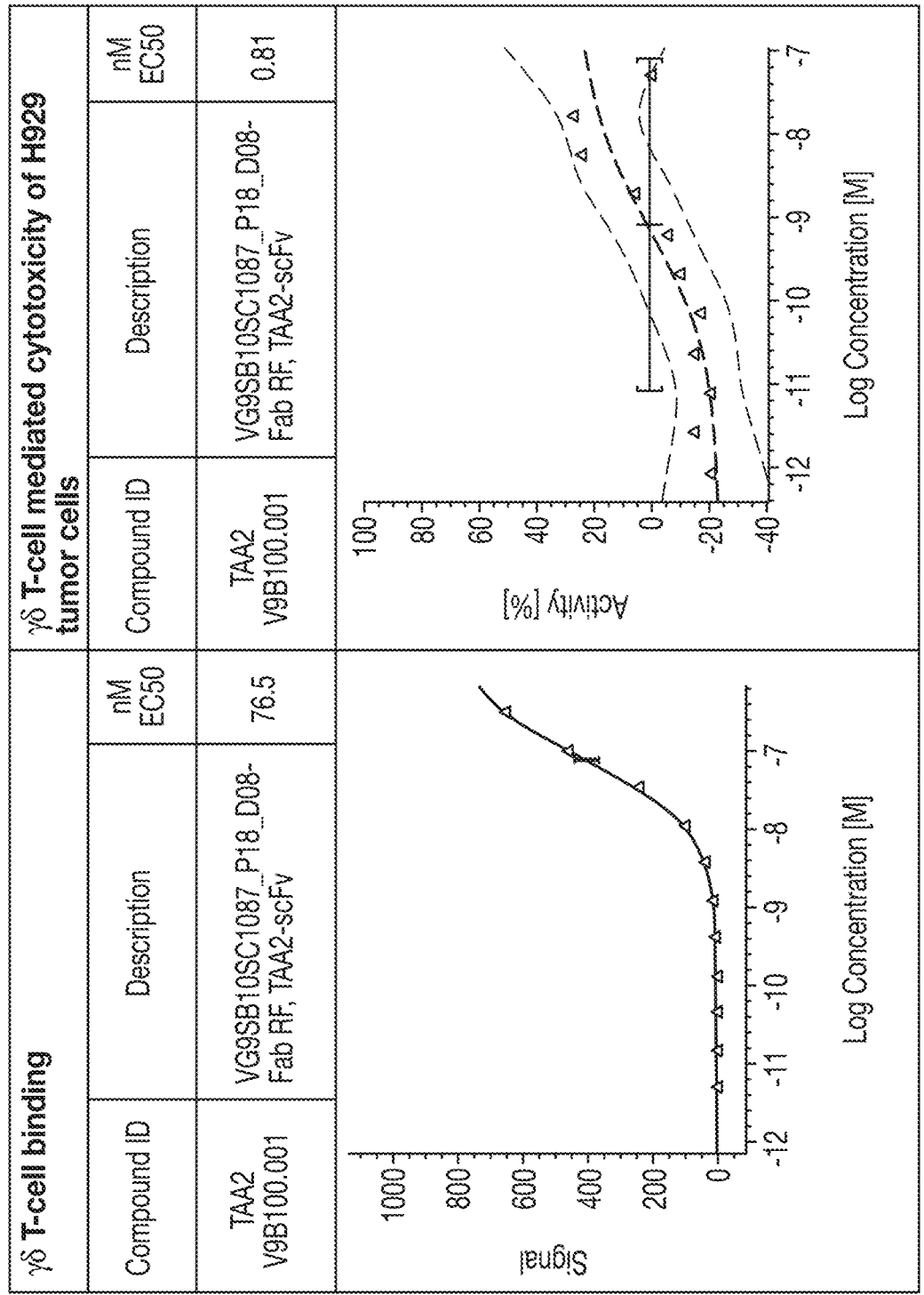
FIG. 14 shows that the anti-TRGV9/anti-TAA2 bispecific antibody (VG9SB10SC1087_P18_D08-Fab RF, TAA2-scFv (TAA2V9B100.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.
Figure 15:
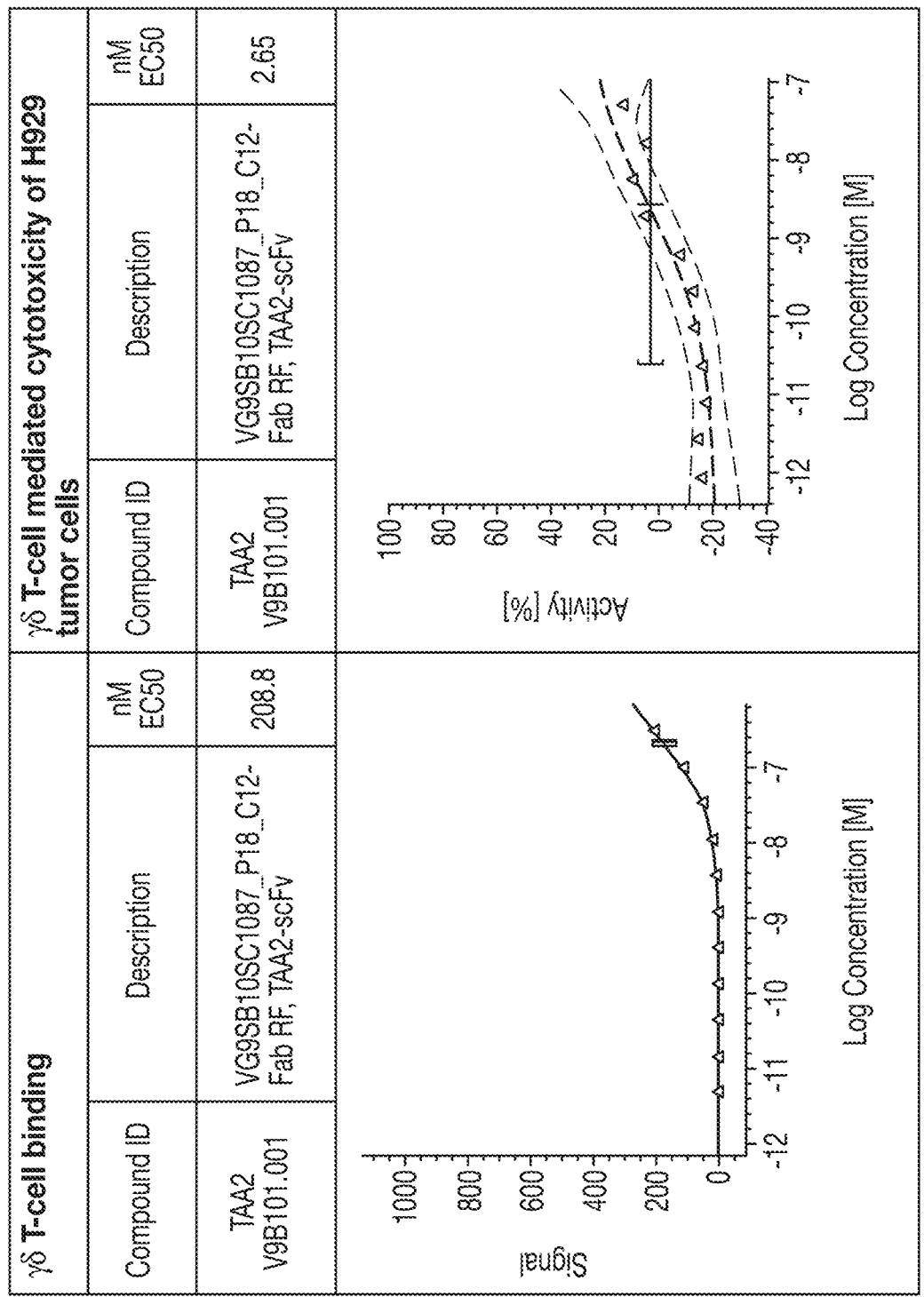
FIG. 15 shows that the anti-TRGV9/anti-TAA2 bispecific antibody (VG9SB10SC1087_P18_C12-Fab RF, TAA2-scFv (TAA2V9B101.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.
Figure 16:
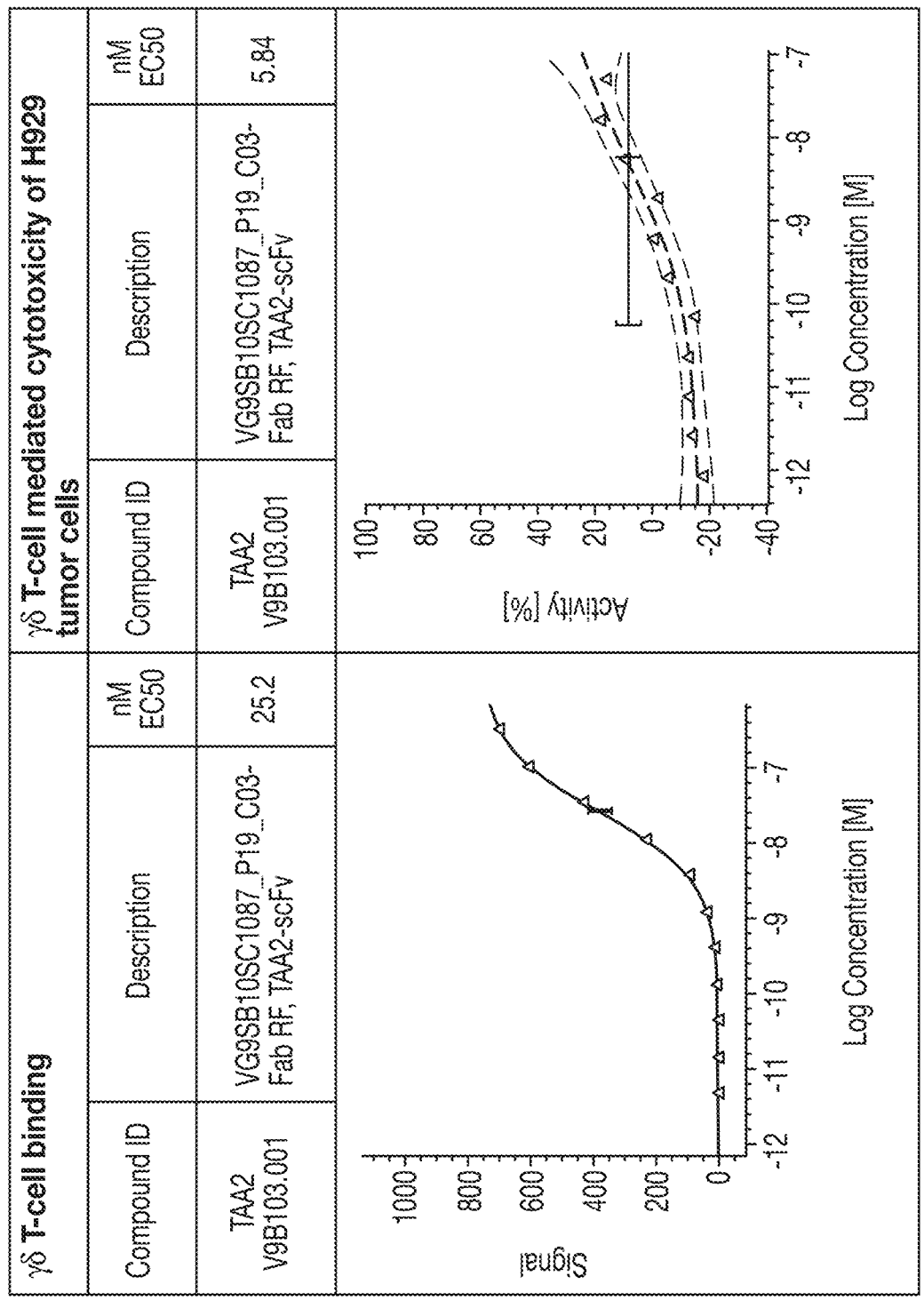
FIG. 16 shows that the anti-TRGV9/anti-TAA2 bispecific antibody (VG9SB10SC1087_P19_C03-Fab RF, TAA2-scFv (TAA2V9B103.001)) binds γδ T cells (left panel) and mediates γδ T cell cytotoxicity against TAA2 expressing H929 cells in vitro (right panel). $EC_{50}$ values were calculated as described in methods. Representative data shown here are from a single experiment.

The two antibodies (VG9B2) were expressed in CHO-Expi cells. The purified chimera human IgG1 mAb (silent Fc) demonstrated binding to human γδ T cells showing specificity toward TCR Vγ9, as shown in FIG. 12 (left panel).

Example 5.3: Production and De Novo Sequencing of Anti-TAA2 MAB

An anti-TAA2 clone was obtained and sequenced (data not shown).

Example 5.4: Preparation of ANTI-TRGV9/ANTI-TAA2 Bispecific Antibodies

The variable region sequence of anti-TRGV9 and anti-TAA2 antibodies was used to generate a bispecific human IgG1 antibody to be tested for T cell re-directed killing of H929 cells, which express TAA2. A summary of Vγ9 and TAA2 clones is provided in Table 29.

TABLE 29

Summary of Vγ9 and TAA2 clones

| | | B # |
|---|---|---|
| i. | VG9B420-LH-scFv Half Ab | TAA2V9B101 |
| ii. | VG9SB10SC1087_P18_D08-Fab Half Ab | TAA2V9B100 |
| iii. | VG9SB10SC1087_P18_C12-Fab Half Ab | TAA2V9B101 |
| iv. | TAA2 | Not Shown |
| v. | VG9SB10SC1087_P19_C03-Fab Half Ab | TAA2V9B103 |

The bispecific antibodies were produced as Fab (Vg9)× scFv (TAA2) and scFv (Vg9)×Fab (TAA2) antibodies in the knob-into-hole format as human IgG1 with silent Fc. Nucleic acid sequences encoding variable regions were subcloned into a custom mammalian expression vectors containing constant region of human IgG1 expression cassettes using standard PCR restriction enzyme based standard cloning techniques, and sequenced verified. The bispecific antibodies were expressed by transient transfection in Chinese hamster ovary cell line.

The sequences of the bispecific antibodies expressed in the CHO cells are shown in Table 30 below.

TABLE 30

Sequences of antibodies expressed in CHO cells

| mAb ID | 'Knob' arm and 'hole' arm amino acid sequence | | SEQ ID NO: |
|---|---|---|---|
| TAA2-Fab (half-mAb) | Heavy Chain B TAA2V9B71 | SEQUENCE NOT SHOWN | — |
| | Light Chain TAA2V9B71 | SEQUENCE NOT SHOWN | — |
| VG9SB10SC1087_P18_D08-Fab (half-mAb) | Heavy Chain A TAA2V9B100 | MAWVWTLLFLMAAAQSIQAEVQLV QSGAEVKKPGSSVKVSCKASGDTF NNYAISWVRQAPGQGLEWMGGIIP FFGTPDYAQKFQGRVTITADKSTS TAYMELSGLRSEDTAVYYCARPGS GSPDYYYYDMDVWGQGTTVTVSSA STKGPSVFPLAPSSKSTSGGTAAL GCLVKDYFPEPVTVSWNSGALTSG VHTFPAVLQSSGLYSLSSVVTVPS SSLGTQTYICNVNHKPSNTKVDKK VEPKSCDKTHTCPPCPAPEAAGGP SVFLFPPKPKDTLMISRTPEVTCV VVSVSHEDPEVKFNWYVDGVEVHN AKTKPREEQYNSTYRVVSVLTVLH QDWLNGKEYKCKVSNKALPAPIEK TISKAKGQPREPQVYVYPPSREEM TKNQVSLTCLVKGFYPSDIAVEWE SNGQPENNYKTTPPVLDSDGSFAL VSKLTVDKSRWQQGNVFSCSVMHE ALHNRFTQKSLSLSPGK | 150 |
| | Light Chain A TAA2V9B100 | MAWVWTLLFLMAAAQSIQADIVMT QTPLSSPVTLGQPASISCRSSQSL VHSDGNTYLSWLQQRPGQPPRLLI YKISNRFSGVPDRFSGSGAGTDFT LKINRVEAEDVGVYYCMQATQFPL TFGGGTKVEIKRTVAAPSVFIFPP SDEQLKSGTASVVCLLNNFYPREA KVQWKVDNALQSGNSQESVTEQDS KDSTYSLSSTLTLSKADYEKHKVY ACEVTHQGLSSPVTKSFNRGEC | 151 |
| VG9SB10SC1087_P18_C12-Fab (half-mAb) | Heavy Chain A TAA2V9B101 | MAWVWTLLFLMAAAQSIQAEVQLV QSGAEVKKPGSSVKVSCKASGGTF SSYAISWVRQAPGQGLEWMGGNIP IFNTANYAQKFQDRVTITADKSTS TAYMELSSLRSEDTAVYYCVREGT GYSYGLDYWGQGTPVTVSSASTKG PSVFPLAPSSKSTSGGTAALGCLV KDYFPEPVTVSWNSGALTSGVHTF PAVLQSSGLYSLSSVVTVPSSSLG TQTYICNVNHKPSNTKVDKKVEPK SCDKTHTCPPCPAPEAAGGPSVFL FPPKPKDTLMISRTPEVTCVVVSV SHEDPEVKFNWYVDGVEVHNAKTK PREEQYNSTYRVVSVLTVLHQDWL NGKEYKCKVSNKALPAPIEKTISK AKGQPREPQVYVYPPSREEMTKNQ VSLTCLVKGFYPSDIAVEWESNGQ PENNYKTTPPVLDSDGSFALVSKL TVDKSRWQQGNVFSCSVMHEALHN RFTQKSLSLSPGK | 152 |
| | Light Chain A TAA2V9B101 | MAWVWTLLFLMAAAQSIQAEIVMT QSPLSSPVTLGQPASISCRSSQSL IHSDGNTYLSWLQQRPGQPPRLLI YKISNRFSGVPDRFSGSGAGTDFT LKISRVEAEDVGIYYCMQAKQFPI TFGQGTKVDIKRTVAAPSVFIFPP SDEQLKSGTASVVCLLNNFYPREA KVQWKVDNALQSGNSQESVTEQDS KDSTYSLSSTLTLSKADYEKHKVY ACEVTHQGLSSPVTKSFNRGEC | 153 |

TABLE 30-continued

Sequences of antibodies expressed in CHO cells

| mAb ID | 'Knob' arm and 'hole' arm amino acid sequence | | SEQ ID NO: |
|---|---|---|---|
| VG9SB10 SC1087_ P 19_C03- Fab (half- mAb) | Heavy Chain A TAA2V9B1 03 | MAWVWTLLFLMAAAQSIQAQVQLQ ESGPGLVKPSQTLSLTCTVSGGSI SSGGSYWSWIRQHPGKGLEWIGYI YNSGSTYYNPSLKSRVSMSVDTSK NQFSLKLSSVTAADTAVYYCARDS NYEWFFDLWGPGTLVTVSSASTKG PSVFPLAPSSKSTSGGTAALGCLV KDYFPEPVTVSWNSGALTSGVHTF PAVLQSSGLYSLSSVVTVPSSSLG TQTYICNVNHKPSNTKVDKKVEPK SCDKTHTCPPCPAPEAAGGPSVFL FPPKPKDTLMISRTPEVTCVVVSV SHEDPEVKFNWYVDGVEVHNAKTK PREEQYNSTYRVVSVLTVLHQDWL NGKEYKCKVSNKALPAPIEKTISK AKGQPREPQVYVPPPSREEMTKNQ VSLTCLVKGFYPSDIAVEWESNGQ PENNYKTTPPVLDSDGSFALVSKL TVDKSRWQQGNVFSCSVMHEALHN RFTQKSLSLSPGK | 154 |
| | Light Chain A TAA2V9B1 03 | MAWVWTLLFLMAAAQSIQAEIVMT QSPATLSLSPGERATLSCRASQSV SSYLAWYQQKPGQAPRLLIYDASN RATGIPARFSGSGSGTDFTLTISS LEPEDFAVYYCQQRSNWPLTFGGG TKVEIKRTVAAPSVFIFPPSDEQL KSGTASVVCLLNNFYPREAKVQWK VDNALQSGNSQESVTEQDSKDSTY SLSSTLTLSKADYEKHKVYACEVT HQGLSSPVTKSFNRGEC | 155 | scFv Sequences

| Vg9-B3- LH-scFv (half- mAb) | Heavy Chain A TAA2V9B1 06 | MAWVWTLLFLMAAAQSIQADIQMT QSPASLSASVGETVTITCRASENI HNYLAWYQQKQGKSPQLLVYNAKT LADGVPSRFSGSGSGTQYSLKINS LQPEDFGNYYCQHFWSYPLTFGAG TKLELKGGSEGKSSGSGSESKSTG GSQGQMQQSGAELVKPGASVKLSC KTSGFTFSSNYISWLKQKPGQSLE WIAWIHGGTGGIGYNQKFTGKAQL TVDTSSTTAYMQFSSLTTEDSAIY YCARRGYGAWFAYWGQGTLVTVSA EPKSSDKTHTCPPCPAPEAAGGPS VFLFPPKPKDTLMISRTPEVTCVV VSVSHEDPEVKFNWYVDGVEVHNA KTKPREEQYNSTYRVVSVLTVLHQ DWLNGKEYKCKVSNKALPAPIEKT ISKAKGQPREPQVYVPPPSREEMT KNQVSLTCLVKGFYPSDIAVEWES NGQPENNYKTTPPVLDSDGSFALV SKLTVDKSRWQQGNVFSCSVMHEA LHNHYTQKSLSLSPGK | SEQ ID NO: 97 |
| VG9B420- LH-scFv (half- mAb) | Heavy Chain A TAA2V9B7 1 | MAWVWTLLFLMAAAQSIQAEIVMT QSPGTLSLSPGDRATLSCRASQSV ASSYLAWYQQKPGQSPRLLIYGAS SRATGIPDRFSGSGSGTDFTLTIS RLEPEDFAVYYCQQYGSSPPYTFG QGTRLEIKGGSEGKSSGSGSESKS TGGSEVQLVESGGGLVKPGGSLRL SCSASGFTFSNYDMNWVRQAPGKG LEWVSSISSSSSYIYYADSVKGRF TISRDNAKNSLYLQMNSLRAEDTA VYHCARDVGTTDYYYYGMDVWGQ GTMVTVSSEPKSSDKTHTCPPCPA PEAAGGPSVFLFPPKPKDTLMISR TPEVTCVVVSVSHEDPEVKFNWYV DGVEVHNAKTKPREEQYNSTYRVV SVLTVLHQDWLNGKEYKCKVSNKA LPAPIEKTISKAKGQPREPQVYVY PPSREEMTKNQVSLTCLVKGFYPS DIAVEWESNGQPENNYKTTPPVLD | SEQ ID NO: 106 |

TABLE 30-continued

Sequences of antibodies expressed in CHO cells

| mAb ID | 'Knob' arm and 'hole' arm amino acid sequence | | SEQ ID NO: |
|---|---|---|---|
| | | SDGSFALVSKLTVDKSRWQQGNVF SCSVMHEALHNHYTQKSLSLSPGK | |
| TAA2- scFv (half- mAb) | Heavy Chain B TAA2V9B1 01 | SEQUENCE NOT SHOWN | — |

TABLE 31

Anti-TRGV9 and Anti-TAA2 Heavy and Light Chain Sequences

| Antibody | Heavy Chain | Light Chain |
|---|---|---|
| VG9SB10 SC1087_ P18_D08 | EVQLVQSGAEVKKPGSSVKVS CKASGDTFNNYAISWVRQAPG QGLEWMGGIIPFFGTPDYAQK FQGRVTITADKSTSTAYMELS GLRSEDTAVYYCARPGSGSPD YYYYDMDVWGQGTTVTVSSAS TKGPSVFPLAPSSKSTSGGTA ALGCLVKDYFPEPVTVSWNSG ALTSGVHTFPAVLQSSGLYSL SSVVTVPSSSLGTQTYICNVN HKPSNTKVDKKVEPKSCDKTH TCPPCPAPEAAGGPSVFLFPP KPKDTLMISRTPEVTCVVVSV SHEDPEVKFNWYVDGVEVHNA KTKPREEQYNSTYRVVSVLTV LHQDWLNGKEYKCKVSNKALP APIEKTISKAKGQPREPQVYV YPPSREEMTKNQVSLTCLVKG FYPSDIAVEWESNGQPENNYK TTPPVLDSDGSFALVSKLTVD KSRWQQGNVFSCSVMHEALHN RFTQKSLSLSPGK (SEQ ID NO: 115) | DIVMTQTPLSSPVT LGQPASISCRSSQS LVHSDGNTYLSWLQ QRPGQPPRLLIYKI SNRFSGVPDRFSGS GAGTDFTLKINRVE AEDVGYYCMQATQ FPLTFGGGTKVEIK RTVAAPSVFIFPPS DEQLKSGTASVVCL LNNFYPREAKVQWK VDNALQSGNSQESV TEQDSKDSTYSLSS TLTLSKADYEKHKV YACEVTHQGLSSPV TKSFNRGEC (SEQ ID NO: 116) |
| VG9SB1 0SC108 7_P18_ C12 | EVQLVQSGAEVKKPGSSVKVS CKASGGTFSSYAISWVRQAPG QGLEWMGGNIPIFNTANYAQK FQDRVTITADKSTSTAYMELS SLRSEDTAVYYCVREGTGYSY GLDYWGQGTPVTVSSASTKGP SVTSGGTAALGCLVKDYFPEP VTVSWNSGALTSGVHTFPAVL QSSGLYSLSSVVTVPSSSLGT QTYICNVNHKPSNTKVDKKVE PKSCDKTHTCPPCPAPEAAGG PSVFLFPPKPKDTLMISRTPE VTCVVVSVSHEDPEVKFNWYV DGVEVHNAKTKPREEQYNSTY RVVSVLTVLHQDWLNGKEYKC KVSNKALPAPIEKTISKAKGQ PREPQVYVPPSREEMTKNQV SLTCLVKGFYPSDIAVEWESN GQPENNYKTTPPVLDSDGSFA LVSKLTVDKSRWQQGNVFSCS VMHEALHNRFTQKSLSLSPGK (SEQ ID NO: 125) | EIVMTQSPLSSPVT LGQPASISCRSSQS LIHSDGNTYLSWLQ QRPGQPPRLLIYKI SNRFSGVPDRFSGS GAGTDFTLKISRVE AEDVGIYYCMQAKQ FPITFGQGTKVDIK RTVAAPSVFIFPPS DEQLKSGTASVVCL LNNFYPREAKVQWK VDNALQSGNSQESV TEQDSKDSTYSLSS TLTLSKADYEKHKV YACEVTHQGLSSPV TKSFNRGEC (SEQ ID NO: 126) |
| VG9SB1 0SC108 7_P19_ C03 | QVQLQESGPGLVKPSQTLSLT CTVSGGSISSGGSYWSWIRQH PGKGLEWIGYIYNSGSTYYNP SLKSRVSMSVDTSKNQFSLKL SSVTAADTAVYYCARDSNYEW FFDLWGPGTLVTVSSASTKGP SVFPLAPSSKSTSGGTAALGC LVKDYFPEPVTVSWNSGALTS | EIVMTQSPATLSLS PGERATLSCRASQS VSSYLAWYQQKPGQ APRLLIYDASNRAT GIPARFSGSGSGTD FTLTISSLEPEDFA VYYCQQRSNWPLTE GGGTKVEIKRTVAA |

TABLE 31-continued

Anti-TRGV9 and Anti-TAA2 Heavy and Light Chain Sequences

| Antibody | Heavy Chain | Light Chain |
|---|---|---|
|  | GVHTFPAVLQSSGLYSLSSVV TVPSSSLGTQTYICNVNHKPS NTKVDKKVEPKSCDKTHTCPP CPAPEAAGGPSVFLFPPKPKD TLMISRTPEVTCVVVSVSHED PEVKFNWYVDGVEVHNAKTKP REEQYNSTYRVVSVLTVLHQD WLNGKEYKCKVSNKALPAPIE KTISKAKGQPREPQVYVYPPS REEMTKNQVSLTCLVKGFYPS DIAVEWESNGQPENNYKTTPP VLDSDGSFALVSKLTVDKSRW QQGNVFSCSVMHEALHNRFTQ KSLSLSPGK (SEQ ID NO: 135) | PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC (SEQ ID NO: 136) |
| TAA2 | SEQUENCE NOT SHOWN | SEQUENCE NOT SHOWN |

The antibodies were initially purified by MAB SELECT SURE PROTEIN A column (GE Healthcare). The column was equilibrated with PBS pH 7.2 and loaded with fermentation supernatant at a flow rate of 2 mL/min. After loading, the column was washed with 4 column volumes of PBS followed by elution in 30 mM sodium acetate, pH 3.5. Fractions containing protein peaks as monitored by absorbance at 280 nm were pooled and neutralized to pH 5.0 by adding 1% 3 M sodium acetate pH 9.0. The bispecific mAbs were further purified on a preparative SUPERDEX 200 10/300 GL (GE healthcare) size exclusion chromatography (SEC) column equilibrated with PBS buffer. The integrity of sample was assessed by endotoxin measurement (<3.0 EU/mg), SDS-PAGE under reducing and non-reducing conditions, SEC, and intact mass by MS.

Example 5.5: Evaluation of Binding and Cytotoxic Properties of the ANTI-TRGV9/ANTI-TAA2 Bispecific Antibody Using H929 Cells and Human γδ T Cells Each of FIGS. 12-16 shows that the anti-TRGV9/anti-TAA2 bispecific antibodies bind γδ T cells (left panels) and mediate γδ T cell cytotoxicity against TAA2 expressing H929 cells in vitro (right panels). For the binding assays, γδ-enriched T cells were used, and samples incubated for 1 hour at 37° C. prior to measurements. For the killing assays, expanded γδ T cells (effectors) were co-cultured with H929 at 5:1 E:T ratios in the presence of various concentrations of the bispecific antibody for 72 hours at 37° C. Bispecific constructs were tested in 11-point titration curve with a 3-fold dilution series starting at 50 nM antibody concentration. Human pan T cells were used as effector cells, as was done previously (see above). H929-WT tumor cell line was used as target cells. Dose response curves show anti-TRGV9/anti-TAA2 bispecific mediated γδ T cell cytotoxicity against TAA2 expressing H929 cells in a dose dependent manner. $EC_{50}$ values were calculated as described in methods. Representative data shown are from a single experiment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

What is claimed is:

1. An antibody that binds to T Cell Receptor Gamma Variable 9 (TRGV9), wherein the antibody comprises a heavy chain variable region (VH) and a light chain variable region (VL), wherein the antibody comprises: (i) a VH comprising a VH complementarity determining region (CDR) 1 having the amino acid sequence of SEQ ID NO: 1, a VH CDR2 having the amino acid sequence of SEQ ID NO:2, and a VH CDR3 having the amino acid sequence of SEQ ID NO:31, SEQ ID NO:32 or SEQ ID NO:33; and (ii) a VL comprising a VL CDR1 having the amino acid sequence of SEQ ID NO:4, a VL CDR2 having the amino acid sequence of SEQ ID NO: 5, and a VL CDR3 having the amino acid sequence of SEQ ID NO:6.

2. The antibody of claim 1, wherein the antibody comprises: (i) a VH comprising a VH complementarity determining region (CDR) 1 having the amino acid sequence of SEQ ID NO: 1, a VH CDR2 having the amino acid sequence of SEQ ID NO:2, and a VH CDR3 having the amino acid sequence of SEQ ID NO:31; and (ii) a VL comprising a VL CDR1 having the amino acid sequence of SEQ ID NO:4, a VL CDR2 having the amino acid sequence of SEQ ID NO:5, and a VL CDR3 having the amino acid sequence of SEQ ID NO:6.

3. The antibody of claim 2, wherein the antibody comprises a VH having the amino acid sequence of SEQ ID NO:34.

4. The antibody of claim 2, wherein the antibody comprises a VL having the amino acid sequence of SEQ ID NO:8.

5. The antibody of claim 2, wherein the antibody comprises a VH having the amino acid sequence of SEQ ID NO:34, and a VL having the amino acid sequence of SEQ ID NO:8.

6. The antibody of claim 1, wherein the antibody comprises: (i) a VH comprising a VH CDR1 having the amino acid sequence of SEQ ID NO:1, a VH CDR2 having the amino acid sequence of SEQ ID NO:2, and a VH CDR3 having the amino acid sequence of SEQ ID NO:32; and (ii) a VL comprising a VL CDR1 having the amino acid sequence of SEQ ID NO:4, a VL CDR2 having the amino acid sequence of SEQ ID NO: 5, and a VL CDR3 having the amino acid sequence of SEQ ID NO:6.

7. The antibody of claim 6, wherein the antibody comprises a VH having the amino acid sequence of SEQ ID NO:35.

8. The antibody of claim 6, wherein the antibody comprises a VL having the amino acid sequence of SEQ ID NO:8.

9. The antibody of claim 6, wherein the antibody comprises a VH having the amino acid sequence of SEQ ID NO:35, and a VL having the amino acid sequence of SEQ ID NO:8.

10. The antibody of claim 1, wherein the antibody comprises: (i) a VH comprising a VH CDR1 having the amino acid sequence of SEQ ID NO:1, a VH CDR2 having the amino acid sequence of SEQ ID NO:2, and a VH CDR3 having the amino acid sequence of SEQ ID NO:33; and (ii) a VL comprising a VL CDR1 having the amino acid sequence of SEQ ID NO:4, a VL CDR2 having the amino acid sequence of SEQ ID NO:5, and a VL CDR3 having the amino acid sequence of SEQ ID NO:6.

11. The antibody of claim 10, wherein the antibody comprises a VH having the amino acid sequence of SEQ ID NO:36.

12. The antibody of claim 10, wherein the antibody comprises a VL having the amino acid sequence of SEQ ID NO:8.

13. The antibody of claim 10, wherein the antibody comprises a VH having the amino acid sequence of SEQ ID NO:36, and a VL having the amino acid sequence of SEQ ID NO:8.

14. The antibody of any one of claims 1 to 13, wherein the TRGV9 is present on the surface of a γ5 T cell.

15. The antibody of any one of claims 1 to 13, wherein the antibody is a humanized antibody.

16. The antibody of any one of claims 1 to 13, wherein the antibody is an IgG antibody.

17. The antibody of claim 16, wherein the IgG antibody is an IgG1, IgG2, IgG3, or IgG4 antibody.

18. A nucleic acid encoding the antibody of any one of claims 1 to 13.

19. A vector comprising the nucleic acid of claim 18.

20. A host cell comprising the vector of claim 19.

21. A kit comprising the vector of claim 19 and packaging for the same.

22. The antibody of claim 2, wherein the antibody comprises a VH having at least 95% identity to the amino acid sequence of SEQ ID NO:34.

23. The antibody of claim 2, wherein the antibody comprises a VL having at least 95% identity to the amino acid sequence of SEQ ID NO:8.

24. The antibody of claim 2, wherein the antibody comprises a VH having at least 95% identity to the amino acid sequence of SEQ ID NO:34, and a VL having at least 95% identity to the amino acid sequence of SEQ ID NO:8.

25. The antibody of claim 6, wherein the antibody comprises a VH having at least 95% identity to the amino acid sequence of SEQ ID NO:35.

26. The antibody of claim 6, wherein the antibody comprises a VL having at least 95% identity to the amino acid sequence of SEQ ID NO:8.

27. The antibody of claim 6, wherein the antibody comprises a VH having at least 95% identity to the amino acid sequence of SEQ ID NO:35, and a VL having at least 95% identity to the amino acid sequence of SEQ ID NO:8.

28. The antibody of claim 10, wherein the antibody comprises a VH having at least 95% identity to the amino acid sequence of SEQ ID NO:36.

29. The antibody of claim 10, wherein the antibody comprises a VL having at least 95% identity to the amino acid sequence of SEQ ID NO:8.

30. The antibody of claim 10, wherein the antibody comprises a VH having at least 95% identity to the amino acid sequence of SEQ ID NO:36, and a VL having at least 95% identity to the amino acid sequence of SEQ ID NO:8.

31. A nucleic acid encoding the antibody of any one of claims 22 to 30.

32. A vector comprising the nucleic acid of claim 31.

33. A host cell comprising the vector of claim 32.

34. A kit comprising the vector of claim 32 and packaging for the same.

35. A kit comprising the antibody of any one of claims 1 to 13 and instructions for use.

36. A kit comprising the antibody of any one of claims 22 to 30 and instructions for use.

37. A pharmaceutical composition comprising the antibody of any one of claims 1-13 and 22-30, and a pharmaceutically acceptable carrier.

38. A pharmaceutical composition comprising the antibody of claim 14, and a pharmaceutically acceptable carrier.

39. A pharmaceutical composition comprising the antibody of claim 15, and a pharmaceutically acceptable carrier.

40. A pharmaceutical composition comprising the antibody of claim 16, and a pharmaceutically acceptable carrier.

41. A pharmaceutical composition comprising the antibody of claim 17, and a pharmaceutically acceptable carrier.

* * * * *

SEQUENCE LISTING

```
<160> NUMBER OF SEQ ID NOS: 762

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5 HCDR1

<400> SEQUENCE: 1

Asp His Tyr Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5 HCDR2

<400> SEQUENCE: 2

Gln Ile Tyr Pro Gly Asp Gly Asn Thr Tyr Tyr Asn Gln Lys Phe Lys
1               5                   10                  15

Gly
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5_1 HCDR3

<400> SEQUENCE: 3

Asn Tyr Gly Asp Tyr Thr Ile Asp Phe
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5 LCDR1

<400> SEQUENCE: 4

Lys Ser Ser Gln Ser Leu Leu Tyr Ser Ser Asn Gln Lys Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5 LCDR2

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5 LCDR3

<400> SEQUENCE: 6

Gln Gln Tyr Tyr Arg Tyr His Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LP7A5 Heavy Chain Variable Region

<400> SEQUENCE: 7
```

Glu Val Gln Leu Gln Gln Ser Gly Ala Glu Leu Ala Arg Pro Gly Ala
1               5                   10                  15

Ser Val Lys Leu Ser Cys Lys Ala Ser Gly Phe Thr Phe Thr Asp His
            20                  25                  30

Tyr Ile Asn Trp Val Lys Gln Arg Thr Gly Gln Gly Leu Glu Trp Ile
            35                  40                  45

Gly Gln Ile Tyr Pro Gly Asp Gly Asn Thr Tyr Tyr Asn Gln Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Pro Asn Tyr Gly Asp Tyr Thr Ile Asp Phe Trp Gly Gln Gly Thr
            100                 105                 110

Ser Val Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LP7A5 Light Chain Variable Region

<400> SEQUENCE: 8

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr His Thr Phe Gly Thr Gly Thr Lys Leu Glu Ile Lys
            100                 105                 110

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I3RB217 HCDR1

<400> SEQUENCE: 9

Ser Tyr Trp Ile Ser
1               5

<210> SEQ ID NO 10
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I3RB217 HCDR2

<400> SEQUENCE: 10

Ile Ile Asp Pro Ser Asp Ser Asp Thr Arg Tyr Ser Pro Ser Phe Gln
1               5                   10                  15

Gly

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I3RB217 HCDR3

<400> SEQUENCE: 11

Gly Asp Gly Ser Thr Asp Leu Asp Tyr
1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I3RB217 LCDR1

<400> SEQUENCE: 12

Arg Ala Ser Gln Ser Val Ser Ser Ser Tyr Leu
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I3RB217 LCDR2

<400> SEQUENCE: 13

Gly Ala Ser Ser Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: I3RB217 LCDR3

<400> SEQUENCE: 14

Gln Gln Asp Tyr Gly Phe Pro Trp Thr
1               5
```

-continued

```
<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: I3RB217 Heavy Chain Variable Region

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: I3RB217 Light Chain Variable Region

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys
            100                 105

<210> SEQ ID NO 17
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Vgamma9 half antibody

<400> SEQUENCE: 17

```
Met Ala Trp Val Trp Thr Leu Leu Phe Leu Met Ala Ala Ala Gln Ser
 1               5                  10                  15

Ile Gln Ala Asp Ile Val Met Ser Gln Ser Pro Ser Ser Leu Ala Val
            20                  25                  30

Ser Val Gly Glu Lys Val Thr Met Ser Cys Lys Ser Ser Gln Ser Leu
        35                  40                  45

Leu Tyr Ser Ser Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Lys Ala Glu Asp Leu Ala Val Tyr Tyr
            100                 105                 110

Cys Gln Gln Tyr Tyr Arg Tyr His Thr Phe Gly Thr Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Gly Gly
225                 230                 235                 240

Ser Glu Gly Lys Ser Ser Gly Ser Gly Ser Glu Ser Lys Ser Thr Glu
                245                 250                 255

Gly Lys Ser Ser Gly Ser Gly Ser Glu Ser Lys Ser Thr Gly Gly Ser
            260                 265                 270

Glu Val Gln Leu Gln Gln Ser Gly Ala Glu Leu Ala Arg Pro Gly Ala
        275                 280                 285

Ser Val Lys Leu Ser Cys Lys Ala Ser Gly Phe Thr Phe Thr Asp His
    290                 295                 300

Tyr Ile Asn Trp Val Lys Gln Arg Thr Gly Gln Gly Leu Glu Trp Ile
305                 310                 315                 320

Gly Gln Ile Tyr Pro Gly Asp Gly Asn Thr Tyr Tyr Asn Gln Lys Phe
                325                 330                 335

Lys Gly Lys Ala Thr Leu Thr Ala Asp Lys Ser Ser Ser Thr Ala Tyr
            340                 345                 350

Met Gln Leu Ser Ser Leu Thr Ser Glu Asp Ser Ala Val Tyr Phe Cys
        355                 360                 365

Ala Pro Asn Tyr Gly Asp Tyr Thr Ile Asp Phe Trp Gly Gln Gly Thr
    370                 375                 380

Ser Val Thr Val Ser Ser Ala Ser Thr Lys Gly Pro Ser Val Phe Pro
385                 390                 395                 400
```

```
Leu Ala Pro Cys Ser Arg Ser Thr Ser Glu Ser Thr Ala Ala Leu Gly
                405                 410                 415

Cys Leu Val Lys Asp Tyr Phe Pro Glu Pro Val Thr Val Ser Trp Asn
            420                 425                 430

Ser Gly Ala Leu Thr Ser Gly Val His Thr Phe Pro Ala Val Leu Gln
        435                 440                 445

Ser Ser Gly Leu Tyr Ser Leu Ser Ser Val Val Thr Val Pro Ser Ser
    450                 455                 460

Ser Leu Gly Thr Lys Thr Tyr Thr Cys Asn Val Asp His Lys Pro Ser
465                 470                 475                 480

Asn Thr Lys Val Asp Lys Arg Val Glu Ser Lys Tyr Gly Pro Pro Cys
                485                 490                 495

Pro Pro Cys Pro Ala Pro Glu Ala Ala Gly Gly Pro Ser Val Phe Leu
            500                 505                 510

Phe Pro Pro Lys Pro Lys Asp Thr Leu Met Ile Ser Arg Thr Pro Glu
        515                 520                 525

Val Thr Cys Val Val Val Asp Val Ser Gln Glu Asp Pro Glu Val Gln
    530                 535                 540

Phe Asn Trp Tyr Val Asp Gly Val Glu Val His Asn Ala Lys Thr Lys
545                 550                 555                 560

Pro Arg Glu Glu Gln Phe Asn Ser Thr Tyr Arg Val Val Ser Val Leu
                565                 570                 575

Thr Val Leu His Gln Asp Trp Leu Asn Gly Lys Glu Tyr Lys Cys Lys
            580                 585                 590

Val Ser Asn Lys Gly Leu Pro Ser Ser Ile Glu Lys Thr Ile Ser Lys
        595                 600                 605

Ala Lys Gly Gln Pro Arg Glu Pro Gln Val Tyr Thr Leu Pro Pro Ser
    610                 615                 620

Gln Glu Glu Met Thr Lys Asn Gln Val Ser Leu Ser Cys Ala Val Lys
625                 630                 635                 640

Gly Phe Tyr Pro Ser Asp Ile Ala Val Glu Trp Glu Ser Asn Gly Gln
                645                 650                 655

Pro Glu Asn Asn Tyr Lys Thr Thr Pro Pro Val Leu Asp Ser Asp Gly
            660                 665                 670

Ser Phe Phe Leu Val Ser Arg Leu Thr Val Asp Lys Ser Arg Trp Gln
        675                 680                 685

Glu Gly Asn Val Phe Ser Cys Ser Val Met His Glu Ala Leu His Asn
    690                 695                 700

Arg Phe Thr Gln Lys Ser Leu Ser Leu Gly Lys
705                 710                 715

<210> SEQ ID NO 18
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD123 half antibody

<400> SEQUENCE: 18

Met Ala Trp Val Trp Thr Leu Leu Phe Leu Met Ala Ala Ala Gln Ser
1               5                   10                  15

Ile Gln Ala Glu Ile Val Leu Thr Gln Ser Pro Gly Thr Leu Ser Leu
            20                  25                  30
```

Ser Pro Gly Glu Arg Ala Thr Leu Ser Cys Arg Ala Ser Gln Ser Val
             35                  40                  45

Ser Ser Ser Tyr Leu Ala Trp Tyr Gln Gln Lys Pro Gly Gln Ala Pro
 50                  55                  60

Arg Leu Leu Ile Tyr Gly Ala Ser Ser Arg Ala Thr Gly Ile Pro Asp
 65                  70                  75                  80

Arg Phe Ser Gly Ser Gly Ser Gly Thr Asp Phe Thr Leu Thr Ile Ser
                 85                  90                  95

Arg Leu Glu Pro Glu Asp Phe Ala Val Tyr Tyr Cys Gln Gln Asp Tyr
                100                 105                 110

Gly Phe Pro Trp Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Gly Ser Glu Gly Lys
225                 230                 235                 240

Ser Ser Gly Ser Gly Ser Glu Ser Lys Ser Thr Glu Gly Lys Ser Ser
                245                 250                 255

Gly Ser Gly Ser Glu Ser Lys Ser Thr Gly Gly Ser Glu Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Ser Trp
    290                 295                 300

Val Arg Gln Met Pro Gly Lys Gly Leu Glu Trp Met Gly Ile Ile Asp
305                 310                 315                 320

Pro Ser Asp Ser Asp Thr Arg Tyr Ser Pro Ser Phe Gln Gly Gln Val
                325                 330                 335

Thr Ile Ser Ala Asp Lys Ser Ile Ser Thr Ala Tyr Leu Gln Trp Ser
            340                 345                 350

Ser Leu Lys Ala Ser Asp Thr Ala Met Tyr Tyr Cys Ala Arg Gly Asp
        355                 360                 365

Gly Ser Thr Asp Leu Asp Tyr Trp Gly Gln Gly Thr Leu Val Thr Val
    370                 375                 380

Ser Ser Ala Ser Thr Lys Gly Pro Ser Val Phe Pro Leu Ala Pro Cys
385                 390                 395                 400

Ser Arg Ser Thr Ser Glu Ser Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
        435                 440                 445

Tyr Ser Leu Ser Ser Val Val Thr Val Pro Ser Ser Ser Leu Gly Thr

```
                    450                 455                 460

Lys Thr Tyr Thr Cys Asn Val Asp His Lys Pro Ser Asn Thr Lys Val
465                 470                 475                 480

Asp Lys Arg Val Glu Ser Lys Tyr Gly Pro Pro Cys Pro Pro Cys Pro
                485                 490                 495

Ala Pro Glu Ala Ala Gly Gly Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser Gln Glu Asp Pro Glu Val Gln Phe Asn Trp Tyr
    530                 535                 540

Val Asp Gly Val Glu Val His Asn Ala Lys Thr Lys Pro Arg Glu Glu
545                 550                 555                 560

Gln Phe Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Gly Leu Pro Ser Ser Ile Glu Lys Thr Ile Ser Lys Ala Lys Gly Gln
        595                 600                 605

Pro Arg Glu Pro Gln Val Tyr Thr Leu Pro Pro Ser Gln Glu Glu Met
    610                 615                 620

Thr Lys Asn Gln Val Ser Leu Trp Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Arg Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Leu Gly Lys
705                 710

<210> SEQ ID NO 19
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B23B49 half antibody

<400> SEQUENCE: 19

Met Ala Trp Val Trp Thr Leu Leu Phe Leu Met Ala Ala Ala Gln Ser
1               5                   10                  15

Ile Gln Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp Tyr Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
```

```
                85                  90                  95
Arg Leu Glu Pro Glu Asp Phe Ala Val Tyr Tyr Cys Gln Gln Asp Tyr
            100                 105                 110
Gly Phe Pro Trp Thr Phe Gly Gln Gly Thr Lys Val Glu Ile Lys Arg
            115                 120                 125
Thr Val Ala Ala Pro Ser Val Phe Ile Phe Pro Pro Ser Asp Glu Gln
            130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
            195                 200                 205
His Lys Val Tyr Ala Cys Glu Val Thr His Gln Gly Leu Ser Ser Pro
        210                 215                 220
Val Thr Lys Ser Phe Asn Arg Gly Glu Cys Gly Gly Ser Glu Gly Lys
225                 230                 235                 240
Ser Ser Gly Ser Gly Ser Glu Ser Lys Ser Thr Glu Gly Lys Ser Ser
                245                 250                 255
Gly Ser Gly Ser Glu Ser Lys Ser Thr Gly Gly Ser Glu Val Gln Leu
            260                 265                 270
Val Gln Ser Gly Ala Glu Val Lys Lys Pro Gly Glu Ser Leu Lys Ile
            275                 280                 285
Ser Cys Lys Gly Ser Gly Tyr Ser Phe Thr Ser Tyr Trp Ile Ser Trp
290                 295                 300
Val Arg Gln Met Pro Gly Lys Gly Leu Glu Trp Met Gly Ile Ile Asp
305                 310                 315                 320
Pro Ser Asp Ser Asp Thr Arg Tyr Ser Pro Ser Phe Gln Gly Gln Val
                325                 330                 335
Thr Ile Ser Ala Asp Lys Ser Ile Ser Thr Ala Tyr Leu Gln Trp Ser
            340                 345                 350
Ser Leu Lys Ala Ser Asp Thr Ala Met Tyr Tyr Cys Ala Arg Gly Asp
            355                 360                 365
Gly Ser Thr Asp Leu Asp Tyr Trp Gly Gln Gly Thr Leu Val Thr Val
            370                 375                 380
Ser Ser Ala Ser Thr Lys Gly Pro Ser Val Phe Pro Leu Ala Pro Cys
385                 390                 395                 400
Ser Arg Ser Thr Ser Glu Ser Thr Ala Ala Leu Gly Cys Leu Val Lys
                405                 410                 415
Asp Tyr Phe Pro Glu Pro Val Thr Val Ser Trp Asn Ser Gly Ala Leu
            420                 425                 430
Thr Ser Gly Val His Thr Phe Pro Ala Val Leu Gln Ser Ser Gly Leu
            435                 440                 445
Tyr Ser Leu Ser Ser Val Val Thr Val Pro Ser Ser Ser Leu Gly Thr
            450                 455                 460
Lys Thr Tyr Thr Cys Asn Val Asp His Lys Pro Ser Asn Thr Lys Val
465                 470                 475                 480
Asp Lys Arg Val Glu Ser Lys Tyr Gly Pro Pro Cys Pro Pro Cys Pro
                485                 490                 495
Ala Pro Glu Ala Ala Gly Gly Pro Ser Val Phe Leu Phe Pro Pro Lys
            500                 505                 510
```

-continued

```
Pro Lys Asp Thr Leu Met Ile Ser Arg Thr Pro Glu Val Thr Cys Val
        515                 520                 525

Val Val Asp Val Ser Gln Glu Asp Pro Glu Val Gln Phe Asn Trp Tyr
    530                 535                 540

Val Asp Gly Val Glu Val His Asn Ala Lys Thr Lys Pro Arg Glu Glu
545                 550                 555                 560

Gln Phe Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Gly Leu Pro Ser Ser Ile Glu Lys Thr Ile Ser Lys Ala Lys Gly Gln
        595                 600                 605

Pro Arg Glu Pro Gln Val Tyr Thr Leu Pro Pro Ser Gln Glu Glu Met
    610                 615                 620

Thr Lys Asn Gln Val Ser Leu Trp Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Arg Leu Thr Val Asp Lys Ser Arg Trp Gln Glu Gly Asn Val
        675                 680                 685

Phe Ser Cys Ser Val Met His Glu Ala Leu His Asn His Tyr Thr Gln
    690                 695                 700

Lys Ser Leu Ser Leu Ser Leu Gly Lys
705                 710
```

<210> SEQ ID NO 20
<211> LENGTH: 2151
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Vgamma9 half antibody

<400> SEQUENCE: 20

```
atggcctggg tgtggaccct gctgttcctg atggccgccg cccagagcat ccaggccgac      60
atcgtgatga gccagagccc aagcagcctg gccgtgagcg tgggcgagaa ggtgaccatg     120
agctgcaaga gcagccagag cctgctgtac agcagcaacc agaagaacta cctggcctgg     180
taccagcaga agccaggcca gagcccaaag ctgctgatct actgggccag cacccgcgag     240
agcggcgtgc cagaccgctt caccggcagc ggcagcggca ccgacttcac cctgaccatc     300
agcagcgtga aggccgagga cctggccgtg tactactgcc agcagtacta ccgctaccac     360
accttcggca ccggcaccaa gctggagatc aagcgcaccg tggccgcccc aagcgtgttc     420
atcttcccac caagcgacga gcagctgaag agcggcaccg ccagcgtggt gtgcctgctg     480
aacaacttct acccacgcga ggccaaggtg cagtggaagg tggacaacgc cctgcagagc     540
ggcaacagcc aggagagcgt gaccgagcag gacagcaagg acagcaccta cagcctgagc     600
agcaccctga ccctgagcaa ggccgactac gagaagcaca aggtgtacgc ctgcgaggtg     660
acccaccagg gcctgagcag cccagtgacc aagagcttca accgcggcga gtgcggcggc     720
agcgagggca gagcagcgg cagcggcagc gagagcaaga gcaccgaggg caagagcagc     780
```

| | |
|---|---|
| ggcagcggca gcgagagcaa gagcaccggc ggcagcgagg tgcagctgca gcagagcggc | 840 |
| gccgagctgg cccgcccagg cgccagcgtg aagctgagct gcaaggccag cggcttcacc | 900 |
| ttcaccgacc actacatcaa ctgggtgaag cagcgcaccg gccagggcct ggagtggatc | 960 |
| ggccagatct acccaggcga cggcaacacc tactacaacc agaagttcaa gggcaaggcc | 1020 |
| accctgaccg ccgacaagag cagcagcacc gcctacatgc agctgagcag cctgaccagc | 1080 |
| gaggacagcg ccgtgtactt ctgcgcccca aactacggcg actacaccat cgacttctgg | 1140 |
| ggccagggca ccagcgtgac cgtgagcagc gccagcacca agggcccaag cgtgttccca | 1200 |
| ctggccccat gcagccgcag caccagcgag agcaccgccg ccctgggctg cctggtgaag | 1260 |
| gactacttcc cagagccagt gaccgtgagc tggaacagcg gcgccctgac cagcggcgtg | 1320 |
| cacaccttcc cagccgtgct gcagagcagc ggcctgtaca gcctgagcag cgtggtgacc | 1380 |
| gtgccaagca gcagcctggg caccaagacc tacacctgca acgtggacca caagccaagc | 1440 |
| aacaccaagg tggacaagcg cgtggagagc aagtacggcc caccatgccc accatgccca | 1500 |
| gccccagagg ccgccggcgg cccaagcgtg ttcctgttcc caccaaagcc aaaggacacc | 1560 |
| ctgatgatca gccgcacccc agaggtgacc tgcgtggtgg tggacgtgag ccaggaggac | 1620 |
| ccagaggtgc agttcaactg gtacgtggac ggcgtggagg tgcacaacgc caagaccaag | 1680 |
| ccacgcgagg agcagttcaa cagcacctac cgcgtggtga gcgtgctgac cgtgctgcac | 1740 |
| caggactggc tgaacggcaa ggagtacaag tgcaaggtgc gcaacaaggg cctgccaagc | 1800 |
| agcatcgaga agaccatcag caaggccaag ggccagccac gcgagccaca ggtgtacacc | 1860 |
| ctgccaccaa gccaggagga gatgaccaag aaccaggtga gcctgtggtg cctggtgaag | 1920 |
| ggcttctacc caagcgacat cgccgtggag tgggagagca acggccagcc agagaacaac | 1980 |
| tacaagacca cccaccagt gctggacagc gacggcagct tcttcctgta cagccgcctg | 2040 |
| accgtggaca gagccgctg caggagggc aacgtgttca gctgcagcgt gatgcacgag | 2100 |
| gccctgcaca accactacac ccagaagagc ctgagcctga gcctgggcaa g | 2151 |

<210> SEQ ID NO 21
<211> LENGTH: 2139
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD123 half antibody

<400> SEQUENCE: 21

| | |
|---|---|
| atggcctggg tgtggaccct gctgttcctg atggccgccg cccagagcat ccaggccgag | 60 |
| atcgtgctga cccagagccc aggcaccctg agcctgagcc caggcgagcg cgccaccctg | 120 |
| agctgccgcg ccagccagag cgtgagcagc agctacctgg cctggtacca gcagaagcca | 180 |
| ggccaggccc cacgcctgct gatctacggc gccagcagcc gcgccaccgg catcccagac | 240 |
| cgcttcagcg gcagcggcag cggcaccgac ttcaccctga ccatcagccg cctggagcca | 300 |
| gaggacttcg ccgtgtacta ctgccagcag gactacggct cccatggac cttcggccag | 360 |
| ggcaccaagg tggagatcaa agcgaccgtg gccgccccaa gcgtgttcat cttcccacca | 420 |
| agcgacgagc agctgaagag cggcaccgcc agcgtggtgt gcctgctgaa caacttctac | 480 |
| ccacgcgagg ccaaggtgca gtggaaggtg gacaacgccc tgcagagcgg caacagccag | 540 |
| gagagcgtga ccgagcagga cagcaaggac agcacctaca gcctgagcag caccctgacc | 600 |

| | |
|---|---|
| ctgagcaagg ccgactacga gaagcacaag gtgtacgcct cgaggtgac ccaccagggc | 660 |
| ctgagcagcc cagtgaccaa gagcttcaac cgcggcgagt gcggcggcag cgagggcaag | 720 |
| agcagcggca gcggcagcga gagcaagagc accgagggca gagcagcgg cagcggcagc | 780 |
| gagagcaaga gcaccggcgg cagcgaggtg cagctggtgc agagcggcgc cgaggtgaag | 840 |
| aagccaggcg agagcctgaa gatcagctgc aagggcagcg gctacagctt caccagctac | 900 |
| tggatcagct gggtgcgcca gatgccaggc aagggcctgg agtggatggg catcatcgac | 960 |
| ccaagcgaca gcgacacccg ctacagccca agcttccagg gccaggtgac catcagcgcc | 1020 |
| gacaagagca tcagcaccgc ctacctgcag tggagcagcc tgaaggccag cgacaccgcc | 1080 |
| atgtactact gcgcccgcgg cgacggcagc accgacctgg actactgggg ccagggcacc | 1140 |
| ctggtgaccg tgagcagcgc cagcaccaag ggcccaagcg tgttcccact ggccccatgc | 1200 |
| agccgcagca ccagcgagag caccgccgcc ctgggctgcc tggtgaagga ctacttccca | 1260 |
| gagccagtga ccgtgagctg aacagcggc gccctgacca gcggcgtgca caccttccca | 1320 |
| gccgtgctgc agagcagcgg cctgtacagc ctgagcagcg tggtgaccgt gccaagcagc | 1380 |
| agcctgggca ccaagaccta cacctgcaac gtggaccaca agccaagcaa caccaaggtg | 1440 |
| gacaagcgcg tggagagcaa gtacggccca ccatgcccac catgcccagc ccagaggcc | 1500 |
| gccggcggcc caagcgtgtt cctgttccca caaagccaa aggacaccct gatgatcagc | 1560 |
| cgcacccag aggtgacctg cgtggtggtg gacgtgagcc aggaggaccc agaggtgcag | 1620 |
| ttcaactggt acgtggacgg cgtggaggtg cacaacgcca agaccaagcc acgcgaggag | 1680 |
| cagttcaaca gcacctaccg cgtggtgagc gtgctgaccg tgctgcacca ggactggctg | 1740 |
| aacggcaagg agtacaagtg caaggtgagc aacaagggcc tgccaagcag catcgagaag | 1800 |
| accatcagca aggccaaggg ccagccacgc gagccacagg tgtacaccct gccaccaagc | 1860 |
| caggaggaga tgaccaagaa ccaggtgagc ctgtggtgcc tggtgaaggg cttctaccca | 1920 |
| agcgacatcg ccgtggagtg ggagagcaac ggccagccag agaacaacta caagaccacc | 1980 |
| ccaccagtgc tggacagcga cggcagcttc ttcctgtaca gccgcctgac cgtggacaag | 2040 |
| agccgctggc aggagggcaa cgtgttcagc tgcagcgtga tgcacgaggc cctgcacaac | 2100 |
| cactacaccc agaagagcct gagcctgagc ctgggcaag | 2139 |

<210> SEQ ID NO 22
<211> LENGTH: 2154
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: B23B49 half antibody

<400> SEQUENCE: 22

| | |
|---|---|
| atggcctggg tgtggaccct gctgttcctg atggccgccg cccagagcat ccaggccgac | 60 |
| atcgtgatga cccagagccc agacagcctg gccgtgagcc tgggcgagcg cgccaccatc | 120 |
| aactgccgcg ccagccagag cgtggactac aacggcatca gctacatgca ctggtaccag | 180 |
| cagaagccag gccagccacc aaagctgctg atctacgccg ccagcaaccc agagagcggc | 240 |
| gtgccagacc gcttcagcgg cagcggcagc ggcaccgact tcaccctgac catcagcagc | 300 |
| ctgcaggccg aggacgtggc cgtgtactac tgccagcaga tcatcgagga ccatggacc | 360 |
| ttcggccagg gcaccaaggt ggagatcaag cgcaccgtgg ccgccccaag cgtgttcatc | 420 |

-continued

| | |
|---|---|
| ttcccaccaa gcgacgagca gctgaagagc ggcaccgcca gcgtggtgtg cctgctgaac | 480 |
| aacttctacc cacgcgaggc caaggtgcag tggaaggtgg acaacgccct gcagagcggc | 540 |
| aacagccagg agagcgtgac cgagcaggac agcaaggaca gcacctacag cctgagcagc | 600 |
| accctgaccc tgagcaaggc cgactacgag aagcacaagg tgtacgcctg cgaggtgacc | 660 |
| caccagggcc tgagcagccc agtgaccaag agcttcaacc gcggcgagtg cggcggcagc | 720 |
| gagggcaaga gcagcggcag cggcagcgag agcaagagca ccgagggcaa gagcagcggc | 780 |
| agcggcagcg agagcaagag caccggcggc agccagatca ccctgaagga gagcggccca | 840 |
| accctggtga agccaaccca gaccctgacc ctgacctgca ccttcagcgg cttcagcctg | 900 |
| agcaccagcg gcatgggcgt gagctggatc cgccagccac caggcaaggc cctggagtgg | 960 |
| ctggcccaca tctactggga cgacgacaag cgctacaacc caagcctgaa gagccgcctg | 1020 |
| accatcacca aggacaccag caagaaccag gtggtgctga ccatgaccaa catggaccca | 1080 |
| gtggacaccg ccacctacta ctgcgcccgc ctgtacggct tcacctacgg cttcgcctac | 1140 |
| tggggccagg gcaccctggt gaccgtgagc agcgccagcc caagggccc aagcgtgttc | 1200 |
| ccactggccc catgcagccg cagcaccagc gagagcaccg ccgccctggg ctgcctggtg | 1260 |
| aaggactact cccagagcc agtgaccgtg agctggaaca gcggcgccct gaccagcggc | 1320 |
| gtgcacacct cccagccgt gctgcagagc agcggcctgt acagcctgag cagcgtggtg | 1380 |
| accgtgccaa gcagcagcct gggcaccaag acctacacct gcaacgtgga ccacaagcca | 1440 |
| agcaacacca aggtggacaa gcgcgtggag agcaagtacg gcccaccatg cccaccatgc | 1500 |
| ccagccccag gggccgccgg cggcccaagc gtgttcctgt tcccaccaaa gccaaaggac | 1560 |
| accctgatga tcagccgcac cccagaggtg acctgcgtgg tggtggacgt gagccaggag | 1620 |
| gacccagagg tgcagttcaa ctggtacgtg gacggcgtgg aggtgcacaa cgccaagacc | 1680 |
| aagccacgcg aggagcagtt caacagcacc taccgcgtgg tgagcgtgct gaccgtgctg | 1740 |
| caccaggact ggctgaacgg caaggagtac aagtgcaagg tgagcaacaa gggcctgcca | 1800 |
| agcagcatcg agaagaccat cagcaaggcc aagggccagc cacgcgagcc acaggtgtac | 1860 |
| accctgccac caagccagga ggagatgacc aagaaccagg tgagcctgtg gtgcctggtg | 1920 |
| aagggcttct acccaagcga catcgccgtg gagtgggaga gcaacggcca gccagagaac | 1980 |
| aactacaaga ccaccccacc agtgctggac agcgacggca gcttcttcct gtacagccgc | 2040 |
| ctgaccgtgg acaagagccg ctggcaggag ggcaacgtgt tcagctgcag cgtgatgcac | 2100 |
| gaggccctgc acaaccacta cacccagaag agcctgagcc tgagcctggg caag | 2154 |

<210> SEQ ID NO 23
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG1 heavy chain 1

<400> SEQUENCE: 23

Glu Val Gln Leu Gln Gln Ser Gly Ala Glu Leu Ala Arg Pro Gly Ala
1               5                   10                  15

Ser Val Lys Leu Ser Cys Lys Ala Ser Gly Phe Thr Phe Thr Asp His
            20                  25                  30

Tyr Ile Asn Trp Val Lys Gln Arg Thr Gly Gln Gly Leu Glu Trp Ile
        35                  40                  45

Gly Gln Ile Tyr Pro Gly Asp Gly Asn Thr Tyr Tyr Asn Gln Lys Phe
 50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Pro Asn Tyr Gly Asp Tyr Thr Ile Asp Phe Trp Gly Gln Gly Thr
                100                 105                 110

Ser Val Thr Val Ser Ser Ala Ser Thr Lys Gly Pro Ser Val Phe Pro
             115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Val Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

Arg Phe Thr Gln Lys Ser Leu Ser Leu Ser Leu Gly Lys
        435                 440                 445

<210> SEQ ID NO 24
<211> LENGTH: 219

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG1 light chain 1

<400> SEQUENCE: 24

Asp Ile Val Met Ser Gln Ser Pro Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr His Thr Phe Gly Thr Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 25
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG1 heavy chain 2

<400> SEQUENCE: 25

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Gly Asp Gly Ser Thr Asp Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Trp Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 26
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: VG1 light chain 2

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Tyr Gly Phe Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG3 heavy chain 1

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Ile Ser Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Pro Ser Pro Gly Thr Gly Tyr Ala Val Asp Tyr Trp Gly Gln
            100                 105                 110

-continued

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn Arg Phe Thr Gln Lys Ser Leu Ser Leu Ser Leu Gly Lys
        435                 440                 445

<210> SEQ ID NO 28
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG3 light chain 1

<400> SEQUENCE: 28

Asp Ile Gln Met Thr Gln Ser Pro Ser Ser Leu Ser Ala Ser Val Gly
1               5                   10                  15

```
Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Phe Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG3 heavy chain 2

<400> SEQUENCE: 29

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Phe Tyr Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Trp Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys
    435                 440                 445

<210> SEQ ID NO 30
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VG3 light chain 2

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
        35                  40                  45
```

```
Lys Leu Leu Ile Tyr Ala Ala Ser Asn Pro Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ile Ile
                 85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5_2 HCDR3

<400> SEQUENCE: 31

Asn Met Gly Met Tyr Thr Ile Asp Phe
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5_3 HCDR3

<400> SEQUENCE: 32

Asn Met Gly Met Tyr Thr Leu Asp Phe
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LP7A5_4 HCDR3

<400> SEQUENCE: 33
```

Asn Tyr Gly Asp Tyr Thr Leu Asp Phe
1               5

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LP7A5_2 Heavy Chain Variable Region

<400> SEQUENCE: 34

Glu Val Gln Leu Gln Gln Ser Gly Ala Glu Leu Ala Arg Pro Gly Ala
1               5                   10                  15

Ser Val Lys Leu Ser Cys Lys Ala Ser Gly Phe Thr Phe Thr Asp His
                20                  25                  30

Tyr Ile Asn Trp Val Lys Gln Arg Thr Gly Gln Gly Leu Glu Trp Ile
            35                  40                  45

Gly Gln Ile Tyr Pro Gly Asp Gly Asn Thr Tyr Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Pro Asn Met Gly Met Tyr Thr Ile Asp Phe Trp Gly Gln Gly Thr
            100                 105                 110

Ser Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LP7A5_3 Heavy Chain Variable Region

<400> SEQUENCE: 35

Glu Val Gln Leu Gln Gln Ser Gly Ala Glu Leu Ala Arg Pro Gly Ala
1               5                   10                  15

Ser Val Lys Leu Ser Cys Lys Ala Ser Gly Phe Thr Phe Thr Asp His
                20                  25                  30

Tyr Ile Asn Trp Val Lys Gln Arg Thr Gly Gln Gly Leu Glu Trp Ile
            35                  40                  45

Gly Gln Ile Tyr Pro Gly Asp Gly Asn Thr Tyr Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Pro Asn Met Gly Met Tyr Thr Leu Asp Phe Trp Gly Gln Gly Thr
            100                 105                 110

Ser Val Thr Val Ser Ser
        115

<210> SEQ ID NO 36

<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: LP7A5_4 Heavy Chain Variable Region

<400> SEQUENCE: 36

Glu Val Gln Leu Gln Gln Ser Gly Ala Glu Leu Ala Arg Pro Gly Ala
1               5                   10                  15

Ser Val Lys Leu Ser Cys Lys Ala Ser Gly Phe Thr Phe Thr Asp His
            20                  25                  30

Tyr Ile Asn Trp Val Lys Gln Arg Thr Gly Gln Gly Leu Glu Trp Ile
        35                  40                  45

Gly Gln Ile Tyr Pro Gly Asp Gly Asn Thr Tyr Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Pro Asn Tyr Gly Asp Tyr Thr Leu Asp Phe Trp Gly Gln Gly Thr
            100                 105                 110

Ser Val Thr Val Ser Ser
        115

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46
<211> LENGTH: 713
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Anti-RSV ('knob'-arm) sequence expressed in CHO
    cells

<400> SEQUENCE: 46

```
Met Ala Trp Val Trp Thr Leu Leu Phe Leu Met Ala Ala Gln Ser
1               5                   10                  15

Ile Gln Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp Tyr Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Asp Tyr
            100                 105                 110

Gly Phe Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Gly Gly Ser Gly Gly Lys
225                 230                 235                 240

Ser Ser Gly Ser Gly Ser Glu Ser Lys Ser Thr Glu Gly Lys Ser Ser
```

-continued

```
                245                 250                 255
Gly Ser Gly Ser Glu Ser Lys Ser Thr Gly Ser Glu Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Ser Trp
    290                 295                 300

Val Arg Gln Met Pro Gly Lys Gly Leu Glu Trp Met Gly Ile Ile Asp
305                 310                 315                 320

Pro Ser Asp Ser Asp Thr Arg Tyr Ser Pro Ser Phe Gln Gly Gln Val
                325                 330                 335

Thr Ile Ser Ala Asp Lys Ser Ile Ser Thr Ala Tyr Leu Gln Trp Ser
            340                 345                 350

Ser Leu Lys Ala Ser Asp Thr Ala Met Tyr Tyr Cys Ala Arg Gly Asp
        355                 360                 365

Gly Ser Thr Asp Leu Asp Tyr Trp Gly Gln Gly Thr Leu Val Thr Val
    370                 375                 380

Ser Ser Ala Ser Thr Lys Gly Pro Ser Val Phe Pro Leu Ala Pro Cys
385                 390                 395                 400

Ser Arg Ser Thr Ser Glu Ser Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
        435                 440                 445

Tyr Ser Leu Ser Ser Val Val Thr Val Pro Ser Ser Ser Leu Gly Thr
    450                 455                 460

Lys Thr Tyr Thr Cys Asn Val Asp His Lys Pro Ser Asn Thr Lys Val
465                 470                 475                 480

Asp Lys Arg Val Glu Ser Lys Tyr Gly Pro Pro Cys Pro Pro Cys Pro
                485                 490                 495

Ala Pro Glu Ala Ala Gly Gly Pro Ser Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser Gln Glu Asp Pro Glu Val Gln Phe Asn Trp Tyr
    530                 535                 540

Val Asp Gly Val Glu Val His Asn Ala Lys Thr Lys Pro Arg Glu Glu
545                 550                 555                 560

Gln Phe Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Gly Leu Pro Ser Ser Ile Glu Lys Thr Ile Ser Lys Ala Lys Gly Gln
        595                 600                 605

Pro Arg Glu Pro Gln Val Tyr Thr Leu Pro Pro Ser Gln Glu Glu Met
    610                 615                 620

Thr Lys Asn Gln Val Ser Leu Trp Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670
```

Tyr Ser Arg Leu Thr Val Asp Lys Ser Arg Trp Gln Glu Gly Asn Val
            675                 680                 685

Phe Ser Cys Ser Val Met His Glu Ala Leu His Asn His Tyr Thr Gln
        690                 695                 700

Lys Ser Leu Ser Leu Ser Leu Gly Lys
705                 710

<210> SEQ ID NO 47
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C33B904 Heavy Chain

<400> SEQUENCE: 47

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Gly Trp Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Pro Tyr Gly Asp Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Trp Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys
            435                 440                 445

<210> SEQ ID NO 48
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C33B904 Light Chain

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Phe Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Val Ser Ser Leu Gln Ala Glu Asp Val Ala Val Tyr Tyr Cys Gln His
            85                  90                  95

Tyr Tyr Ser Thr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

```
Ser Pro Val Thr Lys Ser Phe Asn Arg Gly Glu Cys
    210                 215                 220

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRBC1 Heavy Chain

<400> SEQUENCE: 58
```

-continued

```
Glu Val Arg Leu Gln Gln Ser Gly Pro Asp Leu Ile Lys Pro Gly Ala
1               5                   10                  15

Ser Val Lys Met Ser Cys Lys Ala Ser Gly Tyr Thr Phe Thr Gly Tyr
            20                  25                  30

Val Met His Trp Val Lys Gln Arg Pro Gly Gln Gly Leu Glu Trp Ile
        35                  40                  45

Gly Phe Ile Asn Pro Tyr Asn Asp Asp Ile Gln Ser Asn Glu Arg Phe
    50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Ser
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Val Leu Pro Pro Ser Arg Glu Glu Met Thr Lys Asn
        355                 360                 365

Gln Val Ser Leu Leu Cys Leu Val Lys Gly Phe Tyr Pro Ser Asp Ile
    370                 375                 380

Ala Val Glu Trp Glu Ser Asn Gly Gln Pro Glu Asn Asn Tyr Leu Thr
385                 390                 395                 400

Trp Pro Pro Val Leu Asp Ser Asp Gly Ser Phe Phe Leu Tyr Ser Lys
                405                 410                 415
```

```
Leu Thr Val Asp Lys Ser Arg Trp Gln Gly Asn Val Phe Ser Cys
            420             425             430

Ser Val Met His Glu Ala Leu His Asn Arg Phe Thr Gln Lys Ser Leu
        435             440             445

Ser Leu Ser Pro Gly Lys
    450
```

<210> SEQ ID NO 59
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRBC1 Light Chain

<400> SEQUENCE: 59

```
Asp Val Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TRGV9Ab HCDR1

<400> SEQUENCE: 60

```
Gly Phe Thr Phe Thr Asp His Tyr
1               5
```

```
<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TRGV9Ab HCDR2

<400> SEQUENCE: 61

Ile Tyr Pro Gly Ser Gly Asn Thr
1               5

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TRGV9Ab HCDR3

<400> SEQUENCE: 62

Ala Arg Asn Tyr Gly Asp Tyr Thr Ile Asp Phe
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TRGV9Ab LCDR1

<400> SEQUENCE: 63

Gln Ser Val Leu Tyr Ser Ser Asn Asn Lys Asn Tyr
1               5                   10

<210> SEQ ID NO 64
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TRGV9Ab LCDR2

<400> SEQUENCE: 64

Trp Ala Ser
1

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9Ab_var17 Heavy Chain Variable Region

<400> SEQUENCE: 65

Gln Val Gln Leu Val Gln Ser Gly Ala Glu Val Lys Lys Pro Gly Ala
```

-continued

```
                1               5                  10                 15
            Ser Val Lys Val Ser Cys Lys Ala Ser Gly Phe Thr Phe Thr Asp His
                            20                  25                  30

Tyr Ile Asn Trp Val Arg Gln Ala Thr Gly Gln Gly Leu Glu Trp Met
                        35                  40                  45

Gly Gln Ile Tyr Pro Gly Ser Gly Asn Thr Tyr Tyr Asn Gln Lys Phe
                    50                  55                  60

Lys Gly Arg Val Thr Met Thr Arg Asp Thr Ser Ile Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Asn Tyr Gly Asp Tyr Thr Ile Asp Phe Trp Gly Gln Gly Thr
                            100                 105                 110

Ser Val Thr Val Ser Ser
                        115

<210> SEQ ID NO 66
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9Ab_var17 Light Chain Variable Region

<400> SEQUENCE: 66

Asp Ile Val Met Thr Gln Ser Pro Asp Ser Leu Ala Val Ser Leu Gly
            1               5                  10                 15

Glu Arg Ala Thr Ile Asn Cys Lys Ser Ser Gln Ser Val Leu Tyr Ser
                            20                  25                  30

Ser Asn Asn Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                    50                  55                  60

Pro Asp Arg Phe Ser Gly Ser Gly Ser Gly Thr Asp Phe Thr Leu Thr
            65                  70                  75                  80

Ile Ser Ser Leu Gln Ala Glu Asp Val Ala Val Tyr Tyr Cys Gln Gln
                            85                  90                  95

Tyr Tyr Arg Tyr His Thr Phe Gly Thr Gly Thr Lys Leu Glu Ile Lys
                            100                 105                 110

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9Ab_var29 Heavy Chain Variable Region

<400> SEQUENCE: 67

Gln Val Gln Leu Val Gln Ser Gly Ala Glu Val Lys Lys Pro Gly Ala
            1               5                  10                 15

Ser Val Lys Val Ser Cys Lys Ala Ser Gly Phe Thr Phe Thr Asp His
                            20                  25                  30

Tyr Ile Asn Trp Val Arg Gln Ala Thr Gly Gln Gly Leu Glu Trp Met
                        35                  40                  45
```

Gly Gln Ile Tyr Pro Gly Ser Gly Asn Thr Tyr Tyr Asn Gln Lys Phe
            50                  55                  60

Lys Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Gly Asp Tyr Thr Ile Asp Phe Trp Gly Gln Gly Thr
                100                 105                 110

Ser Val Thr Val Ser Ser
            115

<210> SEQ ID NO 68
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9Ab_var29 Light Chain Variable Region

<400> SEQUENCE: 68

Asp Ile Val Met Thr Gln Ser Pro Asp Ser Leu Ala Val Ser Leu Gly
 1               5                  10                  15

Glu Arg Ala Thr Ile Ser Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Tyr His Thr Phe Gly Thr Gly Thr Lys Leu Glu Ile Lys
                100                 105                 110

<210> SEQ ID NO 69
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_7A5_1 Heavy  Chain

<400> SEQUENCE: 69

Glu Val Gln Leu Gln Gln Ser Gly Ala Glu Leu Ala Arg Pro Gly Ala
 1               5                  10                  15

Ser Val Lys Leu Ser Cys Lys Ala Ser Gly Phe Thr Phe Thr Asp His
                 20                  25                  30

Tyr Ile Asn Trp Val Lys Gln Arg Thr Gly Gln Gly Leu Glu Trp Ile
             35                  40                  45

Gly Gln Ile Tyr Pro Gly Asp Gly Asn Thr Tyr Tyr Asn Gln Lys Phe
            50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Pro Asn Tyr Gly Asp Tyr Thr Ile Asp Phe Trp Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Ser Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Val Tyr
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Ala Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn Arg Phe Thr Gln Lys Ser Leu Ser Leu Ser Pro Gly Lys
            435                 440                 445

<210> SEQ ID NO 70
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_var17 scFv

<400> SEQUENCE: 70

```
Met Ala Trp Val Trp Thr Leu Leu Phe Leu Met Ala Ala Gln Ser
1               5                   10                  15

Ile Gln Ala Asp Ile Val Met Thr Gln Ser Pro Asp Ser Leu Ala Val
                20                  25                  30

Ser Leu Gly Glu Arg Ala Thr Ile Asn Cys Lys Ser Gln Ser Val
            35                  40                  45

Leu Tyr Ser Ser Asn Asn Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
                100                 105                 110

Cys Gln Gln Tyr Tyr Arg Tyr His Thr Phe Gly Thr Gly Thr Lys Leu
            115                 120                 125

Glu Ile Lys Gly Gly Ser Glu Gly Lys Ser Ser Gly Ser Gly Ser Glu
    130                 135                 140

Ser Lys Ser Thr Gly Gly Ser Gln Val Gln Leu Val Gln Ser Gly Ala
145                 150                 155                 160

Glu Val Lys Lys Pro Gly Ala Ser Val Lys Val Ser Cys Lys Ala Ser
                165                 170                 175

Gly Phe Thr Phe Thr Asp His Tyr Ile Asn Trp Val Arg Gln Ala Thr
            180                 185                 190

Gly Gln Gly Leu Glu Trp Met Gly Gln Ile Tyr Pro Gly Ser Gly Asn
    195                 200                 205

Thr Tyr Tyr Asn Gln Lys Phe Lys Gly Arg Val Thr Met Thr Arg Asp
210                 215                 220

Thr Ser Ile Ser Thr Ala Tyr Met Glu Leu Ser Ser Leu Arg Ser Glu
225                 230                 235                 240

Asp Thr Ala Val Tyr Tyr Cys Ala Arg Asn Tyr Gly Asp Tyr Thr Ile
                245                 250                 255

Asp Phe Trp Gly Gln Gly Thr Ser Val Thr Val Ser Ser Glu Pro Lys
            260                 265                 270

Ser Ser Asp Lys Thr His Thr Cys Pro Pro Cys Pro Ala Pro Glu Ala
    275                 280                 285

Ala Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Ser Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
    355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Val Tyr Pro Pro Ser Arg Glu Glu Met Thr Lys Asn Gln
                405                 410                 415
```

```
Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Ala Leu Val Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500

<210> SEQ ID NO 71
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_var17 Heavy Chain

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp His
            20                  25                  30

Tyr Ile Asn Trp Val Arg Gln Ala Thr Gly Gln Gly Leu Glu Trp Met
        35                  40                  45

Gly Gln Ile Tyr Pro Gly Ser Gly Asn Thr Tyr Tyr Asn Gln Lys Phe
50                  55                  60

Lys Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Gly Asp Tyr Thr Ile Asp Phe Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Ser Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Val Tyr
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Ala Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Phe Thr Gln Lys Ser Leu Ser Leu Ser Pro Gly Lys
        435                 440                 445

<210> SEQ ID NO 72
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_var17 Light Chain

<400> SEQUENCE: 72

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Tyr His Thr Phe Gly Thr Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 73
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_var29 scFv

<400> SEQUENCE: 73

Met Ala Trp Val Trp Thr Leu Leu Phe Leu Met Ala Ala Ala Gln Ser
1               5                   10                  15

Ile Gln Ala Asp Ile Val Met Thr Gln Ser Pro Asp Ser Leu Ala Val
            20                  25                  30

Ser Leu Gly Glu Arg Ala Thr Ile Ser Cys Lys Ser Ser Gln Ser Val
            35                  40                  45

Leu Tyr Ser Ser Asn Asn Lys Asn Tyr Leu Ala Trp Tyr Gln Gln Lys
        50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
            85                  90                  95

Thr Leu Thr Ile Ser Ser Leu Gln Ala Glu Asp Val Ala Val Tyr Tyr
            100                 105                 110

Cys Gln Gln Tyr Tyr Arg Tyr His Thr Phe Gly Thr Gly Thr Lys Leu
            115                 120                 125

Glu Ile Lys Gly Gly Ser Glu Gly Lys Ser Ser Gly Ser Gly Ser Glu
            130                 135                 140

Ser Lys Ser Thr Gly Gly Ser Gln Val Gln Leu Val Gln Ser Gly Ala
145                 150                 155                 160

Glu Val Lys Lys Pro Gly Ala Ser Val Lys Val Ser Cys Lys Ala Ser
            165                 170                 175

Gly Phe Thr Phe Thr Asp His Tyr Ile Asn Trp Val Arg Gln Ala Thr
            180                 185                 190

Gly Gln Gly Leu Glu Trp Met Gly Gln Ile Tyr Pro Gly Ser Gly Asn
            195                 200                 205

Thr Tyr Tyr Asn Gln Lys Phe Lys Gly Arg Val Thr Met Thr Arg Asn
            210                 215                 220

Thr Ser Ile Ser Thr Ala Tyr Met Glu Leu Ser Ser Leu Arg Ser Glu
225                 230                 235                 240

Asp Thr Ala Val Tyr Tyr Cys Ala Arg Asn Tyr Gly Asp Tyr Thr Ile
            245                 250                 255

Asp Phe Trp Gly Gln Gly Thr Ser Val Thr Val Ser Ser Glu Pro Lys
            260                 265                 270

Ser Ser Asp Lys Thr His Thr Cys Pro Pro Cys Pro Ala Pro Glu Ala
            275                 280                 285

Ala Gly Gly Pro Ser Val Phe Leu Phe Pro Pro Lys Pro Lys Asp Thr
            290                 295                 300

Leu Met Ile Ser Arg Thr Pro Glu Val Thr Cys Val Val Val Ser Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Val Tyr Pro Pro Ser Arg Glu Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Ala Leu Val Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500

<210> SEQ ID NO 74
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_var29 Heavy Chain

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp His
            20                  25                  30

Tyr Ile Asn Trp Val Arg Gln Ala Thr Gly Gln Gly Leu Glu Trp Met
        35                  40                  45

Gly Gln Ile Tyr Pro Gly Ser Gly Asn Thr Tyr Tyr Asn Gln Lys Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Gly Asp Tyr Thr Ile Asp Phe Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ser Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Val Tyr
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Ala Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Phe Thr Gln Lys Ser Leu Ser Leu Ser Pro Gly Lys
        435                 440                 445

<210> SEQ ID NO 75
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TRGV9_var29 Light Chain

<400> SEQUENCE: 75

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Val Leu Tyr Ser
            20                  25                  30

-continued

```
Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Tyr His Thr Phe Gly Gly Thr Lys Leu Glu Ile Lys
                100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: TRGV9Ab HCDR2

<400> SEQUENCE: 76

```
Gln Ile Tyr Pro Gly Ser Gly Asn Thr Tyr Tyr Asn Gln Lys Phe Lys
1               5                   10                  15

Gly
```

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide
<220> FEATURE:
<223> OTHER INFORMATION: TRGV9Ab LCDR1

<400> SEQUENCE: 77

```
Lys Ser Ser Gln Ser Val Leu Tyr Ser Ser Asn Lys Asn Tyr Leu
1               5                   10                  15

Ala
```

<210> SEQ ID NO 78
<211> LENGTH: 467
<212> TYPE: PRT
<213> ORGANISM: Artificial Sequence
<220> FEATURE:
<223> OTHER INFORMATION: Description of Artificial Sequence: Synthetic

```
           polypeptide
<220> FEATURE:
<223> OTHER INFORMATION: Anti-TRGV9_7A5_1 (half-mAb) Heavy Chain A

<400> SEQUENCE: 78

Met Ala Trp Val Trp Thr Leu Leu Phe Leu Met Ala Ala Ala Gln Ser
1               5                   10                  15

Ile Gln Ala Glu Val Gln Leu Gln Gln Ser Gly Ala Glu Leu Ala Arg
            20                  25                  30

Pro Gly Ala Ser Val Lys Leu Ser Cys Lys Ala Ser Gly Phe Thr Phe
        35                  40                  45

Thr Asp His Tyr Ile Asn Trp Val Lys Gln Arg Thr Gly Gln Gly Leu
    50                  55                  60

Glu Trp Ile Gly Gln Ile Tyr Pro Gly Asp Gly Asn Thr Tyr Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Pro Asn Tyr Gly Asp Tyr Thr Ile Asp Phe Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Ser Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Val Tyr Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
```

```
                385                 390                 395                 400
Trp Glu Ser Asn Gly Gln Pro Glu Asn Tyr Lys Thr Thr Pro Pro
                405                 410                 415

Val Leu Asp Ser Asp Gly Ser Phe Ala Leu Val Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn Arg Phe Thr Gln Lys Ser Leu Ser Leu Ser
                450                 455                 460

Pro Gly Lys
465

<210> SEQ ID NO 79
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-TRGV9_7A5_1 (half-mAb) Light Chain

<400> SEQUENCE: 79

Met Ala Trp Val Trp Thr Leu Leu Phe Leu Met Ala Ala Ala Gln Ser
1               5                   10                  15

Ile Gln Ala Asp Ile Val Met Ser Gln Ser Pro Ser Ser Leu Ala Val
                20                  25                  30

Ser Val Gly Glu Lys Val Thr Met Ser Cys Lys Ser Ser Gln Ser Leu
            35                  40                  45

Leu Tyr Ser Ser Asn Gln Lys Asn Tyr Leu Ala Trp Tyr Gln Gln Lys
        50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Lys Ala Glu Asp Leu Ala Val Tyr Tyr
                100                 105                 110

Cys Gln Gln Tyr Tyr Arg Tyr His Thr Phe Gly Thr Gly Thr Lys Leu
                115                 120                 125

Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 80
<211> LENGTH: 467
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti- TRGV9_7A5_var17 Heavy Chain A

<400> SEQUENCE: 80

Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Thr Asp His Tyr Ile Asn Trp Val Arg Gln Ala Thr Gly Gln Gly Leu
    50                  55                  60

Glu Trp Met Gly Gln Ile Tyr Pro Gly Ser Gly Asn Thr Tyr Tyr Asn
65                  70                  75                  80

Gln Lys Phe Lys Gly Arg Val Thr Met Thr Arg Asp Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg Asn Tyr Gly Asp Tyr Thr Ile Asp Phe Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Ala Ala Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Ser Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Val Tyr Pro Pro Ser Arg Glu Glu Met Thr Lys Asn Gln Val Ser
```

```
                370                 375                 380
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Ala Leu Val Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn Arg Phe Thr Gln Lys Ser Leu Ser Leu Ser
                450                 455                 460

Pro Gly Lys
465

<210> SEQ ID NO 81
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti- TRGV9_7A5_var17 Light Chain

<400> SEQUENCE: 81

Met Ala Trp Val Trp Thr Leu Leu Phe Leu Met Ala Ala Ala Gln Ser
1               5                   10                  15

Ile Gln Ala Asp Ile Val Met Thr Gln Ser Pro Asp Ser Leu Ala Val
                20                  25                  30

Ser Leu Gly Glu Arg Ala Thr Ile Asn Cys Lys Ser Ser Gln Ser Val
            35                  40                  45

Leu Tyr Ser Ser Asn Asn Lys Asn Tyr Leu Ala Trp Tyr Gln Gln Lys
        50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
                100                 105                 110

Cys Gln Gln Tyr Tyr Arg Tyr His Thr Phe Gly Thr Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235
```

<210> SEQ ID NO 82
<211> LENGTH: 467
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: Anti- TRGV9_7A5_var29 Heavy Chain A

<400> SEQUENCE: 82

```
Met Ala Trp Val Trp Thr Leu Leu Phe Leu Met Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Thr Asp His Tyr Ile Asn Trp Val Arg Gln Ala Thr Gly Gln Gly Leu
    50                  55                  60

Glu Trp Met Gly Gln Ile Tyr Pro Gly Ser Gly Asn Thr Tyr Tyr Asn
65                  70                  75                  80

Gln Lys Phe Lys Gly Arg Val Thr Met Thr Arg Asn Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg Asn Tyr Gly Asp Tyr Thr Ile Asp Phe Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Ala Ala Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Ser Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
```

```
              355                 360                 365
Tyr Val Tyr Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Ala Leu Val Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn Arg Phe Thr Gln Lys Ser Leu Ser Leu Ser
    450                 455                 460

Pro Gly Lys
465

<210> SEQ ID NO 83
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti- TRGV9_7A5_var29 Light Chain

<400> SEQUENCE: 83

Met Ala Trp Val Trp Thr Leu Leu Phe Leu Met Ala Ala Ala Gln Ser
1               5                   10                  15

Ile Gln Ala Asp Ile Val Met Thr Gln Ser Pro Asp Ser Leu Ala Val
            20                  25                  30

Ser Leu Gly Glu Arg Ala Thr Ile Ser Cys Lys Ser Ser Gln Ser Val
        35                  40                  45

Leu Tyr Ser Ser Asn Asn Lys Asn Tyr Leu Ala Trp Tyr Gln Gln Lys
    50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110

Cys Gln Gln Tyr Tyr Arg Tyr His Thr Phe Gly Thr Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
```

<210> SEQ ID NO 84
<211> LENGTH: 473
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Anti-TRBC1 (half-mAb) Heavy Chain B

<400> SEQUENCE: 84

```
Met Ala Trp Val Trp Thr Leu Leu Phe Leu Met Ala Ala Ala Gln Ser
1               5                   10                  15

Ile Gln Ala Glu Val Arg Leu Gln Gln Ser Gly Pro Asp Leu Ile Lys
            20                  25                  30

Pro Gly Ala Ser Val Lys Met Ser Cys Lys Ala Ser Gly Tyr Thr Phe
        35                  40                  45

Thr Gly Tyr Val Met His Trp Val Lys Gln Arg Pro Gly Gln Gly Leu
    50                  55                  60

Glu Trp Ile Gly Phe Ile Asn Pro Tyr Asn Asp Asp Ile Gln Ser Asn
65                  70                  75                  80

Glu Arg Phe Arg Gly Lys Ala Thr Leu Thr Ser Asp Lys Ser Ser Thr
                85                  90                  95

Thr Ala Tyr Met Glu Leu Ser Ser Leu Thr Ser Glu Asp Ser Ala Val
            100                 105                 110

Tyr Tyr Cys Ala Arg Gly Ala Gly Tyr Asn Phe Asp Gly Ala Tyr Arg
        115                 120                 125

Phe Phe Asp Phe Trp Gly Gln Gly Thr Thr Leu Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Ser Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
```

```
                340                 345                 350
Ala Leu Pro Ala Pro Ile Glu Lys Thr Ile Ser Lys Ala Lys Gly Gln
            355                 360                 365

Pro Arg Glu Pro Gln Val Tyr Val Leu Pro Pro Ser Arg Glu Glu Met
        370                 375                 380

Thr Lys Asn Gln Val Ser Leu Leu Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Leu Thr Trp Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn Arg Phe Thr Gln
    450                 455                 460

Lys Ser Leu Ser Leu Ser Pro Gly Lys
465                 470

<210> SEQ ID NO 85
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-TRBC1 (half-mAb) Light Chain

<400> SEQUENCE: 85

Met Ala Trp Val Trp Thr Leu Leu Phe Leu Met Ala Ala Ala Gln Ser
1               5                   10                  15

Ile Gln Ala Asp Val Val Met Thr Gln Ser Pro Leu Ser Leu Pro Val
            20                  25                  30

Ser Leu Gly Asp Gln Ala Ser Ile Ser Cys Arg Ser Ser Gln Arg Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Arg Val Ser Asn Arg Phe Pro
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Phe Cys
            100                 105                 110

Ser Gln Ser Thr His Val Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
```

-continued

```
            210                 215                 220
Leu Ser Ser Pro Val Thr Lys Ser Phe Asn Arg Gly Glu Cys
225                 230                 235

<210> SEQ ID NO 86
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-RSV (half-mAb) Heavy Chain B

<400> SEQUENCE: 86

Met Ala Trp Val Trp Thr Leu Leu Phe Leu Met Ala Ala Ala Gln Ser
1               5                   10                  15

Ile Gln Ala Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Gly Val Ser Trp Ile Arg Gln Pro Pro Gly Lys
    50                  55                  60

Ala Leu Glu Trp Leu Ala His Ile Tyr Trp Asp Asp Lys Arg Tyr
65                  70                  75                  80

Asn Pro Ser Leu Lys Ser Arg Leu Thr Ile Thr Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Leu Tyr Gly Phe Thr Tyr Gly Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Ser Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
```

325                 330                 335
Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Val Leu Pro Pro Ser Arg Glu Glu Met Thr Lys Asn Gln
        370                 375                 380

Val Ser Leu Leu Cys Leu Val Lys Gly Phe Tyr Pro Ser Asp Ile Ala
385                 390                 395                 400

Val Glu Trp Glu Ser Asn Gly Gln Pro Glu Asn Asn Tyr Leu Thr Trp
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 87
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-RSV (half-mAb) Light Chain

<400> SEQUENCE: 87

Met Glu Thr His Ser Gln Val Phe Val Tyr Met Leu Leu Trp Leu Ser
1               5                   10                  15

Gly Val Glu Gly Asp Ile Val Met Thr Gln Ser Pro Asp Ser Leu Ala
            20                  25                  30

Val Ser Leu Gly Glu Arg Ala Thr Ile Asn Cys Arg Ala Ser Gln Ser
        35                  40                  45

Val Asp Tyr Asn Gly Ile Ser Tyr Met His Trp Tyr Gln Gln Lys Pro
    50                  55                  60

Gly Gln Pro Pro Lys Leu Leu Ile Tyr Ala Ala Ser Asn Pro Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ile Ile Glu Asp Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala

```
            195                 200                 205
Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 88
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-Null-scFv Heavy Chain B

<400> SEQUENCE: 88

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Ile
        35                  40                  45

Ser Ser Tyr Leu Asn Trp Tyr Gln Gln Lys Pro Gly Cys Ala Pro Lys
    50                  55                  60

Leu Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Ser
            100                 105                 110

Thr Pro Leu Thr Phe Gly Gln Gly Thr Lys Val Glu Ile Lys Gly Gly
        115                 120                 125

Gly Ser Gly Gly Ser Gly Gly Cys Pro Pro Cys Gly Gly Ser Gly Gly
    130                 135                 140

Glu Val Gln Leu Leu Glu Ser Gly Gly Gly Leu Val Gln Pro Gly Gly
145                 150                 155                 160

Ser Leu Arg Leu Ser Cys Ala Ala Ser Gly Phe Thr Phe Ser Ser Tyr
                165                 170                 175

Ala Met Ser Trp Val Arg Gln Ala Pro Gly Lys Gly Leu Glu Trp Val
            180                 185                 190

Ser Ala Ile Ser Gly Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Ala Lys Tyr Asp Gly Ile Tyr Gly Glu Leu Asp Phe Trp Gly Cys Gly
                245                 250                 255

Thr Leu Val Thr Val Ser Ser Glu Pro Lys Ser Ser Asp Lys Thr His
            260                 265                 270

Thr Cys Pro Pro Cys Pro Ala Pro Glu Ala Ala Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Ser Val Ser His Glu Asp Pro Glu
```

```
              305                 310                 315                 320
Val Lys Phe Asn Trp Tyr Val Asp Gly Val Glu Val His Asn Ala Lys
                    325                 330                 335

Thr Lys Pro Arg Glu Glu Gln Tyr Asn Ser Thr Tyr Arg Val Val Ser
                340                 345                 350

Val Leu Thr Val Leu His Gln Asp Trp Leu Asn Gly Lys Glu Tyr Lys
            355                 360                 365

Cys Lys Val Ser Asn Lys Ala Leu Pro Ala Pro Ile Glu Lys Thr Ile
        370                 375                 380

Ser Lys Ala Lys Gly Gln Pro Arg Glu Pro Gln Val Tyr Val Leu Pro
385                 390                 395                 400

Pro Ser Arg Glu Glu Met Thr Lys Asn Gln Val Ser Leu Leu Cys Leu
                405                 410                 415

Val Lys Gly Phe Tyr Pro Ser Asp Ile Ala Val Glu Trp Glu Ser Asn
                420                 425                 430

Gly Gln Pro Glu Asn Asn Tyr Leu Thr Trp Pro Pro Val Leu Asp Ser
            435                 440                 445

Asp Gly Ser Phe Phe Leu Tyr Ser Lys Leu Thr Val Asp Lys Ser Arg
        450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Phe Thr Phe Ser Ser Asn Tyr
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile His Gly Gly Thr Gly Gly Ile
1               5

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Arg Gly Tyr Gly Ala Trp Phe Ala Tyr
1               5                   10

<210> SEQ ID NO 92
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Asn Ile His Asn Tyr
1               5

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asn Ala Lys
1

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln His Phe Trp Ser Tyr Pro Leu Thr
1               5

<210> SEQ ID NO 95
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Asn
            20                  25                  30

Tyr Ile Ser Trp Leu Lys Gln Lys Pro Gly Gln Ser Leu Glu Trp Ile
        35                  40                  45

Ala Trp Ile His Gly Gly Thr Gly Gly Ile Gly Tyr Asn Gln Lys Phe
    50                  55                  60

Thr Gly Lys Ala Gln Leu Thr Val Asp Thr Ser Ser Thr Thr Ala Tyr
65                  70                  75                  80

Met Gln Phe Ser Ser Leu Thr Thr Glu Asp Ser Ala Ile Tyr Tyr Cys
                85                  90                  95

Ala Arg Arg Gly Tyr Gly Ala Trp Phe Ala Tyr Trp Gly Gln Gly Thr
            100                 105                 110

Leu Val Thr Val Ser Ala
        115

<210> SEQ ID NO 96
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Asn Tyr Tyr Cys Gln His Phe Trp Ser Tyr Pro Leu
                85                  90                  95

Thr Phe Gly Ala Gly Thr Lys Leu Glu Leu Lys
            100                 105

<210> SEQ ID NO 97
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Ala Trp Val Trp Thr Leu Leu Phe Leu Met Ala Ala Ala Gln Ser
1               5                   10                  15

Ile Gln Ala Asp Ile Gln Met Thr Gln Ser Pro Ala Ser Leu Ser Ala
            20                  25                  30

Ser Val Gly Glu Thr Val Thr Ile Thr Cys Arg Ala Ser Glu Asn Ile
        35                  40                  45

His Asn Tyr Leu Ala Trp Tyr Gln Gln Lys Gln Gly Lys Ser Pro Gln
    50                  55                  60

Leu Leu Val Tyr Asn Ala Lys Thr Leu Ala Asp Gly Val Pro Ser Arg
65                  70                  75                  80

Phe Ser Gly Ser Gly Ser Gly Thr Gln Tyr Ser Leu Lys Ile Asn Ser
                85                  90                  95

Leu Gln Pro Glu Asp Phe Gly Asn Tyr Tyr Cys Gln His Phe Trp Ser
            100                 105                 110

Tyr Pro Leu Thr Phe Gly Ala Gly Thr Lys Leu Glu Leu Lys Gly Gly
        115                 120                 125

Ser Glu Gly Lys Ser Ser Gly Ser Gly Ser Glu Ser Lys Ser Thr Gly
    130                 135                 140

Gly Ser Gln Gly Gln Met Gln Gln Ser Gly Ala Glu Leu Val Lys Pro
145                 150                 155                 160

Gly Ala Ser Val Lys Leu Ser Cys Lys Thr Ser Gly Phe Thr Phe Ser
                165                 170                 175

Ser Asn Tyr Ile Ser Trp Leu Lys Gln Lys Pro Gly Gln Ser Leu Glu
            180                 185                 190

Trp Ile Ala Trp Ile His Gly Gly Thr Gly Gly Ile Gly Tyr Asn Gln
        195                 200                 205

Lys Phe Thr Gly Lys Ala Gln Leu Thr Val Asp Thr Ser Ser Thr Thr

```
            210                 215                 220
Ala Tyr Met Gln Phe Ser Ser Leu Thr Thr Glu Asp Ser Ala Ile Tyr
225                 230                 235                 240

Tyr Cys Ala Arg Arg Gly Tyr Gly Ala Trp Phe Ala Tyr Trp Gly Gln
                245                 250                 255

Gly Thr Leu Val Thr Val Ser Ala Glu Pro Lys Ser Ser Asp Lys Thr
                260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Ser Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Val Tyr
385                 390                 395                 400

Pro Pro Ser Arg Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Tyr Lys Thr Thr Pro Pro Val Leu Asp
            435                 440                 445

Ser Asp Gly Ser Phe Ala Leu Val Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Thr Phe Ser Asn Tyr Asp
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Ser Ser Ser Ser Ser Tyr Ile
```

```
<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Arg Asp Val Gly Val Thr Asp Tyr Tyr Tyr Gly Met Asp Val
1               5                   10                  15

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Ser Val Ala Ser Ser Tyr
1               5

<210> SEQ ID NO 102
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Ala Ser
1

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Gln Tyr Gly Ser Ser Pro Pro Tyr Thr
1               5                   10

<210> SEQ ID NO 104
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Thr Phe Ser Asn Tyr
            20                  25                  30

Asp Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr His Cys
                 85                  90                  95

Ala Arg Asp Val Gly Val Thr Thr Asp Tyr Tyr Tyr Gly Met Asp
                100                 105                 110

Val Trp Gly Gln Gly Thr Met Val Thr Val Ser Ser
            115                 120

<210> SEQ ID NO 105
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Ile Val Met Thr Gln Ser Pro Gly Thr Leu Ser Leu Ser Pro Gly
 1               5                  10                  15

Asp Arg Ala Thr Leu Ser Cys Arg Ala Ser Gln Ser Val Ala Ser Ser
             20                  25                  30

Tyr Leu Ala Trp Tyr Gln Gln Lys Pro Gly Gln Ser Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Tyr Thr Phe Gly Gln Gly Thr Arg Leu Glu Ile Lys
            100                 105

<210> SEQ ID NO 106
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Ala Trp Val Trp Thr Leu Leu Phe Leu Met Ala Ala Ala Gln Ser
 1               5                  10                  15

Ile Gln Ala Glu Ile Val Met Thr Gln Ser Pro Gly Thr Leu Ser Leu
             20                  25                  30

Ser Pro Gly Asp Arg Ala Thr Leu Ser Cys Arg Ala Ser Gln Ser Val
         35                  40                  45

Ala Ser Ser Tyr Leu Ala Trp Tyr Gln Gln Lys Pro Gly Gln Ser Pro
 50                  55                  60

Arg Leu Leu Ile Tyr Gly Ala Ser Ser Arg Ala Thr Gly Ile Pro Asp
 65                  70                  75                  80

Arg Phe Ser Gly Ser Gly Ser Gly Thr Asp Phe Thr Leu Thr Ile Ser
                 85                  90                  95

Arg Leu Glu Pro Glu Asp Phe Ala Val Tyr Tyr Cys Gln Gln Tyr Gly
                100                 105                 110

Ser Ser Pro Pro Tyr Thr Phe Gly Gln Gly Thr Arg Leu Glu Ile Lys
```

```
                115                 120                 125
Gly Gly Ser Glu Gly Lys Ser Ser Gly Ser Glu Ser Lys Ser
            130                 135                 140
Thr Gly Gly Ser Glu Val Gln Leu Val Glu Ser Gly Gly Leu Val
145                 150                 155                 160
Lys Pro Gly Gly Ser Leu Arg Leu Ser Cys Ser Ala Ser Gly Phe Thr
                165                 170                 175
Phe Ser Asn Tyr Asp Met Asn Trp Val Arg Gln Ala Pro Gly Lys Gly
            180                 185                 190
Leu Glu Trp Val Ser Ser Ile Ser Ser Ser Ser Tyr Ile Tyr Tyr
            195                 200                 205
Ala Asp Ser Val Lys Gly Arg Phe Thr Ile Ser Arg Asp Asn Ala Lys
            210                 215                 220
Asn Ser Leu Tyr Leu Gln Met Asn Ser Leu Arg Ala Glu Asp Thr Ala
225                 230                 235                 240
Val Tyr His Cys Ala Arg Asp Val Gly Val Thr Thr Asp Tyr Tyr
                245                 250                 255
Tyr Gly Met Asp Val Trp Gly Gln Gly Thr Met Val Thr Val Ser Ser
            260                 265                 270
Glu Pro Lys Ser Ser Asp Lys Thr His Thr Cys Pro Pro Cys Pro Ala
            275                 280                 285
Pro Glu Ala Ala Gly Gly Pro Ser Val Phe Leu Phe Pro Pro Lys Pro
            290                 295                 300
Lys Asp Thr Leu Met Ile Ser Arg Thr Pro Glu Val Thr Cys Val Val
305                 310                 315                 320
Val Ser Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
            340                 345                 350
Tyr Asn Ser Thr Tyr Arg Val Val Ser Val Leu Thr Val Leu His Gln
            355                 360                 365
Asp Trp Leu Asn Gly Lys Glu Tyr Lys Cys Lys Val Ser Asn Lys Ala
370                 375                 380
Leu Pro Ala Pro Ile Glu Lys Thr Ile Ser Lys Ala Lys Gly Gln Pro
385                 390                 395                 400
Arg Glu Pro Gln Val Tyr Val Tyr Pro Pro Ser Arg Glu Glu Met Thr
                405                 410                 415
Lys Asn Gln Val Ser Leu Thr Cys Leu Val Lys Gly Phe Tyr Pro Ser
            420                 425                 430
Asp Ile Ala Val Glu Trp Glu Ser Asn Gly Gln Pro Glu Asn Asn Tyr
            435                 440                 445
Lys Thr Thr Pro Pro Val Leu Asp Ser Asp Gly Ser Phe Ala Leu Val
            450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly Lys
            500

<210> SEQ ID NO 107
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 107

Gly Asp Thr Phe Asn Asn Tyr Ala
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Ile Pro Phe Phe Gly Thr Pro
1               5

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Arg Pro Gly Ser Gly Ser Pro Asp Tyr Tyr Tyr Tyr Asp Met Asp
1               5                   10                  15

Val

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ser Leu Val His Ser Asp Gly Asn Thr Tyr
1               5                   10

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Ile Ser
1

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Gln Ala Thr Gln Phe Pro Leu Thr
```

<210> SEQ ID NO 113
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Asn Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Pro Asp Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Pro Gly Ser Gly Ser Pro Asp Tyr Tyr Tyr Tyr Asp Met Asp
            100                 105                 110

Val Trp Gly Gln Gly Thr Thr Val Thr Val Ser Ser
        115                 120

<210> SEQ ID NO 114
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Asn Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110

<210> SEQ ID NO 115
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

-continued

```
Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Asn Asn Tyr
            20                  25                  30

Ala Ile Ser Trp Val Arg Gln Ala Pro Gly Gln Gly Leu Glu Trp Met
        35                  40                  45

Gly Gly Ile Ile Pro Phe Phe Gly Thr Pro Asp Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Gly Leu Arg Ser Glu Asp Thr Ala Val Tyr Tyr Cys
            85                  90                  95

Ala Arg Pro Gly Ser Gly Ser Pro Asp Tyr Tyr Tyr Asp Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Ser
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Val Tyr Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Ala Leu Val Ser Lys
            405                 410                 415
```

```
Leu Thr Val Asp Lys Ser Arg Trp Gln Gln Gly Asn Val Phe Ser Cys
            420                 425                 430

Ser Val Met His Glu Ala Leu His Asn Arg Phe Thr Gln Lys Ser Leu
            435                 440                 445

Ser Leu Ser Pro Gly Lys
            450
```

<210> SEQ ID NO 116
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Asn Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Gly Gly Thr Phe Ser Ser Tyr Ala
1               5
```

<210> SEQ ID NO 118
<211> LENGTH: 8

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asn Ile Pro Ile Phe Asn Thr Ala
1               5

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Val Arg Glu Gly Thr Gly Tyr Ser Tyr Gly Leu Asp Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Ser Leu Ile His Ser Asp Gly Asn Thr Tyr
1               5                   10

<210> SEQ ID NO 121
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Ile Ser
1

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Met Gln Ala Lys Gln Phe Pro Ile Thr
1               5

<210> SEQ ID NO 123
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Gln Ser Gly Ala Glu Val Lys Lys Pro Gly Ser
```

```
                1               5                  10                 15
Ser Val Lys Val Ser Cys Lys Ala Ser Gly Gly Thr Phe Ser Ser Tyr
            20                  25                 30

Ala Ile Ser Trp Val Arg Gln Ala Pro Gly Gln Gly Leu Glu Trp Met
            35                  40                 45

Gly Gly Asn Ile Pro Ile Phe Asn Thr Ala Asn Tyr Ala Gln Lys Phe
            50                  55                 60

Gln Asp Arg Val Thr Ile Thr Ala Asp Lys Ser Thr Ser Thr Ala Tyr
65                  70                  75                 80

Met Glu Leu Ser Ser Leu Arg Ser Glu Asp Thr Ala Val Tyr Tyr Cys
            85                  90                 95

Val Arg Glu Gly Thr Gly Tyr Ser Tyr Gly Leu Asp Tyr Trp Gly Gln
            100                 105                110

Gly Thr Pro Val Thr Val Ser Ser
            115                 120
```

<210> SEQ ID NO 124
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 124

```
Glu Ile Val Met Thr Gln Ser Pro Leu Ser Ser Pro Val Thr Leu Gly
1               5                   10                 15

Gln Pro Ala Ser Ile Ser Cys Arg Ser Ser Gln Ser Leu Ile His Ser
            20                  25                 30

Asp Gly Asn Thr Tyr Leu Ser Trp Leu Gln Gln Arg Pro Gly Gln Pro
            35                  40                 45

Pro Arg Leu Leu Ile Tyr Lys Ile Ser Asn Arg Phe Ser Gly Val Pro
            50                  55                 60

Asp Arg Phe Ser Gly Ser Gly Ala Gly Thr Asp Phe Thr Leu Lys Ile
65                  70                  75                 80

Ser Arg Val Glu Ala Glu Asp Val Gly Ile Tyr Tyr Cys Met Gln Ala
            85                  90                 95

Lys Gln Phe Pro Ile Thr Phe Gly Gln Gly Thr Lys Val Asp Ile Lys
            100                 105                110
```

<210> SEQ ID NO 125
<211> LENGTH: 441
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 125

```
Glu Val Gln Leu Val Gln Ser Gly Ala Glu Val Lys Lys Pro Gly Ser
1               5                   10                 15

Ser Val Lys Val Ser Cys Lys Ala Ser Gly Gly Thr Phe Ser Ser Tyr
            20                  25                 30

Ala Ile Ser Trp Val Arg Gln Ala Pro Gly Gln Gly Leu Glu Trp Met
            35                  40                 45

Gly Gly Asn Ile Pro Ile Phe Asn Thr Ala Asn Tyr Ala Gln Lys Phe
            50                  55                 60

Gln Asp Arg Val Thr Ile Thr Ala Asp Lys Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Val Arg Glu Gly Thr Gly Tyr Ser Tyr Gly Leu Asp Tyr Trp Gly Gln
                100                 105                 110

Gly Thr Pro Val Thr Val Ser Ser Ala Ser Thr Lys Gly Pro Ser Val
                115                 120                 125

Thr Ser Gly Gly Thr Ala Ala Leu Gly Cys Leu Val Lys Asp Tyr Phe
            130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Leu Gly Thr Gln Thr Tyr
                180                 185                 190

Ile Cys Asn Val Asn His Lys Pro Ser Asn Thr Lys Val Asp Lys Lys
            195                 200                 205

Val Glu Pro Lys Ser Cys Asp Lys Thr His Thr Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Ser Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
            275                 280                 285

Gln Tyr Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Val Tyr Pro Pro Ser Arg Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Ala Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn Arg Phe Thr Gln
                420                 425                 430

Lys Ser Leu Ser Leu Ser Pro Gly Lys
            435                 440

<210> SEQ ID NO 126
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 126

Glu Ile Val Met Thr Gln Ser Pro Leu Ser Pro Val Thr Leu Gly
1               5                   10                  15

Gln Pro Ala Ser Ile Ser Cys Arg Ser Ser Gln Ser Leu Ile His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Lys Gln Phe Pro Ile Thr Phe Gly Gln Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Ser Ile Ser Ser Gly Gly Ser Tyr
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Tyr Asn Ser Gly Ser Thr
1               5

<210> SEQ ID NO 129
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 129

Ala Arg Asp Ser Asn Tyr Glu Trp Phe Phe Asp Leu
1               5                   10

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Ser Val Ser Ser Tyr
1               5

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Ala Ser
1

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Gln Arg Ser Asn Trp Pro Leu Thr
1               5

<210> SEQ ID NO 133
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Ser Tyr Trp Ser Trp Ile Arg Gln His Pro Gly Lys Gly Leu Glu
            35                  40                  45

Trp Ile Gly Tyr Ile Tyr Asn Ser Gly Ser Thr Tyr Tyr Asn Pro Ser
        50                  55                  60

Leu Lys Ser Arg Val Ser Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Asn Tyr Glu Trp Phe Phe Asp Leu Trp Gly Pro
                100                 105                 110

Gly Thr Leu Val Thr Val Ser Ser
        115                 120

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 135
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Ser Tyr Trp Ser Trp Ile Arg Gln His Pro Gly Lys Gly Leu Glu
        35                  40                  45

Trp Ile Gly Tyr Ile Tyr Asn Ser Gly Ser Thr Tyr Tyr Asn Pro Ser
    50                  55                  60

Leu Lys Ser Arg Val Ser Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Asn Tyr Glu Trp Phe Phe Asp Leu Trp Gly Pro
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Val Tyr Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
        435                 440                 445

Gly Lys
    450

<210> SEQ ID NO 136
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 136

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

-continued

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Met Ala Trp Val Trp Thr Leu Leu Phe Leu Met Ala Ala Ala Gln Ser
1               5                   10                  15

Ile Gln Ala Glu Val Gln Leu Val Gln Ser Gly Ala Glu Val Lys Lys
            20                  25                  30

Pro Gly Ser Ser Val Lys Val Ser Cys Lys Ala Ser Gly Asp Thr Phe
        35                  40                  45

Asn Asn Tyr Ala Ile Ser Trp Val Arg Gln Ala Pro Gly Gln Gly Leu
    50                  55                  60

Glu Trp Met Gly Gly Ile Ile Pro Phe Phe Gly Thr Pro Asp Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Gly Leu Arg Ser Glu Asp Thr Ala Val
            100                 105                 110

Tyr Tyr Cys Ala Arg Pro Gly Ser Gly Ser Pro Asp Tyr Tyr Tyr Tyr
        115                 120                 125

Asp Met Asp Val Trp Gly Gln Gly Thr Thr Val Thr Val Ser Ser Ala
```

```
            130                 135                 140
Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Ala Ala Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Ser Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Val Tyr Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Ala Leu
            420                 425                 430

Val Ser Lys Leu Thr Val Asp Lys Ser Arg Trp Gln Gln Gly Asn Val
        435                 440                 445

Phe Ser Cys Ser Val Met His Glu Ala Leu His Asn Arg Phe Thr Gln
    450                 455                 460

Lys Ser Leu Ser Leu Ser Pro Gly Lys
465                 470

<210> SEQ ID NO 151
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Ala Trp Val Trp Thr Leu Leu Phe Leu Met Ala Ala Ala Gln Ser
1               5                   10                  15
```

```
Ile Gln Ala Asp Ile Val Met Thr Gln Thr Pro Leu Ser Ser Pro Val
            20                  25                  30

Thr Leu Gly Gln Pro Ala Ser Ile Ser Cys Arg Ser Ser Gln Ser Leu
        35                  40                  45

Val His Ser Asp Gly Asn Thr Tyr Leu Ser Trp Leu Gln Gln Arg Pro
 50                  55                  60

Gly Gln Pro Pro Arg Leu Leu Ile Tyr Lys Ile Ser Asn Arg Phe Ser
 65                  70                  75                  80

Gly Val Pro Asp Arg Phe Ser Gly Ser Gly Ala Gly Thr Asp Phe Thr
                85                  90                  95

Leu Lys Ile Asn Arg Val Glu Ala Glu Asp Val Gly Val Tyr Tyr Cys
            100                 105                 110

Met Gln Ala Thr Gln Phe Pro Leu Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 152
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Ala Trp Val Trp Thr Leu Leu Phe Leu Met Ala Ala Ala Gln Ser
1               5                   10                  15

Ile Gln Ala Glu Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Asn Ile Pro Ile Phe Asn Thr Ala Asn Tyr Ala
65                  70                  75                  80

Gln Lys Phe Gln Asp Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Val Arg Glu Gly Thr Gly Tyr Ser Tyr Gly Leu Asp Tyr
        115                 120                 125

Trp Gly Gln Gly Thr Pro Val Thr Val Ser Ser Ala Ser Thr Lys Gly
    130                 135                 140
```

```
Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Ser Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Val Tyr Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Ala Leu Val Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn Arg Phe Thr Gln Lys Ser Leu Ser
450                 455                 460

Leu Ser Pro Gly Lys
465

<210> SEQ ID NO 153
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Ala Trp Val Trp Thr Leu Leu Phe Leu Met Ala Ala Ala Gln Ser
1               5                   10                  15

Ile Gln Ala Glu Ile Val Met Thr Gln Ser Pro Leu Ser Ser Pro Val
```

```
                    20                  25                  30
Thr Leu Gly Gln Pro Ala Ser Ile Ser Cys Arg Ser Ser Gln Ser Leu
                35                  40                  45
Ile His Ser Asp Gly Asn Thr Tyr Leu Ser Trp Leu Gln Gln Arg Pro
            50                  55                  60
Gly Gln Pro Pro Arg Leu Leu Ile Tyr Lys Ile Ser Asn Arg Phe Ser
 65                 70                  75                  80
Gly Val Pro Asp Arg Phe Ser Gly Ser Gly Ala Gly Thr Asp Phe Thr
                    85                  90                  95
Leu Lys Ile Ser Arg Val Glu Ala Glu Asp Val Gly Ile Tyr Tyr Cys
                100                 105                 110
Met Gln Ala Lys Gln Phe Pro Ile Thr Phe Gly Gln Gly Thr Lys Val
            115                 120                 125
Asp Ile Lys Arg Thr Val Ala Ala Pro Ser Val Phe Ile Phe Pro Pro
        130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys
225                 230                 235

<210> SEQ ID NO 154
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Ala Trp Val Trp Thr Leu Leu Phe Leu Met Ala Ala Ala Gln Ser
 1               5                  10                  15
Ile Gln Ala Gln Val Gln Leu Gln Glu Ser Gly Pro Gly Leu Val Lys
                20                  25                  30
Pro Ser Gln Thr Leu Ser Leu Thr Cys Thr Val Ser Gly Gly Ser Ile
            35                  40                  45
Ser Ser Gly Gly Ser Tyr Trp Ser Trp Ile Arg Gln His Pro Gly Lys
        50                  55                  60
Gly Leu Glu Trp Ile Gly Tyr Ile Tyr Asn Ser Gly Ser Thr Tyr Tyr
 65                 70                  75                  80
Asn Pro Ser Leu Lys Ser Arg Val Ser Met Ser Val Asp Thr Ser Lys
                85                  90                  95
Asn Gln Phe Ser Leu Lys Leu Ser Ser Val Thr Ala Ala Asp Thr Ala
            100                 105                 110
Val Tyr Tyr Cys Ala Arg Asp Ser Asn Tyr Glu Trp Phe Phe Asp Leu
        115                 120                 125
Trp Gly Pro Gly Thr Leu Val Thr Val Ser Ser Ala Ser Thr Lys Gly
    130                 135                 140
```

```
Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
    195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Ser Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Val Tyr Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Ala Leu Val Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn Arg Phe Thr Gln Lys Ser Leu Ser
    450                 455                 460

Leu Ser Pro Gly Lys
465

<210> SEQ ID NO 155
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Ala Trp Val Trp Thr Leu Leu Phe Leu Met Ala Ala Ala Gln Ser
1               5                   10                  15

Ile Gln Ala Glu Ile Val Met Thr Gln Ser Pro Ala Thr Leu Ser Leu
            20                  25                  30
```

```
Ser Pro Gly Glu Arg Ala Thr Leu Ser Cys Arg Ala Ser Gln Ser Val
        35                  40                  45

Ser Ser Tyr Leu Ala Trp Tyr Gln Gln Lys Pro Gly Gln Ala Pro Arg
 50                  55                  60

Leu Leu Ile Tyr Asp Ala Ser Asn Arg Ala Thr Gly Ile Pro Ala Arg
 65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Leu Thr Phe Gly Gly Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 156
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Ala Trp Val Trp Thr Leu Leu Phe Leu Met Ala Ala Ala Gln Ser
1               5                   10                  15

Ile Gln Ala Ala Gly His Leu Glu Gln Pro Gln Ile Ser Ser Thr Lys
            20                  25                  30

Thr Leu Ser Lys Thr Ala Arg Leu Glu Cys Val Val Ser Gly Ile Thr
        35                  40                  45

Ile Ser Ala Thr Ser Val Tyr Trp Tyr Arg Glu Arg Pro Gly Glu Val
 50                  55                  60

Ile Gln Phe Leu Val Ser Ile Ser Tyr Asp Gly Thr Val Arg Lys Glu
65                  70                  75                  80

Ser Gly Ile Pro Ser Gly Lys Phe Glu Val Asp Arg Ile Pro Glu Thr
                85                  90                  95

Ser Thr Ser Thr Leu Thr Ile His Asn Val Glu Lys Gln Asp Ile Ala
            100                 105                 110

Thr Tyr Tyr Cys Ala Leu Trp Glu Ala Gln Gln Glu Leu Gly Lys Lys
            115                 120                 125

Ile Lys Val Phe Gly Pro Gly Thr Lys Leu Ile Ile Thr Asp Lys Gln
        130                 135                 140

Leu Asp Ala Asp Val Ser Pro Lys Pro Thr Ile Phe Leu Pro Ser Ile
```

```
            145                 150                 155                 160
Ala Glu Thr Lys Leu Gln Lys Ala Gly Thr Tyr Leu Cys Leu Leu Glu
                165                 170                 175

Lys Phe Phe Pro Asp Val Ile Lys Ile His Trp Glu Lys Lys Ser
            180                 185                 190

Asn Thr Ile Leu Gly Ser Gln Glu Gly Asn Thr Met Lys Thr Asn Asp
                195                 200                 205

Thr Tyr Met Lys Phe Ser Trp Leu Thr Val Pro Glu Lys Ser Leu Asp
        210                 215                 220

Lys Glu His Arg Cys Ile Val Arg His Glu Asn Asn Lys Asn Gly Val
225                 230                 235                 240

Asp Gln Glu Ile Ile Phe Pro Pro Ile Lys Thr Asp Val Ile Thr Met
                245                 250                 255

Asp Pro Lys Asp Asn Glu Pro Lys Ser Cys Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
370                 375                 380

Ala Lys Gly Gln Pro Arg Glu Pro Gln Val Tyr Val Tyr Pro Pro Ser
385                 390                 395                 400

Arg Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Ala Leu Val Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 157
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Ala Trp Val Trp Thr Leu Leu Phe Leu Met Ala Ala Ala Gln Ser
1               5                   10                  15
```

```
Ile Gln Ala Ala Ile Glu Leu Val Pro Glu His Gln Thr Val Pro Val
         20                  25                  30

Ser Ile Gly Val Pro Ala Thr Leu Arg Cys Ser Met Lys Gly Glu Ala
         35                  40                  45

Ile Gly Asn Tyr Tyr Ile Asn Trp Tyr Arg Lys Thr Gln Gly Asn Thr
         50                  55                  60

Met Thr Phe Ile Tyr Arg Glu Lys Asp Ile Tyr Gly Pro Gly Phe Lys
65                       70                  75                  80

Asp Asn Phe Gln Gly Asp Ile Asp Ile Ala Lys Asn Leu Ala Val Leu
                 85                  90                  95

Lys Ile Leu Ala Pro Ser Glu Arg Asp Glu Gly Ser Tyr Tyr Cys Ala
             100                 105                 110

Cys Asp Thr Leu Gly Met Gly Gly Glu Tyr Thr Asp Lys Leu Ile Phe
             115                 120                 125

Gly Lys Gly Thr Arg Val Thr Val Glu Pro Arg Ser Gln Pro His Thr
             130                 135                 140

Lys Pro Ser Val Phe Val Met Lys Asn Gly Thr Asn Val Ala Cys Leu
145                 150                 155                 160

Val Lys Glu Phe Tyr Pro Lys Asp Ile Arg Ile Asn Leu Val Ser Ser
                 165                 170                 175

Lys Lys Ile Thr Glu Phe Asp Pro Ala Ile Val Ile Ser Pro Ser Gly
             180                 185                 190

Lys Tyr Asn Ala Val Lys Leu Gly Lys Tyr Glu Asp Ser Asn Ser Val
             195                 200                 205

Thr Cys Ser Val Gln His Asp Asn Lys Thr Val His Ser Thr Asp Phe
210                 215                 220

Glu Val Lys Thr Asp Ser Thr Asp His Val Lys Pro Lys Glu Thr Glu
225                 230                 235                 240

Asn Thr Lys Gln Pro Ser Lys Ser Glu Pro Lys Ser Cys Asp Lys Thr
                 245                 250                 255

His Thr Cys Pro Pro Cys Pro Ala Pro Glu Leu Leu Gly Gly Pro Ser
             260                 265                 270

Val Phe Leu Phe Pro Pro Lys Pro Lys Asp Thr Leu Met Ile Ser Arg
             275                 280                 285

Thr Pro Glu Val Thr Cys Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
             325                 330                 335

Ser Val Leu Thr Val Leu His Gln Asp Trp Leu Asn Gly Lys Glu Tyr
             340                 345                 350

Lys Cys Lys Val Ser Asn Lys Ala Leu Pro Ala Pro Ile Glu Lys Thr
             355                 360                 365

Ile Ser Lys Ala Lys Gly Gln Pro Arg Glu Pro Gln Val Tyr Val Leu
             370                 375                 380

Pro Pro Ser Arg Glu Glu Met Thr Lys Asn Gln Val Ser Leu Leu Cys
385                 390                 395                 400

Leu Val Lys Gly Phe Tyr Pro Ser Asp Ile Ala Val Glu Trp Glu Ser
                 405                 410                 415

Asn Gly Gln Pro Glu Asn Asn Tyr Leu Thr Trp Pro Pro Val Leu Asp
             420                 425                 430

Ser Asp Gly Ser Phe Phe Leu Tyr Ser Lys Leu Thr Val Asp Lys Ser
```

```
                    435                 440                 445
Arg Trp Gln Gln Gly Asn Val Phe Ser Cys Ser Val Met His Glu Ala
            450                 455                 460

Leu His Asn His Tyr Thr Gln Lys Ser Leu Ser Leu Ser Pro Gly Lys
465                 470                 475                 480

<210> SEQ ID NO 158

<400> SEQUENCE: 158

000

<210> SEQ ID NO 159

<400> SEQUENCE: 159

000

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Phe Thr Phe Thr Asp His Tyr Ile Asn
1               5                   10

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Ile Tyr Pro Gly Asp Gly Asn Thr Tyr Tyr Asn Gln Lys Phe Lys
1               5                   10                  15
Gly

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asn Tyr Gly Asp Tyr Thr Ile Asp Phe
1               5

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Lys Ser Ser Gln Ser Leu Leu Tyr Ser Ser Asn Gln Lys Asn Tyr Leu
1               5                   10                  15
```

Ala

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Trp Ala Ser Thr Arg Glu Ser
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Gln Tyr Tyr Arg Tyr His Thr
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Phe Thr Phe Thr Asp His Tyr
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ile Tyr Pro Gly Asp Gly Asn Thr
1               5

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Pro Asn Tyr Gly Asp Tyr Thr Ile Asp Phe
1               5                   10

<210> SEQ ID NO 169
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 169

Gln Ser Leu Leu Tyr Ser Ser Asn Gln Lys Asn Tyr
1               5                   10

<210> SEQ ID NO 170
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Trp Ala Ser
1

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Gln Tyr Tyr Arg Tyr His Thr
1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asp His Tyr Ile Asn
1               5

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Ile Tyr Pro Gly Asp Gly Asn Thr Tyr Tyr Asn Gln Lys Phe Lys
1               5                   10                  15

Gly

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asn Tyr Gly Asp Tyr Thr Ile Asp Phe
1               5

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Ser Ser Gln Ser Leu Leu Tyr Ser Ser Asn Gln Lys Asn Tyr Leu
1               5                   10                  15

Ala

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Ala Ser Thr Arg Glu Ser
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Gln Tyr Tyr Arg Tyr His Thr
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Phe Thr Phe Thr Asp His
1               5

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Pro Gly Asp Gly
1

<210> SEQ ID NO 180
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 180

Tyr Gly Asp Tyr Thr Ile Asp
1               5

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Gln Ser Leu Leu Tyr Ser Ser Asn Gln Lys Asn Tyr
1               5                   10

<210> SEQ ID NO 182
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Trp Ala Ser
1

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Tyr Tyr Arg Tyr His
1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Asp His Tyr Ile Asn
1               5

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Trp Ile Gly Gln Ile Tyr Pro Gly Asp Gly Asn Thr Tyr
1               5                   10

-continued

```
<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Pro Asn Tyr Gly Asp Tyr Thr Ile Asp
1               5                   10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Leu Tyr Ser Ser Asn Gln Lys Asn Tyr Leu Ala Trp Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Leu Leu Ile Tyr Trp Ala Ser Thr Arg Glu
1               5                   10

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Gln Tyr Tyr Arg Tyr His
1               5

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Thr Phe Thr Asp His Tyr Ile Asn
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191
```

Gln Ile Tyr Pro Gly Asp Gly Asn Thr Tyr
1               5                   10

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asn Tyr Gly Asp Tyr Thr Ile Asp Phe
1               5

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Lys Ser Ser Gln Ser Leu Leu Tyr Ser Ser Asn Gln Lys Asn Tyr Leu
1               5                   10                  15
Ala

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Ala Ser Thr Arg Glu Ser
1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Gln Tyr Tyr Arg Tyr His Thr
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Phe Thr Phe Thr Asp His Tyr Ile Asn
1               5                   10

<210> SEQ ID NO 197
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Ile Tyr Pro Gly Asp Gly Asn Thr Tyr Tyr Asn Gln Lys Phe Lys
1               5                   10                  15
Gly

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Asn Met Gly Met Tyr Thr Ile Asp Phe
1               5

<210> SEQ ID NO 199
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Lys Ser Ser Gln Ser Leu Leu Tyr Ser Asn Gln Lys Asn Tyr Leu
1               5                   10                  15
Ala

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Trp Ala Ser Thr Arg Glu Ser
1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gln Gln Tyr Tyr Arg Tyr His Thr
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 202

Gly Phe Thr Phe Thr Asp His Tyr
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ile Tyr Pro Gly Asp Gly Asn Thr
1               5

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Pro Asn Met Gly Met Tyr Thr Ile Asp Phe
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln Ser Leu Leu Tyr Ser Ser Asn Gln Lys Asn Tyr
1               5                   10

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Ala Ser
1

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Gln Tyr Tyr Arg Tyr His Thr
1               5

<210> SEQ ID NO 208
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asp His Tyr Ile Asn
1               5

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gln Ile Tyr Pro Gly Asp Gly Asn Thr Tyr Tyr Asn Gln Lys Phe Lys
1               5                   10                  15

Gly

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asn Met Gly Met Tyr Thr Ile Asp Phe
1               5

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Lys Ser Ser Gln Ser Leu Leu Tyr Ser Ser Asn Gln Lys Asn Tyr Leu
1               5                   10                  15

Ala

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Trp Ala Ser Thr Arg Glu Ser
1               5

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 213

Gln Gln Tyr Tyr Arg Tyr His Thr
1               5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Phe Thr Phe Thr Asp His
1               5

<210> SEQ ID NO 215
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Pro Gly Asp Gly
1

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Met Gly Met Tyr Thr Ile Asp
1               5

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Gln Ser Leu Leu Tyr Ser Ser Asn Gln Lys Asn Tyr
1               5                   10

<210> SEQ ID NO 218
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Trp Ala Ser
1

<210> SEQ ID NO 219
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Tyr Tyr Arg Tyr His
1               5

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Asp His Tyr Ile Asn
1               5

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Trp Ile Gly Gln Ile Tyr Pro Gly Asp Gly Asn Thr Tyr
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Pro Asn Met Gly Met Tyr Thr Ile Asp
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Leu Tyr Ser Ser Asn Gln Lys Asn Tyr Leu Ala Trp Tyr
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Leu Leu Ile Tyr Trp Ala Ser Thr Arg Glu
```

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gln Gln Tyr Tyr Arg Tyr His
1               5

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Phe Thr Phe Thr Asp His Tyr Ile Asn
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gln Ile Tyr Pro Gly Asp Gly Asn Thr Tyr
1               5                   10

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Asn Met Gly Met Tyr Thr Ile Asp Phe
1               5

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Lys Ser Ser Gln Ser Leu Leu Tyr Ser Ser Asn Gln Lys Asn Tyr Leu
1               5                   10                  15

Ala

<210> SEQ ID NO 230
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 230

Trp Ala Ser Thr Arg Glu Ser
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Gln Gln Tyr Tyr Arg Tyr His Thr
1               5

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gly Phe Thr Phe Thr Asp His Tyr Ile Asn
1               5                   10

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gln Ile Tyr Pro Gly Asp Gly Asn Thr Tyr Tyr Asn Gln Lys Phe Lys
1               5                   10                  15

Gly

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asn Met Gly Met Tyr Thr Leu Asp Phe
1               5

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Lys Ser Ser Gln Ser Leu Leu Tyr Ser Ser Asn Gln Lys Asn Tyr Leu
```

```
1               5                   10                  15

Ala

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Trp Ala Ser Thr Arg Glu Ser
1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gln Gln Tyr Tyr Arg Tyr His Thr
1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Phe Thr Phe Thr Asp His Tyr
1               5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ile Tyr Pro Gly Asp Gly Asn Thr
1               5

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ala Pro Asn Met Gly Met Tyr Thr Leu Asp Phe
1               5                   10

<210> SEQ ID NO 241
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 241

Gln Ser Leu Leu Tyr Ser Ser Asn Gln Lys Asn Tyr
1               5                   10

<210> SEQ ID NO 242
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Trp Ala Ser
1

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gln Gln Tyr Tyr Arg Tyr His Thr
1               5

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asp His Tyr Ile Asn
1               5

<210> SEQ ID NO 245
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Ile Tyr Pro Gly Asp Gly Asn Thr Tyr Tyr Asn Gln Lys Phe Lys
1               5                   10                  15

Gly

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Asn Met Gly Met Tyr Thr Leu Asp Phe
```

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Lys Ser Ser Gln Ser Leu Leu Tyr Ser Ser Asn Gln Lys Asn Tyr Leu
1               5                   10                  15

Ala

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Ala Ser Thr Arg Glu Ser
1               5

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Tyr Tyr Arg Tyr His Thr
1               5

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Phe Thr Phe Thr Asp His
1               5

<210> SEQ ID NO 251
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Pro Gly Asp Gly
1

<210> SEQ ID NO 252
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 252

Met Gly Met Tyr Thr Leu Asp
1               5

<210> SEQ ID NO 253
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ser Gln Ser Leu Leu Tyr Ser Ser Asn Gln Lys Asn Tyr
1               5                   10

<210> SEQ ID NO 254
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Ala Ser
1

<210> SEQ ID NO 255
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Tyr Tyr Arg Tyr His
1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Thr Asp His Tyr Ile Asn
1               5

<210> SEQ ID NO 257
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Trp Ile Gly Gln Ile Tyr Pro Gly Asp Gly Asn Thr Tyr
1               5                   10
```

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Pro Asn Met Gly Met Tyr Thr Leu Asp
1               5                   10

<210> SEQ ID NO 259
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Leu Tyr Ser Ser Asn Gln Lys Asn Tyr Leu Ala Trp Tyr
1               5                   10

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Leu Leu Ile Tyr Trp Ala Ser Thr Arg Glu
1               5                   10

<210> SEQ ID NO 261
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Gln Tyr Tyr Arg Tyr His
1               5

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Phe Thr Phe Thr Asp His Tyr Ile Asn
1               5                   10

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 263

Gln Ile Tyr Pro Gly Asp Gly Asn Thr Tyr
1               5                   10

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asn Met Gly Met Tyr Thr Leu Asp Phe
1               5

<210> SEQ ID NO 265
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Lys Ser Ser Gln Ser Leu Leu Tyr Ser Ser Asn Gln Lys Asn Tyr Leu
1               5                   10                  15

Ala

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Trp Ala Ser Thr Arg Glu Ser
1               5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gln Gln Tyr Tyr Arg Tyr His Thr
1               5

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Phe Thr Phe Thr Asp His Tyr Ile Asn
1               5                   10

<210> SEQ ID NO 269
```

-continued

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gln Ile Tyr Pro Gly Asp Gly Asn Thr Tyr Tyr Asn Gln Lys Phe Lys
1               5                   10                  15

Gly

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asn Tyr Gly Asp Tyr Thr Leu Asp Phe
1               5

<210> SEQ ID NO 271
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Lys Ser Ser Gln Ser Leu Leu Tyr Ser Ser Asn Gln Lys Asn Tyr Leu
1               5                   10                  15

Ala

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Trp Ala Ser Thr Arg Glu Ser
1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Gln Tyr Tyr Arg Tyr His Thr
1               5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 274

Gly Phe Thr Phe Thr Asp His Tyr
1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ile Tyr Pro Gly Asp Gly Asn Thr
1               5

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ala Pro Asn Tyr Gly Asp Tyr Thr Leu Asp Phe
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gln Ser Leu Leu Tyr Ser Ser Asn Gln Lys Asn Tyr
1               5                   10

<210> SEQ ID NO 278
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Trp Ala Ser
1

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Gln Tyr Tyr Arg Tyr His Thr
1               5

<210> SEQ ID NO 280

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Asp His Tyr Ile Asn
1               5

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Ile Tyr Pro Gly Asp Gly Asn Thr Tyr Tyr Asn Gln Lys Phe Lys
1               5                   10                  15

Gly

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asn Tyr Gly Asp Tyr Thr Leu Asp Phe
1               5

<210> SEQ ID NO 283
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Lys Ser Ser Gln Ser Leu Leu Tyr Ser Ser Asn Gln Lys Asn Tyr Leu
1               5                   10                  15

Ala

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Trp Ala Ser Thr Arg Glu Ser
1               5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 285

Gln Gln Tyr Tyr Arg Tyr His Thr
1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Phe Thr Phe Thr Asp His
1               5

<210> SEQ ID NO 287
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Pro Gly Asp Gly
1

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Tyr Gly Asp Tyr Thr Leu Asp
1               5

<210> SEQ ID NO 289
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ser Gln Ser Leu Leu Tyr Ser Ser Asn Gln Lys Asn Tyr
1               5                   10

<210> SEQ ID NO 290
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Trp Ala Ser
1

<210> SEQ ID NO 291

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Tyr Tyr Arg Tyr His
1               5

<210> SEQ ID NO 292
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Thr Asp His Tyr Ile Asn
1               5

<210> SEQ ID NO 293
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Trp Ile Gly Gln Ile Tyr Pro Gly Asp Gly Asn Thr Tyr
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Pro Asn Tyr Gly Asp Tyr Thr Leu Asp
1               5                   10

<210> SEQ ID NO 295
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Leu Tyr Ser Ser Asn Gln Lys Asn Tyr Leu Ala Trp Tyr
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296
```

```
Leu Leu Ile Tyr Trp Ala Ser Thr Arg Glu
1               5                   10

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gln Gln Tyr Tyr Arg Tyr His
1               5

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Phe Thr Phe Thr Asp His Tyr Ile Asn
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gln Ile Tyr Pro Gly Asp Gly Asn Thr Tyr
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Asn Tyr Gly Asp Tyr Thr Leu Asp Phe
1               5

<210> SEQ ID NO 301
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Lys Ser Ser Gln Ser Leu Leu Tyr Ser Ser Asn Gln Lys Asn Tyr Leu
1               5                   10                  15

Ala

<210> SEQ ID NO 302
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 302

Trp Ala Ser Thr Arg Glu Ser
1               5

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gln Gln Tyr Tyr Arg Tyr His Thr
1               5

<210> SEQ ID NO 304
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Phe Thr Phe Thr Asp His Tyr Ile Asn
1               5                   10

<210> SEQ ID NO 305
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gln Ile Tyr Pro Gly Ser Gly Asn Thr Tyr Tyr Asn Gln Lys Phe Lys
1               5                   10                  15

Gly

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Asn Tyr Gly Asp Tyr Thr Ile Asp Phe
1               5

<210> SEQ ID NO 307
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307
```

```
Lys Ser Ser Gln Ser Val Leu Tyr Ser Ser Asn Asn Lys Asn Tyr Leu
1               5                   10                  15
Ala

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Trp Ala Ser Thr Arg Glu Ser
1               5

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Gln Tyr Tyr Arg Tyr His Thr
1               5

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Phe Thr Phe Thr Asp His Tyr
1               5

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ile Tyr Pro Gly Ser Gly Asn Thr
1               5

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ala Arg Asn Tyr Gly Asp Tyr Thr Ile Asp Phe
1               5                   10

<210> SEQ ID NO 313
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 313

Gln Ser Val Leu Tyr Ser Ser Asn Asn Lys Asn Tyr
1               5                   10

<210> SEQ ID NO 314
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Trp Ala Ser
1

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Gln Tyr Tyr Arg Tyr His Thr
1               5

<210> SEQ ID NO 316
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Asp His Tyr Ile Asn
1               5

<210> SEQ ID NO 317
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Ile Tyr Pro Gly Ser Gly Asn Thr Tyr Tyr Asn Gln Lys Phe Lys
1               5                   10                  15

Gly

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318
```

```
Asn Tyr Gly Asp Tyr Thr Ile Asp Phe
1               5
```

```
<210> SEQ ID NO 319
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Lys Ser Ser Gln Ser Val Leu Tyr Ser Ser Asn Asn Lys Asn Tyr Leu
1               5                   10                  15

Ala
```

```
<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Trp Ala Ser Thr Arg Glu Ser
1               5
```

```
<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Gln Tyr Tyr Arg Tyr His Thr
1               5
```

```
<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Phe Thr Phe Thr Asp His
1               5
```

```
<210> SEQ ID NO 323
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Pro Gly Ser Gly
1
```

```
<210> SEQ ID NO 324
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 324

Tyr Gly Asp Tyr Thr Ile Asp
1               5

<210> SEQ ID NO 325
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ser Gln Ser Val Leu Tyr Ser Ser Asn Asn Lys Asn Tyr
1               5                   10

<210> SEQ ID NO 326
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Trp Ala Ser
1

<210> SEQ ID NO 327
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Tyr Tyr Arg Tyr His
1               5

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Thr Asp His Tyr Ile Asn
1               5

<210> SEQ ID NO 329
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Trp Met Gly Gln Ile Tyr Pro Gly Ser Gly Asn Thr Tyr
1               5                   10

<210> SEQ ID NO 330
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ala Arg Asn Tyr Gly Asp Tyr Thr Ile Asp
1               5                   10

<210> SEQ ID NO 331
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Leu Tyr Ser Ser Asn Asn Lys Asn Tyr Leu Ala Trp Tyr
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Leu Leu Ile Tyr Trp Ala Ser Thr Arg Glu
1               5                   10

<210> SEQ ID NO 333
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gln Gln Tyr Tyr Arg Tyr His
1               5

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gly Phe Thr Phe Thr Asp His Tyr Ile Asn
1               5                   10

<210> SEQ ID NO 335
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gln Ile Tyr Pro Gly Ser Gly Asn Thr Tyr
1               5                   10

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Asn Tyr Gly Asp Tyr Thr Ile Asp Phe
1               5

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Lys Ser Ser Gln Ser Val Leu Tyr Ser Ser Asn Asn Lys Asn Tyr Leu
1               5                   10                  15

Ala

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Trp Ala Ser Thr Arg Glu Ser
1               5

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gln Gln Tyr Tyr Arg Tyr His Thr
1               5

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Phe Thr Phe Thr Asp His Tyr Ile Asn
1               5                   10

```
<210> SEQ ID NO 341
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gln Ile Tyr Pro Gly Ser Gly Asn Thr Tyr Tyr Asn Gln Lys Phe Lys
1               5                   10                  15

Gly

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asn Tyr Gly Asp Tyr Thr Ile Asp Phe
1               5

<210> SEQ ID NO 343
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Lys Ser Ser Gln Ser Val Leu Tyr Ser Ser Asn Asn Lys Asn Tyr Leu
1               5                   10                  15

Ala

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Trp Ala Ser Thr Arg Glu Ser
1               5

<210> SEQ ID NO 345
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gln Gln Tyr Tyr Arg Tyr His Thr
1               5

<210> SEQ ID NO 346
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 346

Gly Phe Thr Phe Thr Asp His Tyr
1               5

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ile Tyr Pro Gly Ser Gly Asn Thr
1               5

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ala Arg Asn Tyr Gly Asp Tyr Thr Ile Asp Phe
1               5                   10

<210> SEQ ID NO 349
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gln Ser Val Leu Tyr Ser Ser Asn Asn Lys Asn Tyr
1               5                   10

<210> SEQ ID NO 350
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Trp Ala Ser
1

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Gln Tyr Tyr Arg Tyr His Thr
1               5
```

```
<210> SEQ ID NO 352
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asp His Tyr Ile Asn
1               5

<210> SEQ ID NO 353
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Gln Ile Tyr Pro Gly Ser Gly Asn Thr Tyr Tyr Asn Gln Lys Phe Lys
1               5                   10                  15

Gly

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asn Tyr Gly Asp Tyr Thr Ile Asp Phe
1               5

<210> SEQ ID NO 355
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Lys Ser Ser Gln Ser Val Leu Tyr Ser Ser Asn Asn Lys Asn Tyr Leu
1               5                   10                  15

Ala

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Trp Ala Ser Thr Arg Glu Ser
1               5

<210> SEQ ID NO 357
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 357

Gln Gln Tyr Tyr Arg Tyr His Thr
1               5

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Phe Thr Phe Thr Asp His
1               5

<210> SEQ ID NO 359
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Pro Gly Ser Gly
1

<210> SEQ ID NO 360
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Tyr Gly Asp Tyr Thr Ile Asp
1               5

<210> SEQ ID NO 361
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ser Gln Ser Val Leu Tyr Ser Ser Asn Asn Lys Asn Tyr
1               5                   10

<210> SEQ ID NO 362
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Trp Ala Ser
1
```

```
<210> SEQ ID NO 363
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Tyr Tyr Arg Tyr His
1               5

<210> SEQ ID NO 364
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Thr Asp His Tyr Ile Asn
1               5

<210> SEQ ID NO 365
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Trp Met Gly Gln Ile Tyr Pro Gly Ser Gly Asn Thr Tyr
1               5                   10

<210> SEQ ID NO 366
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ala Arg Asn Tyr Gly Asp Tyr Thr Ile Asp
1               5                   10

<210> SEQ ID NO 367
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Leu Tyr Ser Ser Asn Asn Lys Asn Tyr Leu Ala Trp Tyr
1               5                   10

<210> SEQ ID NO 368
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368
```

Leu Leu Ile Tyr Trp Ala Ser Thr Arg Glu
1               5                   10

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gln Gln Tyr Tyr Arg Tyr His
1               5

<210> SEQ ID NO 370
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Phe Thr Phe Thr Asp His Tyr Ile Asn
1               5                   10

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gln Ile Tyr Pro Gly Ser Gly Asn Thr Tyr
1               5                   10

<210> SEQ ID NO 372
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Asn Tyr Gly Asp Tyr Thr Ile Asp Phe
1               5

<210> SEQ ID NO 373
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Lys Ser Ser Gln Ser Val Leu Tyr Ser Ser Asn Asn Lys Asn Tyr Leu
1               5                   10                  15

Ala

<210> SEQ ID NO 374
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Trp Ala Ser Thr Arg Glu Ser
1               5

<210> SEQ ID NO 375
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gln Gln Tyr Tyr Arg Tyr His Thr
1               5

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Phe Thr Phe Ser Ser Asn Tyr Ile Ser
1               5                   10

<210> SEQ ID NO 377
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Trp Ile His Gly Gly Thr Gly Gly Ile Gly Tyr Asn Gln Lys Phe Thr
1               5                   10                  15

Gly

<210> SEQ ID NO 378
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Arg Gly Tyr Gly Ala Trp Phe Ala Tyr
1               5

<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379
```

Arg Ala Ser Glu Asn Ile His Asn Tyr Leu Ala
1               5                   10

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Asn Ala Lys Thr Leu Ala Asp
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gln His Phe Trp Ser Tyr Pro Leu Thr
1               5

<210> SEQ ID NO 382
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gly Phe Thr Phe Ser Ser Asn Tyr
1               5

<210> SEQ ID NO 383
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ile His Gly Gly Thr Gly Gly Ile
1               5

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Ala Arg Arg Gly Tyr Gly Ala Trp Phe Ala Tyr
1               5                   10

<210> SEQ ID NO 385
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 385

Glu Asn Ile His Asn Tyr
1               5

<210> SEQ ID NO 386
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Asn Ala Lys
1

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln His Phe Trp Ser Tyr Pro Leu Thr
1               5

<210> SEQ ID NO 388
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ser Asn Tyr Ile Ser
1               5

<210> SEQ ID NO 389
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Trp Ile His Gly Gly Thr Gly Gly Ile Gly Tyr Asn Gln Lys Phe Thr
1               5                   10                  15

Gly

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Gly Tyr Gly Ala Trp Phe Ala Tyr
```

```
1               5
```

<210> SEQ ID NO 391
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

```
Arg Ala Ser Glu Asn Ile His Asn Tyr Leu Ala
1               5                   10
```

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

```
Asn Ala Lys Thr Leu Ala Asp
1               5
```

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

```
Gln His Phe Trp Ser Tyr Pro Leu Thr
1               5
```

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

```
Gly Phe Thr Phe Ser Ser Asn
1               5
```

<210> SEQ ID NO 395
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

```
Gly Gly Thr Gly
1
```

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 396

Gly Tyr Gly Ala Trp Phe Ala
1               5

<210> SEQ ID NO 397
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Ser Glu Asn Ile His Asn Tyr
1               5

<210> SEQ ID NO 398
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asn Ala Lys
1

<210> SEQ ID NO 399
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Phe Trp Ser Tyr Pro Leu
1               5

<210> SEQ ID NO 400
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ser Ser Asn Tyr Ile Ser
1               5

<210> SEQ ID NO 401
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Trp Ile Ala Trp Ile His Gly Gly Thr Gly Gly Ile Gly
1               5                   10

<210> SEQ ID NO 402
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Ala Arg Arg Gly Tyr Gly Ala Trp Phe Ala
1               5                   10

<210> SEQ ID NO 403
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

His Asn Tyr Leu Ala Trp Tyr
1               5

<210> SEQ ID NO 404
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Leu Leu Val Tyr Asn Ala Lys Thr Leu Ala
1               5                   10

<210> SEQ ID NO 405
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gln His Phe Trp Ser Tyr Pro Leu
1               5

<210> SEQ ID NO 406
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gly Phe Thr Phe Ser Ser Asn Tyr Ile Ser
1               5                   10

<210> SEQ ID NO 407
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407
```

```
Trp Ile His Gly Gly Thr Gly Gly Ile Gly
1               5                   10

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Arg Gly Tyr Gly Ala Trp Phe Ala Tyr
1               5

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Arg Ala Ser Glu Asn Ile His Asn Tyr Leu Ala
1               5                   10

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Asn Ala Lys Thr Leu Ala Asp
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gln His Phe Trp Ser Tyr Pro Leu Thr
1               5

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Phe Thr Phe Ser Asn Tyr Asp Met Asn
1               5                   10

<210> SEQ ID NO 413
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 413

Ser Ile Ser Ser Ser Ser Tyr Ile Tyr Tyr Ala Asp Ser Val Lys
1               5                   10                  15

Gly

<210> SEQ ID NO 414
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Asp Val Gly Val Thr Thr Asp Tyr Tyr Tyr Tyr Gly Met Asp Val
1               5                   10                  15

<210> SEQ ID NO 415
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Arg Ala Ser Gln Ser Val Ala Ser Ser Tyr Leu Ala
1               5                   10

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Ala Ser Ser Arg Ala Thr
1               5

<210> SEQ ID NO 417
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gln Gln Tyr Gly Ser Ser Pro Pro Tyr Thr
1               5                   10

<210> SEQ ID NO 418
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gly Phe Thr Phe Ser Asn Tyr Asp
1               5
```

```
<210> SEQ ID NO 419
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Ile Ser Ser Ser Ser Ser Tyr Ile
1               5

<210> SEQ ID NO 420
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ala Arg Asp Val Gly Val Thr Thr Asp Tyr Tyr Tyr Gly Met Asp
1               5                   10                  15

Val

<210> SEQ ID NO 421
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gln Ser Val Ala Ser Ser Tyr
1               5

<210> SEQ ID NO 422
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gly Ala Ser
1

<210> SEQ ID NO 423
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gln Gln Tyr Gly Ser Ser Pro Pro Tyr Thr
1               5                   10

<210> SEQ ID NO 424
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 424

Asn Tyr Asp Met Asn
1               5

<210> SEQ ID NO 425
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ser Ile Ser Ser Ser Ser Ser Tyr Ile Tyr Tyr Ala Asp Ser Val Lys
1               5                   10                  15
Gly

<210> SEQ ID NO 426
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Asp Val Gly Val Thr Thr Asp Tyr Tyr Tyr Tyr Gly Met Asp Val
1               5                   10                  15

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Arg Ala Ser Gln Ser Val Ala Ser Ser Tyr Leu Ala
1               5                   10

<210> SEQ ID NO 428
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Gly Ala Ser Ser Arg Ala Thr
1               5

<210> SEQ ID NO 429
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gln Gln Tyr Gly Ser Ser Pro Pro Tyr Thr
1               5                   10

```
<210> SEQ ID NO 430
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly Phe Thr Phe Ser Asn Tyr
1               5

<210> SEQ ID NO 431
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ser Ser Ser Ser
1

<210> SEQ ID NO 432
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Val Gly Val Thr Thr Asp Tyr Tyr Tyr Tyr Gly Met Asp
1               5                   10

<210> SEQ ID NO 433
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ser Gln Ser Val Ala Ser Ser Tyr
1               5

<210> SEQ ID NO 434
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gly Ala Ser
1

<210> SEQ ID NO 435
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 435

Tyr Gly Ser Ser Pro Pro Tyr
1               5

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Ser Asn Tyr Asp Met Asn
1               5

<210> SEQ ID NO 437
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Trp Val Ser Ser Ile Ser Ser Ser Ser Tyr Ile Tyr
1               5                   10

<210> SEQ ID NO 438
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ala Arg Asp Val Gly Val Thr Thr Asp Tyr Tyr Tyr Tyr Gly Met Asp
1               5                   10                  15

<210> SEQ ID NO 439
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Ala Ser Ser Tyr Leu Ala Trp Tyr
1               5

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Leu Leu Ile Tyr Gly Ala Ser Ser Arg Ala
1               5                   10

<210> SEQ ID NO 441
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gln Gln Tyr Gly Ser Ser Pro Pro Tyr
1               5

<210> SEQ ID NO 442
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Gly Phe Thr Phe Ser Asn Tyr Asp Met Asn
1               5                   10

<210> SEQ ID NO 443
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Ser Ile Ser Ser Ser Ser Ser Tyr Ile Tyr
1               5                   10

<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Asp Val Gly Val Thr Thr Asp Tyr Tyr Tyr Tyr Gly Met Asp Val
1               5                   10                  15

<210> SEQ ID NO 445
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Arg Ala Ser Gln Ser Val Ala Ser Ser Tyr Leu Ala
1               5                   10

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Gly Ala Ser Ser Arg Ala Thr
```

```
1               5
```

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

```
Gln Gln Tyr Gly Ser Ser Pro Pro Tyr Thr
1               5                   10
```

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

```
Gly Asp Thr Phe Asn Asn Tyr Ala Ile Ser
1               5                   10
```

<210> SEQ ID NO 449
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

```
Gly Ile Ile Pro Phe Phe Gly Thr Pro Asp Tyr Ala Gln Lys Phe Gln
1               5                   10                  15

Gly
```

<210> SEQ ID NO 450
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

```
Pro Gly Ser Gly Ser Pro Asp Tyr Tyr Tyr Tyr Asp Met Asp Val
1               5                   10                  15
```

<210> SEQ ID NO 451
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

```
Arg Ser Ser Gln Ser Leu Val His Ser Asp Gly Asn Thr Tyr Leu Ser
1               5                   10                  15
```

<210> SEQ ID NO 452
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 452

Lys Ile Ser Asn Arg Phe Ser
1               5

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Met Gln Ala Thr Gln Phe Pro Leu Thr
1               5

<210> SEQ ID NO 454
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Gly Asp Thr Phe Asn Asn Tyr Ala
1               5

<210> SEQ ID NO 455
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Ile Ile Pro Phe Phe Gly Thr Pro
1               5

<210> SEQ ID NO 456
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Ala Arg Pro Gly Ser Gly Ser Pro Asp Tyr Tyr Tyr Tyr Asp Met Asp
1               5                   10                  15

Val

<210> SEQ ID NO 457
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Gln Ser Leu Val His Ser Asp Gly Asn Thr Tyr
```

```
1               5                   10
```

<210> SEQ ID NO 458
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

```
Lys Ile Ser
1
```

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

```
Met Gln Ala Thr Gln Phe Pro Leu Thr
1               5
```

<210> SEQ ID NO 460
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

```
Asn Tyr Ala Ile Ser
1               5
```

<210> SEQ ID NO 461
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

```
Gly Ile Ile Pro Phe Phe Gly Thr Pro Asp Tyr Ala Gln Lys Phe Gln
1               5                   10                  15

Gly
```

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

```
Pro Gly Ser Gly Ser Pro Asp Tyr Tyr Tyr Tyr Asp Met Asp Val
1               5                   10                  15
```

<210> SEQ ID NO 463
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 463

Arg Ser Ser Gln Ser Leu Val His Ser Asp Gly Asn Thr Tyr Leu Ser
1               5                   10                  15

<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Lys Ile Ser Asn Arg Phe Ser
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Met Gln Ala Thr Gln Phe Pro Leu Thr
1               5

<210> SEQ ID NO 466
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Gly Asp Thr Phe Asn Asn Tyr
1               5

<210> SEQ ID NO 467
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Pro Phe Phe Gly
1

<210> SEQ ID NO 468
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Gly Ser Gly Ser Pro Asp Tyr Tyr Tyr Tyr Asp Met Asp
1               5                   10
```

<210> SEQ ID NO 469
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ser Gln Ser Leu Val His Ser Asp Gly Asn Thr Tyr
1               5                   10

<210> SEQ ID NO 470
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Lys Ile Ser
1

<210> SEQ ID NO 471
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Ala Thr Gln Phe Pro Leu
1               5

<210> SEQ ID NO 472
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Asn Asn Tyr Ala Ile Ser
1               5

<210> SEQ ID NO 473
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Trp Met Gly Gly Ile Ile Pro Phe Phe Gly Thr Pro Asp
1               5                   10

<210> SEQ ID NO 474
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 474

Ala Arg Pro Gly Ser Gly Ser Pro Asp Tyr Tyr Tyr Asp Met Asp
1               5                   10                  15

<210> SEQ ID NO 475
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Val His Ser Asp Gly Asn Thr Tyr Leu Ser Trp Leu
1               5                   10

<210> SEQ ID NO 476
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Leu Leu Ile Tyr Lys Ile Ser Asn Arg Phe
1               5                   10

<210> SEQ ID NO 477
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Met Gln Ala Thr Gln Phe Pro Leu
1               5

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gly Asp Thr Phe Asn Asn Tyr Ala Ile Ser
1               5                   10

<210> SEQ ID NO 479
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Gly Ile Ile Pro Phe Phe Gly Thr Pro Asp
1               5                   10

<210> SEQ ID NO 480
<211> LENGTH: 15
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 480

Pro Gly Ser Gly Ser Pro Asp Tyr Tyr Tyr Asp Met Asp Val
1               5                   10                  15

<210> SEQ ID NO 481
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 481

Arg Ser Ser Gln Ser Leu Val His Ser Asp Gly Asn Thr Tyr Leu Ser
1               5                   10                  15

<210> SEQ ID NO 482
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 482

Lys Ile Ser Asn Arg Phe Ser
1               5

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 483

Met Gln Ala Thr Gln Phe Pro Leu Thr
1               5

<210> SEQ ID NO 484
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 484

Gly Gly Thr Phe Ser Ser Tyr Ala Ile Ser
1               5                   10

<210> SEQ ID NO 485
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 485

Gly Asn Ile Pro Ile Phe Asn Thr Ala Asn Tyr Ala Gln Lys Phe Gln
1               5                   10                  15

Asp

<210> SEQ ID NO 486
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Glu Gly Thr Gly Tyr Ser Tyr Gly Leu Asp Tyr
1               5                   10

<210> SEQ ID NO 487
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Arg Ser Ser Gln Ser Leu Ile His Ser Asp Gly Asn Thr Tyr Leu Ser
1               5                   10                  15

<210> SEQ ID NO 488
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Lys Ile Ser Asn Arg Phe Ser
1               5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Met Gln Ala Lys Gln Phe Pro Ile Thr
1               5

<210> SEQ ID NO 490
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gly Gly Thr Phe Ser Ser Tyr Ala
1               5

<210> SEQ ID NO 491
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 491

Asn Ile Pro Ile Phe Asn Thr Ala
1               5

<210> SEQ ID NO 492
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Val Arg Glu Gly Thr Gly Tyr Ser Tyr Gly Leu Asp Tyr
1               5                   10

<210> SEQ ID NO 493
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Gln Ser Leu Ile His Ser Asp Gly Asn Thr Tyr
1               5                   10

<210> SEQ ID NO 494
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Lys Ile Ser
1

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Met Gln Ala Lys Gln Phe Pro Ile Thr
1               5

<210> SEQ ID NO 496
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Ser Tyr Ala Ile Ser
1               5
```

```
<210> SEQ ID NO 497
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Gly Asn Ile Pro Ile Phe Asn Thr Ala Asn Tyr Ala Gln Lys Phe Gln
1               5                   10                  15

Asp

<210> SEQ ID NO 498
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Glu Gly Thr Gly Tyr Ser Tyr Gly Leu Asp Tyr
1               5                   10

<210> SEQ ID NO 499
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Arg Ser Ser Gln Ser Leu Ile His Ser Asp Gly Asn Thr Tyr Leu Ser
1               5                   10                  15

<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Lys Ile Ser Asn Arg Phe Ser
1               5

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Met Gln Ala Lys Gln Phe Pro Ile Thr
1               5

<210> SEQ ID NO 502
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 502

Gly Gly Thr Phe Ser Ser Tyr
1               5

<210> SEQ ID NO 503
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Pro Ile Phe Asn
1

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Gly Thr Gly Tyr Ser Tyr Gly Leu Asp
1               5

<210> SEQ ID NO 505
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Ser Gln Ser Leu Ile His Ser Asp Gly Asn Thr Tyr
1               5                   10

<210> SEQ ID NO 506
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Lys Ile Ser
1

<210> SEQ ID NO 507
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ala Lys Gln Phe Pro Ile
1               5

<210> SEQ ID NO 508
<211> LENGTH: 6
```

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Ser Ser Tyr Ala Ile Ser
1               5

<210> SEQ ID NO 509
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Trp Met Gly Gly Asn Ile Pro Ile Phe Asn Thr Ala Asn
1               5                   10

<210> SEQ ID NO 510
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Val Arg Glu Gly Thr Gly Tyr Ser Tyr Gly Leu Asp
1               5                   10

<210> SEQ ID NO 511
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Ile His Ser Asp Gly Asn Thr Tyr Leu Ser Trp Leu
1               5                   10

<210> SEQ ID NO 512
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Leu Leu Ile Tyr Lys Ile Ser Asn Arg Phe
1               5                   10

<210> SEQ ID NO 513
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Met Gln Ala Lys Gln Phe Pro Ile
```

```
1               5
```

<210> SEQ ID NO 514
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

```
Gly Gly Thr Phe Ser Ser Tyr Ala Ile Ser
1               5                   10
```

<210> SEQ ID NO 515
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

```
Gly Asn Ile Pro Ile Phe Asn Thr Ala Asn
1               5                   10
```

<210> SEQ ID NO 516
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

```
Glu Gly Thr Gly Tyr Ser Tyr Gly Leu Asp Tyr
1               5                   10
```

<210> SEQ ID NO 517
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

```
Arg Ser Ser Gln Ser Leu Ile His Ser Asp Gly Asn Thr Tyr Leu Ser
1               5                   10                  15
```

<210> SEQ ID NO 518
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

```
Lys Ile Ser Asn Arg Phe Ser
1               5
```

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 519

Met Gln Ala Lys Gln Phe Pro Ile Thr
1               5

<210> SEQ ID NO 520
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Gly Gly Ser Ile Ser Ser Gly Gly Ser Tyr Trp Ser
1               5                   10

<210> SEQ ID NO 521
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Tyr Ile Tyr Asn Ser Gly Ser Thr Tyr Tyr Asn Pro Ser Leu Lys Ser
1               5                   10                  15

<210> SEQ ID NO 522
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Asp Ser Asn Tyr Glu Trp Phe Phe Asp Leu
1               5                   10

<210> SEQ ID NO 523
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Arg Ala Ser Gln Ser Val Ser Ser Tyr Leu Ala
1               5                   10

<210> SEQ ID NO 524
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Asp Ala Ser Asn Arg Ala Thr
1               5

<210> SEQ ID NO 525

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gln Gln Arg Ser Asn Trp Pro Leu Thr
1               5

<210> SEQ ID NO 526
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Gly Gly Ser Ile Ser Ser Gly Gly Ser Tyr
1               5                   10

<210> SEQ ID NO 527
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Ile Tyr Asn Ser Gly Ser Thr
1               5

<210> SEQ ID NO 528
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ala Arg Asp Ser Asn Tyr Glu Trp Phe Phe Asp Leu
1               5                   10

<210> SEQ ID NO 529
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gln Ser Val Ser Ser Tyr
1               5

<210> SEQ ID NO 530
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530
```

Asp Ala Ser
1

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gln Gln Arg Ser Asn Trp Pro Leu Thr
1               5

<210> SEQ ID NO 532
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Ser Gly Gly Ser Tyr Trp Ser
1               5

<210> SEQ ID NO 533
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Tyr Ile Tyr Asn Ser Gly Ser Thr Tyr Tyr Asn Pro Ser Leu Lys Ser
1               5                   10                  15

<210> SEQ ID NO 534
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Asp Ser Asn Tyr Glu Trp Phe Phe Asp Leu
1               5                   10

<210> SEQ ID NO 535
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Arg Ala Ser Gln Ser Val Ser Ser Tyr Leu Ala
1               5                   10

<210> SEQ ID NO 536
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 536

Asp Ala Ser Asn Arg Ala Thr
1               5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Gln Gln Arg Ser Asn Trp Pro Leu Thr
1               5

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Gly Gly Ser Ile Ser Ser Gly Gly Ser
1               5

<210> SEQ ID NO 539
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Asn Ser Gly
1

<210> SEQ ID NO 540
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Ser Asn Tyr Glu Trp Phe Phe Asp
1               5

<210> SEQ ID NO 541
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Ser Gln Ser Val Ser Ser Tyr
1               5
```

```
<210> SEQ ID NO 542
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Asp Ala Ser
1

<210> SEQ ID NO 543
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Arg Ser Asn Trp Pro Leu
1               5

<210> SEQ ID NO 544
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Ser Ser Gly Gly Ser Tyr Trp Ser
1               5

<210> SEQ ID NO 545
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Trp Ile Gly Tyr Ile Tyr Asn Ser Gly Ser Thr Tyr
1               5                   10

<210> SEQ ID NO 546
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Ala Arg Asp Ser Asn Tyr Glu Trp Phe Phe Asp
1               5                   10

<210> SEQ ID NO 547
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547
```

```
Ser Ser Tyr Leu Ala Trp Tyr
1               5

<210> SEQ ID NO 548
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Leu Leu Ile Tyr Asp Ala Ser Asn Arg Ala
1               5                   10

<210> SEQ ID NO 549
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gln Gln Arg Ser Asn Trp Pro Leu
1               5

<210> SEQ ID NO 550
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Gly Gly Ser Ile Ser Ser Gly Gly Ser Tyr Trp Ser
1               5                   10

<210> SEQ ID NO 551
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Tyr Ile Tyr Asn Ser Gly Ser Thr Tyr
1               5

<210> SEQ ID NO 552
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Asp Ser Asn Tyr Glu Trp Phe Phe Asp Leu
1               5                   10

<210> SEQ ID NO 553
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 553

Arg Ala Ser Gln Ser Val Ser Ser Tyr Leu Ala
1               5                   10

<210> SEQ ID NO 554
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Asp Ala Ser Asn Arg Ala Thr
1               5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Gln Gln Arg Ser Asn Trp Pro Leu Thr
1               5

<210> SEQ ID NO 556
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gly Tyr Ser Phe Thr Ser Tyr Trp Ile Ser
1               5                   10

<210> SEQ ID NO 557
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Ile Ile Asp Pro Ser Asp Ser Asp Thr Arg Tyr Ser Pro Ser Phe Gln
1               5                   10                  15

Gly

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gly Asp Gly Ser Thr Asp Leu Asp Tyr
```

```
<210> SEQ ID NO 559
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Arg Ala Ser Gln Ser Val Ser Ser Ser Tyr Leu Ala
1               5                   10

<210> SEQ ID NO 560
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gly Ala Ser Ser Arg Ala Thr
1               5

<210> SEQ ID NO 561
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Gln Gln Asp Tyr Gly Phe Pro Trp Thr
1               5

<210> SEQ ID NO 562
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Gly Tyr Ser Phe Thr Ser Tyr Trp
1               5

<210> SEQ ID NO 563
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Ile Asp Pro Ser Asp Ser Asp Thr
1               5

<210> SEQ ID NO 564
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 564

Ala Arg Gly Asp Gly Ser Thr Asp Leu Asp Tyr
1               5                   10

<210> SEQ ID NO 565
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Gln Ser Val Ser Ser Ser Tyr
1               5

<210> SEQ ID NO 566
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Gly Ala Ser
1

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gln Gln Asp Tyr Gly Phe Pro Trp Thr
1               5

<210> SEQ ID NO 568
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Ser Tyr Trp Ile Ser
1               5

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Ile Ile Asp Pro Ser Asp Ser Asp Thr Arg Tyr Ser Pro Ser Phe Gln
1               5                   10                  15

Gly

```
<210> SEQ ID NO 570
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gly Asp Gly Ser Thr Asp Leu Asp Tyr
1               5

<210> SEQ ID NO 571
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Arg Ala Ser Gln Ser Val Ser Ser Ser Tyr Leu Ala
1               5                   10

<210> SEQ ID NO 572
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Gly Ala Ser Ser Arg Ala Thr
1               5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Gln Gln Asp Tyr Gly Phe Pro Trp Thr
1               5

<210> SEQ ID NO 574
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Tyr Ser Phe Thr Ser Tyr
1               5

<210> SEQ ID NO 575
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 575

Pro Ser Asp Ser
1

<210> SEQ ID NO 576
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Asp Gly Ser Thr Asp Leu Asp
1               5

<210> SEQ ID NO 577
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Ser Gln Ser Val Ser Ser Ser Tyr
1               5

<210> SEQ ID NO 578
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gly Ala Ser
1

<210> SEQ ID NO 579
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Asp Tyr Gly Phe Pro Trp
1               5

<210> SEQ ID NO 580
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Thr Ser Tyr Trp Ile Ser
1               5

<210> SEQ ID NO 581
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 581

Trp Met Gly Ile Ile Asp Pro Ser Asp Ser Asp Thr Arg
1               5                   10

<210> SEQ ID NO 582
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Ala Arg Gly Asp Gly Ser Thr Asp Leu Asp
1               5                   10

<210> SEQ ID NO 583
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Ser Ser Ser Tyr Leu Ala Trp Tyr
1               5

<210> SEQ ID NO 584
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Leu Leu Ile Tyr Gly Ala Ser Ser Arg Ala
1               5                   10

<210> SEQ ID NO 585
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gln Gln Asp Tyr Gly Phe Pro Trp
1               5

<210> SEQ ID NO 586
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Gly Tyr Ser Phe Thr Ser Tyr Trp Ile Ser
1               5                   10
```

```
<210> SEQ ID NO 587
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Ile Ile Asp Pro Ser Asp Ser Asp Thr Arg
1               5                   10

<210> SEQ ID NO 588
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Gly Asp Gly Ser Thr Asp Leu Asp Tyr
1               5

<210> SEQ ID NO 589
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Arg Ala Ser Gln Ser Val Ser Ser Ser Tyr Leu Ala
1               5                   10

<210> SEQ ID NO 590
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Gly Ala Ser Ser Arg Ala Thr
1               5

<210> SEQ ID NO 591
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gln Gln Asp Tyr Gly Phe Pro Trp Thr
1               5

<210> SEQ ID NO 592

<400> SEQUENCE: 592

000
```

```
<210> SEQ ID NO 593
<400> SEQUENCE: 593
000

<210> SEQ ID NO 594
<400> SEQUENCE: 594
000

<210> SEQ ID NO 595
<400> SEQUENCE: 595
000

<210> SEQ ID NO 596
<400> SEQUENCE: 596
000

<210> SEQ ID NO 597
<400> SEQUENCE: 597
000

<210> SEQ ID NO 598
<400> SEQUENCE: 598
000

<210> SEQ ID NO 599
<400> SEQUENCE: 599
000

<210> SEQ ID NO 600
<400> SEQUENCE: 600
000

<210> SEQ ID NO 601
<400> SEQUENCE: 601
000

<210> SEQ ID NO 602
<400> SEQUENCE: 602
000

<210> SEQ ID NO 603
<400> SEQUENCE: 603
000

<210> SEQ ID NO 604
```

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

-continued

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

-continued

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

```
<210> SEQ ID NO 695
<400> SEQUENCE: 695

000

<210> SEQ ID NO 696
<400> SEQUENCE: 696

000

<210> SEQ ID NO 697
<400> SEQUENCE: 697

000

<210> SEQ ID NO 698
<400> SEQUENCE: 698

000

<210> SEQ ID NO 699
<400> SEQUENCE: 699

000

<210> SEQ ID NO 700
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Tyr Pro Gly Asp Gly Asn
1               5

<210> SEQ ID NO 701
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Asn Tyr Gly Asp Tyr Thr Ile Asp
1               5

<210> SEQ ID NO 702
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Tyr Pro Gly Asp Gly Asn
1               5
```

```
<210> SEQ ID NO 703
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Asn Met Gly Met Tyr Thr Ile Asp
1               5

<210> SEQ ID NO 704
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Tyr Pro Gly Asp Gly Asn
1               5

<210> SEQ ID NO 705
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Asn Met Gly Met Tyr Thr Leu Asp
1               5

<210> SEQ ID NO 706
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Tyr Pro Gly Asp Gly Asn
1               5

<210> SEQ ID NO 707
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Asn Tyr Gly Asp Tyr Thr Leu Asp
1               5

<210> SEQ ID NO 708
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 708

Tyr Pro Gly Ser Gly Asn
1               5

<210> SEQ ID NO 709
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Asn Tyr Gly Asp Tyr Thr Ile Asp
1               5

<210> SEQ ID NO 710
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Tyr Pro Gly Ser Gly Asn
1               5

<210> SEQ ID NO 711
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Asn Tyr Gly Asp Tyr Thr Ile Asp
1               5

<210> SEQ ID NO 712
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

His Gly Gly Thr Gly Gly
1               5

<210> SEQ ID NO 713
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Arg Gly Tyr Gly Ala Trp Phe Ala
1               5

<210> SEQ ID NO 714
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 714

Ser Ser Ser Ser Ser Tyr
1               5

<210> SEQ ID NO 715
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Asp Val Gly Val Thr Thr Asp Tyr Tyr Tyr Tyr Gly Met Asp
1               5                   10

<210> SEQ ID NO 716
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

Ile Pro Phe Phe Gly Thr
1               5

<210> SEQ ID NO 717
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

Pro Gly Ser Gly Ser Pro Asp Tyr Tyr Tyr Tyr Asp Met Asp
1               5                   10

<210> SEQ ID NO 718
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Ile Pro Ile Phe Asn Thr
1               5

<210> SEQ ID NO 719
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Glu Gly Thr Gly Tyr Ser Tyr Gly Leu Asp
1               5                   10
```

```
<210> SEQ ID NO 720
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Tyr Asn Ser Gly Ser
1               5

<210> SEQ ID NO 721
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Asp Ser Asn Tyr Glu Trp Phe Phe Asp
1               5

<210> SEQ ID NO 722
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 722

Asp Pro Ser Asp Ser Asp
1               5

<210> SEQ ID NO 723
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Gly Asp Gly Ser Thr Asp Leu Asp
1               5

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000
```

```
<210> SEQ ID NO 727
<400> SEQUENCE: 727

000

<210> SEQ ID NO 728
<400> SEQUENCE: 728

000

<210> SEQ ID NO 729
<400> SEQUENCE: 729

000

<210> SEQ ID NO 730
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Gly Arg Thr Phe Ser Arg Tyr Thr Met Gly
1               5                   10

<210> SEQ ID NO 731
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Ala Ile Ser Trp Ser Gly Gly Arg Thr Asn Phe Ala Gly Ser Val Lys
1               5                   10                  15

Gly

<210> SEQ ID NO 732
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Asp Trp Leu Pro Val Pro Gly Arg Glu Ser Tyr Asp Tyr
1               5                   10

<210> SEQ ID NO 733
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Gly Arg Thr Phe Ser Ser Tyr Ala Met Gly
1               5                   10
```

```
<210> SEQ ID NO 734
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Ala Ile Ser Trp Ser Gly Gly Thr Thr Tyr Tyr Ala Asp Ser Val Lys
1               5                   10                  15

Gly

<210> SEQ ID NO 735
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Ser Leu Asp Cys Ser Gly Pro Gly Cys His Thr Ala Glu Tyr Asp Tyr
1               5                   10                  15

<210> SEQ ID NO 736
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Gly Arg Thr Phe Ser Glu Tyr Ala Met Gly
1               5                   10

<210> SEQ ID NO 737
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Ala Ile Ser Trp Thr Gly Ser Lys Thr Tyr Tyr Ala Asp Ser Val Lys
1               5                   10                  15

Gly

<210> SEQ ID NO 738
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Ser Ser Asp Cys Ser Gly Pro Gly Cys His Thr Glu Glu Tyr Asp Tyr
1               5                   10                  15

<210> SEQ ID NO 739
<211> LENGTH: 10
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 739

Gly Arg Thr Phe Ser Ser Tyr Ala Met Gly
1               5                   10

<210> SEQ ID NO 740
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 740

Ala Val Ser Trp Ser Gly Gly Ser Thr Tyr Tyr Ala Asp Ser Val Lys
1               5                   10                  15

Gly

<210> SEQ ID NO 741
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 741

Ser Gln Asp Cys Ser Gly Pro Gly Cys Tyr Thr Asn Glu Tyr Asp Ser
1               5                   10                  15

<210> SEQ ID NO 742
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 742

Gly Ser Ile Phe Ser Asn Tyr Ala Met Ala
1               5                   10

<210> SEQ ID NO 743
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 743

Ala Val Ser Trp Ser Gly Gly Arg Thr Tyr Tyr Ala Asp Ser Val Lys
1               5                   10                  15

Gly

<210> SEQ ID NO 744
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 744

```
Ser Leu Ser Cys Ser Gly Pro Gly Cys Ser Leu Glu Glu Tyr Asp Tyr
1               5                   10                  15
```

<210> SEQ ID NO 745
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

```
Gly Arg Pro Phe Ser Asn Tyr Gly Met Gly
1               5                   10
```

<210> SEQ ID NO 746
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

```
Gly Ile Thr Trp Ser Gly Gly Ser Thr His Tyr Ala Asp Leu Val Lys
1               5                   10                  15

Gly
```

<210> SEQ ID NO 747
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

```
Val Phe Ser Gly Ala Glu Thr Ala Tyr Tyr Pro Ser Thr Glu Tyr Asp
1               5                   10                  15

Tyr
```

<210> SEQ ID NO 748
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

```
Val Arg Thr Phe Ser Asp Tyr Arg Met Gly
1               5                   10
```

<210> SEQ ID NO 749
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

```
Thr Ile Ser Trp Ser Gly Gly Leu Thr Tyr Tyr Ala Asp Ser Val Lys
1               5                   10                  15

Gly
```

<210> SEQ ID NO 750
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Gly Gly Gly Tyr Ala Gly Gly Thr Tyr Tyr His Pro Glu Glu
1               5                   10

<210> SEQ ID NO 751
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 751

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Gly Arg Thr Asn Phe Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Trp Leu Pro Val Pro Gly Arg Glu Ser Tyr Asp Tyr Trp
            100                 105                 110

Gly Gln Gly Thr Gln Val Thr Val Ser Ser
        115                 120

<210> SEQ ID NO 752
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 752

Glu Val Gln Leu Val Glu Ser Gly Gly Gly Leu Val Gln Ala Gly Gly
1               5                   10                  15

Ser Leu Arg Leu Ser Cys Thr Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Thr Thr Tyr Tyr Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asn Ser Leu Lys Pro Glu Asp Thr Ala Val Tyr Phe Cys
                85                  90                  95

Ala Ala Ser Leu Asp Cys Ser Gly Pro Gly Cys His Thr Ala Glu Tyr

```
                    100                 105                 110
Asp Tyr Trp Gly Gln Gly Thr Gln Val Thr Val Ser Ser
            115                 120                 125

<210> SEQ ID NO 753
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 753

Glu Val Gln Leu Val Glu Ser Gly Gly Gly Leu Val Gln Ala Gly Gly
1               5                   10                  15

Ser Leu Arg Leu Ser Cys Ala Ala Thr Gly Arg Thr Phe Ser Glu Tyr
            20                  25                  30

Ala Met Gly Trp Phe Arg Gln Ala Pro Gly Lys Glu Arg Glu Phe Ala
        35                  40                  45

Ala Ala Ile Ser Trp Ile Gly Ser Lys Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ser Asp Cys Ser Gly Pro Gly Cys His Thr Glu Glu Tyr
            100                 105                 110

Asp Tyr Trp Gly Gln Gly Thr Gln Val Thr Val Ser Ser
            115                 120                 125

<210> SEQ ID NO 754
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 754

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Val Ser Trp Ser Gly Gly Ser Thr Tyr Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Asn Pro Glu Asp Thr Ala Val Tyr Tyr Cys
                85                  90                  95

Ala Ala Ser Gln Asp Cys Ser Gly Pro Gly Cys Tyr Thr Asn Glu Tyr
            100                 105                 110

Asp Ser Trp Gly Gln Gly Thr Gln Val Thr Val Ser Ser
            115                 120                 125

<210> SEQ ID NO 755
<211> LENGTH: 125
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 755

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Asn Tyr
            20                  25                  30

Ala Met Ala Trp Phe Arg Gln Ala Pro Glu Lys Glu Arg Asp Phe Leu
        35                  40                  45

Ala Ala Val Ser Trp Ser Gly Arg Thr Tyr Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Ser Leu Ser Cys Ser Gly Pro Gly Cys Ser Leu Glu Glu Tyr
            100                 105                 110

Asp Tyr Trp Gly Gln Gly Thr Gln Val Thr Val Ser Ser
        115                 120                 125

<210> SEQ ID NO 756
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 756

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Pro Phe Ser Asn Tyr
            20                  25                  30

Gly Met Gly Trp Phe Arg Gln Ala Pro Gly Lys Glu Arg Glu Phe Val
        35                  40                  45

Ala Gly Ile Thr Trp Ser Gly Gly Ser Thr His Tyr Ala Asp Leu Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Thr Glu
            100                 105                 110

Tyr Asp Tyr Trp Gly Gln Gly Thr Gln Val Thr Val Ser Ser
        115                 120                 125

<210> SEQ ID NO 757
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 757

Glu Val Gln Leu Val Glu Ser Gly Gly Gly Leu Val Gln Ala Gly Gly
1               5                   10                  15

```
Ser Leu Arg Leu Ser Cys Ala Val Ser Val Arg Thr Phe Ser Asp Tyr
        20                  25                  30

Arg Met Gly Trp Phe Arg Gln Ala Pro Gly Lys Glu Arg Glu Phe Val
        35                  40                  45

Ser Thr Ile Ser Trp Ser Gly Gly Leu Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                    85                  90                  95

Ala Ala Gly Gly Gly Tyr Ala Gly Thr Tyr Tyr His Pro Glu Glu
            100                 105                 110

Trp Gly Gln Gly Thr Gln Val Thr Val Ser Ser
        115                 120

<210> SEQ ID NO 758
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr or Met
<220> FEATURE:
<221> NAME/KEY: MOD_RES
<222> LOCATION: (6)..(6)
<223> OTHER INFORMATION: Met or Asp
<220> FEATURE:
<221> NAME/KEY: MOD_RES
<222> LOCATION: (9)..(9)
<223> OTHER INFORMATION: Ile or Leu

<400> SEQUENCE: 758

Ala Pro Asn Xaa Gly Xaa Tyr Thr Xaa Asp Phe
1               5                   10

<210> SEQ ID NO 759

<400> SEQUENCE: 759

000

<210> SEQ ID NO 760

<400> SEQUENCE: 760

000

<210> SEQ ID NO 761
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Asp, or Gly
<220> FEATURE:
<221> NAME/KEY: MOD_RES
<222> LOCATION: (5)..(6)
<223> OTHER INFORMATION: Ser or Asn
```

```
<400> SEQUENCE: 761

Gly Xaa Thr Phe Xaa Xaa
1               5

<210> SEQ ID NO 762
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (6)..(6)
<223> OTHER INFORMATION: Val or Leu

<400> SEQUENCE: 762

Arg Xaa Ser Gln Ser Xaa
1               5
```